United States Patent
Agbandje-McKenna et al.

(10) Patent No.: US 12,163,152 B2
(45) Date of Patent: Dec. 10, 2024

(54) AAV CHIMERAS

(71) Applicant: University of Florida Research Foundation, Incorporated, Gainesville, FL (US)

(72) Inventors: Mavis Agbandje-McKenna, Gainesville, FL (US); Mario Mietzsch, Gainesville, FL (US); Robert McKenna, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 18/150,430

(22) Filed: Jan. 5, 2023

(65) Prior Publication Data

US 2023/0399658 A1    Dec. 14, 2023

Related U.S. Application Data

(63) Continuation of application No. 16/978,657, filed as application No. PCT/US2019/021048 on Mar. 6, 2019, now Pat. No. 11,905,524.

(60) Provisional application No. 62/639,466, filed on Mar. 6, 2018.

(51) Int. Cl.
C12N 7/00    (2006.01)
C12N 15/861    (2006.01)

(52) U.S. Cl.
CPC .. *C12N 15/861* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | |
|---|---|---|
| 6,491,907 B1 | 12/2002 | Rabinowitz et al. |
| 11,905,524 B2 | 2/2024 | Agbandje-Mckenna et al. |
| 2003/0040101 A1 | 2/2003 | Wilson et al. |
| 2003/0148506 A1 | 8/2003 | Kotin et al. |
| 2013/0109742 A1 | 5/2013 | Hewitt et al. |

FOREIGN PATENT DOCUMENTS

| | | |
|---|---|---|
| CN | 1461805 A | 12/2003 |
| CN | 101724608 A | 6/2010 |
| WO | WO 2003/104392 A2 | 12/2003 |
| WO | WO 2011/088081 A1 | 7/2011 |
| WO | WO 2017/100674 A1 | 6/2017 |

OTHER PUBLICATIONS

Extended European Search Report mailed Feb. 4, 2022 for Application No. EP19764877.7.
Invitation to Pay Additional Fees mailed May 9, 2019 in connection with Application No. PCT/US2019/021048.
International Search Report and Written Opinion mailed Jul. 5, 2019 in connection with Application No. PCT/US2019/021048.

(Continued)

*Primary Examiner* — M Franco G Salvoza
(74) *Attorney, Agent, or Firm* — Wolf, Greenfield & Sacks, P.C.

(57) ABSTRACT

Provided herein are compositions and methods for packaging a recombinant adeno-associated virus (rAAV) particle comprising using inverted terminal repeats (ITRs) and rep genes of different serotypes and/or using chimeric rep genes.

13 Claims, 22 Drawing Sheets

Specification includes a Sequence Listing.

(56) References Cited

OTHER PUBLICATIONS

International Preliminary Report on Patentability mailed Sep. 17, 2020 in connection with Application No. PCT/US2019/021048.

Chiorini et al., Adeno-associated virus (AAV) type 5 Rep protein cleaves a unique terminal resolution site compared with other AAV serotypes. J Virol. May 1999;73(5):4293-8. doi: 10.1128/JVI.73.5.4293-4298.1999.

Hewitt et al., Creating a novel origin of replication through modulating DNA-protein interfaces. PLoS One. Jan. 22, 2010;5(1):e8850. doi: 10.1371/journal.pone.0008850.

Hickman et al., Structural unity among viral origin binding proteins: crystal structure of the nuclease domain of adeno-associated virus Rep. Mol Cell. Aug. 2002;10(2):327-37. doi: 10.1016/s1097-2765(02)00592-0.

Mietzsch et al., Improved Genome Packaging Efficiency of Adeno-associated Virus Vectors Using Rep Hybrids. J Virol. Sep. 9, 2021;95(19):e0077321. doi: 10.1128/JVI.00773-21. Epub Jul. 21, 2021.

Mori et al., Two novel adeno-associated viruses from cynomolgus monkey: pseudotyping characterization of capsid protein. Virology. Dec. 20, 2004;330(2):375-83. doi: 10.1016/j.virol.2004.10.012.

Rabinowitz et al., Cross-packaging of a single adeno-associated virus (AAV) type 2 vector genome into multiple AAV serotypes enables transduction with broad specificity. J Virol. Jan. 2002;76(2):791-801. doi: 10.1128/jvi.76.2.791-801.2002.

Smith et al., An adeno-associated virus (AAV) initiator protein, Rep78, catalyzes the cleavage and ligation of single-stranded AAV ori DNA. J Virol. Apr. 2000;74(7):3122-9. doi: 10.1128/jvi.74.7.3122-3129.2000.

Yoon et al., Amino-terminal domain exchange redirects origin-specific interactions of adeno-associated virus rep78 in vitro. J Virol. Apr. 2001;75(7):3230-9. doi: 10.1128/JVI.75.7.3230-3239.2001.

Grimm et al., Liver transduction with recombinant adeno-associated virus is primarily restricted by capsid serotype not vector genotype. J Virol. Jan. 2006;80(1):426-39. doi: 10.1128/JVI.80.1.426-439.2006.

|      | AAV1 | AAV2 | AAV3 | AAV4 | AAV5 | AAV6 | AAV7 | AAV8 | AAV9 |
|------|------|------|------|------|------|------|------|------|------|
| AAV1 |      | 81.6 | 85.1 | 77.7 | 56.3 | 81.6 | 95.9 | N/A  | N/A  |
| AAV2 | 87.3 |      | 82.3 | 81.1 | 54.5 | 100  | 83.6 | N/A  | N/A  |
| AAV3 | 88.5 | 88.9 |      | 78.5 | 55.1 | 82.3 | 87.8 | N/A  | N/A  |
| AAV4 | 89.8 | 90.2 | 92.6 |      | 54.5 | 81.1 | 80.4 | N/A  | N/A  |
| AAV5 | 57.7 | 58.0 | 58.0 | 58.3 |      | 54.4 | 55.1 | N/A  | N/A  |
| AAV6 | 99.4 | 87.3 | 88.5 | 89.4 | 58.0 |      | 83.6 | N/A  | N/A  |
| AAV7 | 97.6 | 88.3 | 89.6 | 90.2 | 58.3 | 97.6 |      | N/A  | N/A  |
| AAV8 | 95.0 | 85.4 | 87.2 | 87.7 | 57.2 | 95.0 | 96.0 |      | N/A  |
| AAV9 | N/A  | N/A  | N/A  | N/A  | N/A  | N/A  | N/A  |      |      |

ITR DNA sequence identity [%]

Rep78 amino acid sequence identity [%]

FIG. 5

| Rep variant plasmid | genome packaging efficiency |
|---|---|
| R2V1 | reference |
| R2n1V1 | 1.7-fold higher |
| R2d1V1 | 4.9-fold higher |
| R2h1V1 | 3.8-fold higher |

| Rep variant plasmid | genome packaging efficiency |
|---|---|
| R1c2V1 | 3.0-fold higher |
| R1nc2V1 | 1.4-fold higher |
| R1dc2V1 | 2.0-fold higher |
| R1hc2V1 | 4.5-fold higher |

FIG. 7B

| | AAV1 expression plasmids (all encode the AAV1 cap gene) | | |
|---|---|---|---|
| plasmid name | description of rep gene | VP expression | genome packaging efficiency |
| pR1c2V1 | AAV1 rep gene (ATG start codon) with AAV2 Rep C-terminus (aa 371-621) | similar to pR2V1 | 3.0-fold higher than pR2V1 |
| pR1hc2V1 | AAV1 rep gene (ATG start codon) with AAV2 Rep helicase domain (aa 243-370) + C-terminus (aa 371-621) | similar to pR2V1 | 4.5-fold higher than pR2V1 |
| pR2d1V1 | AAV2 rep gene (ACG start codon) with AAV1 Rep DNA-binding domain (aa 103-242) | similar to pR2V1 | 4.9-fold higher than pR2V1 |
| pR2h1V1 | AAV2 rep gene (ACG start codon) with AAV1 Rep helicase domain (aa 243-370) | similar to pR2V1 | 3.8-fold higher than pR2V1 |
| variants to be tested | | | |
| pR1y2V1 | AAV1 rep gene (ATG start codon) with AAV2 Rep p40 region (aa 371-529) | | |
| pR1z2V1 | AAV1 rep gene (ATG start codon) with AAV2 zinc finger domain (aa 530-621) | | |
| pR1hy2V1 | AAV1 rep gene (ATG start codon) with AAV2 Rep helicase domain (aa 243-370) + AAV2 Rep p40 region (aa 371-529) | | |
| pR1hz2V1 | AAV1 rep gene (ATG start codon) with AAV2 Rep helicase domain (aa 243-370) + AAV2 zinc finger domain (aa 530-621) | | |
| pR2dy1V1 | AAV2 rep gene (ACG start codon) with AAV1 Rep DNA-binding domain (aa 103-242) + AAV1 Rep p40 region (aa 371-530) | | |
| pR2dz1V1 | AAV2 rep gene (ACG start codon) with AAV1 Rep DNA-binding domain (aa 103-242) + AAV1 zinc finger domain (aa 531-623) | | |

FIG. 8

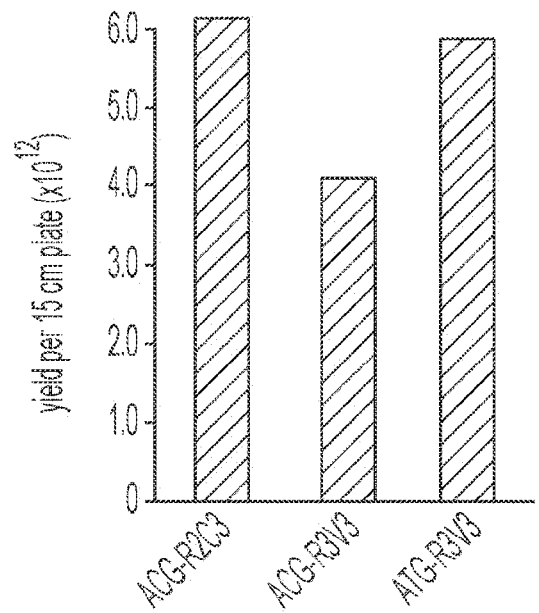

FIG. 9C

| AAV3 expression plasmids (all contain AAV3 cap gene) | |
|---|---|
| plasmid name | description of rep gene |
| pR2V3 | AAV2 rep gene (ACG start codon) |
| pACG-R3V3 | AAV3 rep gene (ACG start codon) |
| pATG-R3V3 | AAV3 rep gene (ATG start codon) |
| pR1c2V3 | AAV1 rep gene (ACG start codon) with AAV2 Rep C-terminus (aa 371-621) |
| pR1hc2V3 | AAV1 rep gene (ATG start codon) with AAV2 Rep helicase domain (aa 243-370) + C-terminus (aa 371-621) |
| pR2d1V3 | AAV2 rep gene (ACG start codon) with AAV1 Rep DNA-binding domain (aa 103-242) |
| pR2h1V3 | AAV2 rep gene (ACG start codon) with AAV1 Rep helicase domain (aa 243-370) |
| pR8d1c2V3 | AAV8 rep gene (ATG start codon) with AAV1 Rep DNA-binding domain (aa 103-242) + AAV2 C-terminus (aa 371-621) |
| pR3h2V3 | AAV3 rep gene (ATG start codon) with AAV2 Rep helicase domain (aa 243-370) |
| pR3d2V3 | AAV3 rep gene (ATG start codon) with AAV2 Rep DNA-binding domain (aa 103-242) |
| variants to be tested | |

FIG. 9D

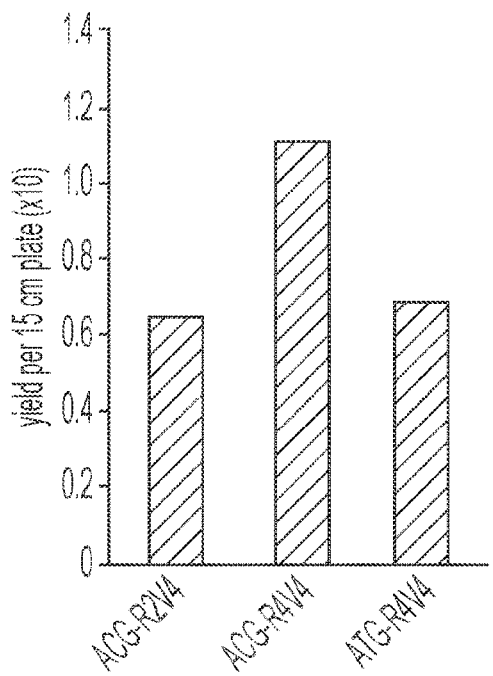

FIG. 10C

| AAV4 expression plasmids (all contain AAV4 cap gene) | |
|---|---|
| plasmid name | description of rep gene |
| pR2V4 | AAV2 rep gene (ACG start codon) |
| pACG-R4V4 | AAV4 rep gene (ACG start codon) |
| pATG-R4V4 | AAV4 rep gene (ATG start codon) |
| pR1c2V4 | AAV1 rep gene (ACG start codon) with AAV2 Rep C-terminus (aa 371-621) |
| pR1hc2V4 | AAV1 rep gene (ATG start codon) with AAV2 Rep helicase domain (aa 243-370) + C-terminus (aa 371-621) |
| pR2d1V4 | AAV2 rep gene (ACG start codon) with AAV1 Rep DNA-binding domain (aa 103-242) |
| pR2h1V4 | AAV2 rep gene (ACG start codon) with AAV1 Rep helicase domain (aa 243-370) |
| pR8d1c2V4 | AAV8 rep gene (ATG start codon) with AAV1 Rep DNA-binding domain (aa 103-242) + AAV2 C-terminus (aa 371-621) |
| pR4h2V4 | AAV4 rep gene (ACG start codon) with AAV2 Rep helicase domain (aa 243-370) |
| pR4d2V4 | AAV4 rep gene (ACG start codon) with AAV2 Rep DNA-binding domain (aa 103-242) |
| variants to be tested | |

FIG. 10D

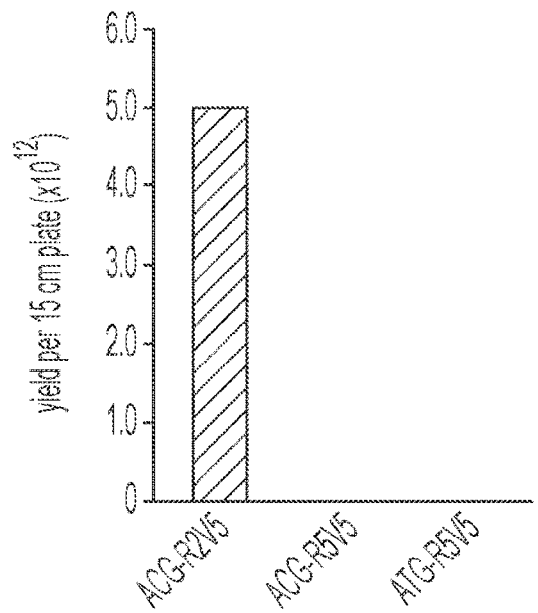

FIG. 11C

| AAV5 expression plasmids (all contain AAV5 cap gene) | |
|---|---|
| plasmid name | description of rep gene |
| pR2V5 | AAV2 rep gene (ACG start codon) |
| pACG-R5V5 | AAV5 rep gene (ACG start codon) |
| pATG-R5V5 | AAV5 rep gene (ATG start codon) |
| pR1c2V5 | AAV1 rep gene (ACG start codon) with AAV2 Rep C-terminus (aa 371-621) |
| pR1hc2V5 | AAV1 rep gene (ATG start codon) with AAV2 Rep helicase domain (aa 243-370) + C-terminus (aa 371-621) |
| pR2d1V5 | AAV2 rep gene (ACG start codon) with AAV1 Rep DNA-binding domain (aa 103-242) |
| pR2h1V5 | AAV2 rep gene (ACG start codon) with AAV1 Rep helicase domain (aa 243-370) |
| pR8d1c2V5 | AAV8 rep gene (ATG start codon) with AAV1 Rep DNA-binding domain (aa 103-242) + AAV2 C-terminus (aa 371-621) |
| pR5h2V5 | AAV5 rep gene (ACG start codon) with AAV2 Rep helicase domain (aa 243-370) |
| pR5d2V5 | AAV5 rep gene (ACG start codon) with AAV2 Rep DNA-binding domain (aa 103-242) |
| variants to be tested | |

FIG. 11D

| Rep variant plasmid | genome packaging efficiency |
|---|---|
| R2V6 | reference |
| R8d1c2V6 | ~2.9-fold higher |
| R1hc2V6 | ~2.4-fold higher |

FIG. 12B

| plasmid name | description of rep gene | AAV1 expression plasmids (all encode the AAV1 cap gene) | | |
|---|---|---|---|---|
| | | | VP expression | genome packaging efficiency |
| pR8d1c2v6 | AAV8 rep gene (ATG start codon) with AAV1 Rep DNA-binding domain (aa 103-242) + AAV2 Rep C-terminus (aa 371-621) | | similar to pR2v6 | 2.9-fold higher than pR2v6 |
| pR1hc2v6 | AAV1 rep gene (ATG start codon) with AAV2 Rep helicase domain (aa 243-370) + C-terminus (aa 371-621) | | similar to pR2v6 | 2.4-fold higher than pR2v6 |
| variants to be tested | | | | |
| pR8d1v2v6 | AAV8 rep gene (ATG start codon) with AAV1 Rep DNA-binding domain (aa 103-242) + AAV2 Rep p40 region (aa 371-529) | | | |
| pR8d12v6 | AAV8 rep gene (ATG start codon) with AAV1 Rep DNA-binding domain (aa 103-242) + AAV2 zinc finger domain (aa 530-621) | | | |
| pR1hv2v6 | AAV1 rep gene (ATG start codon) with AAV2 Rep helicase domain (aa 243-370) + AAV2 Rep p40 region (aa 371-529) | | | |
| pR1hz2v6 | AAV1 rep gene (ATG start codon) with AAV2 Rep helicase domain (aa 243-370) + AAV2 zinc finger domain (aa 530-621) | | | |

FIG. 12C

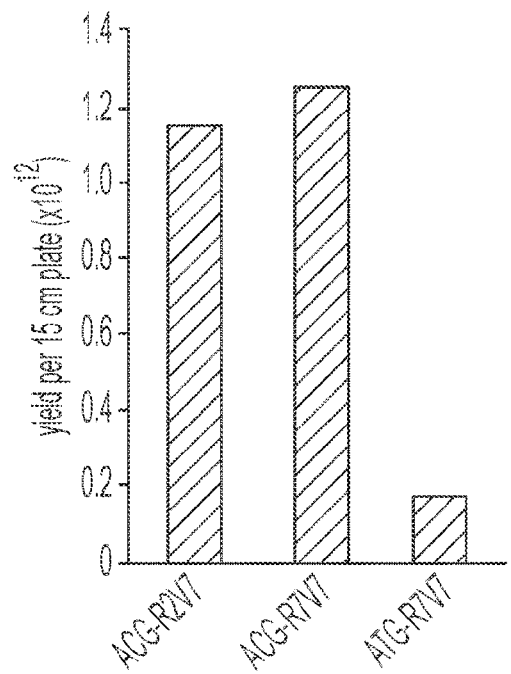

FIG. 13C

| AAV7 expression plasmids (all contain AAV7 cap gene) | |
|---|---|
| plasmid name | description of rep gene |
| pR2V7 | AAV2 rep gene (ACG start codon) |
| pACG-R7V7 | AAV6 rep gene (ACG start codon) |
| pATG-R7V7 | AAV6 rep gene (ATG start codon) |
| pR1c2V7 | AAV1 rep gene (ACG start codon) with AAV2 Rep C-terminus (aa 371-621) |
| pR1hc2V7 | AAV1 rep gene (ATG start codon) with AAV2 Rep helicase domain (aa 243-370) + C-terminus (aa 371-621) |
| pR2d1V7 | AAV2 rep gene (ACG start codon) with AAV1 Rep DNA-binding domain (aa 103-242) |
| pR2h1V7 | AAV2 rep gene (ACG start codon) with AAV1 Rep helicase domain (aa 243-370) |
| pR8d1c2V7 | AAV8 rep gene (ATG start codon) with AAV1 Rep DNA-binding domain (aa 103-242) + AAV2 C-terminus (aa 371-621) |
| pR7hc2V7 | AAV7 rep gene (ACG start codon) with AAV2 Rep helicase domain (aa 243-370) + AAV2 C-terminus (aa 371-621) |
| pR7dc2V7 | AAV7 rep gene (ACG start codon) with AAV2 Rep DNA-binding domain (aa 103-242) + AAV2 C-terminus (aa 371-621) |
| variants to be tested | |

FIG. 13D

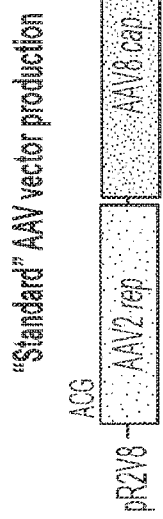
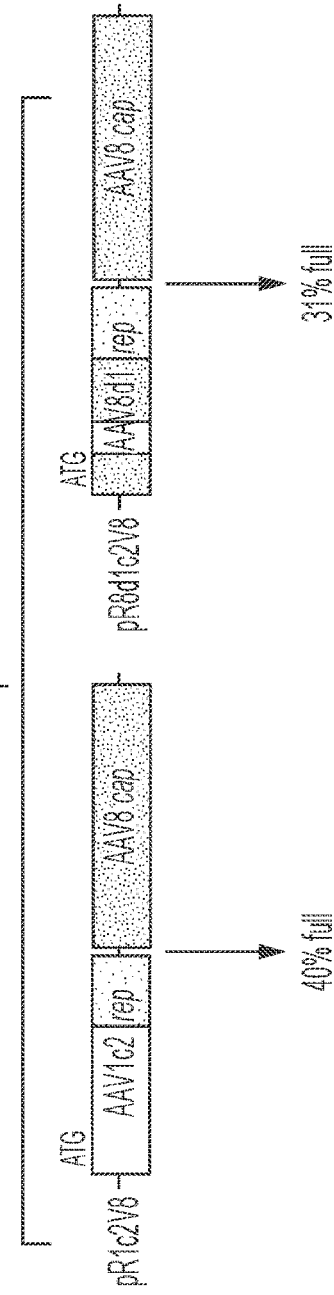
FIG. 15A
FIG. 15B

| AAV8 expression plasmids (all contain AAV8 cap gene) | | | |
|---|---|---|---|
| plasmid name | description of rep gene | VP expression | genome packaging |
| pR8d1c2V8 | AAV8 rep gene (ATG start codon) with AAV1 Rep DNA-binding domain (aa 103-242) + AAV2 Rep C-terminus (aa 371-621) | high, similar to pR2V8 | higher than pR2V8 (~3 fold) |
| pR1c2V8 | AAV1 rep gene (ATG start codon) with AAV2 Rep C-terminus (aa 371-621) | high, similar to pR2V8 | higher than pR2V8 (~4 fold) |
| pR8p1c2V8 | AAV8 rep gene (ATG start codon) with six nucleotide deletions in the AAV8 DNA-binding domain + AAV2 Rep C-terminus (aa 371-621) | high, similar to pR2V8 | higher than pR2V8 (~4 fold) |

FIG. 16A

SEQ ID NO: 186 Query AAGTCCATGGTGCTAGGCCGCTTCCTGAGTCAGATTCGGGGAAAAGCTTGGTCCAGACCAT
SEQ ID NO: 187 Sbjct AAGTCCATGGTGCTAGGCCGCTTCCTGAGTCAGATTCGGGGAAAAGCTTGGTCCAGACCAT Query CTACCTCGGGGGTCGAGCCCCACCTTGCCCAACTGGTTCGGGTGACCAAAGACGCGGTA
Sbjct CTACCCCGGGGGTCGAGCCCCACCTTGCCCAACTGGTTCGGGTGACCAAAGACGCGGTA Query ATGGCGCCGGCGGGGGGAACAAGGTGCTGGACGAGTGCTACATCCCCAACTACCTCCTG
Sbjct ATGGCGCCGGCGGGGGGAACAAGGTGCTGGACGAGTGCTACATCCCCAACTACCTCCTG

FIG. 16B

AAV CHIMERAS

RELATED APPLICATIONS

This application is a continuation of U.S. patent application Ser. No. 16/978,657, filed Sep. 4, 2020, which is a national stage filing under 35 U.S.C. § 371 of International Patent Application Serial No. PCT/US2019/021048, filed Mar. 6, 2019, which claims the benefit of U.S. Provisional Application No. 62/639,466, filed on Mar. 6, 2018, each of which is incorporated herein by reference in its entirety.

REFERENCE TO AN ELECTRONIC SEQUENCE LISTING

The contents of the electronic sequence listing (U119670055US02-SEQ-KSB.xml; Size: 266,249 bytes; and Date of Creation: Jan. 5, 2023) is herein incorporated by reference in its entirety.

BACKGROUND

Adeno-associated virus (AAV) particles are commonly used for research and also for gene therapy applications, including several in clinical development.

Methods and compositions for producing recombinant adeno-associated virus (rAAV) particles, in both small and large scale, are useful for research, pre-clinical, and clinical applications.

SUMMARY

Recombinant AAV particle production can involve culturing cells, introducing to those cells AAV genes and genes of interest that are desired to be packaged in rAAV particles, and allowing the cells to package (or produce) rAAV particles. Cells that package or produce rAAV particles are also referred to herein as "producer cells." AAV genes that are introduced to a producer cell generally include rep, cap, helper genes and inverted terminal repeats (ITRs) which flank one or more genes of interest. In the last decade numerous AAV cap genes from multiple natural serotypes and variants have been utilized for different gene therapy applications. In contrast, variation of rep and ITR sequences and how they influence rAAV particle packaging has not been explored. This application is related, at least in part, to the finding that both rep and ITR sequences can be varied to improve the packaging of rAAV particles of difference serotypes. In some embodiments, recombinant Rep proteins (e.g., chimeric Rep proteins) and/or genes encoding them as described in this application can be used in the production of rAAV particles comprising recombinant rAAV nucleic acids including one or more genes of interest flanked by ITR sequences (e.g., of different serotypes) as described in this application.

Accordingly, in one aspect, provided herein is a composition comprising a nucleic acid comprising a rep gene, wherein the rep gene is chimeric. In some embodiments, a rep gene comprises an N-terminus and a C-terminus (c). In some embodiments, an N terminus comprises an N-terminus domain (n), a DNA binding domain (d), and a helicase domain (h). In some embodiments, a C terminus comprises a NLS/p40 promoter domain (y) and a Zinc finger domain (z). In some embodiments, a rep gene is of serotype AAV1, AAV2, AAV3, AAV4, AAV6, AAV12, AAV13, AAV1 and AAV2, or AAV5 and AAV2, or is chimeric.

In some embodiments, an N terminus is of AAV1 serotype and the C terminus is of AAV2 serotype. In some embodiments, an N terminus is of AAV2 serotype and the C terminus is of AAV1 serotype. In some embodiments, an N terminus is of AAV2 serotype and the C terminus is of AAV5 serotype. In some embodiments, an N terminus is of AAV5 serotype and the C terminus is of AAV2 serotype.

In some embodiments, n, d, y, and z domains are of AAV2 serotype and an h domain is of AAV1 serotype. In some embodiments, n, h, y, and z domains are of AAV2 serotype and a d domain is of AAV1 serotype. In some embodiments, d, h, y, and z domains are of AAV2 serotype and a n domain is of AAV1 serotype. In some embodiments, n, d, and h domains are of AAV1 serotype and y and z domains are of AAV1 serotype. In some embodiments, d and h domains are of AAV1 serotype and n, y and z domains are of AAV2 serotype. In some embodiments, n and d domains are of AAV1 serotype and h, y, and z domains is of AAV2 serotype.

In some embodiments, n, d, and h domains are of AAV2 serotype and y and z domains are of AAV3 serotype. In some embodiments, a rep gene having n, d, and h domains are of AAV2 serotype and y and z domains are of AAV3 serotype has a start codon of sequence ACG. In some embodiments, a rep gene is of AAV3 serotype, and has a start codon of sequence ATG.

In some embodiments, a rep gene is of AAV4 serotype, and has a start codon of sequence ACG.

In some embodiments, a rep gene is of AAV2 serotype, and has a start codon of sequence ACG.

In some embodiments, n and h domains are of AAV8 serotype and d, y and z domains are of AAV2 serotype. In some embodiments, n and d domains are of AAV1 serotype and h, y, and z domains are of AAV2 serotype.

In some embodiments, a rep gene is of AAV2 serotype, and has a start codon of sequence ACG. In some embodiments, a rep gene is of AAV7 serotype, and has a start codon of sequence ACG.

In some embodiments, n and h domains are of AAV8 serotype and the d, y, and z domains are of AAV2 serotype, and a rep gene has a start codon of sequence ATG. In some embodiments, n, h and d domains are of AAV1 serotype and the y and z domains are of AAV2 serotype, and a rep gene has a start codon of sequence ATG. In some embodiments, n and h domains are of AAV8 serotype, the following nucleotides are deleted in the d domain: T574, C592, C607, A637, G644, AND C657 according to SEQ ID NO: 125 (and resulting in SEQ ID NO: 126), y and z domains are of AAV2 serotype, and a rep gene has a start codon of sequence ATG.

In some embodiments, any one of the compositions described herein further comprises a nucleic acid comprising a cap gene. The cap gene may be of any serotype (e.g., 1, 2, 3, 4, 5, 6, 7, 8, 9, 10, 11, 12, or 13).

In some embodiments, the nucleic acid comprising the rep gene and the nucleic acid comprising the cap gene are comprised by a nucleic acid vector. In some embodiments, a nucleic acid vector comprising nucleic acid comprising a rep gene and the nucleic acid comprising a cap gene further comprises a nucleic acid comprising a pair of ITRs. In some embodiments, a gene of interest is flanked by the pair of ITRs.

Accordingly, in one aspect, provided herein is a method of packaging a recombinant adeno-associated virus (AAV) particle comprising contacting a cell that expresses a rep gene of a first serotype with a recombinant nucleic acid that comprises a pair of inverted terminal repeats (ITRs) of a second serotype. In some embodiments, a rep gene is expressed by transfecting or infecting the cell with a nucleic acid encoding the rep gene. In some embodiments, a rep gene is chimeric. A chimeric rep gene is one that comprises corresponding nucleic acid bases of more than AAV one serotype. In some embodiments, a rep gene is of serotype 1, 2, 3, 4, 6, 12, 13, 1 and 2, or 5 and 2.

In some embodiments of any one of the methods disclosed herein, Rep proteins encoded by a rep gene of serotype 1 and 2 comprise amino acids of serotype 1 in the N terminus and amino acids of serotype 2 in the C terminus. In some embodiments, Rep proteins encoded by a rep gene of serotype 1 and 2 comprise amino acids of serotype 2 in the N terminus and amino acids of serotype 1 in the C terminus. In some embodiments, Rep proteins encoded by a rep gene of serotype 2 and 5 comprise amino acids of serotype 2 in the N terminus and amino acids of serotype 5 in the C terminus. In some embodiments, Rep proteins encoded by a rep gene of serotype 5 and 2 comprise amino acids of serotype 5 in the N terminus and amino acids of serotype 2 in the C terminus.

In some embodiments of any one of the methods disclosed herein, the first serotype of the rep gene is serotype 1. In some embodiments, the first serotype of the rep gene is serotype 1, and the second serotype of the ITRs is serotype 1, 2, 3, 4, or 7. In some embodiments, the first serotype of the rep gene is serotype 1, and the second serotype of the ITRs is serotype 1. In some embodiments, the first serotype of the rep gene is serotype 1, and the second serotype of the ITRs is serotype 2. In some embodiments, the first serotype of the rep gene is serotype 1, and the second serotype of the ITRs is serotype 3. In some embodiments, the first serotype of the rep gene is serotype 1, and the second serotype of the ITRs is serotype 4. In some embodiments, the first serotype of the rep gene is serotype 1, and the second serotype of the ITRs is serotype 7.

In some embodiments of any one of the methods disclosed herein, the second serotype of the ITRs is serotype 6. In some embodiments of any one of the methods disclosed herein, the second serotype of the ITRs is serotype 6, and the first serotype of the rep gene is serotype 2, 3, 4, 6, 12, or 13. In some embodiments of any one of the methods disclosed herein, the second serotype of the ITRs is serotype 6, and the first serotype of the rep gene is serotype 2. In some embodiments of any one of the methods disclosed herein, the second serotype of the ITRs is serotype 6, and the first serotype of the rep gene is serotype 3. In some embodiments of any one of the methods disclosed herein, the second serotype of the ITRs is serotype 6, and the first serotype of the rep gene is serotype 4. In some embodiments of any one of the methods disclosed herein, the second serotype of the ITRs is serotype 6, and the first serotype of the rep gene is serotype 6. In some embodiments of any one of the methods disclosed herein, the second serotype of the ITRs is serotype 6, and the first serotype of the rep gene is serotype 12. In some embodiments of any one of the methods disclosed herein, the second serotype of the ITRs is serotype 6, and the first serotype of the rep gene is serotype 13.

In some embodiments of any one of the methods disclosed herein, the second serotype of the ITRs is serotype 1. In some embodiments of any one of the methods disclosed herein, the second serotype of the ITRs is serotype 1, and the first serotype of the rep gene is serotype 2, 3, 4, 12, or 13. In some embodiments of any one of the methods disclosed herein, the second serotype of the ITRs is serotype 1, and the first serotype of the rep gene is serotype 2. In some embodiments of any one of the methods disclosed herein, the second serotype of the ITRs is serotype 1, and the first serotype of the rep gene is serotype 3. In some embodiments of any one of the methods disclosed herein, the second serotype of the ITRs is serotype 1, and the first serotype of the rep gene is serotype 4. In some embodiments of any one of the methods disclosed herein, the second serotype of the ITRs is serotype 1, and the first serotype of the rep gene is serotype 12. In some embodiments of any one of the methods disclosed herein, the second serotype of the ITRs is serotype 1, and the first serotype of the rep gene is serotype 13.

In some embodiments, the Rep proteins encoded by a rep gene of serotype 1 and 2 comprise amino acids of serotype 1 in the N terminus and amino acids of serotype 2 in the C terminus, and the second serotype of the ITRs is serotype 1. In some embodiments, the Rep proteins encoded by a rep gene of serotype 1 and 2 comprise amino acids of serotype 1 in the N terminus and amino acids of serotype 2 in the C terminus, and the second serotype of the ITRs is serotype 6.

In some embodiments, the Rep proteins encoded by a rep gene of serotype 2 and 1 comprise amino acids of serotype 2 in the N terminus and amino acids of serotype 1 in the C terminus, and the second serotype of the ITRs is serotype 1. In some embodiments, the Rep proteins encoded by a rep gene of serotype 2 and 1 comprise amino acids of serotype 2 in the N terminus and amino acids of serotype 1 in the C terminus, and the second serotype of the ITRs is serotype 6.

In some embodiments, the Rep proteins encoded by a rep gene of serotype 2 and 5 comprise amino acids of serotype 2 in the N terminus and amino acids of serotype 5 in the C terminus, and the second serotype of the ITRs is serotype 2.

In some embodiments, the Rep proteins encoded by a rep gene of serotype 5 and 2 comprise amino acids of serotype 5 in the N terminus and amino acids of serotype 2 in the C terminus, and the second serotype of the ITRs is serotype 5.

In some embodiments, n, d, y, and z domains are of AAV2 serotype and an h domain is of AAV1 serotype. In some embodiments, n, h, y, and z domains are of AAV2 serotype and a d domain is of AAV1 serotype. In some embodiments, d, h, y, and z domains are of AAV2 serotype and a n domain is of AAV1 serotype. In some embodiments, n, d, and h domains are of AAV1 serotype and y and z domains are of AAV1 serotype. In some embodiments, d and h domains are of AAV1 serotype and n, y and z domains are of AAV2 serotype. In some embodiments, n and d domains are of AAV1 serotype and h, y, and z domains are of AAV2 serotype.

In some embodiments, n, d, and h domains are of AAV2 serotype and y and z domains are of AAV3 serotype. In some embodiments, a rep gene having n, d, and h domains are of AAV2 serotype and y and z domains are of AAV3 serotype has a start codon of sequence ACG. In some embodiments, a rep gene is of AAV3 serotype, and has a start codon of sequence ATG.

In some embodiments, a rep gene is of AAV4 serotype, and has a start codon of sequence ACG.

In some embodiments, a rep gene is of AAV2 serotype, and has a start codon of sequence ACG.

In some embodiments, n and h domains are of AAV8 serotype and d, y and z domains are of AAV2 serotype. In some embodiments, n and d domains are of AAV1 serotype and h, y, and z domains are of AAV2 serotype.

In some embodiments, a rep gene is of AAV2 serotype, and has a start codon of sequence ACG. In some embodiments, a rep gene is of AAV7 serotype, and has a start codon of sequence ACG.

In some embodiments, n and h domains are of AAV8 serotype and the d, y, and z domains are of AAV2 serotype, and a rep gene has a start codon of sequence ATG. In some embodiments, n, h and d domains are of AAV1 serotype and the y and z domains are of AAV2 serotype, and a rep gene has a start codon of sequence ATG. In some embodiments, n and h domains are of AAV8 serotype, the following nucleotides are deleted in the d domain: T574, C592, C607, A637, G644, AND C657 according to SEQ ID NO: 125 (and resulting in SEQ ID NO: 126), y and z domains are of AAV2 serotype, and a rep gene has a start codon of sequence ATG.

In some embodiments, any one of the compositions described herein further comprises a nucleic acid comprising a cap gene. The cap gene may be of any serotype (e.g., 1, 2, 3, 4, 5, 6, 7, 8, 9, 10, 11, 12, or 13)

In some embodiments of any one of the methods disclosed herein, a cells is also contacted with a recombinant nucleic acid that comprises a cap gene. In some embodiments of any one of the methods disclosed herein, a cell that expresses a rep gene and is contacted with a recombinant nucleic acid that comprises a pair of inverted terminal repeats (ITRs) of a second serotype also expresses a cap gene.

In some aspects, the present application also provides a cell comprising a rep gene of a first serotype and a pair of ITRs of a second serotype. A cell as provided herein may comprise any one of the combinations of ITRs and rep genes disclosed herein. In some embodiments, any one of the cells provided herein further comprises a cap gene.

BRIEF DESCRIPTION OF THE DRAWINGS

The following drawings form part of the present specification and are included to further demonstrate certain aspects of the present application, which can be better understood by reference to one or more of these drawings in combination with the detailed description of specific embodiments presented herein. It is to be understood that the data illustrated in the drawings in no way limit the scope of the application.

FIG. 5 shows percent sequence identity analysis for AAV ITR and Rep78 for AAV serotypes 1-9.

FIGS. 7A-7B show characterization and optimization of the rep gene for AAV1 vector production. FIG. 7A shows examples of AAV plasmid designs with variations in the rep gene. pR2V1 denotes a plasmid with a cap gene of AAV1 sequence, and a rep gene of AAV2 sequence. pR2h1V1 denotes a plasmid with a cap gene of AAV1 sequence, and a rep gene of AAV2 sequence with the exception that the helicase domain (h) is of AAV1 sequence. pR2d1V1 denotes a plasmid with a cap gene of AAV1 sequence, and a rep gene of AAV2 sequence with the exception that the DNA binding domain (d) is of AAV1 sequence. pR2n1V1 denotes a plasmid with a cap gene of AAV1 sequence, and a rep gene of AAV2 sequence with the exception that the N-terminus domain (n) is of AAV1 sequence. pR1c2V1 denotes a plasmid with a cap gene of AAV1 sequence, and a rep gene of AAV1 sequence with the exception that the C terminus (c), which consists of the NLS/p40 promoter domain (y) and the zinc-finger domain (z) is of AAV2 sequence. pR1hc2V1 denotes a plasmid with a cap gene of AAV1 sequence, and a rep gene of AAV1 sequence with the exception that the C terminus (c) and the helicase domain (h) are of AAV2 sequence. pR1dc2V1 denotes a plasmid with a cap gene of AAV1 sequence, and a rep gene of AAV1 sequence with the exception that the DNA binding domain (d), and the C terminus (c) are of AAV2 sequence. pR1nc2V1 denotes a plasmid with a cap gene of AAV1 sequence, and a rep gene of AAV1 sequence with the exception that the N-terminus domain (n), and the C terminus (c) are of AAV2 sequence.

FIG. 7B shows the genome packaging efficiencies of the plasmids shown in FIG. 7A. The genome packaging efficiency is calculated as the amount of genome packaged in a rAAV particle compared to a particle with capsid proteins of serotype 1 and rep proteins of serotype 2 (reference).

FIG. 8 provides an overview of the newly generated AAV1 production plasmids and their phenotype. The plasmid names, descriptions of rep genes, VP expressions, and genome packaging efficiencies are shown.

FIGS. 9A-9D provide characterization and optimization of the rep gene for AAV3 vector production. FIG. 9A is a schematic showing examples of the AAV2 and AAV3 rep variations with either the naturally occurring ACG start codon, or a ATG start codon. FIG. 9B shows expression of capsid proteins or VP proteins and Rep proteins for the plasmids shown in FIG. 9A. AAV3 Rep78 is not visible with the ACG start codon. FIG. 9C provides yield of vector genomes per 15 cm plate ($\times 10^{12}$) of ACG-R2C3, ACG-R3V3, and ATG-R3V3 as shown in FIG. 9A. FIG. 9D is a chart showing the plasmid names and descriptions of the AAV3 expression plasmids tested.

FIGS. 10A-10D provide characterization and optimization of the rep gene for AAV4 vector production. FIG. 10A is a schematic showing examples of the AAV2 and AAV4 rep variations with either the naturally occurring ACG start codon, or a ATG start codon. FIG. 10B shows expression of capsid proteins or VP proteins and Rep proteins for the plasmids shown in FIG. 10A. The asterisk denotes known cross-reactivity of the A1 antibody. FIG. 10C provides yield of vector genomes per 15 cm plate ($\times 10^{12}$) of ACG-R2C3, ACG-R3V3, and ATG-R3V3 as shown in FIG. 10A.4. FIG. 10D is a chart showing the names and descriptions of AAV4 expression plasmids.

FIGS. 11A-11D provide characterization and optimization of the rep gene for AAV5 vector production. FIG. 11A is a schematic showing examples of the AAV2 and AAV5 rep variations with either the naturally occurring ACG start codon, or a ATG start codon. FIG. 11B shows expression of capsid proteins or VP proteins and Rep proteins for the plasmids shown in FIG. 10A. AAV5 Rep78 is not visible with the ACG start codon. FIG. 11C shows the plasmid yield per 15 cm plate ($\times 10^{12}$) of ACG-R2V5, ACG-R5V5, and ATG-R5V5. FIG. 10D is a chart showing the names and descriptions of AAV5 expression plasmids, all of which contain the AAV5 cap gene.

FIGS. 12A-12C provide characterization and optimization of the rep gene for AAV6 vector production. FIG. 12A shows expression of capsid proteins or VP proteins and Rep proteins for denoted plasmids, as well as their yields relative to the control (untransfected cells). FIG. 12B provides genome packaging efficiency for R8d1c3V6 and R1hc2V6 relative to R2V6. FIG. 12C is a chart showing the names and descriptions of AAV6 expression plasmids.

FIGS. 13A-13D provide characterization and optimization of the rep gene for AAV7 vector production. FIG. 13A is a schematic showing examples of the AAV2 and AAV7 rep variations with either the naturally occurring ACG start codon, or a ATG start codon. FIG. 13B shows expression of capsid proteins or VP proteins and Rep proteins for the plasmids shown in FIG. 13A. FIG. 13C shows the plasmid yield per 15 cm plate ($\times 10^{12}$) of ACG-R2V7, ACG-R7V7, and ATG-R7V7. FIG. 13D is a chart showing the names and descriptions of AAV7 expression plasmids.

FIG. 14A shows the plasmid yield per 15 cm plate (gp) for R2V8, R8c2V8, R1c2V8, R8n1c2V8, R8d1c2V8, and R8h1c2V8. FIG. 14B shows schematics of example AAV1, AAV2 and AAV8 rep variations.

FIGS. 15A-15B show an example of the ratio of genome-containing AAV8 particles for 'standard' AAV vector production compared to the vector production using rep chimeras as described herein.

FIG. 16A is a chart showing the names and descriptions of AAV8 expression plasmids, along with their genome packaging efficiencies and expression of VP proteins relative to pR2V8. FIG. 16B shows nucleotides are deleted in the DNA binding (d) domain of AAV8 for the last hybrid listed in FIG. 16A.

DETAILED DESCRIPTION

To package rAAV particles, the viral genome that is found between two flanking ITRs is replaced with one or more genes of interest along with one or more control sequences (e.g., a promoter). Generally, when constructing rAAV particles, a gene to be packaged is flanked by cis-active ITRs while the rep and cap genes, which are in encoded in the wild-type genome, can be supplied in trans. The cap gene encodes capsid proteins that encapsidate packaged genetic material. The rep gene encodes proteins involved in replication of viral DNA. In the last decade, numerous AAV cap genes from multiple natural serotypes and variants have been utilized for different gene therapy applications. Generally, ITRs and rep gene of serotype 2 are used for packaging rAAV particles of various serotypes. The present application provides novel methods and compositions for packaging rAAV particles using ITRs and rep genes of different serotypes. As used herein, "packaging of rAAV particles" implies packing of nucleic acid sequences that are flanked by ITRs, which may comprises one or more genes of interest, into rAAV particles.

The inventors of the present application have explored how the sequences of ITRs and rep genes can be varied to improve the packaging of rAAV particles. Accordingly, provided herein are compositions of nucleic acids (e.g., comprised in vectors such as plasmids) that comprise ITRs and/or rep of different serotypes, including chimeric rep genes, for use in transfecting a producer cell, as well as cells that express a Rep proteins of a serotype that is different from the serotype of the ITRs used in producing rAAV particles. As defined herein, a "chimeric" AAV gene (e.g., rep or cap), also referred to as a "hybrid" AAV gene, or chimeric" AAV protein (e.g., Rep (e.g., Rep78, Rep68, Rep52, or Rep40) or capsid protein (e.g., VP1, VP2, and VP3)), also referred to as a "hybrid" AAV protein, is gene or protein having nucleotides or amino acids of more than one AAV serotype, respectively.

Methods of using ITRs and rep genes of different serotypes to improve rAAV particle packaging are also disclosed herein. In some embodiments, chimeric ITRs and/or chimeric rep genes are used for rAAV particle packaging.

AAV Structure

The AAV genome is built of single-stranded deoxyribonucleic acid (ssDNA), which is either positive- or negative-sensed. At each end of the DNA strand is an inverted terminal repeat (ITR). Between the ITRs are two open reading frames (ORFs): rep and cap. The cap ORF contains overlapping nucleotide sequences of capsid proteins: VP1, VP2 and VP3, which interact together to form a capsid of an icosahedral symmetry. The serotype of an AAV particle is attributed to the sequence of comprising capsid proteins.

Figures 1, 2:
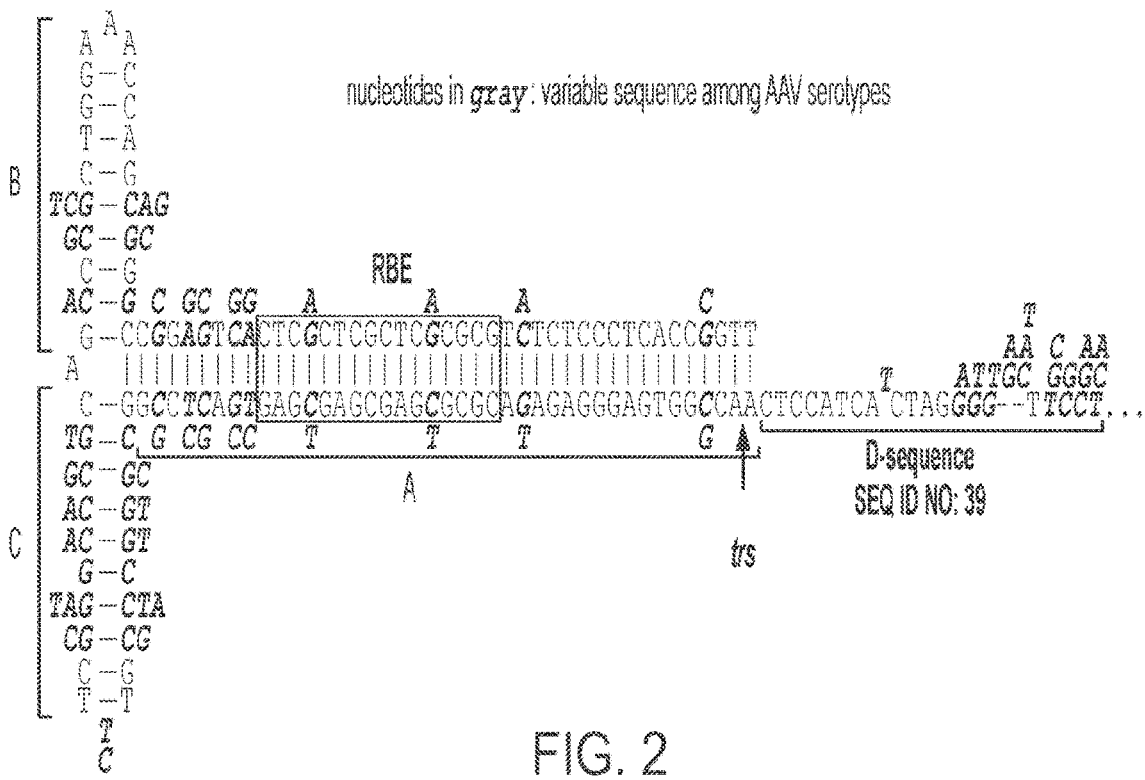
FIG. 1 shows alignment of rep and ITR sequences of AAV serotypes 1-13.
FIG. 2 shows a structure of an AAV ITR with variations in base pairs found between different AAV serotypes. RBE: Rep binding element where AAV Rep78 and Rep68 proteins bind.

FIG. 2 shows the structure of an AAV ITR. Each AAV ITR forms a hairpin, which contributes to so-called self-priming that allows primase-independent synthesis of the second DNA strand. ITRs are required for integration of AAV DNA into host DNA, efficient encapsidation and generation of a fully assembled DNAse-resistant AAV particle. ITRs are generally considered to be required in cis next to the one or more genes that are desired to be packaged into a rAAV particle. SEQ ID NOs: 1-7 correspond to examples of wild-type ITR sequences of serotypes 1-7 (AAV1-AAV7), respectively.

Example Sequence of Wild-Type AAV1 ITR

```
                                        (SEQ ID NO: 1)
ttgcccactccctctctgcgcgctcgctcgctcggtggggcctgcggacc aaaggtccgcagacggcagagctctgctctgccggccccaccgagcgagc gagcgcgcagagagggagtgggcaactccatcactaggggtaatcgc
```

Example Sequence of Wild-Type AAV2 ITR

```
                                        (SEQ ID NO: 2)
ttggccactccctctctgcgcgctcgctcgctcactgaggccgggcgacc aaaggtcgcccgacgcccgggctttgcccgggcggcctcagtgagcgagc gagcgcgcagagagggagtggccaactccatcactaggggttcct
```

Example Sequence of Wild-Type AAV3 ITR

```
                                        (SEQ ID NO: 3)
tggccactccctctatgcgcactcgctcgctcggtggggcctggcgacca aaggtcgccagacggacgtgctttgcacgtccggccccaccgagcgagcg agtgcgcatagagggagtggccaactccatcactagaggtatggca
```

Example Sequence of Wild-Type AAV4 ITR

```
                                        (SEQ ID NO: 4)
ttggccactccctctatgcgcgctcgctcactcactcggccctggagacc aaaggtctccagactgccggcctctggccggcagggccgagtgagtgagc gagcgcgcatagagggagtggccaactccatcatctaggtttgcccac
```

Example Sequence of Wild-Type AAV5 ITR (SEQ ID NO: 5)
ctctcccccctgtcgcgttcgctcgctcgctggctcgtttggggggtgg cagctcaaagagctgccagacgacggccctctggccgtcgcccccccaaa cgagccagcgagcgagcgaacgcgacagggggagagtgccacactctca agcaagggggttttgtaagcagtgat Example Sequence of Wild-Type AAV6 ITR (SEQ ID NO: 6)
ttggccactccctctctgcgcgctcgctcgctcactgaggccgggcgacc aaaggtcgcccgacgcccgggctttgcccgggcggcctcagtgagcgagc gagcgcgcagagagggagtggccaactccatcactaggggttcct Example Sequence of Wild-Type AAV7 ITR (SEQ ID NO: 7)
ttggccactccctctatgcgcgctcgctcgctcggtggggcctgcggacc aaaggtccgcagacggcagagctctgctctgccggccccaccgagcgagc gagcgcgcatagagggagtggccaactccatcactaggggtaccgc The rep ORF is composed of four overlapping genes encoding Rep proteins required for the AAV life cycle. The names of the four Rep proteins depict their sizes in kilodaltons (kDa): Rep78, Rep68, Rep52 and Rep40. Rep78 and Rep68 bind the hairpin formed by the ITR in the self-priming act and cleave at a specific region, designated terminal resolution site, within the hairpin. All four Rep proteins bind to ATP and possess helicase activity. They upregulate the transcription from the p40 promoter, and downregulate both p5 and p19 promoter activity.

SEQ ID NOs: 8-20 correspond to example sequences of wild-type AAV rep genes of serotypes 1-13, respectively.

SEQ ID NOs: 21-33 correspond to example sequences of wild-type AAV Rep78 protein of serotypes 1-13, respectively. Rep78 has 621 amino acids. Rep68 comprises of amino acids 1-529 of Rep78 and a sequence LARGHSL (SEQ ID NO: 38) in the C terminus. Rep52 comprises amino acids 225-621 of Rep78. Rep40 comprises of amino acids 225-621 of Rep78 and LARGHSL (SEQ ID NO: 38) in the C terminus.

Example of Wild-Type AAV1 Rep Nucleic Acid Sequence (SEQ ID NO: 8)
atgccgggcttctacgagatcgtgatcaaggtgccgagcgacctggacga gcacctgccgggcatttctgactcgtttgtgagctgggtggccgagaagg aatgggagctgcccccggattctgacatggatctgaatctgattgagcag gcaccctgaccgtggccgagaagctgcagcgcgacttcctggtccaatg gcgccgcgtgagtaaggccccggaggccctcttctttgttcagttcgaga agggcgagtcctacttccacctccatattctggtggagaccacggggtc aaatccatggtgctgggccgcttcctgagtcagattagggacaagctggt gcagaccatctaccgcgggatcgagccgaccctgcccaactggttcgcgg tgaccaagacgcgtaatggcgccggaggggggaacaaggtggtggacgag tgctacatccccaactacctcctgccaagactcagcccgagctgcagtg Example of Wild-Type AAV2 Rep Nucleic Acid Sequence (SEQ ID NO: 9)
atgccgggggttttacgagattgtgattaaggtccccagcgaccttgacgg gcatctgcccggcatttctgacagctttgtgaactgggtggccgagaagg aatgggagttgccgccagattctgacatggatctgaatctgattgagcag gcaccctgaccgtggccgagaagctgcagcgcgactttctgacggaatg gcgccgtgtgagtaaggccccggaggcccttttctttgtgcaatttgaga agggagagagctacttccacatgcacgtgctcgtggaaaccaccggggtg aaatccatggttttgggacgtttcctgagtcagattcgcgaaaactgat tcagagaatttaccgcgggatcgagccgactttgccaaactggttcgcgg tcacaaagaccagaaatgcgccggagggggaacaaggtggtggatgagt gctacatccccaattacttgctccccaaaacccagcctgagctccagtgg gcgtggactaatatggaacagtatttaagcgcctgtttgaatctcacgga gcgtaaacggttggtggcgcagcatctgacgcacgtgtcgcagacgcagg agcagaacaaagagaatcagaatcccaattctgatgcgccggtgatcaga tcaaaaacttcagccaggtacatggagctggtcgggtggctcgtggacaa ggggattacctcggagaagcagtggatccaggaggaccaggcctcataca tctccttcaatgcggcctccaactcgcggtcccaaatcaaggctgccttg gacaatgcgggaaagattatgagcctgactaaaaccgccccgactacct ggtgggccagcagcccgtggaggacatttccagcaatcggatttataaaa ttttggaactaaacgggtacgatccccaatatgcggcttccgtctttctg ggatgggccacgaaaaagttcggcaagaggaacaccatctggctgtttgg gcctgcaactaccgggaagaccaacatcgcggaggccatagcccacactg tgcccttctacgggtgcgtaaactggaccaatgagaactttcccttcaac gactgtgtcgacaagatggtgatctggtgggaggaggggaagatgaccgc caaggtcgtggagtcggccaaagccattctcggaggaagcaaggtgcgcg tggaccagaaatgcaagtcctcggcccagatagacccgactcccgtgatc gtcacctccaacaccaacatgtgcgccgtgattgacgggaactcaacgac cttcgaacaccagcagccgttgcaagaccggatgttcaaatttgaactca cccgccgtctggatcatgactttgggaaggtcaccaagcaggaagtcaaa gacttttttccggtgggcaaaggatcacgtggttgaggtggagcatgaatt ctacgtcaaaaagggtggagccaagaaaagacccgcccccagtgacgcag atataagtgagcccaaacgggtgcgcgagtcagttgcgcagccatcgacg tcagacgcggaagcttcgatcaactacgcagacaggtaccaaaacaaatg ttctcgtcacgtgggcatgaatctgatgctgtttccctgcagacaatgcg agagaatgaatcagaattcaaatatctgcttcactcacggacagaaagac tgtttagagtgctttcccgtgtcagaatctcaacccgtttctgtcgtcaa aaaggcgtatcagaaactgtgctacattcatcatatcatgggaaaggtgc cagacgcttgcactgcctgcgatctggtcaatgtggatttggatgactgc atctttgaacaataa Example of Wild-Type AAV3 Rep Nucleic Acid Sequence (SEQ ID NO: 10)

atgccggggttctacgagattgtcctgaaggtcccgagtgacctggacga gcacctgccggggcatttctaactcgtttgttaactgggtggccgagaagg aatgggagctgccgccggattctgacatggatccgaatctgattgagcag gcacccctgaccgtggccgaaaagcttcagcgcgagttcctggtggagtg gcgccgcgtgagtaaggcccccggaggccctctttttgtccagttcgaaa agggggagacctacttccacctgcacgtgctgattgagaccatcggggtc aaatccatggtggtcggccgctacgtgagccagattaaagagaagctggt gacccgcatctaccgcggggtcgagccgcagcttccgaactggttcgcgg tgaccaaaacgcgaaatggcgccgggggggaacaaggtggtggacgact gctacatccccaactacctgctccccaagacccagcccgagctccagtgg gcgtggactaacatggaccagtatttaagcgcctgtttgaatctcgcgga gcgtaaacggctggtggcgcagcatctgacgcacgtgtcgcagacgcagg agcagaacaaagagaatcagaaccccaattctgacgcgccggtcatcagg tcaaaaacctcagccaggtacatggagctggtcgggtggctggtggaccg cgggatcacgtcagaaaagcaatggattcaggaggaccaggcctcgtaca tctccttcaacgccgcctccaactcgcggtcccagatcaaggccgcgctg gacaatgcctccaagatcatgagcctgacaaagacggctccggactacct ggtgggcagcaacccgccggaggacattaccaaaaatcggatctaccaaa tcctggagctgaacgggtacgatccgcagtacgcggcctccgtcttcctg ggctgggcgcaaaagaagttcgggaagaggaacaccatctggctctttgg gccggccacgacgggtaaaaccaacatcgcggaagccatcgcccacgccg tgcccttctacggctgcgtaaactggaccaatgagaactttcccttcaac gattgcgtcgacaagatggtgatctggtgggaggagggcaagatgacggc caaggtcgtggagagcgccaaggccattctgggcggaagcaaggtgcgcg tggaccaaaagtgcaagtcatcggcccagatcgaacccactcccgtgatc gtcacctccaacaccaacatgtgcgccgtgattgacgggaacagcaccac cttcgagcatcagcagccgctgcaggaccggatgtttaaatttgaactta cccgccgtttggaccatgactttgggaaggtcaccaaacaggaagtaaag gacttttttccggtgggcttccgatcacgtgactgacgtggctcatgagtt ctacgtcagaaaggtggagctaagaaacgccccgcctccaatgacgcgg atgtaagcgagccaaaacggcagtgcacgtcacttgcgcagccgacaacg tcagacgcggaagcaccggggactacgcggacaggtaccaaaacaaatgt tctcgtcacgtgggcatgaatctgatgctttttccctgtaaaacatgcga gagaatgaatcaaatttccaatgtctgttttacgcatggtcaaagagact gtggggaatgcttccctggaatgtcagaatctcaacccgtttctgtcgtc aaaaagaagacttatcagaaactgtgtccaattcatcatatcctgggaag ggcacccgagattgcctgttcggcctgcgatttggccaatgtggacttgg atgactgtgttctgagcaataa Example of Wild-Type AAV4 Rep Nucleic Acid Sequence (SEQ ID NO: 11)

atgccggggttctacgagatcgtgctgaaggtgcccagcgacctggacga gcacctgcccggcatttctgactcttttgtgagctgggtggccgagaagg aatgggagctgccgccggattctgacatggacttgaatctgattgagcag gcacccctgaccgtggccgaaaagctgcaacgcgagttcctggtcgagtg gcgccgcgtgagtaaggcccccggaggccctcttcttgtccagttcgaga aggggga cagctacttccacctgcacatcctggtggagaccgtgggcgtc aaatccatggtggtgggccgctacgtgagccagattaaagagaagctggt gacccgcatctaccgcggggtcgagccgcagcttccgaactggttcgcgg tgaccaagacgcgtaatgcgccggaggcgggaacaaggtggtggacgac tgctacatccccaactacctgctccccaagacccagcccgagctccagtg -continued

```
ggcgtggactaacatggaccagtatataagcgcctgtttgaatctcgcgg
agcgtaaacggctggtggcgcagcatctgacgcacgtgtcgcagacgcag
gagcagaacaaggaaaaccagaaccccaattctgacgcgccggtcatcag
gtcaaaaacctccgccaggtacatggagctggtcgggtggctggtggacc
gcgggatcacgtcagaaaagcaatggatccaggaggaccaggcgtcctac
atctccttcaacgccgcctccaactcgcggtcacaaatcaaggccgcgct
ggacaatgcctccaaaatcatgagcctgacaaagacggctccggactacc
tggtgggccagaacccgccggaggacatttccagcaaccgcatctaccga
atcctcgagatgaacgggtacgatccgcagtacgcggcctccgtcttcct
gggctgggcgcaaaagaagttcggggaagaggaacaccatctggctctttg
gccggccacgacgggtaaaaccaacatcgcggaagccatcgcccacgcc
gtgcccttctacggctgcgtgaactggaccaatgagaactttccgttcaa
cgattgcgtcgacaagatggtgatctggtgggaggagggcaagatgacgg
ccaaggtcgtagagagcgcaaggccatcctgggcggaagcaaggtgcgc
gtggaccaaaagtgcaagtcatcggcccagatcgacccaactcccgtgat
cgtcacctccaacaccaacatgtgcgcggtcatcgacggaaactcgacca
ccttcgagcaccaacaaccactccaggaccggatgttcaagttcgagctc
accaagcgcctggagcacgactttggcaaggtcaccaagcaggaagtcaa
agacttttttccggtgggcgtcagatcacgtgaccgaggtgactcacgagt
tttacgtcagaaagggtggagctagaaagaggcccgcccccaatgacgca
gatataagtgagcccaagcgggcctgtccgtcagttgcgcagccatcgac
gtcagacgcggaagctccggtggactacgcggacaggtaccaaaacaaat
gttctcgtcacgtgggtatgaatctgatgcttttcccctgccggcaatgc
gagagaatgaatcagaatgtggacatttgcttcacgcacggggtcatgga
ctgtgccgagtgcttccccgtgtcagaatctcaacccgtgtctgtcgtca
gaaagcggacgtatcagaaactgtgtccgattcatcacatcatggggagg
gcgcccgaggtggcctgctcggcctgcgaactggccaatgtggacttgga
tgactgtgacatggaacaataa
```

Example of Wild-Type AAV5 Rep Nucleic Acid Sequence (SEQ ID NO: 12)
```
atggctaccttctatgaagtcattgttcgcgtcccatttgacgtggagga
acatctgcctggaatttctgacagctttgtggactgggtaactggtcaaa
tttgggagctgcctccagagtcagatttaaatttgactctggttgaacag
cctcagttgacggtggctgatagaattcgccgcgtgttcctgtacgagtg
gaacaaattttccaagcaggagtccaaattctttgtgcagtttgaaaagg
gatctgaatattttcatctgcacacgcttgtggagacctccggcatctct
tccatggtcctcggccgctacgtgagtcagattcgcgcccagctggtgaa
agtggtcttccagggaattgaaccccagatcaacgactgggtcgccatca
ccaaggtaaagaagggcggagccaataaggtggtggattctgggtatatt
cccgcctacctgctgccgaaggtccaaccggagcttcagtgggcgtggac
```

Example of Wild-Type AAV6 Rep Nucleic Acid Sequence (SEQ ID NO: 13)
```
atgccggggttttacgagattgtgattaaggtccccagcgaccttgacga
gcatctgccggcatttctgacagctttgtgaactgggtggccgagaagg
aatgggagttgccgccagattctgacatggatctgaatctgattgagcag
gcacccctgaccgtggccgagaagctgcagcgcgacttcctggtccagtg
gcgccgcgtgagtaaggccccggaggccctcttctttgttcagttcgaga
agggcgagtcctacttccacctccatattctggtggagaccacgggggtc
aaatccatggtgctgggccgcttcctgagtcagattagggacaagctggt
gcagaccatctaccgcgggatcgagccgaccctgcccaactggttcgcgg
tgaccaagacgcgtaatggcgccggagggggaacaaggtggtggacgag
tgctacatccccaactacctcctgcccaagactcagcccgagctgcagtg
ggcgtggactaacatggaggagtatataagcgcgtgtttaaacctggccg
```

```
aaacctggacgagtataaattggccgccctgaatctggaggagcgcaaac
ggctcgtcgcgcagtttctggcagaatcctcgcagcgctcgcaggaggcg
gcttcgcagcgtgagttctcggctgacccggtcatcaaaagcaagacttc
ccagaaatacatggcgctcgtcaactggctcgtggagcacggcatcactt
ccgagaagcagtggatccaggaaaatcaggagagctacctctccttcaac
tccaccggcaactctcggagccagatcaaggccgcgctcgacaacgcgac
caaaattatgagtctgacaaaaagcgcggtggactacctcgtggggagct
ccgttcccgaggacatttcaaaaaacagaatctggcaaattttttgagatg
aatggctacgacccggcctacgcgggatccatcctctacggctggtgtca
gcgctccttcaacaagaggaacaccgtctggctctacggacccgccacga
ccggcaagaccaacatcgcgcgaggccatcgcccacactgtgccttttac
ggctgcgtgaactggaccaatgaaaactttcccttttaatgactgtgtgga
caaaatgctcatttggtgggaggagggaaagatgaccaacaaggtggttg
aatccgccaaggccatcctgggggggctcaaaggtgcgggtcgatcagaaa
tgtaaatcctctgttcaaattgattctacccctgtcattgtaacttccaa
tacaaacatgtgtggtggtggatgggaattccacgacctttgaacacc
agcagccgctggaggaccgcatgttcaaatttgaactgactaagcggctc
ccgccagattttggcaagattactaagcaggaagtcaaggactttttttgc
ttgggcaaaggtcaatcaggtgccggtgactcacgagtttaaagttccca
gggaattggcgggaactaaaggggcggagaaatctctaaaacgcccactg
ggtgacgtcaccaatactagctataaaagtctggagaagcgggccaggct
ctcatttgttcccgagacgcctcgcagttcagacgtgactgttgatcccg
ctcctctgcgaccgctcaattggaattcaaggtatgattgcaaatgtgac
tatcatgctcaatttgacaacatttctaacaaatgtgatgaatgtgaata
tttgaatcggggcaaaaatggatgtatctgtcacaatgtaactcactgtc
aaatttgtcatgggattccccctgggaaaaggaaaacttgtcagatttt
ggggattttgacgatgccaataaagaacagtaa
```

-continued agcgcaaacggctcgtggcgcacgacctgacccacgtcagccagacccag
gagcagaacaaggagaatctgaacccccaattctgacgcgcctgtcatccg
gtcaaaaacctccgcacgctacatggagctggtcgggtggctggtggacc
ggggcatcacctccgagaagcagtggatccaggaggaccaggcctcgtac
atctccttcaacgccgcctccaactcgcggtcccagatcaaggccgctct
ggacaatgccggcaagatcatggcgctgaccaaatccgcgcccgactacc
tggtaggccccgctccgcccgccgacattaaaaccaaccgcatttaccgc
atcctggagctgaacggctacgaccctgcctacgccggctccgtctttct
cggctgggcccagaaaaggttcggaaaacgcaacaccatctggctgtttg
ggccggccaccacgggcaagaccaacatcgcggaagccatcgcccacgcc
gtgcccttctacggctgcgtcaactggaccaatgagaactttcccttcaa
cgattgcgtcgacaagatggtgatctggtgggaggagggcaagatgacgg
ccaaggtcgtggagtccgccaaggccattctcggcggcagcaaggtgcgc
gtggaccaaaagtgcaagtcgtccgcccagatcgatcccacccccgtgat
cgtcacctccaacaccaacatgtgcgccgtgattgacgggaacagcacca
ccttcgagcaccagcagccgttgcaggaccggatgttcaaatttgaactc
acccgccgtctggagcatgactttggcaaggtgacaaagcaggaagtcaa
agagttcttccgctgggcgcaggatcacgtgaccgaggtggcgcatgagt
tctacgtcagaaagggtggagccaacaagagacccgcccccgatgacgcg
gataaaagcgagcccaagcgggcctgcccctcagtcgcggatccatcgac
gtcagacgcggaaggagctccggtggactttgccgacaggtaccaaaaca
aatgttctcgtcacgcgggcatgcttcagatgctgtttccctgcaaaaca
tgcgagagaatgaatcagaatttcaacatttgcttcacgcacgggaccag
agactgttcagaatgtttccccggcgtgtcagaatctcaaccggtcgtca
gaaagaggacgtatcggaaactctgtgccattcatcatctgctggggcgg
gctcccgagattgcttgctcggcctgcgatctggtcaacgtggatctgga
tgactgtgtttctgagcaataa Example of Wild-Type AAV7 Rep Nucleic Acid Sequence (SEQ ID NO: 14)
atgccgggtttctacgagatcgtgatcaaggtgccgagcgacctggacga
gcacctgccgggcatttctgactcgtttgtgaactgggtggccgagaagg
aatgggagctgcccccggattctgacatggatctgaatctgatcgagcag
gcaccctgaccgtggccgagaagctgcagcgcgacttcctggtccaatg
gcgccgcgtgagtaaggccccggaggccctgttctttgttcagttcgaga
agggcgagagctacttccaccttcacgttctggtggagaccacggggtc
aagtccatggtgctaggccgcttcctgagtcagattcgggagaagctggt
ccagaccatctaccgcggggtcgagcccacgctgcccaactggttcgcg
tgaccaagacgcgtaatggcgccggcgggggaacaaggtggtggacgag
tgctacatccccaactacctcctgcccaagacccagcccgagctgcagtg
ggcgtggactaacatggaggagtatataagcgcgtgtttgaacctggccg -continued aacgcaaacggctcgtggcgcagcacctgacccacgtcagccagacgcag
gagcagaacaaggagaatctgaacccccaattctgacgcgcccgtgatcag
gtcaaaaacctccgcgcgctacatggagctggtcgggtggctggtggacc
ggggcatcacctccgagaagcagtggatccaggaggaccaggcctcgtac
atctccttcaacgccgcctccaactcgcggtcccagatcaaggccgcgct
ggacaatgccggcaagatcatggcgctgaccaaatccgcgcccgactacc
tggtggggccctcgctgcccgcggacattaaaaccaaccgcatctaccgc
atcctggagctgaacgggtacgatcctgcctacgccggctccgtctttct
cggctgggcccagaaaaagttcgggaagcgcaacaccatctggctgtttg
ggccgccaccaccggcaagaccaacattgcggaagccatcgcccacgcc
gtgcccttctacggctgcgtcaactggaccaatgagaactttcccttcaa
cgattgcgtcgacaagatggtgatctggtgggaggagggcaagatgacgg
ccaaggtcgtggagtccgccaaggccattctcggcggcagcaaggtgcgc
gtggaccaaaagtgcaagtcgtccgcccagatcgaccccacccccgtgat
cgtcacctccaacaccaacatgtgcgccgtgattgacgggaacagcacca
ccttcgagcaccagcagccgttgcaggaccggatgttcaaatttgaactc
acccgccgtctggagcacgactttggcaaggtgacgaagcaggaagtcaa
agagttcttccgctgggccagtgatcacgtgaccgaggtggcgcatgagt
tctacgtcagaaagggcggagccagcaaaagacccgcccccgatgacgcg
gatataagcgagcccaagcgggcctgcccctcagtcgcggatccatcgac
gtcagacgcggaaggagctccggtggactttgccgacaggtaccaaaaca
aatgttctcgtcacgcgggcatgattcagatgctgtttccctgcaaaacg
tgcgagagaatgaatcagaatttcaacatttgcttcacacacgggtcag
agactgtttagagtgtttccccggcgtgtcagaatctcaaccggtcgtca
gaaaaaagacgtatcggaaactctgcgcgattcatcatctgctggggcgg
gcgcccgagattgcttgctcggcctgcgacctggtcaacgtggacctgga
cgactgcgtttctgagcaataa Example of Wild-Type AAV8 Rep Nucleic Acid Sequence (SEQ ID NO: 15)
atgccgggcttctacgagatcgtgatcaaggtgccgagcgacctggacga
gcacctgccgggcatttctgactcgtttgtgaactgggtggccgagaagg
aatgggagctgcccccggattctgacatggatcggaatctgatcgagcag
gcacccctgaccgtggccgagaagctgcagcgcgacttcctggtccaatg
gcgccgcgtgagtaaggccccggaggccctcttctttgttcagttcgaga
agggcgagagctactttcacctgcacgttctggtcgagaccacggggtc
aagtccatggtgctaggccgcttcctgagtcagattcgggaaaagcttgg
tccagaccatctacccgcggggtcgagcccaccttgcccaactggttcg
cggtgaccaaagacgcggtaatggcgccggcggggggaacaaggtggtg
gacgagtgctacatccccaactacctcctgcccaagactcagcccgagct
gcagtgggcgtggactaacatggaggagtatataagcgcgtgcttgaacc tggccgagcgcaaacggctcgtggcgcagcacctgacccacgtcagccag acgcaggagcagaacaaggagaatctgaaccccaattctgacgcgcccgt gatcaggtcaaaaacctccgcgcgctatatggagctggtcgggtggctgg tggaccggggcatcacctccgagaagcagtggatccaggaggaccaggcc tcgtacatctccttcaacgccgcctccaactcgcggtcccagatcaaggc cgcgctggacaatgccggcaagatcatggcgctgaccaaatccgcgcccg actacctggtggggccctcgctgcccgcggacattacccagaaccgcatc taccgcatcctcgctctcaacggctacgaccctgcctacgccggctccgt cttttctcggctgggctcagaaaaagttcgggaaacgcaacaccatctggc tgtttggacccgccaccaccggcaagaccaacattgcggaagccatcgcc cacgccgtgccttctacggctgcgtcaactggaccaatgagaactttcc cttcaatgattgcgtcgacaagatggtgatctggtgggaggagggcaaga tgacggccaaggtcgtggagtccgccaaggccattctcggcggcagcaag gtgcgcgtggaccaaaagtgcaagtcgtccgcccagatcgacccccacccc cgtgatcgtcacctccaacaccaacatgtgcgccgtgattgacgggaaca gcaccaccttcgagcaccagcagcctctccaggaccggatgtttaagttc gaactcacccgccgtctggagcacgactttggcaaggtgacaaagcagga agtcaaagagttcttccgctgggccagtgatcacgtgaccgaggtggcgc atgagttttacgtcagaaagggcggagccagcaaaagacccgcccccgat gacgcggataaaagcgagcccaagcgggcctgcccctcagtcgcggatcc atcgacgtcagacgcggaaggagctccggtggactttgccgacaggtacc aaaacaaatgttctcgtcacgcgggcatgcttcagatgctgtttccctgc aaaacgtgcgagagaatgaatcagaatttcaacatttgcttcacacacgg ggtcagagactgctcagagtgtttccccggcgtgtcagaatctcaaccgg tcgtcagaaagaggacgtatcggaaactctgtgcgattcatcatctgctg gggcgggctcccgagattgcttgctcggcctgcgatctggtcaacgtgga cctggatgactgtgtttctgagcaataa Example of Wild-Type AAVrH.8 Rep Nucleic Acid Sequence (SEQ ID NO: 16)
atgccgggcttctacgagattgtgatcaaggtgccgagcgacctggacga gcacctgccgggcatttctgactcttttgtgaactggggggccgagaagga atgggagctgccccccggattctgacatggatcggaatctgatcgagcagg caccccctgaccgtggccgagaagctgtagcgcgacttcctggtccaatgg cgccgcgtgagtaaggcccggaggccctcttctttgttcagttcgagaa gggcgagagctactttcacctgcacgttctggtcgagaccacgggggtca agtccatggtgctaggccgcttcctgagtcagattcgggagaagctggtc cagaccatctaccgcggggatcgagccgaccctgcccaactggttcgcggt gaccaagacgcgtaatggcgccggcgggggggaacaaggtggtggacgagt gctacatccccaactacctcctgcccaagactcagcccgagctgcagtgg gcgtggactaacatggaggagtatataagcgcgtgcttgaacctggccga gcgcaaacggctcgtggcgcagcacctgacccacgtcagccagacgcagg agcagaacaaggagaatctgaaccccaattctgacgcgcccgtgatcagg tcaaaaacctccgcgcgctacatggagctggtcgggtggctggtggaccg gggcatcacctccgagaagcagtggatccaggaggaccaggcctcgtaca tctccttcaacgccgcctccaactcgcggtcccagatcaaggccgcgctg gacaatgccggcaagatcatggcgctgaccaaatccgcgcccgactacct ggtaggccccttcacttccggtggacattacgcagaaccgcatctaccgca tcctgcagctcaacggctacgaccctgcctacgccggctccgtcttctc ggctgggcacaaaagaagttcgggaaacgcaacaccatctggctgtttgg gccggccaccacgggaaagaccaacatcgcagaagccattgcccacgccg tgcccttctacggctgcgtcaactggaccaatgagaactttcccttcaac gattgcgtcgacaagatggtgatctggtgggaggagggcaagatgacggc caaggtcgtggagtccgccaaggccattctcggcggcagcaaggtgcgcg tggaccaaaagtgcaagtcgtccgcccagatcgaccccactcccgtgatc gtcacctccaacaccaacatgtgcgccgtgattgacgggaacagcaccac cttcgagcaccagcagcctctccaggaccggatgtttaagttcgaactca cccgccgtctggagcacgactttggcaaggtgacaaagcaggaagtcaaa gagttcttccgctgggccagtgatcacgtgaccgaggtggcgcatgagtt ttacgtcagaaagggcggagccagcaaaagacccgcccccgatgacgcgg ataaaagcgagcccaagcgggcctgcccctcagtcgcggatccatcgacg tcagacgcggaaggagctccggtggactttgccgacaggtaccaaaacaa atgttctcgtcacgcgggcatgcttcagatgctgcttccctgcaaaacgt gcgagagaatgaatcagaatttcaacatttgcttcacacacggggtcaga gactgctcagagtgtttccccggcgtgtcagaatctcaaccggtcgtcag aaagaggacgtatcggaaactctgtgcgattcatcatctgctggggcggg ctcccgagattgcttgctcggcctgcgatctggtcaacgtggacctggat gactgtgtttctgagcaataa Example of Wild-Type AAV10 Rep Nucleic Acid Sequence (SEQ ID NO: 17)
atgccgggcttctacgagatcgtgatcaaggtgccgagcgacctggacga gcacctgccgggcatttctgactcgtttgtgaactgggggccgagaagga atgggagctgccccccggattctgacatggatcggaatctgatcgagcagg caccccctgaccgtggccgagaagctgcagcgcgacttcctggtccactgg cgccgcgtgagtaaggcccggaggccctcttctttgttcagttcgagaa gggcgagtcctactttcacctgcacgttctggtcgagaccacgggggtca agtccatggtcctgggccgcttcctgagtcagatcagagacaggctggtg cagaccatctaccgcggggtagagcccacgctgcccaactggttcgcggt gaccaagacgcgaaatggcgccggcgggggggaacaaggtggtggacgagt gctacatccccaactacctcctgcccaagacgcagcccgagctgcagtgg -continued

```
gcgtggactaacatggaggagtatataagcgcgtgtctgaacctcgcgga
gcgtaaacggctcgtggcgcagcacctgacccacgtcagccagacgcagg
agcagaacaaggagaatctgaacccgaattctgacgcgcccgtgatcagg
tcaaaaacctccgcgcgctacatggagctggtcgggtggctggtggaccg
gggcatcacctccgagaagcagtggatccaggaggaccaggcctcgtaca
tctccttcaacgccgcctccaactcgcggtcccagatcaaggccgcgctg
gacaatgccggaaagatcatggcgctgaccaaatccgcgcccgactacct
ggtaggcccgtccttacccgcggacattaaggccaaccgcatctaccgca
tcctggagctcaacggctacgaccccgcctacgccggctccgtcttcctg
ggctgggcgcagaaaaagttcggtaaaaggaatacaatttggctgttcgg
gcccgccaccaccggcaagaccaacatcgcggaagccatcgcccacgccg
tgccctctacggctgcgtcaactggaccaatgagaactttcccttcaac
gattgcgtcgacaagatggtgatctggtgggaggagggcaagatgaccgc
caaggtcgtggagtccgccaaggccattctgggcggaagcaaggtgcgcg
tcgaccaaaagtgcaagtcctcggcccagatcgaccccacgcccgtgatc
gtcacctccaacaccaacatgtgcgccgtgatcgacgggaacagcaccac
cttcgagcaccagcagcccctgcaggaccgcatgttcaagttcgagctca
cccgccgtctggagcacgactttggcaaggtgaccaagcaggaagtcaaa
gagttcttccgctgggctcaggatcacgtgactgaggtgacgcatgagtt
ctacgtcagaaagggcggagccaccaaaagacccgcccccagtgacgcgg
atataagcgagcccaagcgggcctgcccctcagttgcggagccatcgacg
tcagacgcggaagcaccggtggactttgcggacaggtaccaaaacaaatg
ttctcgtcacgcgggcatgcttcagatgctgtttccctgcaagacatgcg
agagaatgaatcagaatttcaacgtctgcttcacgcacggggtcagagac
tgctcagagtgcttccccggcgcgtcagaatctcaacctgtcgtcagaaa
aaagacgtatcagaaactgtgcgcgattcatcatctgctggggcgggcac
ccgagattgcgtgttcggcctgcgatctcgtcaacgtggacttggatgac
tgtgtttctgagcaataa
```

Example of Wild-Type AAV11 Rep Nucleic Acid Sequence (SEQ ID NO: 18)
```
atgccgggcttctacgagatcgtgatcaaggtgccgagcgacctggacga
gcacctgccgggcatttctgactcgtttgtgaactgggtggccgagaagg
aatgggagctgccccccggattctgacatggatcggaatctgatcgagcag
gcacccctgaccgtggccgagaagctgcagcgcgacttcctggtccactg
gcgccgcgtgagtaaggccccggaggccctcttctttgttcagttcgaga
agggcgagtcctacttccacctccacgttctcgtcgagaccacgggggtc
aagtccatggtcctgggccgcttcctgagtcagatcagagacaggctggt
gcagaccatctaccgcggggtcgagcccacgctgcccaactggttcgcgg
tgaccaagacgcgaaatggcgccggcgggggaacaaggtggtggacgag
tgctacatccccaactacctcctgcccaagacccagcccgagctgcagtg
```

Example of Wild-Type AAV12 Rep Nucleic Acid Sequence (SEQ ID NO: 19)
```
atgccggggttctacgaggtggtgatcaaggtgcccagcgacctggacga
gcacctgccggcatttctgactcctttgtgaactgggtggccgagaagg
aatgggagttgccccggattctgacatggatcagaatctgattgagcag
gcacccctgaccgtggccgagaagctgcagcgcgagttcctggtggaatg
gcgccgagtgagtaaatttctggaggccaagttttttgtgcagtttgaaa
agggggactcgtactttcatttgcatattctgattgaaattaccggcgtg
aaatccatggtggtgggccgctacgtgagtcagattagggataaactgat
ccagcgcatctaccgcggggtcgagcccagctgcccaactggttcgcgg
tcacaaagaccgaaatggcgccggaggcgggaacaaggtggtggacgag
tgctacatccccaactacctgctccccaaggtccagcccgagcttcagtg
```

-continued

```
ggcgtggactaacatggaggagtatataagcgcctgtttgaacctcgcgg agcgtaaacggctcgtggcgcagcacctgacgcacgtctcccagacccag gagggcgacaaggagaatctgaacccgaattctgacgcgccggtgatccg gtcaaaaacctccgccaggtacatggagctggtcgggtggctggtggaca agggcatcacgtccgagaagcagtggatccaggaggaccaggcctcgtac atctccttcaacgcggcctccaactcccggtcgcagatcaaggcggccct ggacaatgcctccaaaatcatgagcctcaccaaaacggctccggactatc tcatcgggcagcagcccgtgggggacattaccaccaaccggatctacaaa atcctggaactgaacgggtacgaccccagtacgccgcctccgtctttct cggctgggcccagaaaagtttggaaagcgcaacaccatctggctgtttg ggcccgccaccaccggcaagaccaacatcgcggaagccatcgcccacgcg gtccccttctacggctgcgtcaactggaccaatgagaactttccccttcaa cgactgcgtcgacaaaatggtgattttggtgggaggagggcaagatgaccg ccaaggtcgtagagtccgccaaggccattctgggcggcagcaaggtgcgc gtggaccaaaaatgcaaggcctctgcgcagatcgaccccaccccgtgat cgtcacctccaacaccaacatgtgcgccgtgattgacgggaacagcacca ccttcgagcaccagcagcccctgcaggaccggatgttcaagtttgaactc acccgccgcctcgaccacgactttggcaaggtcaccaagcaggaagtcaa ggacttttccggtgggcggctgatcacgtgactgacgtggctcatgagt tttacgtcacaaagggtggagctaagaaaaggcccgcccctctgacgag gatataagcgagcccaagcggccgcgcgtgtcatttgcgcagccggagac gtcagacgcggaagctcccggagacttcgccgacaggtaccaaaacaaat gttctcgtcacgcgggtatgctgcagatgctcttccctgcaagacgtgc gagagaatgaatcagaattccaacgtctgcttcacgcacggtcagaaaga ttgcggggagtgctttccccgggtcagaatctcaaccggtttctgtcgtca gaaaaacgtatcagaaactgtgcatccttcatcagctccggggggcaccc gagatcgcctgctctgcttgcgaccaactcaaccccgatttggacgattg ccaatttgagcaataa
```

Example of Wild-Type AAV13 Rep Nucleic Acid Sequence (SEQ ID NO: 20)
```
atgccgggattctacgagattgtcctgaaggtgcccagcgacctggacga gcacctgcctggcatttctgactctttttgtaaactgggtggcggagaagg aatgggagctgccgccggattctgacatggatctgaatctgattgagcag gcacccctaaccgtggccgaaaagctgcaacgcgaattcctggtcgagtg gcgccgcgtgagtaaggccccggaggccctcttctttgttcagttcgaga aggggggacagctacttccacctacacattctggtggagaccgtgggcgtg aaatccatggtggtgggccgctacgtgagccagattaaagagaagctggt gacccgcatctaccgcggggtcgagccgcagcttccgaactggttcgcgg tgaccaagacgcgtaatggcgccggaggcgggaacaaggtggtggacgac tgctacatccccaactacctgctccccaagacccagcccgagctccagtg
```

Example of Wild-Type AAV1 Rep78 Amino Acid Sequence

-continued

```
ggcgtggactaatatggaccagtatttaagcgcctgtttgaatctcgcgg agcgtaaacggctggtggcgcagcatctgacgcacgtgtcgcagacgcag gagcagaacaaagagaaccagaatcccaattctgacgcgccggtgatcag atcaaaaacctccgcgaggtacatggagctggtcgggtggctggtggacc gcgggatcacgtcagaaaagcaatggatccaggaggaccaggcctcttac atctccttcaacgccgcctccaactcgcggtcacaaatcaaggccgcact ggacaatgcctccaaatttatgagcctgacaaaaacggctccggactacc tggtggggaaacaacccgccggaggacattaccagcaaccggatctacaaa atcctcgagatgaacgggtacgatccgcagtacgcggcctccgtcttcct gggctgggcgcaaaagaagttcgggaagaggaacaccatctggctctttg ggccggccacgacgggtaaaaccaacatcgctgaagctatcgcccacgcc gtgcccttttacggctgcgtgaactggaccaatgagaactttccgttcaa cgattgcgtcgacaagatggtgatctggtgggaggagggcaagatgacgg ccaaggtcgtggagtccgccaaggccattctgggcggaagcaaggtgcgc gtggaccaaaagtgcaagtcatcggcccagatcgaccccactcccgtcat cgtcacctccaacaccaacatgtgcgcggtcatcgacggaaattccacca ccttcgagcaccaacaaccactccaagaccggatgttcaagttcgagctc accaagcgcctggagcacgactttggcaaggtcaccaagcaggaagtcaa ggacttttccggtgggcgtcagatcacgtgactgaggtgtctcacgagt tttacgtcagaaagggtggagctagaaagaggcccgcccccaatgacgca gatataagtgagcccaagcgggcctgtccgtcagttgcgcagccatcgac gtcagacgcggaagctccggtggactacgcggacaggtaccaaaacaaat gttctcgtcacgtgggcatgaatctgatgcttttcccctgccggcaatgc gagagaatgaatcagaatgtggacatttgcttcacgcacggggtcatgga ctgtgccgagtgcttccccgtgtcagaatctcaaccgtgtctgtcgtca gaaagcggacatatcagaaactgtgtccgattcatcacatcatggggagg gcgcccgaggtggcttgttcggcctgcgatctggccaatgtggacttgga tgactgtgacatggagcaataa
```

(SEQ ID NO: 21)
```
MPGFYEIVIKVPSDLDEHLPGISDSFVSWVAEKEWELPPDSDMDLNLIEQ

APLTVAEKLQRDFLVQWRRVSKAPEALFFVQFEKGESYFHLILVETTGV

KSMVLGRFLSQIRDKLVQTIYRGIEPTLPNWFAVTKTRNGAGGGNKVVDE

CYIPNYLLPKTQPELQWAWTNMEEYISACLNLAERKRLVAQHLTHVSQTQ

EQNKENLNPNSDAPVIRSKTSARYMELVGWLVDRGITSEKQWIQEDQASY

ISFNAASNSRSQIKAALDNAGKIMALTKSAPDYLVGPAPPADIKTNRIYR

ILELNGYEPAYAGSVFLGWAQKRFGKRNTIWLFGPATTGKTNIAEAIAHA

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TRRLEHDFGKVTKQEVKEFFRWAQDHVTEVAHEFYVRKGGANKRPAPDDA
```

```
DKSEPKRACPSVADPSTSDAEGAPVDFADRYQNKCSRHAGMLQMLFPCKT

CERMNQNFNICFTHGTRDCSECFPGVSESQPVVRKRTYRKLCAIHHLLGR

APEIACSACDLVNVDLDDCVSEQ
```

Example of Wild-Type AAV2 Rep78 Amino Acid Sequence

```
                                          (SEQ ID NO: 22)
MPGFYEIVIKVPSDLDGHLPGISDSFVNWVAEKEWELPPDSDMDLNLIEQ

APLTVAEKLQRDFLTEWRRVSKAPEALFFVQFEKGESYFHMHVLVETTGV

KSMVLGRFLSQIREKLIQRIYRGIEPTLPNWFAVTKTRNGAGGGNKVVDE

CYIPNYLLPKTQPELQWAWTNMEQYLSACLNLTERKRLVAQHLTHVSQTQ

EQNKENQNPNSDAPVIRSKTSARYMELVGWLVDKGITSEKQWIQEDQASY

ISFNAASNSRSQIKAALDNAGKIMSLTKTAPDYLVGQQPVEDISSNRIYK

ILELNGYDPQYAASVFLGWATKKFGKRNTIWLFGPATTGKTNIAEAIAHT

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TRRLDHDFGKVTKQEVKDFFRWAKDHVVEVEHEFYVKKGGAKKRPAPSDA

DISEPKRVRESVAQPSTSDAEASINYADRYQNKCSRHVGMNLMLFPCRQC

ERMNQNSNICFTHGQKDCLECFPVSESQPVSVVKKAYQKLCYIHHIMGKV

PDACTACDLVNVDLDDCIFEQ
```

Example of Wild-Type AAV3 Rep78 Amino Acid Sequence

```
                                          (SEQ ID NO: 23)
MPGFYEIVLKVPSDLDEHLPGISNSFVNWVAEKEWELPPDSDMDPNLIEQ

APLTVAEKLQREFLVEWRRVSKAPEALFFVQFEKGETYFHLHVLIETIGV

KSMVVGRYVSQIKEKLVTRIYRGVEPQLPNWFAVTKTRNGAGGGNKVVDD

CYIPNYLLPKTQPELQWAWTNMDQYLSACLNLAERKRLVAQHLTHVSQTQ

EQNKENQNPNSDAPVIRSKTSARYMELVGWLVDRGITSEKQWIQEDQASY

ISFNAASNSRSQIKAALDNASKIMSLTKTAPDYLVGSNPPEDITKNRIYQ

ILELNGYDPQYAASVFLGWAQKKFGKRNTIWLFGPATTGKTNIAEAIAHA

VPFYGCVNWTNENFPFNDCVDKMVIWWEEGKMTAKVVESAKAILGGSKVR

VDQKCKSSAQIEPTPVIVTSNTNMCAVIDGNSTTFEHQQPLQDRMFKFEL

TRRLDHDFGKVTKQEVKDFFRWASDHVTDVAHEFYVRKGGAKKRPASNDA

DVSEPKRQCTSLAQPTTSDAEAPADYADRYQNKCSRHVGMNLMLFPCKTC

ERMNQISNVCFTHGQRDCGECFPGMSESQPVSVVKKKTYQKLCPIHHILG

RAPEIACSACDLANVDLDDCVSEQ
```

Example of Wild-Type AAV4 Rep78 Amino Acid Sequence

```
                                          (SEQ ID NO: 24)
MPGFYEIVLKVPSDLDEHLPGISDSFVSWVAEKEWELPPDSDMDLNLIEQ

APLTVAEKLQREFLVEWRRVSKAPEALFFVQFEKGDSYFHLHILVETVGV

KSMVVGRYVSQIKEKLVTRIYRGVEPQLPNWFAVTKTRNGAGGGNKVVDD

CYIPNYLLPKTQPELQWAWTNMDQYISACLNLAERKRLVAQHLTHVSQTQ

EQNKENQNPNSDAPVIRSKTSARYMELVGWLVDRGITSEKQWIQEDQASY

ISFNAASNSRSQIKAALDNASKIMSLTKTAPDYLVGQNPPEDISSNRIYR

ILEMNGYDPQYAASVFLGWAQKKFGKRNTIWLFGPATTGKTNIAEAIAHA

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TKRLEHDFGKVTKQEVKDFFRWASDHVTEVTHEFYVRKGGARKRPAPNDA

DISEPKRACPSVAQPSTSDAEAPVDYADRYQNKCSRHVGMNLMLFPCRQC

ERMNQNVDICFTHGVMDCAECFPVSESQPVSVVRKRTYQKLCPIHHIMGR

APEVACSACELANVDLDDCDMEQ
```

Example of Wild-Type AAV5 Rep78 Amino Acid Sequence

```
                                          (SEQ ID NO: 25)
MATFYEVIVRVPFDVEEHLPGISDSFVDWVTGQIWELPPESDLNLTLVEQ

PQLTVADRIRRVFLYEWNKFSKQESKFFVQFEKGSEYFHLHTLVETSGIS

SMVLGRYVSQIRAQLVKVVFQGIEPQINDWVAITKVKKGGANKVVDSGYI

PAYLLPKVQPELQWAWTNLDEYKLAALNLEERKRLVAQFLAESSQRSQEA

ASQREFSADPVIKSKTSQKYMALVNWLVEHGITSEKQWIQENQESYLSFN

STGNSRSQIKAALDNATKIMSLTKSAVDYLVGSSVPEDISKNRIWQIFEM

NGYDPAYAGSILYGWCQRSFNKRNTVWLYGPATTGKTNIAEAIAHTVPFY

GCVNWTNENFPFNDCVDKMLIWWEEGKMTNKVVESAKAILGGSKVRVDQK

CKSSVQIDSTPVIVTSNTNMCVVVDGNSTTFEHQQPLEDRMFKFELTKRL

PPDFGKITKQEVKDFFAWAKVNQVPVTHEFKVPRELAGTKGAEKSLKRPL

GDVTNTSYKSLEKRARLSFVPETPRSSDVTVDPAPLRPLNWNSRYDCKCD

YHAQFDNISNKCDECEYLNRGKNGCICHNVTHCQICHGIPPWEKENLSDF

GDFDDANKEQ
```

Example of Wild-Type AAV6 Rep78 Amino Acid Sequence

```
                                          (SEQ ID NO: 26)
MPGFYEIVIKVPSDLDEHLPGISDSFVNWVAEKEWELPPDSDMDLNLIEQ

APLTVAEKLQRDFLVQWRRVSKAPEALFFVQFEKGESYFHLHILVETTGV

KSMVLGRFLSQIRDKLVQTIYRGIEPTLPNWFAVTKTRNGAGGGNKVVDE

CYIPNYLLPKTQPELQWAWTNMEEYISACLNLAERKRLVAHDLTHVSQTQ

EQNKENLNPNSDAPVIRSKTSARYMELVGWLVDRGITSEKQWIQEDQASY

ISFNAASNSRSQIKAALDNAGKIMALTKSAPDYLVGPAPPADIKTNRIYR

ILELNGYDPAYAGSVFLGWAQKRFGKRNTIWLFGPATTGKTNIAEAIAHA

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TRRLEHDFGKVTKQEVKEFFRWAQDHVTEVAHEFYVRKGGANKRPAPDDA

DKSEPKRACPSVADPSTSDAEGAPVDFADRYQNKCSRHAGMLQMLFPCKT

CERMNQNFNICFTHGTRDCSECFPGVSESQPVVRKRTYRKLCAIHHLLGR

APEIACSACDLVNVDLDDCVSEQ
```

Example of Wild-Type AAV7 Rep78 Amino Acid Sequence (SEQ ID NO: 27)
MPGFYEIVIKVPSDLDEHLPGISDSFVNWVAEKEWELPPDSDMDLNLIEQ
APLTVAEKLQRDFLVQWRRVSKAPEALFFVQFEKGESYFHLHVLVETTGV
KSMVLGRFLSQIREKLVQTIYRGVEPTLPNWFAVTKTRNGAGGGNKVVDE
CYIPNYLLPKTQPELQWAWTNMEEYISACLNLAERKRLVAQHLTHVSQTQ
EQNKENLNPNSDAPVIRSKTSARYMELVGWLVDRGITSEKQWIQEDQASY
ISFNAASNSRSQIKAALDNAGKIMALTKSAPDYLVGPSLPADIKTNRIYR
ILELNGYDPAYAGSVFLGWAQKKFGKRNTIWLFGPATTGKTNIAEAIAHA
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLEHDFGKVTKQEVKEFFRWASDHVTEVAHEFYVRKGGASKRPAPDDA
DISEPKRACPSVADPSTSDAEGAPVDFADRYQNKCSRHAGMIQMLFPCKT
CERMNQNFNICFTHGVRDCLECFPGVSESQPVVRKKTYRKLCAIHHLLGR
APEIACSACDLVNVDLDDCVSEQ Example of Wild-Type AAV8 Rep78 Amino Acid Sequence (SEQ ID NO: 28)
MPGFYEIVIKVPSDLDEHLPGISDSFVNWVAEKEWELPPDSDMDRNLIEQ
APLTVAEKLQRDFLVQWRRVSKAPEALFFVQFEKGESYFHLHVLVETTGV
KSMVLGRFLSQIREKLGPDHLPAGSSPTLPNWFAVTKDAVMAPAGGNKVV
DECYIPNYLLPKTQPELQWAWTNMEEYISACLNLAERKRLVAQHLTHVSQ
TQEQNKENLNPNSDAPVIRSKTSARYMELVGWLVDRGITSEKQWIQEDQA
SYISFNAASNSRSQIKAALDNAGKIMALTKSAPDYLVGPSLPADITQNRI
YRILALNGYDPAYAGSVFLGWAQKKFGKRNTIWLFGPATTGKTNIAEAIA
HAVPFYGCVNWTNENFPFNDCVDKMVIWWEEGKMTAKVVESAKAILGGSK
VRVDQKCKSSAQIDPTPVIVTSNTNMCAVIDGNSTTFEHQQPLQDRMFKF
ELTRRLEHDFGKVTKQEVKEFFRWASDHVTEVAHEFYVRKGGASKRPAPD
DADKSEPKRACPSVADPSTSDAEGAPVDFADRYQNKCSRHAGMLQMLFPC
KTCERMNQNFNICFTHGVRDCSECFPGVSESQPVVRKRTYRKLCAIHHLL
GRAPEIACSACDLVNVDLDDCVSEQ Example of Wild-Type AAVrh.8 Rep78 Amino Acid Sequence (SEQ ID NO: 29)
MPGFYEIVIKVPSDLDEHLPGISDSFVNWVAEKEWELPPDSDMDRNLIEQ
APLTVAEKLQRDFLVQWRRVSKAPEALFFVQFEKGESYFHLHVLVETTGV
KSMVLGRFLSQIREKLVQTIYRGIEPTLPNWFAVTKTRNGAGGGNKVVDE
CYIPNYLLPKTQPELQWAWTNMEEYISACLNLAERKRLVAQHLTHVSQTQ
EQNKENLNPNSDAPVIRSKTSARYMELVGWLVDRGITSEKQWIQEDQASY
ISFNAASNSRSQIKAALDNAGKIMALTKSAPDYLVGPSLPVDITQNRIYR
ILQLNGYDPAYAGSVFLGWAQKKFGKRNTIWLFGPATTGKTNIAEAIAHA
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLEHDFGKVTKQEVKEFFRWASDHVTEVAHEFYVRKGGASKRPAPDDA
DKSEPKRACPSVADPSTSDAEGAPVDFADRYQNKCSRHAGMLQMLLPCKT
CERMNQNFNICFTHGVRDCSECFPGVSESQPVVRKRTYRKLCAIHHLLGR
APEIACSACDLVNVDLDDCVSEQ Example of Wild-Type AAV10 Rep78 Amino Acid Sequence (SEQ ID NO: 30)
MPGFYEIVIKVPSDLDEHLPGISDSFVNWVAEKEWELPPDSDMDRNLIEQ
APLTVAEKLQRDFLVHWRRVSKAPEALFFVQFEKGESYFHLHVLVETTGV
KSMVLGRFLSQIRDRLVQTIYRGVEPTLPNWFAVTKTRNGAGGGNKVVDE
CYIPNYLLPKTQPELQWAWTNMEEYISACLNLAERKRLVAQHLTHVSQTQ
EQNKENLNPNSDAPVIRSKTSARYMELVGWLVDRGITSEKQWIQEDQASY
ISFNAASNSRSQIKAALDNAGKIMALTKSAPDYLVGPSLPADIKANRIYR
ILELNGYDPAYAGSVFLGWAQKKFGKRNTIWLFGPATTGKTNIAEAIAHA
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLEHDFGKVTKQEVKEFFRWAQDHVTEVTHEFYVRKGGATKRPAPSDA
DISEPKRACPSVAEPSTSDAEAPVDFADRYQNKCSRHAGMLQMLFPCKTC
ERMNQNFNVCFTHGVRDCSECFPGASESQPVVRKKTYQKLCAIHHLLGRA
PEIACSACDLVNVDLDDCVSEQ Example of Wild-Type AAV11 Rep78 Amino Acid Sequence (SEQ ID NO: 31)
MPGFYEIVIKVPSDLDEHLPGISDSFVNWVAEKEWELPPDSDMDRNLIEQ
APLTVAEKLQRDFLVHWRRVSKAPEALFFVQFEKGESYFHLHVLVETTGV
KSMVLGRFLSQIRDRLVQTIYRGVEPTLPNWFAVTKTRNGAGGGNKVVDE
CYIPNYLLPKTQPELQWAWTNMEEYISACLNLAERKRLVAQHLTHVSQTQ
EQNKENLNPNSDAPVIRSKTSARYMELVGWLVDRGITSEKQWIQEDQASY
ISFNAASNSRSQIKAALDNAGKIMALTKSAPDYLVGPSLPADIKANRIYR
ILELNGYDPAYAGSVFLGWAQKKFGKRNTIWLFGPATTGKTNIAEAIAHA
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLEHDFGKVTKQEVKEFFRWAQDHVTEVAHEFYVRKGGATKRPAPSDA
DISEPKRACPSVPEPSTSDAEAPVDFADRYQNKCSRHAGMLQMLFPCKTC
ERMNQNFNVCFTHGVRDCSECFPGASESQPVVRKKTYQKLCAIHHLLGRA
PEIACSACDLVNVDLDDCVSEQ Example of Wild-Type AAV12 Rep78 Amino Acid Sequence (SEQ ID NO: 32)
MPGFYEVVIKVPSDLDEHLPGISDSFVNWVAEKEWELPPDSDMDQNLIEQ

APLTVAEKLQREFLVEWRRVSKFLEAKFFVQFEKGDSYFHLHILIEITGV

KSMVVGRYVSQIRDKLIQRIYRGVEPQLPNWFAVTKTRNGAGGGNKVVDE

CYIPNYLLPKVQPELQWAWTNMEEYISACLNLAERKRLVAQHLTHVSQTQ

EGDKENLNPNSDAPVIRSKTSARYMELVGWLVDKGITSEKQWIQEDQASY

ISFNAASNSRSQIKAALDNASKIMSLTKTAPDYLIGQQPVGDITTNRIYK

ILELNGYDPQYAASVFLGWAQKKFGKRNTIWLFGPATTGKTNIAEAIAHA

VPFYGCVNWTNENFPFNDCVDKMVIWWEEGKMTAKVVESAKAILGGSKVR

VDQKCKASAQIDPTPVIVTSNTNMCAVIDGNSTTFEHQQPLQDRMFKFEL

TRRLDHDFGKVTKQEVKDFFRWAADHVTDVAHEFYVTKGGAKKRPAPSDE

DISEPKRPRVSFAQPETSDAEAPGDFADRYQNKCSRHAGMLQMLFPCKTC

ERMNQNSNVCFTHGQKDCGECFPGSESQPVSVVRKTYQKLCILHQLRGAP

EIACSACDQLNPDLDDCQFEQ

Example of Wild-Type AAV13 Rep78 Amino Acid Sequence (SEQ ID NO: 33)
MPGFYEIVLKVPSDLDEHLPGISDSFVNWVAEKEWELPPDSDMDLNLIEQ

APLTVAEKLQREFLVEWRRVSKAPEALFFVQFEKGDSYFHLHILVETVGV

KSMVVGRYVSQIKEKLVTRIYRGVEPQLPNWFAVTKTRNGAGGGNKVVDD

CYIPNYLLPKTQPELQWAWTNMDQYLSACLNLAERKRLVAQHLTHVSQTQ

EQNKENQNPNSDAPVIRSKTSARYMELVGWLVDRGITSEKQWIQEDQASY

ISFNAASNSRSQIKAALDNASKFMSLTKTAPDYLVGNNPPEDITSNRIYK

ILEMNGYDPQYAASVFLGWAQKKFGKRNTIWLFGPATTGKTNIAEAIAHA

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TKRLEHDFGKVTKQEVKDFFRWASDHVTEVSHEFYVRKGGARKRPAPNDA

DISEPKRACPSVAQPSTSDAEAPVDYADRYQNKCSRHVGMNLMLFPCRQC

ERMNQNVDICFTHGVMDCAECFPVSESQPVSVVRKRTYQKLCPIHHIMGR

APEVACSACDLANVDLDDCDMEQ

As defined herein, a rep gene or Rep protein comprises an N-terminus and a C-terminus (c), wherein the N terminus comprises an N-terminus domain (n), a DNA binding domain (d), and a helicase domain (h), and C terminus (c) comprises a NLS/p40 promoter domain (y) and a Zinc finger domain (z). Table 1 provides example sequences of these domains for different AAV serotypes.

TABLE 1

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| AAV1 | DNA | n | 1-306 | ATGCCGGGCTTCTACGAGATCGTGATC<br>AAGGTGCCGAGCGACCTGGACGAGCA<br>CCTGCCGGGCATTTCTGACTCGTTTGTG<br>AGCTGGGTGGCCGAGAAGGAATGGGA<br>GCTGCCCCCGGATTCTGACATGGATCT<br>GAATCTGATTGAGCAGGCACCCCTGAC<br>CGTGGCCGAGAAGCTGCAGCGCGACTT<br>CCTGGTCCAATGGCGCCGCGTGAGTAA<br>GGCCCCCGGAGGCCCTCTTCTTTGTTCA<br>GTTCGAGAAGGGCGAGTCCTACTTCCA<br>CCTCCATATTCTGGTGGAGACCACGGG<br>GGTCAAATCC | 40 |
| | | d | 307-726 | ATGGTGCTGGGCCGCTTCCTGAGTCAG<br>ATTAGGGACAAGCTGGTGCAGACCATC<br>TACCGCGGGATCGAGCCGACCCTGCCC<br>AACTGGTTCGCGGTGACCAAGACGCGT<br>AATGGCGCCGGAGGGGGAACAAGGT<br>GGTGGACGAGTGCTACATCCCCAACTA<br>CCTCCTGCCCAAGACTCAGCCCGAGCT<br>GCAGTGGGCGTGGACTAACATGGAGG<br>AGTATATAAGCGCCTGTTTGAACCTGG<br>CCGAGCGCAAACGGCTCGTGGCGCAG<br>CACCTGACCCACGTCAGCCAGACCCAG<br>GAGCAGAACAAGGAGAATCTGAACCC<br>CAATTCTGACGCGCCTGTCATCCGGTC<br>AAAAACCTCCGCGCGCTACATGGAGCT<br>GGTCGGGTGGCTGGTGACCGGGGCAT<br>CACCTCCGAGAAGCAGTGG | 41 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | h | 727-1107 | ATCCAGGAGGACCAGGCCTCGTACATC TCCTTCAACGCCGCTTCCAACTCGCGG TCCCAGATCAAGGCCGCTCTGGACAAT GCCGGCAAGATCATGGCGCTGACCAA ATCCGCGCCCGACTACCTGGTAGGCCC CGCTCCGCCCGCGGACATTAAAACCAA CCGCATCTACCGCATCCTGGAGCTGAA CGGCTACGAACCTGCCTACGCCGGCTC CGTCTTTCTCGGCTGGGCCCAGAAAAG GTTCGGGAAGCGCAACACCATCTGGCT GTTTGGGCCGGCCACCACGGGCAAGAC CAACATCGCGGAAGCCATCGCCCACGC CGTGCCCTTCTACGGCTGCGTCAACTG GACCAATGAGAACTTTCCCTTCAATGA TTGC | 42 |
| | | c | 1108-1872 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA GAGTTCTTCCGCTGGGCGCAGGATCAC GTGACCGAGGTGGCGCATGAGTTCTAC GTCAGAAAGGGTGGAGCCAACAAAAG ACCCGCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAATGTTCTCGTCACG CGGGCATGCTTCAGATGCTGTTTCCCT GCAAGACATGCGAGAGAATGAATCAG AATTTCAACATTTGCTTCACGCACGGG ACGAGAGACTGTTCAGAGTGCTTCCCC GGCGTGTCAGAATCTCAACCGGTCGTC AGAAAGAGGACGTATCGGAAACTCTG TGCCATTCATCATCTGCTGGGGCGGGC TCCCGAGATTGCTTGCTCGGCCTGCGA TCTGGTCAACGTGGACCTGGATGACTG TGTTTCTGAGCAATAA | 43 |
| | | y | 1108-1602 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA GAGTTCTTCCGCTGGGCGCAGGATCAC GTGACCGAGGTGGCGCATGAGTTCTAC GTCAGAAAGGGTGGAGCCAACAAAAG ACCCGCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAA | 44 |
| | | z | 1603-1872 | TGTTCTCGTCACGCGGGCATGCTTCAG ATGCTGTTTCCCTGCAAGACATGCGAG AGAATGAATCAGAATTTCAACATTTGC TTCACGCACGGGACGAGAGACTGTTCA GAGTGCTTCCCCGGCGTGTCAGAATCT CAACCGGTCGTCAGAAAGAGGACGTA TCGGAAACTCTGTGCCATTCATCATCT GCTGGGGCGGGCTCCCGAGATTGCTTG | 45 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CTCGGCCTGCGATCTGGTCAACGTGGA CCTGGATGACTGTGTTTCTGAGCAATA A | |
| | PRT | n | 1-102 | MPGFYEIVIKVPSDLDEHLPGISDSFVSW VAEKEWELPPDSDMDLNLIEQAPLTVAE KLQRDFLVQWRRVSKAPEALFFVQFEK GESYFHLHILVETTGVKS | 46 |
| | | d | 103-242 | MVLGRFLSQIRDKLVQTIYRGIEPTLPNW FAVTKTRNGAGGGNKVVDECYIPNYLLP KTQPELQWAWTNMEEYISACLNLAERK RLVAQHLTHVSQTEQNKENLNPNSDA PVIRSKTSARYMELVGWLVDRGITSEKQ W | 47 |
| | | h | 243-369 | IQEDQASYISFNAASNSRSQIKAALDNAG KIMALTKSAPDYLVGPAPPADIKTNRIYR ILELNGYEPAYAGSVFLGWAQKRFGKR NTIWLFGPATTGKTNIAEAIAHAVPFYGC VNWTNENFPFNDC | 48 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN KCSRHAGMLQMLFPCKTCERMNQNFNI CFTHGTRDCSECFPGVSESQPVVRKRTY RKLCAIHHLLGRAPEIACSACDLVNVDL DDCVSEQ | 49 |
| | | y | 370-534 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN K | 50 |
| | | z | 535-623 | CSRHAGMLQMLFPCKTCERMNQNFNIC FTHGTRDCSECFPGVSESQPVVRKRTYR KLCAIHHLLGRAPEIACSACDLVNVDLD DCVSEQ | 51 |
| AAV2 | DNA | n | 1-306 | ACGCCGGGGTTTTACGAGATTGTGATT AAGGTCCCCAGCGACCTTGACGAGCAT CTGCCCGGCATTTCTGACAGCTTTGTG AACTGGGTGGCCGAGAAGGAATGGGA GTTGCCGCCAGATTCTGACATGGATCT GAATCTGATTGAGCAGGCACCCCTGAC CGTGGCCGAGAAGCTGCAGCGCGACTT TCTGACGGAATGGCGCCGTGTGAGTAA GGCCCCGGAGGCCCTTTTCTTTGTGCA ATTTGAGAAGGGAGAGAGCTACTTCCA CATGCACGTGCTCGTGGAAACCACCGG GGTGAAATCC | 52 |
| | | d | 307-726 | ATGGTTTTGGGACGTTTCCTGAGTCAG ATTCGCGAAAAACTGATTCAGAGAATT TACCGCGGGATCGAGCCGACTTTGCCA AACTGGTTCGCGGTCACAAAGACCAGA AATGGCGCCGGAGGCGGGAACAAGGT GGTGGATGAGTGCTACATCCCCAATTA CTTGCTCCCCAAAACCCAGCCTGAGCT CCAGTGGGCGTGGACTAATATGGAACA GTATTTAAGCGCCTGTTTGAATCTCAC GGAGCGTAAACGGTTGGTGGCGCAGC ATCTGACGCACGTGTCGCAGACGCAGG AGCAGAACAAAGAGAATCAGAATCCC AATTCTGATGCGCCGGTGATCAGATCA AAAACTTCAGCCAGGTACATGGAGCTG GTCGGGTGGCTCGTGGACAAGGGGATT ACCTCGGAGAAGCAGTGG | 53 |
| | | h | 727-1107 | ATCCAGGAGGACCAGGCCTCATACATC TCCTTCAATGCGGCCTCCAACTCGCGG TCCCAAATCAAGGCTGCCTTGGACAAT | 54 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GCGGGAAAGATTATGAGCCTGACTAA AACCGCCCCCGACTACCTGGTGGGCCA GCAGCCCGTGGAGGACATTTCCAGCAA TCGGATTTATAAAATTTTGGAACTAAA CGGGTACGATCCCCAATATGCGGCTTC CGTCTTTCTGGGATGGGCCACGAAAAA GTTCGGCAAGAGGAACACCATCTGGCT GTTTGGGCCTGCAACTACCGGGAAGAC CAACATCGCGGAGGCCATAGCCCACAC TGTGCCCTTCTACGGGTGCGTAAACTG GACCAATGAGAACTTTCCCTTCAACGA CTGT | |
| | c | 1108-1866 | | GTCGACAAGATGGTGATCTGGTGGGAG GAGGGGAAGATGACCGCCAAGGTCGT GGAGTCGGCCAAAGCCATTCTCGGAGG AAGCAAGGTGCGCGTGGACCAGAAAT GCAAGTCCTCGGCCCAGATAGACCCGA CTCCCGTGATCGTCACCTCCAACACCA ACATGTGCGCCGTGATTGACGGGAACT CAACGACCTTCGAACACCAGCAGCCGT TGCAAGACCGGATGTTCAAATTTGAAC TCACCCGCCGTCTGGATCATGACTTTG GGAAGGTCACCAAGCAGGAAGTCAAA GACTTTTTCCGGTGGGCAAAGGATCAC GTGGTTGAGGTGGAGCATGAATTCTAC GTCAAAAAGGGTGGAGCCAAGAAAAG ACCCGCCCCCAGTGACGCAGATATAAG TGAGCCCAAACGGGTGCGCGAGTCAGT TGCGCAGCCATCGACGTCAGACGCGGA AGCTTCGATCAACTACGCAGACAGGTA CCAAAACAAATGTTCTCGTCACGTGGG CATGAATCTGATGCTGTTTCCCTGCAG ACAATGCGAGAGAATGAATCAGAATT CAAATATCTGCTTCACTCACGGACAGA AAGACTGTTTAGAGTGCTTTCCCGTGT CAGAATCTCAACCCGTTTCTGTCGTCA AAAAGGCGTATCAGAAACTGTGCTACA TTCATCATATCATGGGAAAGGTGCCAG ACGCTTGCACTGCCTGCGATCTGGTCA ATGTGGATTTGGATGACTGCATCTTTG AACAATAA | 55 |
| | y | 1108-1599 | | GTCGACAAGATGGTGATCTGGTGGGAG GAGGGGAAGATGACCGCCAAGGTCGT GGAGTCGGCCAAAGCCATTCTCGGAGG AAGCAAGGTGCGCGTGGACCAGAAAT GCAAGTCCTCGGCCCAGATAGACCCGA CTCCCGTGATCGTCACCTCCAACACCA ACATGTGCGCCGTGATTGACGGGAACT CAACGACCTTCGAACACCAGCAGCCGT TGCAAGACCGGATGTTCAAATTTGAAC TCACCCGCCGTCTGGATCATGACTTTG GGAAGGTCACCAAGCAGGAAGTCAAA GACTTTTTCCGGTGGGCAAAGGATCAC GTGGTTGAGGTGGAGCATGAATTCTAC GTCAAAAAGGGTGGAGCCAAGAAAAG ACCCGCCCCCAGTGACGCAGATATAAG TGAGCCCAAACGGGTGCGCGAGTCAGT TGCGCAGCCATCGACGTCAGACGCGGA AGCTTCGATCAACTACGCAGACAGGTA CCAAAACAAA | 56 |
| | z | 1600-1866 | | TGTTCTCGTCACGTGGGCATGAATCTG ATGCTGTTTCCCTGCAGACAATGCGAG AGAATGAATCAGAATTCAAATATCTGC TTCACTCACGGACAGAAAGACTGTTTA GAGTGCTTTCCCGTGTCAGAATCTCAA CCCGTTTCTGTCGTCAAAAAGGCGTAT CAGAAACTGTGCTACATTCATCATATC ATGGGAAAGGTGCCAGACGCTTGCACT GCCTGCGATCTGGTCAATGTGGATTTG GATGACTGCATCTTTGAACAATAA | 57 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | PRT | n | 1-102 | TPGFYEIVIKVPSDLDGHLPGISDSFVNW VAEKEWELPPDSDMDLNLIEQAPLTVAE KLQRDFLTEWRRVSKAPEALFFVQFEKG ESYFHMHVLVETTGVKS | 58 |
| | | d | 103-242 | MVLGRFLSQIREKLIQRIYRGIEPTLPNWF AVTKTRNGAGGGNKVVDECYIPNYLLP KTQPELQWAWTNMEQYLSACLNLTERK RLVAQHLTHVSQTQEQNKENQNPNSDA PVIRSKTSARYMELVGWLVDKGITSEKQ W | 59 |
| | | h | 243-369 | IQEDQASYISFNAASNSRSQIKAALDNAG KIMSLTKTAPDYLVGQQPVEDISSNRIYK ILELNGYDPQYAASVFLGWATKKFGKR NTIWLFGPATTGKTNIAEAIAHTVPFYGC VNWTNENFPFNDC | 60 |
| | | c | 370-621 | VDKMVIWWEEGKMTAKVVESAKAILG GSKVRVDQKCKSSAQIDPTPVIVTSNTN MCAVIDGNSTTFEHQQPLQDRMFKFELT RRLDHDFGKVTKQEVKDFFRWAKDHV VEVEHEFYVKKGGAKKRPAPSDADISEP KRVRESVAQPSTSDAEASINYADRYQNK CSRHVGMNLMLFPCRQCERMNQNSNIC FTHGQKDCLECFPVSESQPVSVVKKAYQ KLCYIHHIMGKVPDACTACDLVNVDLD DCIFEQ | 61 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT RRLDHDFGKVTKQEVKDFFRWAKDHV VEVEHEFYVKKGGAKKRPAPSDADISEP KRVRESVAQPSTSDAEASINYADRYQNK | 62 |
| | | z | 534-621 | CSRHVGMNLMLFPCRQCERMNQNSNIC FTHGQKDCLECFPVSESQPVSVVKKAYQ KLCYIHHIMGKVPDACTACDLVNVDLD DCIFEQ | 63 |
| AAV3 | DNA | n | 1-306 | ATGCCGGGGTTCTACGAGATTGTCCTG AAGGTCCCGAGTGACCTGGACGAGCA CCTGCCGGGCATTTCTAACTCGTTTGTT AACTGGGTGGCCGAGAAGGAATGGGA GCTGCCGCCGGATTCTGACATGGATCC GAATCTGATTGAGCAGGCACCCCTGAC CGTGGCCGAAAAGCTTCAGCGCGAGTT CCTGGTGGAGTGGCGCCGCGTGAGTAA GGCCCCGGAGGCCCTCTTTTTTGTCCA GTTCGAAAAGGGGGAGACCTACTTCCA CCTGCACGTGCTGATTGAGACCATCGG GGTCAAATCC | 64 |
| | | d | 307-726 | ATGGTGGTCGGCCGCTACGTGAGCCAG ATTAAAGAGAAGCTGGTGACCCGCATC TACCGCGGGGTCGAGCCGCAGCTTCCG AACTGGTTCGCGGTGACCAAAACGCGA AATGGCGCCGGGGGCGGGAACAAGGT GGTGGACGACTGCTACATCCCCAACTA CCTGCTCCCCAAGACCCAGCCCGAGCT CCAGTGGGCGTGGACTAACATGGACCA GTATTTAAGCGCCTGTTTGAATCTCGC GGAGCGTAAACGGCTGGTGGCCAGC ATCTGACGCACGTGTCGCAGACGCAGG AGCAGAACAAAGAGAATCAGAACCCC AATTCTGACGCGCCGGTCATCAGGTCA AAAACCTCAGCCAGGTACATGGAGCTG GTCGGGTGGCTGGTGGACCGCGGGATC ACGTCAGAAAAGCAATGG | 65 |
| | | h | 727-1107 | ATTCAGGAGGACCAGGCCTCGTACATC TCCTTCAACGCGCCTCCAACTCGCGG TCCCAGATCAAGGCCGCGCTGGACAAT GCCTCCAAGATCATGAGCCTGACAAAG ACGGCTCCGGACTACCTGGTGGGCAGC AACCCGCCGGAGGACATTACCAAAAA TCGGATCTACCAAATCCTGGAGCTGAA | 66 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CGGGTACGATCCGCAGTACGCGGCCTC CGTCTTCCTGGGCTGGGCGCAAAAGAA GTTCGGGAAGAGGAACACCATCTGGCT CTTTGGGCCGGCCACGACGGGTAAAAC CAACATCGCGGAAGCCATCGCCCACGC CGTGCCCTTCTACGGCTGCGTAAACTG GACCAATGAGAACTTTCCCTTCAACGA TTGC | |
| | | c | 1108-1875 | GTCGACAAGATGGTGATCTGGTGGGAG GAGGGCAAGATGACGGCCAAGGTCGT GGAGAGCGCCAAGGCCATTCTGGGCG GAAGCAAGGTGCGCGTGGACCAAAAG TGCAAGTCATCGGCCCAGATCGAACCC ACTCCCGTGATCGTCACCTCCAACACC AACATGTGCGCCGTGATTGACGGGAAC AGCACCACCTTCGAGCATCAGCAGCCG CTGCAGGACCGGATGTTTAAATTTGAA CTTACCCGCCGTTTGGACCATGACTTT GGGAAGGTCACCAAACAGGAAGTAAA GGACTTTTTCCGGTGGGCTTCCGATCA CGTGACTGACGTGGCTCATGAGTTCTA CGTCAGAAAGGGTGGAGCTAAGAAAC GCCCCGCCTCCAATGACGCGGATGTAA GCGAGCCAAAACGGCAGTGCACGTCA CTTGCGCAGCCGACAACGTCAGACGCG GAAGCACCGGCGGACTACGCGGACAG GTACCAAAACAAATGTTCTCGTCACGT GGGCATGAATCTGATGCTTTTTCCCTGT AAAAACATGCGAGAGAATGAATCAAAT TTCCAATGTCTGTTTTACGCATGGTCAA AGAGACTGTGGGGAATGCTTCCCTGGA ATGTCAGAATCTCAACCCGTTTCTGTC GTCAAAAAGAAGACTTATCAGAAACT GTGTCCAATTCATCATATCCTGGGAAG GGCACCCGAGATTGCCTGTTCGGCCTG CGATTTGGCCAATGTGGACTTGGATGA CTGTGTTTCTGAGCAATAA | 67 |
| | | y | 1108-1599 | GTCGACAAGATGGTGATCTGGTGGGAG GAGGGCAAGATGACGGCCAAGGTCGT GGAGAGCGCCAAGGCCATTCTGGGCG GAAGCAAGGTGCGCGTGGACCAAAAG TGCAAGTCATCGGCCCAGATCGAACCC ACTCCCGTGATCGTCACCTCCAACACC AACATGTGCGCCGTGATTGACGGGAAC AGCACCACCTTCGAGCATCAGCAGCCG CTGCAGGACCGGATGTTTAAATTTGAA CTTACCCGCCGTTTGGACCATGACTTT GGGAAGGTCACCAAACAGGAAGTAAA GGACTTTTTCCGGTGGGCTTCCGATCA CGTGACTGACGTGGCTCATGAGTTCTA CGTCAGAAAGGGTGGAGCTAAGAAAC GCCCCGCCTCCAATGACGCGGATGTAA GCGAGCCAAAACGGCAGTGCACGTCA CTTGCGCAGCCGACAACGTCAGACGCG GAAGCACCGGCGGACTACGCGGACAG GTACCAAAACAAA | 68 |
| | | z | 1600-1875 | TGTTCTCGTCACGTGGGCATGAATCTG ATGCTTTTTCCCTGTAAAACATGCGAG AGAATGAATCAAATTTCCAATGTCTGT TTTACGCATGGTCAAAGAGACTGTGGG GAATGCTTCCCTGGAATGTCAGAATCT CAACCCGTTTCTGTCGTCAAAAAGAAG ACTTATCAGAAACTGTGTCCAATTCAT CATATCCTGGGAAGGGCACCCGAGATT GCCTGTTCGGCCTGCGATTTGGCCAAT GTGGACTTGGATGACTGTGTTTCTGAG CAATAA | 69 |
| | PRT | n | 1-102 | MPGFYEIVLKVPSDLDEHLPGISNSFVNW VAEKEWELPPDSDMDPNLIEQAPLTVAE KLQREFLVEWRRVSKAPEALFFVQFEKG ETYFHLHVLIETIGVKS | 70 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | d | 103-242 | MVVGRYVSQIKEKLVTRIYRGVEPQLPN WFAVTKTRNGAGGGNKVVDDCYIPNYL LPKTQPELQWAWTNMDQYLSACLNLAE RKRLVAQHLTHVSQTQEQNKENQNPNS DAPVIRSKTSARYMELVGWLVDRGITSE KQW | 71 |
| | | h | 243-369 | IQEDQASYISFNAASNSRSQIKAALDNAS KIMSLTKTAPDYLVGSNPPEDITKNRIYQ ILELNGYDPQYAASVFLGWAQKKFGKR NTIWLFGPATTGKTNIAEAIAHAVPFYGC VNWTNENFPFNDC | 72 |
| | | c | 370-624 | VDKMVIWWEEGKMTAKVVESAKAILG GSKVRVDQKCKSSAQIEPTPVIVTSNTN MCAVIDGNSTTFEHQQPLQDRMFKFELT RRLDHDFGKVTKQEVKDFFRWASDHVT DVAHEFYVRKGGAKKRPASNDADVSEP KRQCTSLAQPTTSDAEAPADYADRYQN KCSRHVGMNLMLFPCKTCERMNQISNV CFTHGQRDCGECFPGMSESQPVSVVKKK TYQKLCPIHHILGRAPEIACSACDLANVD LDDCVSEQ | 73 |
| | | y | 370-533 | VDKMVIWWEEGKMTAKVVESAKAILG GSKVRVDQKCKSSAQIEPTPVIVTSNTN MCAVIDGNSTTFEHQQPLQDRMFKFELT RRLDHDFGKVTKQEVKDFFRWASDHVT DVAHEFYVRKGGAKKRPASNDADVSEP KRQCTSLAQPTTSDAEAPADYADRYQN K | 74 |
| | | z | 534-624 | CSRHVGMNLMLFPCKTCERMNQISNVC FTHGQRDCGECFPGMSESQPVSVVKKKT YQKLCPIHHILGRAPEIACSACDLANVDL DDCVSEQ | 75 |
| AAV4 | DNA | n | 1-306 | ACGCCGGGGTTCTACGAGATCGTGCTG AAGGTGCCCAGCGACCTGGACGAGCA CCTGCCCGGCATTTCTGACTCTTTTGTG AGCTGGGTGGCCGAGAAGGAATGGGA GCTGCCGCCGGATTCTGACATGGACTT GAATCTGATTGAGCAGGCACCCCTGAC CGTGGCCGAAAAGCTGCAACGCGAGTT CCTGGTCGAGTGGCGCCGCGTGAGTAA GGCCCCGGAGGCCCTCTTCTTTTGTCCA GTTCGAGAAGGGGGACAGCTACTTCCA CCTGCACATCCTGGTGGAGACCGTGGG CGTCAAATCC | 76 |
| | | d | 307-726 | ATGGTGGTGGGCCGCTACGTGAGCCAG ATTAAAGAGAAGCTGGTGACCCGCATC TACCGCGGGGTCGAGCCGCAGCTTCCG AACTGGTTCGCGGTGACCAAGACGCGT AATGGCGCCGGAGGCGGGAACAAGGT GGTGGACGACTGCTACATCCCCAACTA CCTGCTCCCCAAGACCCAGCCCGAGCT CCAGTGGGCGTGGACTAACATGGACCA GTATATAAGCGCCTGTTTGAATCTCGC GGAGCGTAAACGGCTGGTGGCGCAGC ATCTGACGCACGTGTCGCAGACGCAGG AGCAGAACAAGGAAAACCAGAACCCC AATTCTGACGCGCCGGTCATCAGGTCA AAAACCTCCGCCAGGTACATGGAGCTG GTCGGGTGGCTGGTGGACCGCGGGATC ACGTCAGAAAAGCAATGG | 77 |
| | | h | 727-1107 | ATCCAGGAGGACCAGGCGTCCTACATC TCCTTCAACGCCGCCTCCAACTCGCGG TCACAAATCAAGGCCGCTGGACAAT GCCTCCAAAATCATGAGCCTGACAAAG ACGGCTCCGGACTACCTGGTGGGCCAG AACCCGCCGGAGGACATTTCCAGCAAC CGCATCTACCGAATCCTGGAGATGAAC GGGTACGATCCGCAGTACGCGGCCTCC GTCTTCCTGGGCTGGGCGCAAAAGAAG TTCGGGAAGAGGAACACCATCTGGCTC | 78 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | TTTGGGCCGGCCACGACGGGTAAAACC AACATCGCGGAAGCCATCGCCCACGCC GTGCCCTTCTACGGCTGCGTGAACTGG ACCAATGAGAACTTTCCGTTCAACGAT TGC | |
| | | c | 1108-1872 | GTCGACAAGATGGTGATCTGGTGGGAG GAGGGCAAGATGACGGCCAAGGTCGT AGAGAGCGCCAAGGCCATCCTGGGCG GAAGCAAGGTGCGCGTGGACCAAAAG TGCAAGTCATCGGCCCAGATCGACCCA ACTCCCGTGATCGTCACCTCCAACACC AACATGTGCGCGGTCATCGACGGAAAC TCGACCACCTTCGAGCACCAACAACCA CTCCAGGACCGGATGTTCAAGTTCGAG CTCACCAAGCGCCTGGAGCACGACTTT GGCAAGGTCACCAAGCAGGAAGTCAA AGACTTTTTCCGGTGGGCGTCAGATCA CGTGACCGAGGTGACTCACGAGTTTTA CGTCAGAAAGGGTGGAGCTAGAAAGA GGCCCGCCCCCAATGACGCAGATATAA GTGAGCCCAAGCGGGCCTGTCCGTCAG TTGCGCAGCCATCGACGTCAGACGCGG AAGCTCCGGTGGACTACGCGGACAGGT ACCAAAACAAATGTTCTCGTCACGTGG GTATGAATCTGATGCTTTTTCCCTGCCG GCAATGCGAGAGAATGAATCAGAATG TGGACATTTGCTTCACGCACGGGGTCA TGGACTGTGCCGAGTGCTTCCCCGTGT CAGAATCTCAACCCGTGTCTGTCGTCA GAAAGCGGACGTATCAGAAACTGTGTC CGATTCATCACATCATGGGGAGGGCGC CCGAGGTGGCCTGCTCGGCCTGCGAAC TGGCCAATGTGGACTTGGATGACTGTG ACATGGAACAATAA | 79 |
| | | y | 1108-1599 | GTCGACAAGATGGTGATCTGGTGGGAG GAGGGCAAGATGACGGCCAAGGTCGT AGAGAGCGCCAAGGCCATCCTGGGCG GAAGCAAGGTGCGCGTGGACCAAAAG TGCAAGTCATCGGCCCAGATCGACCCA ACTCCCGTGATCGTCACCTCCAACACC AACATGTGCGCGGTCATCGACGGAAAC TCGACCACCTTCGAGCACCAACAACCA CTCCAGGACCGGATGTTCAAGTTCGAG CTCACCAAGCGCCTGGAGCACGACTTT GGCAAGGTCACCAAGCAGGAAGTCAA AGACTTTTTCCGGTGGGCGTCAGATCA CGTGACCGAGGTGACTCACGAGTTTTA CGTCAGAAAGGGTGGAGCTAGAAAGA GGCCCGCCCCCAATGACGCAGATATAA GTGAGCCCAAGCGGGCCTGTCCGTCAG TTGCGCAGCCATCGACGTCAGACGCGG AAGCTCCGGTGGACTACGCGGACAGGT ACCAAAACAAA | 80 |
| | | z | 1600-1872 | TGTTCTCGTCACGTGGGTATGAATCTG ATGCTTTTTCCCTGCCGGCAATGCGAG AGAATGAATCAGAATGTGGACATTTGC TTCACGCACGGGGTCATGGACTGTGCC GAGTGCTTCCCCGTGTCAGAATCTCAA CCCGTGTCTGTCGTCAGAAAGCGGACG TATCAGAAACTGTGTCCGATTCATCAC ATCATGGGGAGGGCGCCCGAGGTGGC CTGCTCGGCCTGCGAACTGGCCAATGT GGACTTGGATGACTGTGACATGGAACA ATAA | 81 |
| | PRT | n | 1-102 | TPGFYEIVLKVPSDLDEHLPGISDSFVSW VAEKEWELPPDSDMDLNLIEQAPLTVAE KLQREFLVEWRRVSKAPEALFFVQFEKG DSYFHLILVETVGVKS | 82 |
| | | d | 103-242 | MVVGRYVSQIKEKLVTRIYRGVEPQLPN WFAVTKTRNGAGGGNKVVDDCYIPNYL LPKTQPELQWAWTNMDQYISACLNLAE | 83 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | RKRLVAQHLTHVSQTQEQNKENQNPNS DAPVIRSKTSARYMELVGWLVDRGITSE KQW | |
| | | h | 243-369 | IQEDQASYISFNAASNSRSQIKAALDNAS KIMSLTKTAPDYLVGQNPPEDISSNRIYRI LEMNGYDPQYAASVFLGWAQKKFGKR NTIWLFGPATTGKTNIAEAIAHAVPFYGC VNWTNENFPFNDC | 84 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVTHEFYVRKGGARKRPAPNDADISEPK RACPSVAQPSTSDAEAPVDYADRYQNK CSRHVGMNLMLFPCRQCERMNQNVDIC FTHGVMDCAECFPVSESQPVSVVRKRTY QKLCPIHHIMGRAPEVACSACELANVDL DDCDMEQ | 85 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVTHEFYVRKGGARKRPAPNDADISEPK RACPSVAQPSTSDAEAPVDYADRYQNK | 86 |
| | | z | 534-623 | CSRHVGMNLMLFPCRQCERMNQNVDIC FTHGVMDCAECFPVSESQPVSVVRKRTY QKLCPIHHIMGRAPEVACSACELANVDL DDCDMEQ | 87 |
| AAV5 | DNA | n | 1-306 | ATGGCTACCTTCTATGAAGTCATTGTTC GCGTCCCATTTGACGTGGAGGAACATC TGCCTGGAATTTCTGACAGCTTTGTGG ACTGGGTAACTGGTCAAATTTGGGAGC TGCCTCCAGAGTCAGATTTAAATTTGA CTCTGGTTGAACAGCCTCAGTTGACGG TGGCTGATAGAATTCGCCGCGTGTTCC TGTACGAGTGGAACAAATTTTCCAAGC AGGAGTCCAAATTCTTTGTGCAGTTTG AAAAGGGATCTGAATATTTTCATCTGC ACACGCTTGTGGAGACCTCCGGCATCT CTTCC | 88 |
| | | d | 307-714 | ATGGTCCTCGGCCGCTACGTGAGTCAG ATTCGCGCCCAGCTGGTGAAAGTGGTC TTCCAGGGAATTGAACCCCAGATCAAC GACTGGGTCGCCATCACCAAGGTAAAG AAGGGCGGAGCCAATAAGGTGGTGGA TTCTGGGTATATTCCCGCCTACCTGCTG CCGAAGGTCCAACCGGAGCTTCAGTGG GCGTGGACAAACCTGGACGAGTATAA ATTGGCCGCCCTGAATCTGGAGGAGCG CAAACGGCTCGTCGCGCAGTTTCTGGC AGAATCCTCGCAGCGCTCGCAGGAGGC GGCTTCGCAGCGTGAGTTCTCGGCTGA CCCGGTCATCAAAAGCAAGACTTCCCA GAAATACATGGCGCTCGTCAACTGGCT CGTGGAGCACGGCATCACTTCCGAGAA GCAGTGG | 89 |
| | | h | 715-1095 | ATCCAGGAAAATCAGGAGAGCTACCTC TCCTTCAACTCCACCGGCAACTCTCGG AGCCAGATCAAGGCCGCGCTCGACAA CGCGACCAAAATTATGAGTCTGACAAA AAGCGCGGTGGACTACCTCGTGGGGA GCTCCGTTCCCGAGGACATTTCAAAAA ACAGAATCTGGCAAATTTTTGAGATGA ATGGCTACGACCCGGCCTACGCGGGAT CCATCCTCTACGGCTGGTGTCAGCGCT CCTTCAACAAGAGGAACACCGTCTGGC TCTACGGACCCGCCACGACCGGCAAGA | 90 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | c | 1096-1833 | CCAACATCGCGGAGGCCATCGCCCACA CTGTGCCCTTTTACGGCTGCGTGAACT GGACCAATGAAAACTTTCCCTTTAATG ACTGT GTGGACAAAATGCTCATTTGGTGGGAG GAGGGAAAGATGACCAACAAGGTGGT TGAATCCGCCAAGGCCATCCTGGGGGG CTCAAAGGTGCGGGTCGATCAGAAATG TAAATCCTCTGTTCAAATTGATTCTACC CCTGTCATTGTAACTTCCAATACAAAC ATGTGTGTGGTGGTGGATGGGAATTCC ACGACCTTTGAACACCAGCAGCCGCTG GAGGACCGCATGTTCAAATTTGAACTG ACTAAGCGGCTCCCGCCAGATTTTGGC AAGATTACTAAGCAGGAAGTCAAGGA CTTTTTTGCTTGGGCAAAGGTCAATCA GGTGCCGGTGACTCACGAGTTTAAAGT TCCCAGGGAATTGGCGGGAACTAAAG GGGCGGAGAAATCTCTAAAACGCCCA CTGGGTGACGTCACCAATACTAGCTAT AAAAGTCTGGAGAAGCGGGCCAGGCT CTCATTTGTTCCCGAGACGCCTCGCAG TTCAGACGTGACTGTTGATCCCGCTCC TCTGCGACCGCTCAATTGGAATTCAAG GTATGATTGCAAATGTGACTATCATGC TCAATTTGACAACATTTCTAACAAATG TGATGAATGTGAATATTTGAATCGGGG CAAAAATGGATGTATCTGTCACAATGT AACTCACTGTCAAATTTGTCATGGGAT TCCCCCCTGGGAAAGGAAAACTTGTC AGATTTTGGGGATTTTGACGATGCCAA TAAAGAACAGTAA | 91 |
| | | y | 1096-1644 | GTGGACAAAATGCTCATTTGGTGGGAG GAGGGAAAGATGACCAACAAGGTGGT TGAATCCGCCAAGGCCATCCTGGGGGG CTCAAAGGTGCGGGTCGATCAGAAATG TAAATCCTCTGTTCAAATTGATTCTACC CCTGTCATTGTAACTTCCAATACAAAC ATGTGTGTGGTGGTGGATGGGAATTCC ACGACCTTTGAACACCAGCAGCCGCTG GAGGACCGCATGTTCAAATTTGAACTG ACTAAGCGGCTCCCGCCAGATTTTGGC AAGATTACTAAGCAGGAAGTCAAGGA CTTTTTTGCTTGGGCAAAGGTCAATCA GGTGCCGGTGACTCACGAGTTTAAAGT TCCCAGGGAATTGGCGGGAACTAAAG GGGCGGAGAAATCTCTAAAACGCCCA CTGGGTGACGTCACCAATACTAGCTAT AAAAGTCTGGAGAAGCGGGCCAGGCT CTCATTTGTTCCCGAGACGCCTCGCAG TTCAGACGTGACTGTTGATCCCGCTCC TCTGCGACCGCTCAATTGGAATTCAAG GTATGATTGCAAA | 92 |
| | | z | 1645-1833 | TGTGACTATCATGCTCAATTTGACAAC ATTTCTAACAAATGTGATGAATGTGAA TATTTGAATCGGGGCAAAAATGGATGT ATCTGTCACAATGTAACTCACTGTCAA ATTTGTCATGGGATTCCCCCCTGGGAA AAGGAAAACTTGTCAGATTTTGGGGAT TTTGACGATGCCAATAAAGAACAGTAA | 93 |
| | PRT | n | 1-101 | MATFYEVIVRVPFDVEEHLPGISDSFVD WVTGQIWELPPESDLNLTLVEQPQLTVA DRIRRVFLYEWNKFSKQESKFFVQFEKG SEYFHLHTLVETSGISS | 94 |
| | | d | 102-238 | MVLGRYVSQIRAQLVKVVFQGIEPQIND WVAITKVKKGGANKVVDSGYIPAYLLP KVQPELQWAWTNLDEYKLAALNLEERK RLVAQFLAESSQRSQEAASQREFSADPVI KSKTSQKYMALVNWLVEHGITSEKQW | 95 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | h | 239-365 | IQENQESYLSFNSTGNSRSQIKAALDNAT KIMSLTKSAVDYLVGSSVPEDISKNRIWQ IFEMNGYDPAYAGSILYGWCQRSFNKRN TVWLYGPATTGKTNIAEAIAHTVPFYGC VNWTNENFPFNDC | 96 |
| | | c | 366-610 | VDKMLIWWEEGKMTNKVVESAKAILGG SKVRVDQKCKSSVQIDSTPVIVTSNTNM CVVVDGNSTTFEHQQPLEDRMFKFELTK RLPPDFGKITKQEVKDFFAWAKVNQVPV THEFKVPRELAGTKGAEKSLKRPLGDVT NTSYKSLEKRARLSFVPETPRSSDVTVDP APLRPLNWNSRYDCKCDYHAQFDNISN KCDECEYLNRGKNGCICHNVTHCQICHG IPPWEKENLSDFGDFDDANKEQ | 97 |
| | | y | 366-548 | VDKMLIWWEEGKMTNKVVESAKAILGG SKVRVDQKCKSSVQIDSTPVIVTSNTNM CVVVDGNSTTFEHQQPLEDRMFKFELTK RLPPDFGKITKQEVKDFFAWAKVNQVPV THEFKVPRELAGTKGAEKSLKRPLGDVT NTSYKSLEKRARLSFVPETPRSSDVTVDP APLRPLNWNSRYDCK | 98 |
| | | z | 549-610 | CDYHAQFDNISNKCDECEYLNRGKNGCI CHNVTHCQICHGIPPWEKENLSDFGDFD DANKEQ | 99 |
| AAV6 | DNA | n | 1-306 | ATGCCGGGGTTTTACGAGATTGTGATT AAGGTCCCCAGCGACCTTGACGAGCAT CTGCCCGGCATTTCTGACAGCTTTGTG AACTGGGTGGCCGAGAAGGAATGGGA GTTGCCGCCAGATTCTGACATGGATCT GAATCTGATTGAGCAGGCACCCCTGAC CGTGGCCGAGAAGCTGCAGCGCGACTT CCTGGTCCAGTGGCGCCGCGTGAGTAA GGCCCCGGAGGCCCTCTTCTTTGTTCA GTTCGAGAAGGGCGAGTCCTACTTCCA CCTCCATATTCTGGTGGAGACCACGGG GGTCAAATCC | 100 |
| | | d | 307-726 | ATGGTGCTGGGCCGCTTCCTGAGTCAG ATTAGGGACAAGCTGGTGCAGACCATC TACCGCGGGATCGAGCCGACCCTGCCC AACTGGTTCGCGGTGACCAAGACGCGT AATGGCGCCGGAGGGGGGAACAAGGT GGTGGACGAGTGCTACATCCCCAACTA CCTCCTGCCCAAGACTCAGCCCGAGCT GCAGTGGGCGTGGACTAACATGGAGG AGTATATAAGCGCGTGTTTAAACCTGG CCGAGCGCAAACGGCTCGTGGCGCAC GACCTGACCCACGTCAGCCAGACCCAG GAGCAGAACAAGGAGAATCTGAACCC CAATTCTGACGCGCCTGTCATCCGGTC AAAAACCTCCGCACGCTACATGGAGCT GGTCGGGTGGCTGGTGGACCGGGGCAT CACCTCCGAGAAGCAGTGG | 101 |
| | | h | 727-1107 | ATCCAGGAGGACCAGGCCTCGTACATC TCCTTCAACGCCGCCTCCAACTCGCGG TCCCAGATCAAGGCCGCTCTGGACAAT GCCGGCAAGATCATGGCGCTGACCAA ATCCGCGCCCGACTACCTGGTAGGCCC CGCTCCGCCCGCCGACATTAAAACCAA CCGCATTTACCGCATCCTGGAGCTGAA CGGCTACGACCCTGCCTACGCCGGCTC CGTCTTTCTCGGCTGGGCCCAGAAAAG GTTCGGAAAACGCAACACCATCTGGCT GTTTGGGCCGGCCACCACGGGCAAGAC CAACATCGCGGAAGCCATCGCCCACGC CGTGCCCTTCTACGGCTGCGTCAACTG GACCAATGAGAACTTTCCCTTCAACGA TTGC | 102 |
| | | c | 1108-1872 | GTCGACAAGATGGTGATCTGGTGGGAG GAGGGCAAGATGACGGCCAAGGTCGT GGAGTCCGCCAAGGCCATTCTCGGCGG | 103 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CAGCAAGGTGCGCGTGGACCAAAAGT GCAAGTCGTCCGCCCAGATCGATCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA GAGTTCTTCCGCTGGGCGCAGGATCAC GTGACCGAGGTGGCGCATGAGTTCTAC GTCAGAAAGGGTGGAGCCAACAAGAG ACCCGCCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAATGTTCTCGTCACG CGGGCATGCTTCAGATGCTGTTTCCCT GCAAAACATGCGAGAGAATGAATCAG AATTTCAACATTTGCTTCACGCACGGG ACCAGAGACTGTTCAGAATGTTTCCCC GGCGTGTCAGAATCTCAACCGGTCGTC AGAAAGAGGACGTATCGGAAACTCTG TGCCATTCATCATCTGCTGGGGCGGGC TCCCGAGATTGCTTGCTCGGCCTGCGA TCTGGTCAACGTGGATCTGGATGACTG TGTTTCTGAGCAATAA | |
| | | y | 1108-1602 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGATCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCATGACTTTG GCAAGGTGACAAAGCAGGAAGTCAAA GAGTTCTTCCGCTGGGCGCAGGATCAC GTGACCGAGGTGGCGCATGAGTTCTAC GTCAGAAAGGGTGGAGCCAACAAGAG ACCCGCCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAA | 104 |
| | | z | 1603-1872 | TGTTCTCGTCACGCGGGCATGCTTCAG ATGCTGTTTCCCTGCAAAACATGCGAG AGAATGAATCAGAATTTCAACATTTGC TTCACGCACGGGACCAGAGACTGTTCA GAATGTTTCCCCGGCGTGTCAGAATCT CAACCGGTCGTCAGAAAGAGGACGTA TCGGAAACTCTGTGCCATTCATCATCT GCTGGGGCGGGCTCCCGAGATTGCTTG CTCGGCCTGCGATCTGGTCAACGTGGA TCTGGATGACTGTGTTTCTGAGCAATA A | 105 |
| | PRT | n | 1-102 | MPGFYEIVIKVPSDLDEHLPGISDSFVNW VAEKEWELPPDSDMDLNLIEQAPLTVAE KLQRDFLVQWRRVSKAPEALFFVQFEK GESYFHLHILVETTGVKS | 106 |
| | | d | 103-242 | MVLGRFLSQIRDKLVQTIYRGIEPTLPNW FAVTKTRNGAGGGNKVVDECYIPNYLLP KTQPELQWAWTNMEEYISACLNLAERK RLVAHDLTHVSQTQEQNKENLNPNSDA PVIRSKTSARYMELVGWLVDRGITSEKQ W | 107 |
| | | h | 243-369 | IQEDQASYISFNAASNSRSQIKAALDNAG KIMALTKSAPDYLVGPAPPADIKTNRIYR ILELNGYDPAYAGSVFLGWAQKRFGKR NTIWLFGPATTGKTNIAEAIAHAVPFYGC VNWTNENFPFNDC | 108 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN KCSRHAGMLQMLFPCKTCERMNQNFNI CFTHGTRDCSECFPGVSESQPVVRKRTY RKLCAIHHLLGRAPEIACSACDLVNVDL DDCVSEQ | 109 |
| | | y | 370-534 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGANKRPAPDDADKSEP KRACPSVADPSTSDAEGAPVDFADRYQN K | 110 |
| | | z | 535-623 | CSRHAGMLQMLFPCKTCERMNQNFNIC FTHGTRDCSECFPGVSESQPVVRKRTYR KLCAIHHLLGRAPEIACSACDLVNVDLD DCVSEQ | 111 |
| AAV7 | DNA | n | 1-306 | ACGCCGGGTTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCT GAATCTGATCGAGCAGGCACCCCTGAC CGTGGCCGAGAAGCTGCAGCGCGACTT CCTGGTCCAATGGCGCCGCGTGAGTAA GGCCCCGGAGGCCCTGTTCTTTGTTCA GTTCGAGAAGGGCGAGAGCTACTTCCA CCTTCACGTTCTGGTGGAGACCACGGG GGTCAAGTCC | 112 |
| | | d | 307-726 | ATGGTGCTAGGCCGCTTCCTGAGTCAG ATTCGGGAGAAGCTGGTCCAGACCATC TACCGCGGGGTCGAGCCCACGCTGCCC AACTGGTTCGCGGTGACCAAGACGCGT AATGGCGCCGGCGGGGGGAACAAGGT GGTGGACGAGTGCTACATCCCCAACTA CCTCCTGCCCAAGACCCAGCCCGAGCT GCAGTGGGCGTGGACTAACATGGAGG AGTATATAAGCGCGTGTTTGAACCTGG CCGAACGCAAACGGCTCGTGGCGCAG CACCTGACCCACGTCAGCCAGACGCAG GAGCAGAACAAGGAGAATCTGAACCC CAATTCTGACGCGCCCGTGATCAGGTC AAAAACCTCCGCGCGCTACATGGAGCT GGTCGGGTGGCTGGTGGACCGGGGCAT CACCTCCGAGAAGCAGTGG | 113 |
| | | h | 727-1107 | ATCCAGGAGGACCAGGCCTCGTACATC TCCTTCAACGCCGCCTCCAACTCGCGG TCCCAGATCAAGGCCGCGCTGGACAAT GCCGGCAAGATCATGGCGCTGACCAA ATCCGCGCCCGACTACCTGGTGGGGCC CTCGCTGCCCGCGGACATTAAAACCAA CCGCATCTACCGCATCCTGGAGCTGAA CGGGTACGATCCTGCCTACGCCGGCTC CGTCTTTCTCGGCTGGGCCCAGAAAAA GTTCGGGAAGCGCAACACCATCTGGCT GTTTGGGCCCGCCACCACCGGCAAGAC CAACATTGCGGAAGCCATCGCCCACGC CGTGCCCTTCTACGGCTGCGTCAACTG GACCAATGAGAACTTTCCCTTCAACGA TTGC | 114 |
| | | c | 1108-1872 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA | 115 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | ACATGTGCGCCGTGATTGACGGGAACA GCACCACCTTCGAGCACCAGCAGCCGT TGCAGGACCGGATGTTCAAATTTGAAC TCACCCGCCGTCTGGAGCACGACTTTG GCAAGGTGACGAAGCAGGAAGTCAAA GAGTTCTTCCGCTGGGCCAGTGATCAC GTGACCGAGGTGGCGCATGAGTTCTAC GTCAGAAAGGGCGGAGCCAGCAAAAG ACCCGCCCCCGATGACGCGGATATAAG CGAGCCCAAGCGGGCCTGCCCCTCAGT CGCGGATCCATCGACGTCAGACGCGGA AGGAGCTCCGGTGGACTTTGCCGACAG GTACCAAAACAAATGTTCTCGTCACGC GGGCATGATTCAGATGCTGTTTCCCTG CAAAACGTGCGAGAGAATGAATCAGA ATTTCAACATTTGCTTCACACACGGGG TCAGAGACTGTTTAGAGTGTTTCCCCG GCGTGTCAGAATCTCAACCGGTCGTCA GAAAAAAGACGTATCGGAAACTCTGC GCGATTCATCATCTGCTGGGGCGGGCG CCCGAGATTGCTTGCTCGGCCTGCGAC CTGGTCAACGTGGACCTGGACGACTGC GTTTCTGAGCAATAA | |
| | | y | 1108-1602 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCGT TGCAGGACCGGATGTTCAAATTTGAAC TCACCCGCCGTCTGGAGCACGACTTTG GCAAGGTGACGAAGCAGGAAGTCAAA GAGTTCTTCCGCTGGGCCAGTGATCAC GTGACCGAGGTGGCGCATGAGTTCTAC GTCAGAAAGGGCGGAGCCAGCAAAAG ACCCGCCCCCGATGACGCGGATATAAG CGAGCCCAAGCGGGCCTGCCCCTCAGT CGCGGATCCATCGACGTCAGACGCGGA AGGAGCTCCGGTGGACTTTGCCGACAG GTACCAAAACAAA | 116 |
| | | z | 1603-1872 | TGTTCTCGTCACGCGGGCATGATTCAG ATGCTGTTTCCCTGCAAAACGTGCGAG AGAATGAATCAGAATTTCAACATTTGC TTCACACACGGGGTCAGAGACTGTTTA GAGTGTTTCCCCGGCGTGTCAGAATCT CAACCGGTCGTCAGAAAAAAGACGTA TCGGAAACTCTGCGCGATTCATCATCT GCTGGGGCGGGCGCCCGAGATTGCTTG CTCGGCCTGCGACCTGGTCAACGTGGA CCTGGACGACTGCGTTTCTGAGCAATA A | 117 |
| | PRT | n | 1-102 | TPGFYEIVIKVPSDLDEHLPGISDSFVNW VAEKEWELPPDSDMDLNLIEQAPLTVAE KLQRDFLVQWRRVSKAPEALFFVQFEK GESYFHLVLVETTGVKS | 118 |
| | | d | 103-242 | MVLGRFLSQIREKLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSARYMELVGWLVDRGITSE KQW | 119 |
| | | h | 243-369 | IQEDQASYISFNAASNSRSQIKAALDNAG KIMALTKSAPDYLVGPSLPADIKTNRIYR ILELNGYDPAYAGSVFLGWAQKKFGKR NTIWLFGPATTGKTNIAEAIAHAVPFYGC VNWTNENFPFNDC | 120 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT | 121 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | RRLEHDFGKVTKQEVKEFFRWASDHVT EVAHEFYVRKGGASKRPAPDDADISEPK RACPSVADPSTSDAEGAPVDFADRYQNK CSRHAGMIQMLFPCKTCERMNQNFNICF THGVRDCLECFPGVSESQPVVRKKTYRK LCAIHHLLGRAPEIACSACDLVNVDLDD CVSEQ | |
| | | y | 370-534 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWASDHVT EVAHEFYVRKGGASKRPAPDDADISEPK RACPSVADPSTSDAEGAPVDFADRYQNK | 122 |
| | | z | 535-623 | CSRHAGMIQMLFPCKTCERMNQNFNICF THGVRDCLECFPGVSESQPVVRKKTYRK LCAIHHLLGRAPEIACSACDLVNVDLDD CVSEQ | 123 |
| AAV8 | DNA | n | 1-306 | ATGCCGGGCTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCG GAATCTGATCGAGCAGGCACCCCTGAC CGTGGCCGAGAAGCTGCAGCGCGACTT CCTGGTCCAATGGCGCCGCGTGAGTAA GGCCCCGGAGGCCCTCTTCTTTGTTCA GTTCGAGAAGGGCGAGAGCTACTTTCA CCTGCACGTTCTGGTCGAGACCACGGG GGTCAAGTCC | 124 |
| | | d | | ATGGTGCTAGGCCGCTTCCTGAGTCAG ATTCGGGAAAAGCTTGGTCCAGACCAT CTACCCGCGGGGTCGAGCCCCACCTTG CCCAACTGGTTCGCGGTGACCAAAGAC GCGGTAATGGCGCCGGCGGGGGGGAA CAAGGTGGTGGACGAGTGCTACATCCC CAACTACCTCCTGCCCAAGACTCAGCC CGAGCTGCAGTGGGCGTGGACTAACAT GGAGGAGTATATAAGCGCGTGCTTGAA CCTGGCCGAGCGCAAACGGCTCGTGGC GCAGCACCTGACCCACGTCAGCCAGAC GCAGGAGCAGAACAAGGAGAATCTGA ACCCCAATTCTGACGCGCCCGTGATCA GGTCAAAAACCTCCGCGCGCTATATGG AGCTGGTCGGGTGGCTGGTGGACCGGG GCATCACCTCCGAGAAGCAGTGG | 125 |
| | | d | 307-726 | ATGGTGCTAGGCCGCTTCCTGAGTCAG ATTCGGGAAAAGCTTGGTCCAGACCATC TACCGCGGGGTCGAGCCCACCTTGCCC AACTGGTTCGCGGTGACCAAGACGCGT AATGGCGCCGGGGGGGGGAACAAGGT GGTGGACGAGTGCTACATCCCCAACTA CCTCCTGCCCAAGACTCAGCCCGAGCT GCAGTGGGCGTGGACTAACATGGAGG AGTATATAAGCGCGTGCTTGAACCTGG CCGAGCGCAAACGGCTCGTGGCGCAG CACCTGACCCACGTCAGCCAGACGCAG GAGCAGAACAAGGAGAATCTGAACCC CAATTCTGACGCGCCCGTGATCAGGTC AAAAACCTCCGCGCGCTATATGGAGCT GGTCGGGTGGCTGGTGGACCGGGGCAT CACCTCCGAGAAGCAGTGG | 126 |
| | | h | 727-1107 | ATCCAGGAGGACCAGGCCTCGTACATC TCCTTCAACGCCGCCTCCAACTCGCGG TCCCAGATCAAGGCCGCGCTGGACAAT GCCGGCAAGATCATGGCGCTGACCAA ATCCGCGCCCGACTACCTGGTGGGGCC CTCGCTGCCCGCGGACATTACCCAGAA CCGCATCTACCGCATCCTCGCTCTCAA CGGCTACGACCCTGCCTACGCCGGCTC CGTCTTTCTCGGCTGGGCTCAGAAAAA |  127 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | GTTCGGGAAACGCAACACCATCTGGCT GTTTGGACCCGCCACCACCGGCAAGAC CAACATTGCGGAAGCCATCGCCCACGC CGTGCCCTTCTACGGCTGCGTCAACTG GACCAATGAGAACTTTCCCTTCAATGA TTGC | |
| | | c | 1108-1872 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCTC TCCAGGACCGGATGTTTAAGTTCGAAC TCACCCGCCGTCTGGAGCACGACTTTG GCAAGGTGACAAAGCAGGAAGTCAAA GAGTTCTTCCGCTGGGCCAGTGATCAC GTGACCGAGGTGGCGCATGAGTTTTAC GTCAGAAAGGGCGGAGCCAGCAAAAG ACCCGCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAATGTTCTCGTCACG CGGGCATGCTTCAGATGCTGTTTCCCT GCAAAACGTGCGAGAGAATGAATCAG AATTTCAACATTTGCTTCACACACGGG GTCAGAGACTGCTCAGAGTGTTTCCCC GGCGTGTCAGAATCTCAACCGGTCGTC AGAAAGAGGACGTATCGGAAACTCTG TGCGATTCATCATCTGCTGGGGCGGGC TCCCGAGATTGCTTGCTCGGCCTGCGA TCTGGTCAACGTGGACCTGGATGACTG TGTTTCTGAGCAATAA | 128 |
| | | y | 1108-1602 | GTCGACAAGATGGTGATCTGGTGGGAG GAGGGCAAGATGACGGCCAAGGTCGT GGAGTCCGCCAAGGCCATTCTCGGCGG CAGCAAGGTGCGCGTGGACCAAAAGT GCAAGTCGTCCGCCCAGATCGACCCCA CCCCCGTGATCGTCACCTCCAACACCA ACATGTGCGCCGTGATTGACGGGAACA GCACCACCTTCGAGCACCAGCAGCCTC TCCAGGACCGGATGTTTAAGTTCGAAC TCACCCGCCGTCTGGAGCACGACTTTG GCAAGGTGACAAAGCAGGAAGTCAAA GAGTTCTTCCGCTGGGCCAGTGATCAC GTGACCGAGGTGGCGCATGAGTTTTAC GTCAGAAAGGGCGGAGCCAGCAAAAG ACCCGCCCCGATGACGCGGATAAAA GCGAGCCCAAGCGGGCCTGCCCCTCAG TCGCGGATCCATCGACGTCAGACGCGG AAGGAGCTCCGGTGGACTTTGCCGACA GGTACCAAAACAAA | 129 |
| | | z | 1603-1872 | TGTTCTCGTCACGCGGGCATGCTTCAG ATGCTGTTTCCCTGCAAAACGTGCGAG AGAATGAATCAGAATTTCAACATTTGC TTCACACACGGGGTCAGAGACTGCTCA GAGTGTTTCCCCGGCGTGTCAGAATCT CAACCGGTCGTCAGAAAGAGGACGTA TCGGAAACTCTGTGCGATTCATCATCT GCTGGGGCGGGCTCCCGAGATTGCTTG CTCGGCCTGCGATCTGGTCAACGTGGA CCTGGATGACTGTGTTTCTGAGCAATA A | 130 |
| | PRT | n | 1-102 | MPGFYEIVIKVPSDLDEHLPGISDSFVNW VAEKEWELPPDSDMDRNLIEQAPLTVAE KLQRDFLVQWRRVSKAPEALFFVQFEK GESYFHLHVLVETTGVKS | 131 |
| | | d | | MVLGRFLSQIREKLGPDHLPAGSSPTLPN WFAVTKDAVMAPAGGNKVVDECYIPN | 132 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | YLLPKTQPELQWAWTNMEEYISACLNL AERKRLVAQHLTHVSQTQEQNKENLNP NSDAPVIRSKTSARYMELVGWLVDRGIT SEKQW | |
| | | d (p1/2) | 103-224 | MVLGRFLSQIREKLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSA | 133 |
| | | h | 225-369 | RYMELVGWLVDRGITSEKQWIQEDQAS YISFNAASNSRSQIKAALDNAGKIMALT KSAPDYLVGPSLPADITQNRIYRILALNG YDPAYAGSVFLGWAQKKFGKRNTIWLF GPATTGKTNIAEAIAHAVPFYGCVNWTN ENFPFNDC | 134 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWASDHVT EVAHEFYVRKGGASKRPAPDDADKSEP KRACPSVADPSTSDAEGAPVDFADRYQN KCSRHAGMLQMLFPCKTCERMNQNFNI CFTHGVRDCSECFPGVSESQPVVRKRTY RKLCAIHHLLGRAPEIACSACDLVNVDL DDCVSEQ | 135 |
| | | y | 370-536 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWASDHVT EVAHEFYVRKGGASKRPAPDDADKSEP KRACPSVADPSTSDAEGAPVDFADRYQN K | 136 |
| | | z | 537-623 | CSRHAGMLQMLFPCKTCERMNQNFNIC FTHGVRDCSECFPGVSESQPVVRKRTYR KLCAIHHLLGRAPEIACSACDLVNVDLD DCVSEQ | 137 |
| AAV10 | DNA | n | 1-306 | ATGCCGGGCTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCG GAATCTGATCGAGCAGGCACCCCTGAC CGTGGCCGAGAAGCTGCAGCGCGACTT CCTGGTCCACTGGCGCCGCGTGAGTAA GGCCCCGGAGGCCCTCTTCTTTGTTCA GTTCGAGAAGGGCGAGTCCTACTTTCA CCTGCACGTTCTGGTCGAGACCACGGG GGTCAAGTCC | 138 |
| | | d | 307-726 | ATGGTCCTGGGCCGCTTCCTGAGTCAG ATCAGAGACAGGCTGGTGCAGACCATC TACCGCGGGGTAGAGCCCACGCTGCCC AACTGGTTCGCGGTGACCAAGACGCGA AATGGCGCCGGCGGGGGGAACAAGGT GGTGGACGAGTGCTACATCCCCAACTA CCTCCTGCCCAAGACGCAGCCCGAGCT GCAGTGGGCGTGGACTAACATGGAGG AGTATATAAGCGCGTGTCTGAACCTCG CGGAGCGTAAACGGCTCGTGGCGCAG CACCTGACCCACGTCAGCCAGACGCAG GAGCAGAACAAGGAGAATCTGAACCC GAATTCTGACGCGCCCGTGATCAGGTC AAAAACCTCCGCGCGCTACATGGAGCT GGTCGGGTGGCTGGTGGACCGGGGCAT CACCTCCGAGAAGCAGTGG | 139 |
| | | h | 727-1107 | ATCCAGGAGGACCAGGCCTCGTACATC TCCTTCAACGCCGCCTCCAACTCGCGG TCCCAGATCAAGGCCGCGCTGGACAAT GCCGGAAAGATCATGGCGCTGACCAA ATCCGCGCCCGACTACCTGGTAGGCCC GTCCTTACCCGCGGACATTAAGGCCAA | 140 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CCGCATCTACCGCATCCTGGAGCTCAA CGGCTACGACCCCGCCTACGCCGGCTC CGTCTTCCTGGGCTGGGCGCAGAAAAA GTTCGGTAAAAGGAATACAATTTGGCT GTTCGGGCCCGCCACCACCGGCAAGAC CAACATCGCGGAAGCCATCGCCCACGC CGTGCCCTTCTACGGCTGCGTCAACTG GACCAATGAGAACTTTCCCTTCAACGA TTGC | |
| | | c | 1108-1869 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTCGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCCC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGACGCATGAGTTCTAC GTCAGAAAGGGCGGAGCCACCAAAAG ACCCGCCCCCAGTGACGCGGATATAAG CGAGCCCAAGCGGGCCTGCCCCTCAGT TGCGGAGCCATCGACGTCAGACGCGG AAGCACCGGTGGACTTTGCGGACAGGT ACCAAAACAAATGTTCTCGTCACGCGG GCATGCTTCAGATGCTGTTTCCCTGCA AGACATGCGAGAGAATGAATCAGAAT TTCAACGTCTGCTTCACGCACGGGGTC AGAGACTGCTCAGAGTGCTTCCCCGGC GCGTCAGAATCTCAACCTGTCGTCAGA AAAAAGACGTATCAGAAACTGTGCGC GATTCATCATCTGCTGGGGCGGGCACC CGAGATTGCGTGTTCGGCCTGCGATCT CGTCAACGTGGACTTGGATGACTGTGT TTCTGAGCAATAA | 141 |
| | | y | 1108-1599 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTCGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCCC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGACGCATGAGTTCTAC GTCAGAAAGGGCGGAGCCACCAAAAG ACCCGCCCCCAGTGACGCGGATATAAG CGAGCCCAAGCGGGCCTGCCCCTCAGT TGCGGAGCCATCGACGTCAGACGCGG AAGCACCGGTGGACTTTGCGGACAGGT ACCAAAACAAA | 142 |
| | | z | 1600-1869 | TGTTCTCGTCACGCGGGCATGCTTCAG ATGCTGTTTCCCTGCAAGACATGCGAG AGAATGAATCAGAATTTCAACGTCTGC TTCACGCACGGGGTCAGAGACTGCTCA GAGTGCTTCCCCGGCGCGTCAGAATCT CAACCTGTCGTCAGAAAAAAGACGTAT CAGAAACTGTGCGCGATTCATCATCTG CTGGGGCGGGCACCCGAGATTGCGTGT TCGGCCTGCGATCTCGTCAACGTGGAC TTGGATGACTGTGTTTCTGAGCAATAA | 143 |
| | PRT | n | 1-102 | MPGFYEIVIKVPSDLDEHLPGISDSFVNW VAEKEWELPPDSDMDRNLIEQAPLTVAE KLQRDFLVHWRRVSKAPEALFFVQFEK GESYFHLHVLVETTGVKS | 144 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | d | 103-242 | MVLGRFLSQIRDRLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSARYMELVGWLVDRGITSE KQW | 145 |
| | | h | 243-369 | IQEDQASYISFNAASNSRSQIKAALDNAG KIMALTKSAPDYLVGPSLPADIKANRIYR ILELNGYDPAYAGSVFLGWAQKKFGKR NTIWLFGPATTGKTNIAEAIAHAVPFYGC VNWTNENFPFNDC | 146 |
| | | c | 370-622 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVTHEFYVRKGGATKRPAPSDADISEPK RACPSVAEPSTSDAEAPVDFADRYQNKC SRHAGMLQMLFPCKTCERMNQNFNVCF THGVRDCSECFPGASESQPVVRKKTYQK LCAIHHLLGRAPEIACSACDLVNVDLDD CVSEQ | 147 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVTHEFYVRKGGATKRPAPSDADISEPK RACPSVAEPSTSDAEAPVDFADRYQNK | 148 |
| | | z | 534-622 | CSRHAGMLQMLFPCKTCERMNQNFNVC FTHGVRDCSECFPGASESQPVVRKKTYQ KLCAIHHLLGRAPEIACSACDLVNVDLD DCVSEQ | 149 |
| AAV11 | DNA | n | 1-306 | ATGCCGGGCTTCTACGAGATCGTGATC AAGGTGCCGAGCGACCTGGACGAGCA CCTGCCGGGCATTTCTGACTCGTTTGTG AACTGGGTGGCCGAGAAGGAATGGGA GCTGCCCCCGGATTCTGACATGGATCG GAATCTGATCGAGCAGGCACCCCTGAC CGTGGCCGAGAAGCTGCAGCGCGACTT CCTGGTCCACTGGCGCCGCGTGAGTAA GGCCCCGGAGGCCCTCTTCTTTGTTCA GTTCGAGAAGGGCGAGTCCTACTTCCA CCTCCACGTTCTCGTCGAGACCACGGG GGTCAAGTCC | 150 |
| | | d | 307-726 | ATGGTCCTGGGCCGCTTCCTGAGTCAG ATCAGAGACAGGCTGGTGCAGACCATC TACCGCGGGGTCGAGCCCACGCTGCCC AACTGGTTCGCGGTGACCAAGACGCGA AATGGCGCCGGCGGGGGGAACAAGGT GGTGGACGAGTGCTACATCCCCAACTA CCTCCTGCCCAAGACCCAGCCCGAGCT GCAGTGGGCGTGGACTAACATGGAGG AGTATATAAGCGCGTGTCTAAACCTCG CGGAGCGTAAACGGCTCGTGGCGCAG CACCTGACCCACGTCAGCCAGACGCAG GAGCAGAACAAGGAGAATCTGAACCC GAATTCTGACGCGCCCGTGATCAGGTC AAAAACCTCCGCGCTACATGGAGCT GGTCGGGTGGCTGGTGGACCGGGGCAT CACCTCCGAGAAGCAGTGG | 151 |
| | | h | 727-1107 | ATCCAGGAGGACCAGGCCTCGTACATC TCCTTCAACGCCGCCTCCAACTCGCGG TCCCAGATCAAGGCCGCGCTGGACAAT GCCGGAAAGATCATGGCGCTGACCAA ATCCGCGCCCGACTACCTGGTAGGCCC GTCCTTACCCGCGGACATTAAGGCCAA CCGCATCTACCGCATCCTGGAGCTCAA CGGCTACGACCCCGCCTACGCCGGCTC CGTCTTCCTGGGCTGGGCGCAGAAAAA GTTCGGTAAACGCAACACCATCTGGCT GTTTGGGCCCGCCACCACCGGCAAGAC | 152 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | CAACATCGCGGAAGCCATAGCCCACGC CGTGCCCTTCTACGGCTGCGTGAACTG GACCAATGAGAACTTTCCCTTCAACGA TTGC | |
| | | c | 1108-1869 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTGGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCGC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGGCGCATGAGTTCTAC GTCAGAAAGGGCGGAGCCACCAAAAG ACCCGCCCCAGTGACGCGGATATAAG CGAGCCCAAGCGGGCCTGCCCCTCAGT TCCGGAGCCATCGACGTCAGACGCGGA AGCACCGGTGGACTTTGCGGACAGGTA CCAAAACAAATGTTCTCGTCACGCGGG CATGCTTCAGATGCTGTTTCCCTGCAA GACATGCGAGAGAATGAATCAGAATTT CAACGTCTGCTTCACGCACGGGGTCAG AGACTGCTCAGAGTGCTTCCCCGGCGC GTCAGAATCTCAACCCGTCGTCAGAAA AAAGACGTATCAGAAACTGTGCGCGAT TCATCATCTGCTGGGGCGGGCACCCGA GATTGCGTGTTCGGCCTGCGATCTCGT CAACGTGGACTTGGATGACTGTGTTTC TGAGCAATAA | 153 |
| | | y | 1108-1599 | GTCGACAAGATGGTGATCTGGTGGGAG GAGGGCAAGATGACCGCCAAGGTCGT GGAGTCCGCCAAGGCCATTCTGGGCGG AAGCAAGGTGCGCGTGGACCAAAAGT GCAAGTCCTCGGCCCAGATCGACCCCA CGCCCGTGATCGTCACCTCCAACACCA ACATGTGCGCCGTGATCGACGGGAACA GCACCACCTTCGAGCACCAGCAGCCGC TGCAGGACCGCATGTTCAAGTTCGAGC TCACCCGCCGTCTGGAGCACGACTTTG GCAAGGTGACCAAGCAGGAAGTCAAA GAGTTCTTCCGCTGGGCTCAGGATCAC GTGACTGAGGTGGCGCATGAGTTCTAC GTCAGAAAGGGCGGAGCCACCAAAAG ACCCGCCCCAGTGACGCGGATATAAG CGAGCCCAAGCGGGCCTGCCCCTCAGT TCCGGAGCCATCGACGTCAGACGCGGA AGCACCGGTGGACTTTGCGGACAGGTA CCAAAACAAA | 154 |
| | | z | 1600-1869 | TGTTCTCGTCACGCGGGCATGCTTCAG ATGCTGTTTCCCTGCAAGACATGCGAG AGAATGAATCAGAATTTCAACGTCTGC TTCACGCACGGGGTCAGAGACTGCTCA GAGTGCTTCCCCGGCGCGTCAGAATCT CAACCCGTCGTCAGAAAAAAGACGTAT CAGAAACTGTGCGCGATTCATCATCTG CTGGGGCGGGCACCCGAGATTGCGTGT TCGGCCTGCGATCTCGTCAACGTGGAC TTGGATGACTGTGTTTCTGAGCAATAA | 155 |
| | PRT | n | 1-102 | MPGFYEIVIKVPSDLDEHLPGISDSFVNW VAEKEWELPPDSDMDRNLIEQAPLTVAE KLQRDFLVHWRRVSKAPEALFFVQFEK GESYFHLVLVETTGVKS | 156 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | d | 103-242 | MVLGRFLSQIRDRLVQTIYRGVEPTLPN WFAVTKTRNGAGGGNKVVDECYIPNYL LPKTQPELQWAWTNMEEYISACLNLAE RKRLVAQHLTHVSQTQEQNKENLNPNS DAPVIRSKTSARYMELVGWLVDRGITSE KQW | 157 |
| | | h | 243-369 | IQEDQASYISFNAASNSRSQIKAALDNAG KIMALTKSAPDYLVGPSLPADIKANRIYR ILELNGYDPAYAGSVFLGWAQKKFGKR NTIWLFGPATTGKTNIAEAIAHAVPFYGC VNWTNENFPFNDC | 158 |
| | | c | 370-622 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGATKRPAPSDADISEPK RACPSVPEPSTSDAEAPVDFADRYQNKC SRHAGMLQMLFPCKTCERMNQNFNVCF THGVRDCSECFPGASESQPVVRKKTYQK LCAIHHLLGRAPEIACSACDLVNVDLDD CVSEQ | 159 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT RRLEHDFGKVTKQEVKEFFRWAQDHVT EVAHEFYVRKGGATKRPAPSDADISEPK RACPSVPEPSTSDAEAPVDFADRYQNK | 160 |
| | | z | 534-622 | CSRHAGMLQMLFPCKTCERMNQNFNVC FTHGVRDCSECFPGASESQPVVRKKTYQ KLCAIHHLLGRAPEIACSACDLVNVDLD DCVSEQ | 161 |
| AAV12 | DNA | n | 1-306 | ATGCCGGGGTTCTACGAGGTGGTGATC AAGGTGCCCAGCGACCTGGACGAGCA CCTGCCCGGCATTTCTGACTCCTTTGTG AACTGGGTGGCCGAGAAGGAATGGGA GTTGCCCCCGGATTCTGACATGGATCA GAATCTGATTGAGCAGGCACCCCTGAC CGTGGCCGAGAAGCTGCAGCGCGAGTT CCTGGTGGAATGGCGCCGAGTGAGTAA ATTTCTGGAGGCCAAGTTTTTTGTGCA GTTTGAAAAGGGGGACTCGTACTTTCA TTTGCATATTCTGATTGAAATTACCGG CGTGAAATCC | 162 |
| | | d | 307-726 | ATGGTGGTGGGCCGCTACGTGAGTCAG ATTAGGGATAAACTGATCCAGCGCATC TACCGCGGGGTCGAGCCCCAGCTGCCC AACTGGTTCGCGGTCACAAAGACCCGA AATGGCGCCGGAGGCGGGAACAAGGT GGTGGACGAGTGCTACATCCCCAACTA CCTGCTCCCCAAGGTCCAGCCCGAGCT TCAGTGGGCGTGGACTAACATGGAGG AGTATATAAGCGCCTGTTTGAACCTCG CGGAGCGTAAACGGCTCGTGGCGCAG CACCTGACGCACGTCTCCCAGACCCAG GAGGGCGACAAGGAGAATCTGAACCC GAATTCTGACGCGCCGGTGATCCGGTC AAAAACCTCCGCCAGGTACATGGAGCT GGTCGGGTGGCTGGTGGACAAGGGCA TCACGTCCGAGAAGCAGTGG | 163 |
| | | h | 727-1107 | ATCCAGGAGGACCAGGCCTCGTACATC TCCTTCAACGCGGCCTCCAACTCCCGG TCGCAGATCAAGGCGGCCCTGGACAAT GCCTCCAAAATCATGAGCCTCACCAAA ACGGCTCCGGACTATCTCATCGGGCAG CAGCCCGTGGGGGACATTACCACCAAC CGGATCTACAAAATCCTGGAACTGAAC GGGTACGACCCCCAGTACGCCGCCTCC GTCTTTCTCGGCTGGGCCCAGAAAAAG TTTGGAAAGCGCAACACCATCTGGCTG TTTGGGCCCGCCACCACCGGCAAGACC | 164 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | | | AACATCGCGGAAGCCATCGCCCACGCG GTCCCCTTCTACGGCTGCGTCAACTGG ACCAATGAGAACTTTCCCTTCAACGAC TGC | |
| | | c | 1108-1866 | GTCGACAAAATGGTGATTTGGTGGGAG GAGGGCAAGATGACCGCCAAGGTCGT AGAGTCCGCCAAGGCCATTCTGGGCGG CAGCAAGGTGCGCGTGGACCAAAAAT GCAAGGCCTCTGCGCAGATCGACCCCA CCCCCGTGATCGTCACCTCCAACACCA ACATGTGCGCCGTGATTGACGGGAACA GCACCACCTTCGAGCACCAGCAGCCCC TGCAGGACCGGATGTTCAAGTTTGAAC TCACCCGCCGCCTCGACCACGACTTTG GCAAGGTCACCAAGCAGGAAGTCAAG GACTTTTTCCGGTGGGCGGCTGATCAC GTGACTGACGTGGCTCATGAGTTTTAC GTCACAAAGGGTGGAGCTAAGAAAAG GCCCGCCCCTCTGACGAGGATATAAG CGAGCCCAAGCGGCCGCGCGTGTCATT TGCGCAGCCGGAGACGTCAGACGCGG AAGCTCCCGGAGACTTCGCCGACAGGT ACCAAAACAAATGTTCTCGTCACGCGG GTATGCTGCAGATGCTCTTTCCCTGCA AGACGTGCGAGAGAATGAATCAGAAT TCCAACGTCTGCTTCACGCACGGTCAG AAAGATTGCGGGGAGTGCTTTCCCGGG TCAGAATCTCAACCGGTTTCTGTCGTC AGAAAAACGTATCAGAAACTGTGCATC CTTCATCAGCTCCGGGGGGCACCCGAG ATCGCCTGCTCTGCTTGCGACCAACTC AACCCCGATTTGGACGATTGCCAATTT GAGCAATAA | 165 |
| | | y | 1108-1599 | GTCGACAAAATGGTGATTTGGTGGGAG GAGGGCAAGATGACCGCCAAGGTCGT AGAGTCCGCCAAGGCCATTCTGGGCGG CAGCAAGGTGCGCGTGGACCAAAAAT GCAAGGCCTCTGCGCAGATCGACCCCA CCCCCGTGATCGTCACCTCCAACACCA ACATGTGCGCCGTGATTGACGGGAACA GCACCACCTTCGAGCACCAGCAGCCCC TGCAGGACCGGATGTTCAAGTTTGAAC TCACCCGCCGCCTCGACCACGACTTTG GCAAGGTCACCAAGCAGGAAGTCAAG GACTTTTTCCGGTGGGCGGCTGATCAC GTGACTGACGTGGCTCATGAGTTTTAC GTCACAAAGGGTGGAGCTAAGAAAAG GCCCGCCCCTCTGACGAGGATATAAG CGAGCCCAAGCGGCCGCGCGTGTCATT TGCGCAGCCGGAGACGTCAGACGCGG AAGCTCCCGGAGACTTCGCCGACAGGT ACCAAAACAAA | 166 |
| | | z | 1600-1866 | TGTTCTCGTCACGCGGGTATGCTGCAG ATGCTCTTTCCCTGCAAGACGTGCGAG AGAATGAATCAGAATTCCAACGTCTGC TTCACGCACGGTCAGAAAGATTGCGGG GAGTGCTTTCCCGGGTCAGAATCTCAA CCGGTTTCTGTCGTCAGAAAAACGTAT CAGAAACTGTGCATCCTTCATCAGCTC CGGGGGGCACCCGAGATCGCCTGCTCT GCTTGCGACCAACTCAACCCCGATTTG GACGATTGCCAATTTGAGCAATAA | 167 |
| | PRT | n | 1-102 | MPGFYEVVIKVPSDLDEHLPGISDSFVN WVAEKEWELPPDSDMDQNLIEQAPLTV AEKLQREFLVEWRRVSKFLEAKFFVQFE KGDSYFHLHILIEITGVKS | 168 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | d | 103-242 | MVVGRYVSQIRDKLIQRIYRGVEPQLPN WFAVTKTRNGAGGGNKVVDECYIPNYL LPKVQPELQWAWTNMEEYISACLNLAE RKRLVAQHLTHVSQTQEGDKENLNPNS DAPVIRSKTSARYMELVGWLVDKGITSE KQW | 169 |
| | | h | 243-369 | IQEDQASYISFNAASNSRSQIKAALDNAS KIMSLTKTAPDYLIGQQPVGDITTNRIYKI LELNGYDPQYAASVFLGWAQKKFGKRN TIWLFGPATTGKTNIAEAIAHAVPFYGCV NWTNENFPFNDC | 170 |
| | | c | 370-621 | VDKMVIWWEEGKMTAKVVESAKAILG GSKVRVDQKCKASAQIDPTPVIVTSNTN MCAVIDGNSTTFEHQQPLQDRMFKFELT RRLDHDFGKVTKQEVKDFFRWAADHVT DVAHEFYVTKGGAKKRPAPSDEDISEPK RPRVSFAQPETSDAEAPGDFADRYQNKC SRHAGMLQMLFPCKTCERMNQNSNVCF THGQKDCGECFPGSESQPVSVVRKTYQK LCILHQLRGAPEIACSACDQLNPDLDDC QFEQ | 171 |
| | | y | 370-533 | VDKMVIWWEEGKMTAKVVESAKAILG GSKVRVDQKCKASAQIDPTPVIVTSNTN MCAVIDGNSTTFEHQQPLQDRMFKFELT RRLDHDFGKVTKQEVKDFFRWAADHVT DVAHEFYVTKGGAKKRPAPSDEDISEPK RPRVSFAQPETSDAEAPGDFADRYQNK | 172 |
| | | z | 534-621 | CSRHAGMLQMLFPCKTCERMNQNSNVC FTHGQKDCGECFPGSESQPVSVVRKTYQ KLCILHQLRGAPEIACSACDQLNPDLDD CQFEQ | 173 |
| AAV13 | DNA | n | 1-306 | ATGCCGGGATTCTACGAGATTGTCCTG AAGGTGCCCAGCGACCTGGACGAGCA CCTGCCTGGCATTTCTGACTCTTTTGTA AACTGGGTGGCGGAGAAGGAATGGGA GCTGCCGCCGGATTCTGACATGGATCT GAATCTGATTGAGCAGGCACCCCTAAC CGTGGCCGAAAAGCTGCAACGCGAATT CCTGGTCGAGTGGCGCCGCGTGAGTAA GGCCCCGGAGGCCCTCTTCTTTGTTCA GTTCGAGAAGGGGGACAGCTACTTCCA CCTACACATTCTGGTGGAGACCGTGGG CGTGAAATCC | 174 |
| | | d | 307-726 | ATGGTGGTGGGCCGCTACGTGAGCCAG ATTAAAGAGAAGCTGGTGACCCGCATC TACCGCGGGGTCGAGCCGCAGCTTCCG AACTGGTTCGCGGTGACCAAGACGCGT AATGGCGCCGGAGGCGGGAACAAGGT GGTGGACGACTGCTACATCCCCAACTA CCTGCTCCCCAAGACCCAGCCCGAGCT CCAGTGGGCGTGGACTAATATGGACCA GTATTTAAGCGCCTGTTTGAATCTCGC GGAGCGTAAACGGCTGGTGGCGCAGC ATCTGACGCACGTGTCGCAGACGCAGG AGCAGAACAAAGAGAACCAGAATCCC AATTCTGACGCGCCGGTGATCAGATCA AAAACCTCCGCGAGGTACATGGAGCTG GTCGGGTGGCTGGTGGACCGCGGGATC ACGTCAGAAAAGCAATGG | 175 |
| | | h | 727-1107 | ATCCAGGAGGACCAGGCCTCTTACATC TCCTTCAACGCCGCCTCCAACTCGCGG TCACAAATCAAGGCCGCACTGGACAAT GCCTCCAAATTTATGAGCCTGACAAAA ACGGCTCCGGACTACCTGGTGGGAAAC AACCCGCCGGAGGACATTACCAGCAA CCGGATCTACAAAATCCTCGAGATGAA CGGGTACGATCCGCAGTACGCGGCCTC CGTCTTCCTGGGCTGGGCGCAAAAGAA GTTCGGGAAGAGGAACACCATCTGGCT CTTTGGGCCGGCCACGACGGGTAAAAC | 176 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | c | 1108-1872 | CAACATCGCTGAAGCTATCGCCCACGC CGTGCCCTTTTACGGCTGCGTGAACTG GACCAATGAGAACTTTCCGTTCAACGA TTGC GTCGACAAGATGGTGATCTGGTGGGAG GAGGGCAAGATGACGGCCAAGGTCGT GGAGTCCGCCAAGGCCATTCTGGGCGG AAGCAAGGTGCGCGTGGACCAAAAGT GCAAGTCATCGGCCCAGATCGACCCAA CTCCCGTCATCGTCACCTCCAACACCA ACATGTGCGCGGTCATCGACGGAAATT CCACCACCTTCGAGCACCAACAACCAC TCCAAGACCGGATGTTCAAGTTCGAGC TCACCAAGCGCCTGGAGCACGACTTTG GCAAGGTCACCAAGCAGGAAGTCAAG GACTTTTTCCGGTGGGCGTCAGATCAC GTGACTGAGGTGTCTCACGAGTTTTAC GTCAGAAAGGGTGGAGCTAGAAAGAG GCCCGCCCCAATGACGCAGATATAAG TGAGCCCAAGCGGGCCTGTCCGTCAGT TGCGCAGCCATCGACGTCAGACGCGGA AGCTCCGGTGGACTACGCGGACAGGTA CCAAAACAAATGTTCTCGTCACGTGGG CATGAATCTGATGCTTTTTCCCTGCCGG CAATGCGAGAGAATGAATCAGAATGT GGACATTTGCTTCACGCACGGGGTCAT GGACTGTGCCGAGTGCTTCCCCGTGTC AGAATCTCAACCCGTGTCTGTCGTCAG AAAGCGGACATATCAGAAACTGTGTCC GATTCATCACATCATGGGGAGGGCGCC CGAGGTGGCTTGTTCGGCCTGCGATCT GGCCAATGTGGACTTGGATGACTGTGA CATGGAGCAATAA | 177 |
| | | y | 1108-1599 | GTCGACAAGATGGTGATCTGGTGGGAG GAGGGCAAGATGACGGCCAAGGTCGT GGAGTCCGCCAAGGCCATTCTGGGCGG AAGCAAGGTGCGCGTGGACCAAAAGT GCAAGTCATCGGCCCAGATCGACCCAA CTCCCGTCATCGTCACCTCCAACACCA ACATGTGCGCGGTCATCGACGGAAATT CCACCACCTTCGAGCACCAACAACCAC TCCAAGACCGGATGTTCAAGTTCGAGC TCACCAAGCGCCTGGAGCACGACTTTG GCAAGGTCACCAAGCAGGAAGTCAAG GACTTTTTCCGGTGGGCGTCAGATCAC GTGACTGAGGTGTCTCACGAGTTTTAC GTCAGAAAGGGTGGAGCTAGAAAGAG GCCCGCCCCAATGACGCAGATATAAG TGAGCCCAAGCGGGCCTGTCCGTCAGT TGCGCAGCCATCGACGTCAGACGCGGA AGCTCCGGTGGACTACGCGGACAGGTA CCAAAACAAA | 178 |
| | | z | 1600-1872 | TGTTCTCGTCACGTGGGCATGAATCTG ATGCTTTTTCCCTGCCGGCAATGCGAG AGAATGAATCAGAATGTGGACATTTGC TTCACGCACGGGGTCATGGACTGTGCC GAGTGCTTCCCCGTGTCAGAATCTCAA CCCGTGTCTGTCGTCAGAAAGCGGACA TATCAGAAACTGTGTCCGATTCATCAC ATCATGGGGAGGGCGCCCGAGGTGGC TTGTTCGGCCTGCGATCTGGCCAATGT GGACTTGGATGACTGTGACATGGAGCA ATAA | 179 |
| | PRT | n | 1-102 | MPGFYEIVLKVPSDLDEHLPGISDSFVNW VAEKEWELPPDSDMDLNLIEQAPLTVAE KLQREFLVEWRRVSKAPEALFFVQFEKG DSYFHLHILVETVGVKS | 180 |

TABLE 1-continued

Example sequences of rep gene and Rep protein domains for different AAV serotypes

| AAV serotype | seq. type | Domain or terminus | Domain limits per rep gene or rep78 protein | Sequence | SEQ ID NO: |
|---|---|---|---|---|---|
| | | d | 103-242 | MVVGRYVSQIKEKLVTRIYRGVEPQLPN WFAVTKTRNGAGGGNKVVDDCYIPNYL LPKTQPELQWAWTNMDQYLSACLNLAE RKRLVAQHLTHVSQTQEQNKENQNPNS DAPVIRSKTSARYMELVGWLVDRGITSE KQW | 181 |
| | | h | 243-369 | IQEDQASYISFNAASNSRSQIKAALDNAS KFMSLTKTAPDYLVGNNPPEDITSNRIYK ILEMNGYDPQYAASVFLGWAQKKFGKR NTIWLFGPATTGKTNIAEAIAHAVPFYGC VNWTNENFPFNDC | 182 |
| | | c | 370-623 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVSHEFYVRKGGARKRPAPNDADISEPK RACPSVAQPSTSDAEAPVDYADRYQNK CSRHVGMNLMLFPCRQCERMNQNVDIC FTHGVMDCAECFPVSESQPVSVVRKRTY QKLCPIHHIMGRAPEVACSACDLANVDL DDCDMEQ | 183 |
| | | y | 370-533 | VDKMVIWWEEGKMTAKVVESAKAILG GSKVRVDQKCKSSAQIDPTPVIVTSNTN MCAVIDGNSTTFEHQQPLQDRMFKFELT KRLEHDFGKVTKQEVKDFFRWASDHVT EVSHEFYVRKGGARKRPAPNDADISEPK RACPSVAQPSTSDAEAPVDYADRYQNK | 184 |
| | | z | 534-623 | CSRHVGMNLMLFPCRQCERMNQNVDIC FTHGVMDCAECFPVSESQPVSVVRKRTY QKLCPIHHIMGRAPEVACSACDLANVDL DDCDMEQ | 185 |

In some embodiments, disclosed herein is a chimeric rep gene. In some embodiments, a chimeric rep gene has at least one domain (e.g., n, d, h, y, or z) or at least one terminus (e.g., N terminus or C terminus) that is of a serotype that is different than the serotype of majority of the rep gene, or the serotypes of the other domains or terminus. In some embodiments, the N terminus is of serotype (e.g., 1, 2, 3, 4, 5, 6, 7, 8, 9, 10, 11, 12, or 13) different than the serotype of the C terminus (e.g., 1, 2, 3, 4, 5, 6, 7, 8, 9, 10, 11, 12, or 13). In some embodiments, the N terminus is of one serotype and the C-terminus is of a second serotype (e.g., 1, 2, 3, 4, 5, 6, 7, 8, 9, 10, 11, 12, or 13).

In some embodiments, the n domain is of AAV serotype 1, and each of the d, h, y, and z are of a serotype other than AAV1 (e.g., 2, 3, 4, 5, 6, 7, 8, 9, 10, 11, 12, or 13). For example, each of the d, h, y, and z domains may be of the same serotype (e.g., 2, 3, 4, 5, 6, 7, 8, 9, 10, 11, 12, or 13). In some embodiments, each of the d, h, y, and z domains may be of different serotypes relative to each other, e.g., d, h, and y may be of AAV2 serotype, while z may be of AAV3 serotype. In some embodiments, the n domain is of AAV serotype 2, and each of the d, h, y, and z domains are of a serotype other than AAV2 (e.g., 1, 3, 4, 5, 6, 7, 8, 9, 10, 11, 12, or 13). The serotypes of each of the d, h, y, and z domains may be the same, or may be different from each other. In some embodiments, the n domain is of AAV serotype 3, and each of the d, h, y, and z domains are of a serotype other than AAV3 (e.g., 1, 2, 4, 5, 6, 7, 8, 9, 10, 11, 12, or 13). The serotypes of each of the d, h, y, and z domains may be the same, or may be different from each other. In some embodiments, the n domain is of AAV serotype 4, and each of the d, h, y, and z domains are of a serotype other than AAV4 (e.g., 1, 2, 4, 5, 6, 7, 8, 9, 10, 11, 12, or 13). The serotypes of each of the d, h, y, and z domains may be the same, or may be different from each other. In some embodiments, the n domain is of AAV serotype 5, and each of the d, h, y, and z domains are of a serotype other than AAV5 (e.g., 1, 2, 3, 4, 6, 7, 8, 9, 10, 11, 12, or 13). The serotypes of each of the d, h, y, and z domains may be the same, or may be different from each other. In some embodiments, the n domain is of AAV serotype 6, and each of the d, h, y, and z domains are of a serotype other than AAV6 (e.g., 1, 2, 3, 4, 5, 7, 8, 9, 10, 11, 12, or 13). The serotypes of each of the d, h, y, and z domains may be the same, or may be different from each other. In some embodiments, the n domain is of AAV serotype 7, and each of the d, h, y, and z domains are of a serotype other than AAV7 (e.g., 1, 2, 3, 4, 5, 6, 8, 9, 10, 11, 12, or 13). The serotypes of each of the d, h, y, and z domains may be the same, or may be different from each other. In some embodiments, the n domain is of AAV serotype 8, and each of the d, h, y, and z domains are of a serotype other than AAV8 (e.g., 1, 2, 3, 4, 5, 6, 7, 9, 10, 11, 12, or 13). The serotypes of each of the d, h, y, and z domains may be the same, or may be different from each other. In some embodiments, the n domain is of AAV serotype 9, and each of the d, h, y, and z domains are of a serotype other than AAV9 (e.g., 1, 2, 3, 4, 5, 6, 7, 8, 10, 11, 12, or 13). The serotypes of each of the d, h, y, and z domains may be the same, or may be different from each other. In some embodiments, the n domain is of AAV serotype 10, and each of the d, h, y, and z domains are of a serotype other than AAV10 (e.g., 1, 2, 3, 4, 5, 6, 7, 8, 9, 11, 12, or 13). The serotypes of each of the d, h, y, and z domains may be the same, or may be different from each other. In some embodiments, the n domain is of AAV serotype 11, and each of the d, h, y, and z domains are of a serotype other than AAV11 (e.g., 1, 2, 3, 4, 5, 6, 7, 8, 9, 10, 12, or 13). The serotypes of each of the d, h, y, and z domains may be the same, or may be different from each other. In some embodiments, the n domain is of AAV serotype 12, and each of the d, h, y, and z domains are of a serotype other than AAV12 (e.g., 1, 2, 3, 4, 5, 6, 7, 8, 9, 10, 11, or 13). The serotypes of each of the d, h, y, and z domains may be the same, or may be different from each other. In some embodiments, the n domain is of AAV serotype 13, and each of the d, h, y, and z domains are of a serotype other than AAV13 (e.g., 1, 2, 3, 4, 5, 6, 7, 8, 9, 10, 11, or 12). The serotypes of each of the d, h, y, and z domains may be the same, or may be different from each other.

In some embodiments, the d domain is of AAV serotype 1, and each of the n, h, y, and z are of a serotype other than AAV1 (e.g., 2, 3, 4, 5, 6, 7, 8, 9, 10, 11, 12, or 13). For example, each of the n, h, y, and z domains may be of the same serotype (e.g., 2, 3, 4, 5, 6, 7, 8, 9, 10, 11, 12, or 13). In some embodiments, each of the n, h, y, and z domains may be of different serotypes relative to each other, e.g., n, h, and y may be of AAV2 serotype, while z may be of AAV3 serotype. In some embodiments, the d domain is of AAV serotype 2, and each of the n, h, y, and z domains are of a serotype other than AAV2 (e.g., 1, 3, 4, 5, 6, 7, 8, 9, 10, 11, 12, or 13). The serotypes of each of the n, h, y, and z domains may be the same, or may be different from each other. In some embodiments, the d domain is of AAV serotype 3, and each of the n, h, y, and z domains are of a serotype other than AAV3 (e.g., 1, 2, 4, 5, 6, 7, 8, 9, 10, 11, 12, or 13). The serotypes of each of the n, h, y, and z domains may be the same, or may be different from each other. In some embodiments, the d domain is of AAV serotype 4, and each of the n, h, y, and z domains are of a serotype other than AAV4 (e.g., 1, 2, 4, 5, 6, 7, 8, 9, 10, 11, 12, or 13). The serotypes of each of the n, h, y, and z domains may be the same, or may be different from each other. In some embodiments, the d domain is of AAV serotype 5, and each of the n, h, y, and z domains are of a serotype other than AAV5 (e.g., 1, 2, 3, 4, 6, 7, 8, 9, 10, 11, 12, or 13). The serotypes of each of the n, h, y, and z domains may be the same, or may be different from each other. In some embodiments, the n domain is of AAV serotype 6, and each of the n, h, y, and z domains are of a serotype other than AAV6 (e.g., 1, 2, 3, 4, 5, 7, 8, 9, 10, 11, 12, or 13). The serotypes of each of the n, h, y, and z domains may be the same, or may be different from each other. In some embodiments, the d domain is of AAV serotype 7, and each of the n, h, y, and z domains are of a serotype other than AAV7 (e.g., 1, 2, 3, 4, 5, 6, 8, 9, 10, 11, 12, or 13). The serotypes of each of the n, h, y, and z domains may be the same, or may be different from each other. In some embodiments, the n domain is of AAV serotype 8, and each of the n, h, y, and z domains are of a serotype other than AAV8 (e.g., 1, 2, 3, 4, 5, 6, 7, 9, 10, 11, 12, or 13). The serotypes of each of the n, h, y, and z domains may be the same, or may be different from each other. In some embodiments, the d domain is of AAV serotype 9, and each of the n, h, y, and z domains are of a serotype other than AAV9 (e.g., 1, 2, 3, 4, 5, 6, 7, 8, 10, 11, 12, or 13). The serotypes of each of the n, h, y, and z domains may be the same, or may be different from each other. In some embodiments, the d domain is of AAV serotype 10, and each of the n, h, y, and z domains are of a serotype other than AAV10 (e.g., 1, 2, 3, 4, 5, 6, 7, 8, 9, 11, 12, or 13). The serotypes of each of the n, h, y, and z domains may be the same, or may be different from each other. In some embodiments, the d domain is of AAV serotype 11, and each of the n, h, y, and z domains are of a serotype other than AAV11 (e.g., 1, 2, 3, 4, 5, 6, 7, 8, 9, 10, 12, or 13). The serotypes of each of the n, h, y, and z domains may be the same, or may be different from each other. In some embodiments, the d domain is of AAV serotype 12, and each of the n, h, y, and z domains are of a serotype other than AAV12 (e.g., 1, 2, 3, 4, 5, 6, 7, 8, 9, 10, 11, or 13). The serotypes of each of the n, h, y, and z domains may be the same, or may be different from each other. In some embodiments, the d domain is of AAV serotype 13, and each of the n, h, y, and z domains are of a serotype other than AAV13 (e.g., 1, 2, 3, 4, 5, 6, 7, 8, 9, 10, 11, or 12). The serotypes of each of the n, h, y, and z domains may be the same, or may be different from each other.

In some embodiments, the h domain is of AAV serotype 1, and each of the d, n, y, and z are of a serotype other than AAV1 (e.g., 2, 3, 4, 5, 6, 7, 8, 9, 10, 11, 12, or 13). For example, each of the d, n, y, and z domains may be of the same serotype (e.g., 2, 3, 4, 5, 6, 7, 8, 9, 10, 11, 12, or 13). In some embodiments, each of the d, n, y, and z domains may be of different serotypes relative to each other, e.g., d, n, and y may be of AAV2 serotype, while z may be of AAV3 serotype. In some embodiments, the h domain is of AAV serotype 2, and each of the d, n, y, and z domains are of a serotype other than AAV2 (e.g., 1, 3, 4, 5, 6, 7, 8, 9, 10, 11, 12, or 13). The serotypes of each of the d, n, y, and z domains may be the same, or may be different from each other. In some embodiments, the h domain is of AAV serotype 3, and each of the d, n, y, and z domains are of a serotype other than AAV3 (e.g., 1, 2, 4, 5, 6, 7, 8, 9, 10, 11, 12, or 13). The serotypes of each of the d, n, y, and z domains may be the same, or may be different from each other. In some embodiments, the h domain is of AAV serotype 4, and each of the d, n, y, and z domains are of a serotype other than AAV4 (e.g., 1, 2, 4, 5, 6, 7, 8, 9, 10, 11, 12, or 13). The serotypes of each of the d, n, y, and z domains may be the same, or may be different from each other. In some embodiments, the h domain is of AAV serotype 5, and each of the d, n, y, and z domains are of a serotype other than AAV5 (e.g., 1, 2, 3, 4, 6, 7, 8, 9, 10, 11, 12, or 13). The serotypes of each of the d, n, y, and z domains may be the same, or may be different from each other. In some embodiments, the h domain is of AAV serotype 6, and each of the d, n, y, and z domains are of a serotype other than AAV6 (e.g., 1, 2, 3, 4, 5, 7, 8, 9, 10, 11, 12, or 13). The serotypes of each of the d, n, y, and z domains may be the same, or may be different from each other. In some embodiments, the h domain is of AAV serotype 7, and each of the d, n, y, and z domains are of a serotype other than AAV7 (e.g., 1, 2, 3, 4, 5, 6, 8, 9, 10, 11, 12, or 13). The serotypes of each of the d, n, y, and z domains may be the same, or may be different from each other. In some embodiments, the h domain is of AAV serotype 8, and each of the d, n, y, and z domains are of a serotype other than AAV8 (e.g., 1, 2, 3, 4, 5, 6, 7, 9, 10, 11, 12, or 13). The serotypes of each of the d, n, y, and z domains may be the same, or may be different from each other. In some embodiments, the h domain is of AAV serotype 9, and each of the d, n, y, and z domains are of a serotype other than AAV9 (e.g., 1, 2, 3, 4, 5, 6, 7, 8, 10, 11, 12, or 13). The serotypes of each of the d, n, y, and z domains may be the same, or may be different from each other. In some embodiments, the h domain is of AAV serotype 10, and each of the d, n, y, and z domains are of a serotype other than AAV10 (e.g., 1, 2, 3, 4, 5, 6, 7, 8, 9, 11, 12, or 13). The serotypes of each of the d, n, y, and z domains may be the same, or may be different from each other. In some embodiments, the h domain is of AAV serotype 11, and each of the d, n, y, and z domains are of a serotype other than AAV11 (e.g., 1, 2, 3, 4, 5, 6, 7, 8, 9, 10, 12, or 13). The serotypes of each of the d, n, y, and z domains may be the same, or may be different from each other. In some embodiments, the h domain is of AAV serotype 12, and each of the d, n, y, and z domains are of a serotype other than AAV12 (e.g., 1, 2, 3, 4, 5, 6, 7, 8, 9, 10, 11, or 13). The serotypes of each of the d, n, y, and z domains may be the same, or may be different from each other. In some embodiments, the h domain is of AAV serotype 13, and each of the d, n, y, and z domains are of a serotype other than AAV13 (e.g., 1, 2, 3, 4, 5, 6, 7, 8, 9, 10, 11, or 12). The serotypes of each of the d, n, y, and z domains may be the same, or may be different from each other.

In some embodiments, they domain is of AAV serotype 1, and each of the n, d, h, and z are of a serotype other than AAV1 (e.g., 2, 3, 4, 5, 6, 7, 8, 9, 10, 11, 12, or 13). For example, each of the n, d, h, and z domains may be of the same serotype (e.g., 2, 3, 4, 5, 6, 7, 8, 9, 10, 11, 12, or 13). In some embodiments, each of the n, d, h, and z domains may be of different serotypes relative to each other, e.g., d, h may be of AAV2 serotype, while z may be of AAV3 serotype. In some embodiments, the y domain is of AAV serotype 2, and each of the n, d, h, and z domains are of a serotype other than AAV2 (e.g., 1, 3, 4, 5, 6, 7, 8, 9, 10, 11, 12, or 13). The serotypes of each of the n, d, h, and z domains may be the same, or may be different from each other. In some embodiments, the y domain is of AAV serotype 3, and each of the n, d, h, and z domains are of a serotype other than AAV3 (e.g., 1, 2, 4, 5, 6, 7, 8, 9, 10, 11, 12, or 13). The serotypes of each of the n, d, h, and z domains may be the same, or may be different from each other. In some embodiments, the y domain is of AAV serotype 4, and each of the n, d, h, and z domains are of a serotype other than AAV4 (e.g., 1, 2, 4, 5, 6, 7, 8, 9, 10, 11, 12, or 13). The serotypes of each of the n, d, h, and z domains may be the same, or may be different from each other. In some embodiments, the y domain is of AAV serotype 5, and each of the n, d, h, and z domains are of a serotype other than AAV5 (e.g., 1, 2, 3, 4, 6, 7, 8, 9, 10, 11, 12, or 13). The serotypes of each of the n, d, h, and z domains may be the same, or may be different from each other. In some embodiments, the y domain is of AAV serotype 6, and each of the n, d, h, and z domains are of a serotype other than AAV6 (e.g., 1, 2, 3, 4, 5, 7, 8, 9, 10, 11, 12, or 13). The serotypes of each of the n, d, h, and z domains may be the same, or may be different from each other. In some embodiments, the y domain is of AAV serotype 7, and each of the n, d, h, and z domains are of a serotype other than AAV7 (e.g., 1, 2, 3, 4, 5, 6, 8, 9, 10, 11, 12, or 13). The serotypes of each of the n, d, h, and z domains may be the same, or may be different from each other. In some embodiments, the y domain is of AAV serotype 8, and each of the n, d, h, and z domains are of a serotype other than AAV8 (e.g., 1, 2, 3, 4, 5, 6, 7, 9, 10, 11, 12, or 13). The serotypes of each of the n, d, h, and z domains may be the same, or may be different from each other. In some embodiments, the y domain is of AAV serotype 9, and each of the n, d, h, and z domains are of a serotype other than AAV9 (e.g., 1, 2, 3, 4, 5, 6, 7, 8, 10, 11, 12, or 13). The serotypes of each of the n, d, h, and z domains may be the same, or may be different from each other. In some embodiments, the y domain is of AAV serotype 10, and each of the n, d, h, and z domains are of a serotype other than AAV10 (e.g., 1, 2, 3, 4, 5, 6, 7, 8, 9, 11, 12, or 13). The serotypes of each of the n, d, h, and z domains may be the same, or may be different from each other. In some embodiments, the y domain is of AAV serotype 11, and each of the n, d, h, and z domains are of a serotype other than AAV11 (e.g., 1, 2, 3, 4, 5, 6, 7, 8, 9, 10, 12, or 13). The serotypes of each of the n, d, h, and z domains may be the same, or may be different from each other. In some embodiments, the y domain is of AAV serotype 12, and each of the n, d, h, and z domains are of a serotype other than AAV12 (e.g., 1, 2, 3, 4, 5, 6, 7, 8, 9, 10, 11, or 13). The serotypes of each of the n, d, h, and z domains may be the same, or may be different from each other. In some embodiments, the y domain is of AAV serotype 13, and each of the n, d, h, and z domains are of a serotype other than AAV13 (e.g., 1, 2, 3, 4, 5, 6, 7, 8, 9, 10, 11, or 12). The serotypes of each of the n, d, h, and z domains may be the same, or may be different from each other.

In some embodiments, the z domain is of AAV serotype 1, and each of the n, d, h, and y are of a serotype other than AAV1 (e.g., 2, 3, 4, 5, 6, 7, 8, 9, 10, 11, 12, or 13). For example, each of the n, d, h, and y domains may be of the same serotype (e.g., 2, 3, 4, 5, 6, 7, 8, 9, 10, 11, 12, or 13). In some embodiments, each of the n, d, h, and y domains may be of different serotypes relative to each other, e.g., d, h may be of AAV2 serotype, while z may be of AAV3 serotype. In some embodiments, the z domain is of AAV serotype 2, and each of the n, d, h, and y domains are of a serotype other than AAV2 (e.g., 1, 3, 4, 5, 6, 7, 8, 9, 10, 11, 12, or 13). The serotypes of each of the n, d, h, and y domains may be the same, or may be different from each other. In some embodiments, the z domain is of AAV serotype 3, and each of the n, d, h, and y domains are of a serotype other than AAV3 (e.g., 1, 2, 4, 5, 6, 7, 8, 9, 10, 11, 12, or 13). The serotypes of each of the n, d, h, and y domains may be the same, or may be different from each other. In some embodiments, the z domain is of AAV serotype 4, and each of the n, d, h, and y domains are of a serotype other than AAV4 (e.g., 1, 2, 4, 5, 6, 7, 8, 9, 10, 11, 12, or 13). The serotypes of each of the n, d, h, and y domains may be the same, or may be different from each other. In some embodiments, the z domain is of AAV serotype 5, and each of the n, d, h, and y domains are of a serotype other than AAV5 (e.g., 1, 2, 3, 4, 6, 7, 8, 9, 10, 11, 12, or 13). The serotypes of each of the n, d, h, and y domains may be the same, or may be different from each other. In some embodiments, the z domain is of AAV serotype 6, and each of the n, d, h, and y domains are of a serotype other than AAV6 (e.g., 1, 2, 3, 4, 5, 7, 8, 9, 10, 11, 12, or 13). The serotypes of each of the n, d, h, and y domains may be the same, or may be different from each other. In some embodiments, the z domain is of AAV serotype 7, and each of the n, d, h, and y domains are of a serotype other than AAV7 (e.g., 1, 2, 3, 4, 5, 6, 8, 9, 10, 11, 12, or 13). The serotypes of each of the n, d, h, and y domains may be the same, or may be different from each other. In some embodiments, the z domain is of AAV serotype 8, and each of the n, d, h, and y domains are of a serotype other than AAV8 (e.g., 1, 2, 3, 4, 5, 6, 7, 9, 10, 11, 12, or 13). The serotypes of each of the n, d, h, and y domains may be the same, or may be different from each other. In some embodiments, the z domain is of AAV serotype 9, and each of the n, d, h, and y domains are of a serotype other than AAV9 (e.g., 1, 2, 3, 4, 5, 6, 7, 8, 10, 11, 12, or 13). The serotypes of each of the n, d, h, and y domains may be the same, or may be different from each other. In some embodiments, the z domain is of AAV serotype 10, and each of the n, d, h, and y domains are of a serotype other than AAV10 (e.g., 1, 2, 3, 4, 5, 6, 7, 8, 9, 11, 12, or 13). The serotypes of each of the n, d, h, and y domains may be the same, or may be different from each other. In some embodiments, the z domain is of AAV serotype 11, and each of the n, d, h, and y domains are of a serotype other than AAV11 (e.g., 1, 2, 3, 4, 5, 6, 7, 8, 9, 10, 12, or 13). The serotypes of each of the n, d, h, and y domains may be the same, or may be different from each other. In some embodiments, the z domain is of AAV serotype 12, and each of the n, d, h, and y domains are of a serotype other than AAV12 (e.g., 1, 2, 3, 4, 5, 6, 7, 8, 9, 10, 11, or 13). The serotypes of each of the n, d, h, and y domains may be the same, or may be different from each other. In some embodiments, the z domain is of AAV serotype 13, and each of the n, d, h, and y domains are of a serotype other than AAV13 (e.g., 1, 2, 3, 4, 5, 6, 7, 8, 9, 10, 11, or 12). The serotypes of each of the n, d, h, and y domains may be the same, or may be different from each other.

FIGS. 7-16 provide examples of chimeric rep genes. It is to be understood that any combination of domains may be of a serotype that is different from the serotypes of the other domains. For example, only one domain may have a serotype that is different from the serotypes of the other domain. In some embodiments, all five domains have different serotypes. In some embodiments, the domains of a chimeric rep gene is of two different serotypes (e.g., R1h2, i.e., an h domain of AAV2 and other domains of AAV1). In some embodiments, the domains of a chimeric rep gene is of three different serotypes (e.g., R1c3h4, i.e, a C terminus of AAV3, a h domain of AAV4 and n and d domains of AA1). In some embodiments, the domains of a chimeric rep gene is of four different serotypes (e.g., R1h2d3y4, i.e., an h domain of AA2, d domain of AAV3, y domain of AAV3 and n and y domains of AAV1). In some embodiments, the domains of a chimeric rep gene is of five different serotypes (e.g., R1n2d3h4y8).

In some embodiments, a domain is truncated. In some embodiments a domain of a chimeric rep gene is truncated on the N terminal end of the domain. In some embodiments, a chimeric rep gene is truncated on the C terminal end of the domain. In some embodiments, a domain is modified such that non-contiguous nucleotides are deleted. In some embodiments, a domain is truncated by 1-18 nucleotides (e.g., 1, 2, 3, 4, 5, 6, 7, 8, 9, 10, 11, 12, 13, 14, 15, 16, 17, or 18 nucleotides). For example, a d domain may be truncated by 6 nucleotides on either the N terminal end or the C terminal end.

In some embodiments, any of the rep genes described herein comprises a start codon with the sequence ACG. In some embodiments, any of the rep genes described herein comprises a start codon with the sequence other than or different from ACG. In some embodiments, a start codon that has a sequence that is different from ACG is ATG.

It is also to be understood that the present disclosure also provides any chimeric Rep proteins that are encoded by any one of the chimeric rep genes disclosed herein, as well as any chimeric rep genes that may encode any one of the chimeric Rep proteins as disclosed herein.

In some embodiments of the present application, a Rep protein is chimeric in that it comprises amino acid sequences from more than one AAV serotype. In some embodiments, a chimeric Rep protein may comprise an N terminus comprising amino acids from one AAV serotype (e.g., AAV1, 2, 3, 4, 5, 6, 7, 8, 9, 10, 11, 12, or 13) and a C terminus comprising amino acids from another AAV serotype (e.g., AAV1, 2, 3, 4, 5, 6, 7, 8, 9, 10, 11, 12, or 13). For example, a Rep protein may comprise an N terminus comprising corresponding amino acids of AAV1 Rep protein, and a C terminus comprising corresponding amino acids of AAV2 Rep protein (e.g., SEQ ID NO: 34 for Rep78 comprising an N term of AAV1 and a C term of AAV2). A Rep protein may comprise an N terminus comprising corresponding amino acids of AAV2 Rep protein, and a C terminus comprising corresponding amino acids of AAV1 Rep protein (e.g., SEQ ID NO: 35 for Rep78 comprising an N term of AAV2 and a C term of AAV1). In another non-limiting example, a Rep protein comprises an N terminus comprising corresponding amino acids of AAV2 Rep protein, and a C terminus comprising corresponding amino acids of AAV5 Rep protein (e.g., SEQ ID NO: 36 for Rep78 comprising an N term of AAV2 and a C term of AAV5). In another non-limiting example, a Rep protein comprises an N terminus comprising corresponding amino acids of AAV5 Rep protein, and a C terminus comprising corresponding amino acids of AAV2 Rep protein (e.g., SEQ ID NO: 37 for Rep78 comprising an N term of AAV5 and a C term of AAV2). In some embodiments, a Rep protein comprises corresponding amino acids of more than two AAV serotypes (e.g., three, four, or five AAV serotypes). A non-limiting example of a Rep protein comprising corresponding amino acids of three AAV serotypes is Rep protein with corresponding amino acids from AAV1, AAV2 and AAV5. The term "corresponding amino acids" as used herein means amino acids in positions that align with each other in amino acid sequences of different AAV serotypes. In some embodiments, the corresponding amino acids between two AAV serotypes have the same positions. In some embodiments, corresponding amino acids between two AAV serotypes are in positions that are 1-5 amino acids shifted from each other. Methods of aligning amino acid sequences are known in the art, and algorithms to perform such alignments are also readily available. See e.g., Michael S. Rosenberg, Sequence Alignment: Methods, Models, Concepts, and Strategies, 2009, http://www.jstor.org/stable/10.1525/j.ctt1pps7t. For example, alignment of AAV ITRs and/or Rep proteins can be performed using Protein BLAST, https://blast.ncbi.nlm.nih.gov/Blast.cgi?PROGRAM=blastp&PAGE_TYPE=BlastSearch&BLAST_SPEC=blast2seq&LINK_LOC=blasttab.

Example of Rep78 Amino Acid Sequence with an AAV1 N Term and an AAV2 C Term

```
                                        (SEQ ID NO: 34)
MPGFYEIVIKVPSDLDEHLPGISDSFVSWVAEKEWELPPDSDMDLNLIEQ

APLTVAEKLQRDFLVQWRRVSKAPEALFFVQFEKGESYFHLHILVETTGV

KSMVLGRFLSQIRDKLVQTIYRGIEPTLPNWFAVTKTRNGAGGGNKVVDE

CYIPNYLLPKTQPELQWAWTNMEEYISACLNLAERKRLVAQHLTHVSQTQ

EQNKENLNPNSDAPVIRSKTSARYMELVGWLVDKGITSEKQWIQEDQASY

ISFNAASNSRSQIKAALDNAGKIMSLTKTAPDYLVGQQPVEDISSNRIYK

ILELNGYDPQYAASVELGWATKKFGKRNTIWLFGPATTGKTNIAEAIAHT

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TRRLDHDFGKVTKQEVKDFFRWAKDHVVEVEHEFYVKKGGAKKRPAPSDA

DISEPKRVRESVAQPSTSDAEASINYADRYQNKCSRHVGMNLMLFPCRQC
```

-continued
ERMNQNSNICFTHGQKDCLECFPVSESQPVSVVKKAYQKLCYIHHIMGKV

PDACTACDLVNVDLDDCIFEQ

Example of Rep78 Amino Acid Sequence with an AAV2 N Term and an AAV1 C Term (SEQ ID NO: 35)
MPGFYEIVIKVPSDLDGHLPGISDSFVNWVAEKEWELPPDSDMDLNLIEQ

APLTVAEKLQRDFLTEWRRVSKAPEALFFVQFEKGESYFHMHVLVETTGV

KSMVLGRFLSQIREKLIQRIYRGIEPTLPNWFAVTKTRNGAGGGNKVVDE

CYIPNYLLPKTQPELQWAWTNMEQYLSACLNLTERKRLVAQHLTHVSQTQ

EQNKENQNPNSDAPVIRSKTSARYMELVGWLVDRGITSEKQWIQEDQASY

ISFNAASNSRSQIKAALDNAGKIMALTKSAPDYLVGPAPPADIKTNRIYR

ILELNGYEPAYAGSVFLGWAQKRFGKRNTIWLFGPATTGKTNIAEAIAHA

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TRRLEHDFGKVTKQEVKEFFRWAQDHVTEVAHEFYVRKGGANKRPAPDDA

DKSEPKRACPSVADPSTSDAEGAPVDFADRYQNKCSRHAGMLQMLFPCKT

CERMNQNFNICFTHGTRDCSECFPGVSESQPVVRKRTYRKLCAIHHLLGR

APEIACSACDLVNVDLDDCVSEQ

Example of Rep78 Amino Acid Sequence with an AAV2 N Term and an AAV5 C Term (SEQ ID NO: 36)
MPGFYEIVIKVPSDLDGHLPGISDSFVNWVAEKEWELPPDSDMDLNLIEQ

APLTVAEKLQRDFLTEWRRVSKAPEALFFVQFEKGESYFHMHVLVETTGV

KSMVLGRFLSQIREKLIQRIYRGIEPTLPNWFAVTKTRNGAGGGNKVVDE

CYIPNYLLPKTQPELQWAWTNMEQYLSACLNLTERKRLVAQHLTHVSQTQ

EQNKENQNPNSDAPVIRSKTSARYMALVNWLVEHGITSEKQWIQENQESY

LSFNSTGNSRSQIKAALDNATKIMSLTKSAVDYLVGSSVPEDISKNRIWQ

IFEMNGYDPAYAGSILYGWCQRSFNKRNTVWLYGPATTGKTNIAEAIAHT

VPFYGCVNWTNENFPFNDCVDKMLIWWEEGKMTNKVVESAKAILGGSKVR

VDQKCKSSVQIDSTPVIVTSNTNMCVVVDGNSTTFEHQQPLEDRMFKFEL

TKRLPPDFGKITKQEVKDFFAWAKVNQVPVTHEFKVPRELAGTKGAEKSL

KRPLGDVTNTSYKSLEKRARLSFVPETPRSSDVTVDPAPLRPLNWNSRYD

CKCDYHAQFDNISNKCDECEYLNRGKNGCICHNVTHCQICHGIPPWEKEN

LSDFGDFDDANKEQ

Example of Rep78 Amino Acid Sequence with an AAV5 N Term and an AAV2 C Term (SEQ ID NO: 37)
MATFYEVIVRVPFDVEEHLPGISDSFVDWVTGQIWELPPESDLNLTLVEQ

PQLTVADRIRRVFLYEWNKFSKQESKFFVQFEKGSEYFHLHTLVETSGIS

SMVLGRYVSQIRAQLVKVVFQGIEPQINDWVAITKVKKGGANKVVDSGYI

PAYLLPKVQPELQWAWTNLDEYKLAALNLEERKRLVAQFLAESSQRSQEA

ASQREFSADPVIKSKTSQKYMELVGWLVDKGITSEKQWIQEDQASYISFN

AASNSRSQIKAALDNAGKIMSLTKTAPDYLVGQQPVEDISSNRIYKILEL

NGYDPQYAASVFLGWATKKFGKRNTIWLFGPATTGKTNIAEAIAHTVPFY

GCVNWTNENFPFNDCVDKMVIWWEEGKMTAKVVESAKAILGGSKVRVDQK

CKSSAQIDPTPVIVTSNTNMCAVIDGNSTTFEHQQPLQDRMFKFELTRRL

DHDFGKVTKQEVKDFFRWAKDHVVEVEHEFYVKKGGAKKRPAPSDADISE

PKRVRESVAQPSTSDAEASINYADRYQNKCSRHVGMNLMLFPCRQCERMN

QNSNICFTHGQKDCLECFPVSESQPVSVVKKAYQKLCYIHHIMGKVPDAC

TACDLVNVDLDDCIFEQ

Examples of Non-Limiting Chimeric Rep Proteins and Nucleic Acid Sequences Encoding them
R1c2 Amino Acid Sequence:

(SEQ ID NO: 188)
MPGFYEIVIKVPSDLDEHLPGISDSFVSWVAEKEWELPPDSDMDLNLIEQ

APLTVAEKLQRDFLVQWRRVSKAPEALFFVQFEKGESYFHLHILVETTGV

KSMVLGRFLSQIRDKLVQTIYRGIEPTLPNWFAVTKTRNGAGGGNKVVDE

CYIPNYLLPKTQPELQWAWTNMEEYISACLNLAERKRLVAQHLTHVSQTQ

EQNKENLNPNSDAPVIRSKTSARYMELVGWLVDRGITSEKQWIQEDQASY

ISFNAASNSRSQIKAALDNAGKIMALTKSAPDYLVGPAPPADIKTNRIYR

ILELNGYEPAYAGSVFLGWAQKRFGKRNTIWLFGPATTGKTNIAEAIAHA

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TRRLDHDFGKVTKQEVKDFFRWAKDHVVEVEHEFYVKKGGAKKRPAPSDA

DISEPKRVRESVAQPSTSDAEASINYADRYQNKCSRHVGMNLMLFPCRQC

ERMNQNSNICFTHGQKDCLECFPVSESQPVSVVKKAYQKLCYIHHIMGKV

PDACTACDLVNVDLDDCIFEQ

R1hc2 Amino Acid:

(SEQ ID NO: 189)
MPGFYEIVIKVPSDLDEHLPGISDSFVSWVAEKEWELPPDSDMDLNLIEQ

APLTVAEKLQRDFLVQWRRVSKAPEALFFVQFEKGESYFHLHILVETTGV

KSMVLGRFLSQIRDKLVQTIYRGIEPTLPNWFAVTKTRNGAGGGNKVVDE

CYIPNYLLPKTQPELQWAWTNMEEYISACLNLAERKRLVAQHLTHVSQTQ

EQNKENLNPNSDAPVIRSKTSARYMELVGWLVDRGITSEKQWIQEDQASY

ISFNAASNSRSQIKAALDNAGKIMSLTKTAPDYLVGQQPVEDISSNRIYK

ILELNGYDPQYAASVELGWATKKFGKRNTIWLFGPATTGKTNIAEAIAHT

VPFYGCVNWTNENFPFNDCVDKMVIWWEEGKMTAKVVESAKAILGGSKVR

VDQKCKSSAQIDPTPVIVTSNTNMCAVIDGNSTTFEHQQPLQDRMFKFEL

TRRLDHDFGKVTKQEVKDFFRWAKDHVVEVEHEFYVKKGGAKKRPAPSDA

DISEPKRVRESVAQPSTSDAEASINYADRYQNKCSRHVGMNLMLFPCRQC

ERMNQNSNICFTHGQKDCLECFPVSESQPVSVVKKAYQKLCYIHHIMGKV

PDACTACDLVNVDLDDCIFEQ

R2d1 Amino Acid:

(SEQ ID NO: 190)
TPGFYEIVIKVPSDLDEHLPGISDSFVNWVAEKEWELPPDSDMDLNLIEQ
APLTVAEKLQRDFLTEWRRVSKAPEALFFVQFEKGESYFHMHVLVETTGV
KSMVLGRFLSQIRDKLVQTIYRGIEPTLPNWFAVTKTRNGAGGGNKVVDE
CYIPNYLLPKTQPELQWAWTNMEEYISACLNLAERKRLVAQHLTHVSQTQ
EQNKENLNPNSDAPVIRSKTSARYMELVGWLVDRGITSEKQWIQEDQASY
ISFNAASNSRSQIKAALDNAGKIMSLTKTAPDYLVGQQPVEDISSNRIYK
ILELNGYDPQYAASVELGWATKKFGKRNTIWLFGPATTGKTNIAEAIAHT
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLDHDFGKVTKQEVKDFFRWAKDHVVEVEHEFYVKKGGAKKRPAPSDA
DISEPKRVRESVAQPSTSDAEASINYADRYQNKCSRHVGMNLMLFPCRQC
ERMNQNSNICFTHGQKDCLECFPVSEDNASQPVSVVKKAYQKLCYIHHIM
GKVPDACTACDLVNVDLDDCIFEQ

R2h1 Amino Acid:

(SEQ ID NO: 191)
TPGFYEIVIKVPSDLDEHLPGISDSFVNWVAEKEWELPPDSDMDLNLIEQ
APLTVAEKLQRDFLTEWRRVSKAPEALFFVQFEKGESYFHMHVLVETTGV
KSMVLGRFLSQIREKLIQRIYRGIEPTLPNWFAVTKTRNGAGGGNKVVDE
CYIPNYLLPKTQPELQWAWTNMEQYLSACLNLTERKRLVAQHLTHVSQTQ
EQNKENQNPNSDAPVIRSKTSARYMELVGWLVDKGITSEKQWIQEDQASY
ISFNAASNSRSQIKAALDNAGKIMALTKSAPDYLVGPAPPADIKTNRIYR
ILELNGYEPAYAGSVFLGWAQKRFGKRNTIWLFGPATTGKTNIAEAIAHA
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLDHDFGKVTKQEVKDFFRWAKDHVVEVEHEFYVKKGGAKKRPAPSDA
DISEPKRVRESVAQPSTSDAEASINYADRYQNKCSRHVGMNLMLFPCRQC
ERMNQNSNICFTHGQKDCLECFPVSESQPVSVVKKAYQKLCYIHHIMGKV
PDACTACDLVNVDLDDCIFEQ

R8d1c2 Amino Acid:

(SEQ ID NO: 192)
MPGFYEIVIKVPSDLDEHLPGISDSFVNWVAEKEWELPPDSDMDRNLIEQ
APLTVAEKLQRDFLVQWRRVSKAPEALFFVQFEKGESYFHLHVLVETTGV
KSMVLGRFLSQIRDKLVQTIYRGIEPTLPNWFAVTKTRNGAGGGNKVVDE
CYIPNYLLPKTQPELQWAWTNMEEYISACLNLAERKRLVAQHLTHVSQTQ
EQNKENLNPNSDAPVIRSKTSARYMELVGWLVDRGITSEKQWIQEDQASY
ISFNAASNSRSQIKAALDNAGKIMALTKSAPDYLVGPSLPADITQNRIYR
ILALNGYDPAYAGSVFLGWAQKKFGKRNTIWLFGPATTGKTNIAEAIAHA
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLDHDFGKVTKQEVKDFFRWAKDHVVEVEHEFYVKKGGAKKRPAPSDA
DISEPKRVRESVAQPSTSDAEASINYADRYQNKCSRHVGMNLMLFPCRQC
ERMNQNSNICFTHGQKDCLECFPVSESQPVSVVKKAYQKLCYIHHIMGKV
PDACTACDLVNVDLDDCIFEQ

R8p1/2c2 Amino Acid:

(SEQ ID NO: 193)
MPGFYEIVIKVPSDLDEHLPGISDSFVNWVAEKEWELPPDSDMDRNLIEQ
APLTVAEKLQRDFLVQWRRVSKAPEALFFVQFEKGESYFHLHVLVETTGV
KSMVLGRFLSQIREKLVQTIYRGVEPTLPNWFAVTKTRNGAGGGNKVVDE
CYIPNYLLPKTQPELQWAWTNMEEYISACLNLAERKRLVAQHLTHVSQTQ
EQNKENLNPNSDAPVIRSKTSARYMELVGWLVDRGITSEKQWIQEDQASY
ISFNAASNSRSQIKAALDNAGKIMALTKSAPDYLVGPSLPADITQNRIYR
ILALNGYDPAYAGSVFLGWAQKKFGKRNTIWLFGPATTGKTNIAEAIAHA
VPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFEL
TRRLDHDFGKVTKQEVKDFFRWAKDHVVEVEHEFYVKKGGAKKRPAPSDA
DISEPKRVRESVAQPSTSDAEASINYADRYQNKCSRHVGMNLMLFPCRQC
ERMNQNSNICFTHGQKDCLECFPVSESQPVSVVKKAYQKLCYIHHIMGKV
PDACTACDLVNVDLDDCIFEQ

R1c2 Gene Sequence:

(SEQ ID NO: 194)
ATGCCGGGCTTCTACGAGATCGTGATCAAGGTGCCGAGCGACCTGGACGA
GCACCTGCCGGGCATTTCTGACTCGTTTGTGAGCTGGGTGGCCGAGAAGG
AATGGGAGCTGCCCCCGGATTCTGACATGGATCTGAATCTGATTGAGCAG
GCACCCCTGACCGTGGCCGAGAAGCTGCAGCGCGACTTCCTGGTCCAATG
GCGCCGCGTGAGTAAGGCCCCGGAGGCCCTCTTCTTTGTTCAGTTCGAGA
AGGGCGAGTCCTACTTCCACCTCCATATTCTGGTGGAGACCACGGGGGTC
AAATCCATGGTGCTGGGCCGCTTCCTGAGTCAGATTAGGGACAAGCTGGT
GCAGACCATCTACCGCGGGATCGAGCCGACCCTGCCCAACTGGTTCGCGG
TGACCAAGACGCGTAATGGCGCCGGAGGGGGGAACAAGGTGGTGGACGAG
TGCTACATCCCCAACTACCTCCTGCCCAAGACTCAGCCCGAGCTGCAGTG
GGCGTGGACTAACATGGAGGAGTATATAAGCGCCTGTTTGAACCTGGCCG
AGCGCAAACGGCTCGTGGCGCAGCACCTGACCCACGTCAGCCAGACCCAG
GAGCAGAACAAGGAGAATCTGAACCCCAATTCTGACGCGCCTGTCATCCG
GTCAAAAACCTCCGCGCGCTACATGGAGCTGGTCGGGTGGCTGGTGGACC
GGGGCATCACCTCCGAGAAGCAGTGGATCCAGGAGGACCAGGCCTCGTAC
ATCTCCTTCAACGCCGCTTCCAACTCGCGGTCCCAGATCAAGGCCGCTCT
GGACAATGCCGGCAAGATCATGGCGCTGACCAAATCCGCGCCCGACTACC
TGGTAGGCCCCGCTCCGCCCGCGGACATTAAAACCAACCGCATCTACCGC

```
ATCCTGGAGCTGAACGGCTACGAACCTGCCTACGCCGGCTCCGTCTTTCT
CGGCTGGGCCCAGAAAAGGTTCGGGAAGCGCAACACCATCTGGCTGTTTG
GGCCGGCCACCACGGGCAAGACCAACATCGCGGAAGCCATCGCCCACGCC
GTGCCCTTCTACGGCTGCGTCAACTGGACCAATGAGAACTTTCCCTTCAA
TGATTGCGTCGACAAGATGGTGATCTGGTGGGAGGAGGGGAAGATGACCG
CCAAGGTCGTGGAGTCGGCCAAAGCCATTCTCGGAGGAAGCAAGGTGCGC
GTGGACCAGAAATGCAAGTCCTCGGCCCAGATAGACCCGACTCCCGTGAT
CGTCACCTCCAACACCAACATGTGCGCCGTGATTGACGGGAACTCAACGA
CCTTCGAACACCAGCAGCCGTTGCAAGACCGGATGTTCAAATTTGAACTC
ACCCGCCGTCTGGATCATGACTTTGGGAAGGTCACCAAGCAGGAAGTCAA
AGACTTTTTCCGGTGGGCAAAGGATCACGTGGTTGAGGTGGAGCATGAAT
TCTACGTCAAAAAGGGTGGAGCCAAGAAAAGACCCGCCCCCAGTGACGCA
GATATAAGTGAGCCCAAACGGGTGCGCGAGTCAGTTGCGCAGCCATCGAC
GTCAGACGCGGAAGCTTCGATCAACTACGCAGACAGGTACCAAAACAAAT
GTTCTCGTCACGTGGGCATGAATCTGATGCTGTTTCCCTGCAGACAATGC
GAGAGAATGAATCAGAATTCAAATATCTGCTTCACTCACGGACAGAAAGA
CTGTTTAGAGTGCTTTCCCGTGTCAGAATCTCAACCCGTTTCTGTCGTCA
AAAAGGCGTATCAGAAACTGTGCTACATTCATCATATCATGGGAAAGGTG
CCAGACGCTTGCACTGCCTGCGATCTGGTCAATGTGGATTTGGATGACTG
CATCTTTGAACAATAA
```

R1hc2 Gene Sequence:

(SEQ ID NO: 195)
```
ATGCCGGGCTTCTACGAGATCGTGATCAAGGTGCCGAGCGACCTGGACGA
GCACCTGCCGGGCATTTCTGACTCGTTTGTGAGCTGGGTGGCCGAGAAGG
AATGGGAGCTGCCCCCGGATTCTGACATGGATCTGAATCTGATTGAGCAG
GCACCCCTGACCGTGGCCGAGAAGCTGCAGCGCGACTTCCTGGTCCAATG
GCGCCGCGTGAGTAAGGCCCCGGAGGCCCTCTTCTTTGTTCAGTTCGAGA
AGGGCGAGTCCTACTTCCACCTCCATATTCTGGTGGAGACCACGGGGGTC
AAATCCATGGTGCTGGGCCGCTTCCTGAGTCAGATTAGGGACAAGCTGGT
GCAGACCATCTACCGCGGGATCGAGCCGACCCTGCCCAACTGGTTCGCGG
TGACCAAGACGCGTAATGGCGCCGAGGGGGGAACAAGGTGGTGGACGAG
TGCTACATCCCCAACTACCTCCTGCCCAAGACTCAGCCCGAGCTGCAGTG
GGCGTGGACTAACATGGAGGAGTATATAAGCGCCTGTTTGAACCTGGCCG
AGCGCAAACGGCTCGTGGCGCAGCACCTGACCCACGTCAGCCAGACCCAG
GAGCAGAACAAGGAGAATCTGAACCCCAATTCTGACGCGCCTGTCATCCG
GTCAAAAACCTCCGCGCGCTACATGGAGCTGGTCGGGTGGCTGGTGGACC
GGGGCATACACCTCCGAGAAGCAGTGGATCCAGGAGGACCAGGCCTCATAC
ATCTCCTTCAATGCGGCCTCCAACTCGCGGTCCCAAATCAAGGCTGCCTT
GGACAATGCGGGAAAGATTATGAGCCTGACTAAAACCGCCCCCGACTACC
TGGTGGGCCAGCAGCCCGTGGAGGACATTTCCAGCAATCGGATTTATAAA
```

-continued
```
ATTTTGGAACTAAACGGGTACGATCCCCAATATGCGGCTTCCGTCTTTCT
GGGATGGGCCACGAAAAGTTCGGCAAGAGGAACACCATCTGGCTGTTTG
GGCCTGCAACTACCGGGAAGACCAACATCGCGGAGGCCATAGCCCACACT
GTGCCCTTCTACGGGTGCGTAAACTGGACCAATGAGAACTTTCCCTTCAA
CGACTGTGTCGACAAGATGGTGATCTGGTGGGAGGAGGGGAAGATGACCG
CCAAGGTCGTGGAGTCGGCCAAAGCCATTCTCGGAGGAAGCAAGGTGCGC
GTGGACCAGAAATGCAAGTCCTCGGCCCAGATAGACCCGACTCCCGTGAT
CGTCACCTCCAACACCAACATGTGCGCCGTGATTGACGGGAACTCAACGA
CCTTCGAACACCAGCAGCCGTTGCAAGACCGGATGTTCAAATTTGAACTC
ACCCGCCGTCTGGATCATGACTTTGGGAAGGTCACCAAGCAGGAAGTCAA
AGACTTTTTCCGGTGGGCAAAGGATCACGTGGTTGAGGTGGAGCATGAAT
TCTACGTCAAAAAGGGTGGAGCCAAGAAAAGACCCGCCCCCAGTGACGCA
GATATAAGTGAGCCCAAACGGGTGCGCGAGTCAGTTGCGCAGCCATCGAC
GTCAGACGCGGAAGCTTCGATCAACTACGCAGACAGGTACCAAAACAAAT
GTTCTCGTCACGTGGGCATGAATCTGATGCTGTTTCCCTGCAGACAATGC
GAGAGAATGAATCAGAATTCAAATATCTGCTTCACTCACGGACAGAAAGA
CTGTTTAGAGTGCTTTCCCGTGTCAGAATCTCAACCCGTTTCTGTCGTCA
AAAAGGCGTATCAGAAACTGTGCTACATTCATCATATCATGGGAAAGGTG
CCAGACGCTTGCACTGCCTGCGATCTGGTCAATGTGGATTTGGATGACTG
CATCTTTGAACAATAA
```

R2d1 Gene Sequence:

(SEQ ID NO: 196)
```
ACGCCGGGGTTTTACGAGATTGTGATTAAGGTCCCCAGCGACCTTGACGA
GCATCTGCCCGGCATTTCTGACAGCTTTGTGAACTGGGTGGCCGAGAAGG
AATGGGAGTTGCCGCCAGATTCTGACATGGATCTGAATCTGATTGAGCAG
GCACCCCTGACCGTGGCCGAGAAGCTGCAGCGCGACTTTCTGACGGAATG
GCGCCGTGTGAGTAAGGCCCCGGAGGCCCTTTTCTTTGTGCAATTTGAGA
AGGGAGAGAGCTACTTCCACATGCACGTGCTCGTGGAAACCACCGGGGTG
AAATCCATGGTGCTGGGCCGCTTCCTGAGTCAGATTAGGGACAAGCTGGT
GCAGACCATCTACCGCGGGATCGAGCCGACCCTGCCCAACTGGTTCGCGG
TGACCAAGACGCGTAATGGCGCCGGAGGGGGGAACAAGGTGGTGGACGAG
TGCTACATCCCCAACTACCTCCTGCCCAAGACTCAGCCCGAGCTGCAGTG
GGCGTGGACTAACATGGAGGAGTATATAAGCGCCTGTTTGAACCTGGCCG
AGCGCAAACGGCTCGTGGCGCAGCACCTGACCCACGTCAGCCAGACCCAG
GAGCAGAACAAGGAGAATCTGAACCCCAATTCTGACGCGCCTGTCATCCG
GTCAAAAACCTCCGCGCGCTACATGGAGCTGGTCGGGTGGCTGGTGGACC
GGGGCATCACCTCCGAGAAGCAGTGGATCCAGGAGGACCAGGCCTCATAC
ATCTCCTTCAATGCGGCCTCCAACTCGCGGTCCCAAATCAAGGCTGCCTT
GGACAATGCGGGAAAGATTATGAGCCTGACTAAAACCGCCCCCGACTACC
TGGTGGGCCAGCAGCCCGTGGAGGACATTTCCAGCAATCGGATTTATAAA
```

-continued

```
ATTTTGGAACTAAACGGGTACGATCCCCAATATGCGGCTTCCGTCTTTCT
GGGATGGGCCACGAAAAAGTTCGGCAAGAGGAACACCATCTGGCTGTTTG
GGCCTGCAACTACCGGGAAGACCAACATCGCGGAGGCCATAGCCCACACT
GTGCCCTTCTACGGGTGCGTAAACTGGACCAATGAGAACTTTCCCTTCAA
CGACTGTGTCGACAAGATGGTGATCTGGTGGGAGGAGGGGAAGATGACCG
CCAAGGTCGTGGAGTCGGCCAAAGCCATTCTCGGAGGAAGCAAGGTGCGC
GTGGACCAGAAATGCAAGTCCTCGGCCCAGATAGACCCGACTCCCGTGAT
CGTCACCTCCAACACCAACATGTGCGCCGTGATTGACGGGAACTCAACGA
CCTTCGAACACCAGCAGCCGTTGCAAGACCGGATGTTCAAATTTGAACTC
ACCCGCCGTCTGGATCATGACTTTGGGAAGGTCACCAAGCAGGAAGTCAA
AGACTTTTTCCGGTGGGCAAAGGATCACGTGGTTGAGGTGGAGCATGAAT
TCTACGTCAAAAAGGGTGGAGCCAAGAAAAGACCCGCCCCCAGTGACGCA
GATATAAGTGAGCCCAAACGGGTGCGCGAGTCAGTTGCGCAGCCATCGAC
GTCAGACGCGGAAGCTTCGATCAACTACGCAGACAGGTACCAAAACAAAT
GTTCTCGTCACGTGGGCATGAATCTGATGCTGTTTCCCTGCAGACAATGC
GAGAGAATGAATCAGAATTCAAATATCTGCTTCACTCACGGACAGAAAGA
CTGTTTAGAGTGCTTTCCCGTGTCAGAATCTCAACCCGTTTCTGTCGTCA
AAAAGGCGTATCAGAAACTGTGCTACATTCATCATATCATGGGAAAGGTG
CCAGACGCTTGCACTGCCTGCGATCTGGTCAATGTGGATTTGGATGACTG
CATCTTTGAACAATAA
```

R2h1 Gene Sequence:

(SEQ ID NO: 197)
```
ACGCCGGGGTTTTACGAGATTGTGATTAAGGTCCCCAGCGACCTTGACGA
GCATCTGCCCGGCATTTCTGACAGCTTTGTGAACTGGGTGGCCGAGAAGG
AATGGGAGTTGCCGCCAGATTCTGACATGGATCTGAATCTGATTGAGCAG
GCACCCCTGACCGTGGCCGAGAAGCTGCAGCGCGACTTTCTGACGGAATG
GCGCCGTGTGAGTAAGGCCCCGGAGGCCCTTTTCTTTGTGCAATTTGAGA
AGGGAGAGAGCTACTTCCACATGCACGTGCTCGTGGAAACCACCGGGGTG
AAATCCATGGTTTTGGGACGTTTCCTGAGTCAGATTCGCGAAAAACTGAT
TCAGAGAATTTACCGCGGGATCGAGCCGACTTTGCCAAACTGGTTCGCGG
TCACAAAGACCAGAAATGGCGCCGGAGGCGGGAACAAGGTGGTGGATGAG
TGCTACATCCCCAATTACTTGCTCCCCAAAACCCAGCCTGAGCTCCAGTG
GGCGTGGACTAATATGGAACAGTATTTAAGCGCCTGTTTGAATCTCACGG
AGCGTAAACGGTTGGTGGCGCAGCATCTGACGCACGTGTCGCAGACGCAG
GAGCAGAACAAAGAGAATCAGAATCCCAATTCTGATGCGCCGGTGATCAG
ATCAAAAACTTCAGCCAGGTACATGGAGCTGGTCGGGTGGCTCGTGGACA
AGGGGATTACCTCGGAGAAGCAGTGGATCCAGGAGGACCAGGCCTCGTAC
ATCTCCTTCAACGCCGCTTCCAACTCGCGGTCCCAGATCAAGGCCGCTCT
GGACAATGCCGGCAAGATCATGGCGCTGACCAAATCCGCGCCCGACTACC
TGGTAGGCCCCGCTCCGCCCGCGGACATTAAAACCAACCGCATCTACCGC
```

-continued
```
ATCCTGGAGCTGAACGGCTACGAACCTGCCTACGCCGGCTCCGTCTTTCT
CGGCTGGGCCCAGAAAAGGTTCGGGAAGCGCAACACCATCTGGCTGTTTG
GGCCGGCCACCACGGGCAAGACCAACATCGCGGAAGCCATCGCCCACGCC
GTGCCCTTCTACGGCTGCGTCAACTGGACCAATGAGAACTTTCCCTTCAA
TGATTGCGTCGACAAGATGGTGATCTGGTGGGAGGAGGGGAAGATGACCG
CCAAGGTCGTGGAGTCGGCCAAAGCCATTCTCGGAGGAAGCAAGGTGCGC
GTGGACCAGAAATGCAAGTCCTCGGCCCAGATAGACCCGACTCCCGTGAT
CGTCACCTCCAACACCAACATGTGCGCCGTGATTGACGGGAACTCAACGA
CCTTCGAACACCAGCAGCCGTTGCAAGACCGGATGTTCAAATTTGAACTC
ACCCGCCGTCTGGATCATGACTTTGGGAAGGTCACCAAGCAGGAAGTCAA
AGACTTTTTCCGGTGGGCAAAGGATCACGTGGTTGAGGTGGAGCATGAAT
TCTACGTCAAAAAGGGTGGAGCCAAGAAAAGACCCGCCCCCAGTGACGCA
GATATAAGTGAGCCCAAACGGGTGCGCGAGTCAGTTGCGCAGCCATCGAC
GTCAGACGCGGAAGCTTCGATCAACTACGCAGACAGGTACCAAAACAAAT
GTTCTCGTCACGTGGGCATGAATCTGATGCTGTTTCCCTGCAGACAATGC
GAGAGAATGAATCAGAATTCAAATATCTGCTTCACTCACGGACAGAAAGA
CTGTTTAGAGTGCTTTCCCGTGTCAGAATCTCAACCCGTTTCTGTCGTCA
AAAAGGCGTATCAGAAACTGTGCTACATTCATCATATCATGGGAAAGGTG
CCAGACGCTTGCACTGCCTGCGATCTGGTCAATGTGGATTTGGATGACTG
CATCTTTGAACAATAA
```

R8d1c2 Gene Sequence:

(SEQ ID NO: 198)
```
ATGCCGGGCTTCTACGAGATCGTGATCAAGGTGCCGAGCGACCTGGACGA
GCACCTGCCGGGCATTTCTGACTCGTTTGTGAACTGGGTGGCCGAGAAGG
AATGGGAGCTGCCCCCGGATTCTGACATGGATCGGAATCTGATCGAGCAG
GCACCCCTGACCGTGGCCGAGAAGCTGCAGCGCGACTTCCTGGTCCAATG
GCGCCGCGTGAGTAAGGCCCCGGAGGCCCTCTTCTTTGTTCAGTTCGAGA
AGGGCGAGAGCTACTTTCACCTGCACGTTCTGGTCGAGACCACGGGGGTC
AAGTCCATGGTGCTGGCCGCTTCCTGAGTCAGATTAGGGACAAGCTGGT
GCAGACCATCTACCGCGGGATCGAGCCGACCCTGCCCAACTGGTTCGCGG
TGACCAAGACGCGTAATGGCGCCGGAGGGGGGAACAAGGTGGTGGACGAG
TGCTACATCCCCAACTACCTCCTGCCCAAGACTCAGCCCGAGCTGCAGTG
GGCGTGGACTAACATGGAGGAGTATATAAGCGCCTGTTTGAACCTGGCCG
AGCGCAAACGGCTCGTGGCGCAGCACCTGACCCACGTCAGCCAGACCCAG
GAGCAGAACAAGGAGAATCTGAACCCCAATTCTGACGCGCCTGTCATCCG
GTCAAAAACCTCCGCGCGCTATATGGAGCTGGTCGGGTGGCTGGTGGACC
GGGGCATCACCTCCGAGAAGCAGTGGATCCAGGAGGACCAGGCCTCGTAC
ATCTCCTTCAACGCCGCCTCCAACTCGCGGTCCCAGATCAAGGCCGCGCT
GGACAATGCCGGCAAGATCATGGCGCTGACCAAATCCGCGCCCGACTACC
TGGTGGGGCCCTCGCTGCCCGCGGACATTACCCAGAACCGCATCTACCGC
```

```
-continued
ATCCTCGCTCTCAACGGCTACGACCCTGCCTACGCCGGCTCCGTCTTTCT

CGGCTGGGCTCAGAAAAAGTTCGGGAAACGCAACACCATCTGGCTGTTTG

GACCCGCCACCACCGGCAAGACCAACATTGCGGAAGCCATCGCCCACGCC

GTGCCCTTCTACGGCTGCGTCAACTGGACCAATGAGAACTTTCCCTTCAA

TGATTGCGTCGACAAGATGGTGATCTGGTGGGAGGAGGGGAAGATGACCG

CCAAGGTCGTGGAGTCGGCCAAAGCCATTCTCGGAGGAAGCAAGGTGCGC

GTGGACCAGAAATGCAAGTCCTCGGCCCAGATAGACCCGACTCCCGTGAT

CGTCACCTCCAACACCAACATGTGCGCCGTGATTGACGGGAACTCAACGA

CCTTCGAACACCAGCAGCCGTTGCAAGACCGGATGTTCAAATTTGAACTC

ACCCGCCGTCTGGATCATGACTTTGGGAAGGTCACCAAGCAGGAAGTCAA

AGACTTTTTCCGGTGGGCAAAGGATCACGTGGTTGAGGTGGAGCATGAAT

TCTACGTCAAAAAGGGTGGAGCCAAGAAAAGACCCGCCCCCAGTGACGCA

GATATAAGTGAGCCCAAACGGGTGCGCGAGTCAGTTGCGCAGCCATCGAC

GTCAGACGCGGAAGCTTCGATCAACTACGCAGACAGGTACCAAAACAAAT

GTTCTCGTCACGTGGGCATGAATCTGATGCTGTTTCCCTGCAGACAATGC

GAGAGAATGAATCAGAATTCAAATATCTGCTTCACTCACGGACAGAAAGA

CTGTTTAGAGTGCTTTCCCGTGTCAGAATCTCAACCCGTTTCTGTCGTCA

AAAAGGCGTATCAGAAACTGTGCTACATTCATCATATCATGGGAAAGGTG

CCAGACGCTTGCACTGCCTGCGATCTGGTCAATGTGGATTTGGATGACTG

CATCTTTGAACAATAA
```

R8p1/2c2 Gene Sequence:

```
                                          (SEQ ID NO: 199)
ATGCCGGGCTTCTACGAGATCGTGATCAAGGTGCCGAGCGACCTGGACGA

GCACCTGCCGGGCATTTCTGACTCGTTTGTGAACTGGGTGGCCGAGAAGG

AATGGGAGCTGCCCCCGGATTCTGACATGGATCGGAATCTGATCGAGCAG

GCACCCCTGACCGTGGCCGAGAAGCTGCAGCGCGACTTCCTGGTCCAATG

GCGCCGCGTGAGTAAGGCCCCGGAGGCCCTCTTCTTTGTTCAGTTCGAGA

AGGGCGAGAGCTACTTTCACCTGCACGTTCTGGTCGAGACCACGGGGGTC

AAGTCCATGGTGCTAGGCCGCTTCCTGAGTCAGATTCGGGAAAAGCTGGT

CCAGACCATCTACCGCGGGGTCGAGCCCACCTTGCCCAACTGGTTCGCGG

TGACCAAGACGCGTAATGGCGCCGGGGGGGGGAACAAGGTGGTGGACGAG

TGCTACATCCCCAACTACCTCCTGCCCAAGACTCAGCCCGAGCTGCAGTG

GGCGTGGACTAACATGGAGGAGTATATAAGCGCGTGCTTGAACCTGGCCG

AGCGCAAACGGCTCGTGGCGCAGCACCTGACCCACGTCAGCCAGACGCAG

GAGCAGAACAAGGAGAATCTGAACCCCAATTCTGACGCGCCCGTGATCAG

GTCAAAAACCTCCGCGCGCTATATGGAGCTGGTCGGGTGGCTGGTGGACC

GGGGCATCACCTCCGAGAAGCAGTGGATCCAGGAGGACCAGGCCTCGTAC

ATCTCCTTCAACGCCGCCTCCAACTCGCGGTCCCAGATCAAGGCCGCGCT

GGACAATGCCGGCAAGATCATGGCGCTGACCAAATCCGCGCCCGACTACC

TGGTGGGGCCCTCGCTGCCCGCGGACATTACCCAGAACCGCATCTACCGC
```

```
-continued
ATCCTCGCTCTCAACGGCTACGACCCTGCCTACGCCGGCTCCGTCTTTCT

CGGCTGGGCTCAGAAAAAGTTCGGGAAACGCAACACCATCTGGCTGTTTG

GACCCGCCACCACCGGCAAGACCAACATTGCGGAAGCCATCGCCCACGCC

GTGCCCTTCTACGGCTGCGTCAACTGGACCAATGAGAACTTTCCCTTCAA

TGATTGCGTCGACAAGATGGTGATCTGGTGGGAGGAGGGGAAGATGACCG

CCAAGGTCGTGGAGTCGGCCAAAGCCATTCTCGGAGGAAGCAAGGTGCGC

GTGGACCAGAAATGCAAGTCCTCGGCCCAGATAGACCCGACTCCCGTGAT

CGTCACCTCCAACACCAACATGTGCGCCGTGATTGACGGGAACTCAACGA

CCTTCGAACACCAGCAGCCGTTGCAAGACCGGATGTTCAAATTTGAACTC

ACCCGCCGTCTGGATCATGACTTTGGGAAGGTCACCAAGCAGGAAGTCAA

AGACTTTTTCCGGTGGGCAAAGGATCACGTGGTTGAGGTGGAGCATGAAT

TCTACGTCAAAAAGGGTGGAGCCAAGAAAAGACCCGCCCCCAGTGACGCA

GATATAAGTGAGCCCAAACGGGTGCGCGAGTCAGTTGCGCAGCCATCGAC

GTCAGACGCGGAAGCTTCGATCAACTACGCAGACAGGTACCAAAACAAAT

GTTCTCGTCACGTGGGCATGAATCTGATGCTGTTTCCCTGCAGACAATGC

GAGAGAATGAATCAGAATTCAAATATCTGCTTCACTCACGGACAGAAAGA

CTGTTTAGAGTGCTTTCCCGTGTCAGAATCTCAACCCGTTTCTGTCGTCA

AAAAGGCGTATCAGAAACTGTGCTACATTCATCATATCATGGGAAAGGTG

CCAGACGCTTGCACTGCCTGCGATCTGGTCAATGTGGATTTGGATGACTG

CATCTTTGAACAATAA
```

Methods of Packaging Particles

Methods of producing rAAV particles are known in the art and reagents are commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.).

Generally, rAAV production involves culturing cells, introducing AAV genes and any genes of interest (e.g., flanked by ITRs) desired to be packaged to the cells, and allowing the cells to produce or package rAAV. The last step is followed by harvesting rAAV particles and subsequent purification steps. AAV genes and any genes desired to be packaged into rAAV particles may be introduced to cells by either transfection methods (e.g., using plasmid vectors and a transfection agent) or infection methods (e.g., using a viral vector).

In some embodiments, one or more genes of interest, rep gene (e.g., encoding a wild-type or recombinant, for example chimeric, Rep protein as described in this application), cap gene and helper genes (e.g., E1a gene, a E1b gene, a E4 gene, a E2a gene, and a VA gene) are introduced to a cell wherein the genes are comprised in one or more vectors (e.g., plasmids) such that the cell gets transfected or infected by the vectors. For clarity, helper genes are genes that encode helper proteins E1a, E1b, E4, E2a, and VA. In some embodiments, only one or more genes of interest and the control elements to which they are operably linked are comprised in one vector, while one or more of the rep, cap and helper genes are comprised in comprised in one or more of separate vectors. For example, a first vector may comprise one more genes of interest, while a second vector may comprise rep, cap and helper genes. In some embodiments, a first vector may comprise one more genes of interest, while a second vector may comprise rep, and a third vector may comprise helper genes and cap. In some embodiments, a first vector may comprise one more genes of interest, while a second vector may comprise rep, and a third vector may comprise helper genes, and a forth vector may comprise cap.

In some embodiments, a nucleic acid vector used to deliver a gene of interest or AAV gene to a producer cell is circular. In some embodiments, a nucleic acid vector is single-stranded. In some embodiments, a nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector.

In some embodiments of any one of the methods disclosed herein, the regions of nucleic acid (e.g., heterologous nucleic acid regions) that is flanked by ITRs comprises one or more genes of interest. Regions of nucleic acid flanked by ITRs may also comprise control elements that are operably linked to one or more genes of interest. In some embodiments either a rep gene or a cap gene or both the rep and cap genes are flanked by ITRs.

In some embodiments, a cell to which one or more genes of interest are introduced already comprise one or more of one rep gene, cap gene, and/or helper genes useful to package rAAV particles. As a non-limiting example, a cell may already comprise rep and express Rep proteins Rep78, Rep68, Rep52, and Rep40. Such a cell that expresses Rep proteins can be introduced to vectors comprising ITR-flanked genes of interest, and vectors that express cap and helper genes. In some embodiments, a cell may already comprise rep and helper genes.

Methods of transfecting a cell are known in the art. Non-limiting methods of transfecting cells are CaPO4-mediated transfection, transfection using lipids or polymeric molecules such as Polyethylenimine (PEI), and electroporation. Cells can also be introduced to nucleic acid using using viral vectors (e.g., HSV vectors or baculovirus).

After introducing one or more of one or more genes of interest, rep gene, cap gene, and helper genes to a cell in a manner that they enter the cell by transfection or infection, the cell is incubated under conditions in which rAAV particles will be produced in the cell and escape from the cell. The rAAV particles can then be purified using any method known the art or described herein, e.g., by iodixanol step gradient, CsCl gradient, chromatography, or polyethylene glycol (PEG) precipitation.

Improving Packaging of AAV Particles Using Combinations of ITRs and Rep of Different Serotypes, and or Chimeric Rep Genes Disclosed here are combinations of rep and ITRs of different serotypes such that their use in any method to produce or package rAAV particles results in greater packaging or production efficiency compared to similar conditions in which ITRs and rep gene of the same serotype are used. Accordingly, disclosed herein is also a method of packaging a rAAV particle comprising contacting a cell that expresses a rep gene of a first serotype with a recombinant nucleic acid comprising a pair of ITRs of a second serotype. In some embodiments, the first serotype and the second serotype are the same. In some embodiments, the first and second serotypes are different.

In some embodiments on any one of the rAAV particle producing methods disclosed herein, the rep gene is expressed in any one of the producer cells disclosed herein by transfected or infecting the cells with a nucleic acid encoding the rep gene.

In some embodiments, a first serotype of rep gene is any one of serotypes 1, 2, 3, 4, 5, 6, 7, 8, 9, 10, 11, 12, and 13. In some embodiments, a second serotype of AAV ITRs is any one of serotypes 1, 2, 3, 4, 5, 6, 7, 8, 9, 10, 11, 12, and 13. In some embodiments, any one of the first serotype for rep is used with any serotype for ITRs. For example, rep of serotype 1 can be used with ITRs of any one of serotypes 1, 2, 3, 4, 5, 6, 7, 8, 9, 10, 11, 12, and 13. As another example, rep of serotype 2 can be used with ITRs of any one of serotypes 1, 2, 3, 4, 5, 6, 7, 8, 9, 11, 12, and 13, and so on.

In some embodiments, rep of serotype 1 is used with ITRs or serotype 1, 2, 3, 4, or 7.

In some embodiments, ITRs of serotype 6 are used with rep of serotype 2, 3, 4, 6, 12, or 13. In some embodiments, ITRs of serotype 1 are used with rep of serotype 2, 3, 4, 12, or 13.

In some embodiments, a rep gene is chimeric. A chimeric AAV gene is one which comprises amino acids of more than one serotype. SEQ ID NOs 34-37 provide examples of chimeric Rep78 proteins. In some embodiments, ITRs of serotype 6 are used with chimeric rep of serotype 1 and 2. In some embodiments, ITRs of serotype 1 are used with chimeric rep of serotype 1 and 2. In some embodiments, ITRs of serotype 2 are used with chimeric rep of serotype 2 and 5. In some embodiments, ITRs of serotype 5 are used with chimeric rep of serotype 2 and 5.

Chimeric rep genes and Rep proteins are described above and may be used in any one of the methods of packaging rAAV particles as described herein.

In some embodiments, chimeric Rep proteins may comprise corresponding amino acids of a first serotype in the N terminus and corresponding amino acids of a second serotype in the C terminus. For example, a Rep protein may comprise amino acids of serotype 1 in the N terminus and amino acids of serotype 2 in the C terminus. In some embodiments, a Rep protein may comprise amino acids of serotype 2 in the N terminus and amino acids of serotype 1 in the C terminus. In some embodiments, a Rep protein may comprise amino acids of serotype 2 in the N terminus and amino acids of serotype 5 in the C terminus. In some embodiments, a Rep protein may comprise amino acids of serotype 5 in the N terminus and amino acids of serotype 2 in the C terminus. It is to be understood that a chimeric rep gene may be used in combination with ITRs of any serotype for producing rAAV particles or any serotype or pseudo-serotype. Table 2 provides examples of combinations of rep serotypes that can be used with ITRs of different serotypes to improve rAAV particle production. It is to be understood that, in addition the combinations of ITRs and rep genes provided in Table 2, any one chimeric rep genes or chimeric Rep proteins can be used in combination with any one of the ITRs as described herein, which in turn can be used with any one of the cap genes and capsid proteins described herein for producing rAAV particles.

TABLE 2

Examples of ITR and Rep combinations (including examples of chimeras) to be generated and tested

| 1. | AAV1_ITR+AAV1_Rep |
| 2. | AAV2_ITR+AAV1_Rep |
| 3. | AAV3_ITR+AAV1_Rep |
| 4. | AAV4_ITR+AAV1_Rep |

TABLE 2-continued

Examples of ITR and Rep combinations (including examples of chimeras) to be generated and tested

| | |
|---|---|
| 5. | AAV7_ITR+AAV1_Rep |
| 6. | AAV6_ITR+AAV2_Rep |
| 7. | AAV6_ITR+AAV3_Rep |
| 8. | AAV6_ITR+AAV4_Rep |
| 9. | AAV6_ITR+AAV6_Rep |
| 10. | AAV6_ITR+AAV12_Rep |
| 11. | AAV6_ITR+AAV13_Rep |
| 12. | AAV1_ITR+AAV2_Rep |
| 13. | AAV1_ITR+AAV3_Rep |
| 14. | AAV1_ITR+AAV4_Rep |
| 15. | AAV1_ITR+AAV12_Rep |
| 16. | AAV1_ITR+AAV13_Rep |
| 17. | AAV6_ITR+AAV1N/2C_chimeric_Rep |
| 18. | AAV1_ITR+AAV1N/2C_chimeric_Rep |
| 19. | AAV6_ITR+AAV2N/1C_chimeric_Rep |
| 20. | AAV1_ITR+AAV2N/1C_chimeric_Rep |
| 21. | AAV2_ITR+AAV2N/5C_chimeric_Rep |
| 22. | AAV5_ITR+AAV5N/2C_chimeric_Rep |

Producer Cells

Provided herein are cells used to produce rAAV particles using the combinations of ITRs, cap and/or rep of different serotypes as disclosed herein. Accordingly, in some embodiments, a producer cell as disclosed herein comprises rep of a first AAV serotype and ITRs of a second AAV serotype. In some embodiments, a producer cell as disclosed herein comprises a combination of rep and ITRs, wherein the serotypes of the rep and ITRs are any one of the combinations disclosed herein.

In some embodiments, the packaging is performed in a helper cell or producer cell, such as a mammalian cell or an insect cell. Exemplary mammalian cells include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect cells include, but are not limited to Sf9 cells (see, e.g., ATCC® CRL-1711™). The helper cell may comprises rep and/or cap genes that encode the Rep protein and/or Cap proteins for use in a method described herein. In some embodiments, the packaging is performed in vitro.

Improvement in rAAV Particle Yield

Recombinant AAV particle yields may improve by using any one of the methods described herein compared to rAAV production processes that are the same with the exception of the particular combination of serotypes of ITR and Rep proteins. In some embodiments, particle yields are defined by the amount of rAAV particles produced. In some embodiments, particle yields are defined by the amount of full rAAV particles (i.e., those that contain nucleic acid or genomes) produced. In some embodiments, yields of rAAV particles are increased relative to when ITRs of serotype 2 are used for packaging rAAV. In some embodiments, the yield of rAAV production involving any one of the particular combination of serotypes of ITR and Rep protein may increase by 2-20% (e.g., 2-4%. 2-10%, 5-10%, 5-20%, 15-20% or 10-20%), or even by up to 5-10 fold or 100-fold or more (e.g., up to 2-fold, up to 3-fold, up to 5-fold, up to 10-fold, up to 20-fold, up to 50-fold, or up to 100-fold or more) compared to rAAV production processes wherein an ITR of serotype 2 is used.

Recombinant AAV particle yields may improve by using any one of the chimeric rep genes described herein compared to rAAV particles produced using production processes that use rep genes of serotype that is a wild-type serotype closest to the majority of the nucleotides in the chimeric gene. For example, the packaging or particle yields for particles produced using ITRs of AAV2, cap of AAV3, and a chimeric rep of serotype 2 except for having a h domain of serotype 8 (R2h8) may be compared to packaging yields for particles produced using ITRs of AAV2, cap of AAV3 and rep of AAV2. In some embodiments, packaging yields as described herein are compared to that of particles of the same serotype made with ITRs of AAV2 and rep of AAV2. In some embodiments, particle yields achieved by using any one of the chimeric rep genes as described herein is improved by at least 1.5-fold (e.g., at least 1.5-fold, at least 2-fold, at least 3-fold, at least 4-fold, at least 5-fold, at least 6-fold, at least 7-fold, at least 8-fold, at least 9-fold, or at least 10-fold).

Methods of measuring packaging of rAAV particles is known in the art. For example, the quantity of genome can be measured using methods such as PCR (e.g., quantitative PCR). Quantities of capsids or particles can be measured using protein-based assays such as ELISA. In some embodiments, electron microscopy (e.g., cryo-electron microscopy) can be used to differentiate visually empty capsids from full capsids (i.e. those that comprise nucleic acid or genomes).

Cap Genes and Capsid Proteins

A rAAV particle or particle within an rAAV preparation may be of any AAV serotype, including any derivative or pseudotype (e.g., 1, 2, 3, 4, 5, 6, 7, 8, 9, 10, 11, 12, 13, 2/1, 2/5, 2/8, 2/9, 3/1, 3/5, 3/8, or 3/9). A cap gene may be used to package the rAAV genome or any gene of interest flanked by any one of the ITRs as described herein. As a result, a rAAV particle produced from any one of the methods described herein can be of any serotype or pseudotype, which in turn may use any one of the chimeric rep genes described herein. A rAAV particle produced using any one of the methods disclosed herein (e.g., with any one of the rep genes, any one of the cap genes, and/or any one of the ITRs described here) can be used to deliver a gene of interest to a cell (e.g., a cell in a subject's body, or an in vitro cell), or to treat a condition or disease in a subject.

The serotype of an rAAV viral particle refers to the serotype of the capsid proteins of the recombinant virus. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. In some embodiments, cap proteins have one or more amino acid substitutions. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid vector comprising ITRs from one serotype (e.g., AAV2, AAV3) and (b) a capsid comprised of capsid proteins derived from another serotype (e.g., AAV1, AAV2, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 2001).

Helper Genes and Vectors

In some embodiments, the one or more helper vectors (e.g., plasmids) include a first helper plasmid comprising a rep gene and/or a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. In some embodiments, the cap gene is modified such that one or more of the proteins VP1, VP2, and VP3 do not get expressed. In some embodiments, the cap gene is modified such that VP2 does not get expressed. Methods for making such modifications are known in the art (Lux et al. (2005), J Virology, 79: 11776-87)

Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), J Virology, 6:3096-3101).

Gene of Interest and Control Elements

A gene of interest is a gene that encodes a protein of interest. A protein of interest may be a detectable marker or a therapeutic protein. A detectable marker is a molecule that can be visualized (e.g., using a naked eye or under a microscope). In some embodiments, the detectable marker is a fluorescent molecule, a bioluminescent molecule, or a molecule that provides color (e.g., β-galactosidase, β-lactamases, β-glucuronidase, and spheriodenone). In some embodiments, a detectable marker is a fluorescent protein or functional peptide or functional polypeptide thereof.

In some embodiments, a gene of interest encodes a therapeutic protein. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA or other nucleic acid, or protein for gene editing.

In some embodiments, the nucleic acid vector comprises one or more regions comprising a sequence that facilitates expression of the nucleic acid (e.g., the heterologous nucleic acid), e.g., expression control sequences operatively linked to the nucleic acid. Such control elements can be delivered to a producer cell such that it aids in expression of one or more proteins in the producer cells. In some embodiments, a control element is delivered to a producer cells such that it gets packaged with the one or more genes of interest so that the packaged rAAV particle, when used to infect a target cell, tissue, or organ, aids in the expression of the product of the gene of interest in the target cell, tissue, or organ.

Numerous control elements are known in the art. Non-limiting examples of control elements include promoters, insulators, silencers, response elements, introns, enhancers, initiation sites, termination signals, and poly(A) tails. Any combination of such control elements is contemplated herein (e.g., a promoter and an enhancer). To achieve appropriate expression levels of the protein or polypeptide of interest, any of a number of promoters suitable for use in the selected host cell may be employed. The promoter may be, for example, a constitutive promoter, tissue-specific promoter, inducible promoter, or a synthetic promoter. For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A, and cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter. Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline. Tissue-specific promoters and/or regulatory elements are also contemplated herein. Non-limiting examples of such promoters that may be used include airway epithelial cell-specific promoters. Synthetic promoters are also contemplated herein. A synthetic promoter may comprise, for example, regions of known promoters, regulatory elements, transcription factor binding sites, enhancer elements, repressor elements, and the like.

In some embodiments, a gene of interest, optionally including one or more control elements, is flanked by ITRs. In some embodiments, a nucleic acid vector comprising the gene of interest flanked by ITRs is an RNA, a DNA, a ssDNA, or a self-complementary DNA molecule. In some embodiments, the nucleic acid vector is packaged into a viral particle using one or more techniques described in this application (e.g., by introducing the nucleic acid vector, for example via transfection, into a producer cell that expresses a chimeric rep gene or a gene that is of a different serotype than the ITRs flanking the gene of interest, wherein the producer cell further optionally expresses one or more cap genes and/or helper genes).

Without further elaboration, it is believed that one skilled in the art can, based on the above description, utilize the present application to its fullest extent. The following specific embodiments are, therefore, to be construed as merely illustrative, and not limitative of the remainder of the application in any way whatsoever. All publications cited herein are incorporated by reference for the purposes or subject matter referenced herein.

Use of rAAV Particles as Produced by Methods Described Herein

A rAAV particle produced using any one of the methods disclosed herein (e.g., with any one of the rep genes, any one of the cap genes, and/or any one of the ITRs described here) can be used to deliver a gene of interest to a cell (e.g., a cell in a subject's body, or an in vitro cell), or to treat a condition or disease in a subject. In some embodiments, a subject is a mammal (e.g., a human). In some embodiments, a subject is in need of treatment with a gene of interest as described above.

In some embodiments, "administering" or "administration" means providing a material to a subject in a manner that is pharmacologically useful. In some embodiments, a rAAV particle is administered to a subject enterally. In some embodiments, an enteral administration of the essential metal element/s is oral. In some embodiments, a rAAV particle is administered to the subject parenterally. In some embodiments, a rAAV particle is administered to a subject subcutaneously, intraocularly, intravitreally, subretinally, intravenously (IV), intracerebro-ventricularly, intramuscularly, intrathecally (IT), intracisternally, intraperitoneally, via inhalation, topically, or by direct injection to one or more cells, tissues, or organs. In some embodiments, a rAAV particle is administered to the subject by injection into the hepatic artery or portal vein.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a disease, e.g., Friedreich's ataxia. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

In some embodiments, the composition comprises a pharmaceutically acceptable carrier. The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

EXAMPLES

Example 1: Comparison of AAV ITRs and Rep Proteins of Different Serotypes

To begin to explore the impact of using AAV Rep protein and/or AAV ITRs of different serotypes on the genome packaging efficiency, the Rep and available ITR sequences of AAV1 to AAV13 were compared (FIG. 1). The ITR sequences are only available for AAV1-AAV7. AAV1 and AAV6 share high sequence identity in both Rep (99.4%) and Cap (99.2%) proteins. In contrast, their ITR sequences show divergence (81.6%). The AAV6 ITR is identical to that of AAV2 ITR while the Rep and Cap protein sequences are more diverse at 87.3% and 83.4%, respectively. This is consistent with AAV6 being a chimera between AAV1 and AAV2. The AAV1 and AAV6 Rep share high sequence homology (≥95.0%) to AAV7, AAV8, AAV9, AAV10, and AAV11, although their Cap protein sequences are more diverse (FIG. 1). Significantly, AAV5 is consistently diverse in its ITR sequence, Rep protein, and Cap proteins compared to the other AAVs (FIG. 1).

Figure 3:
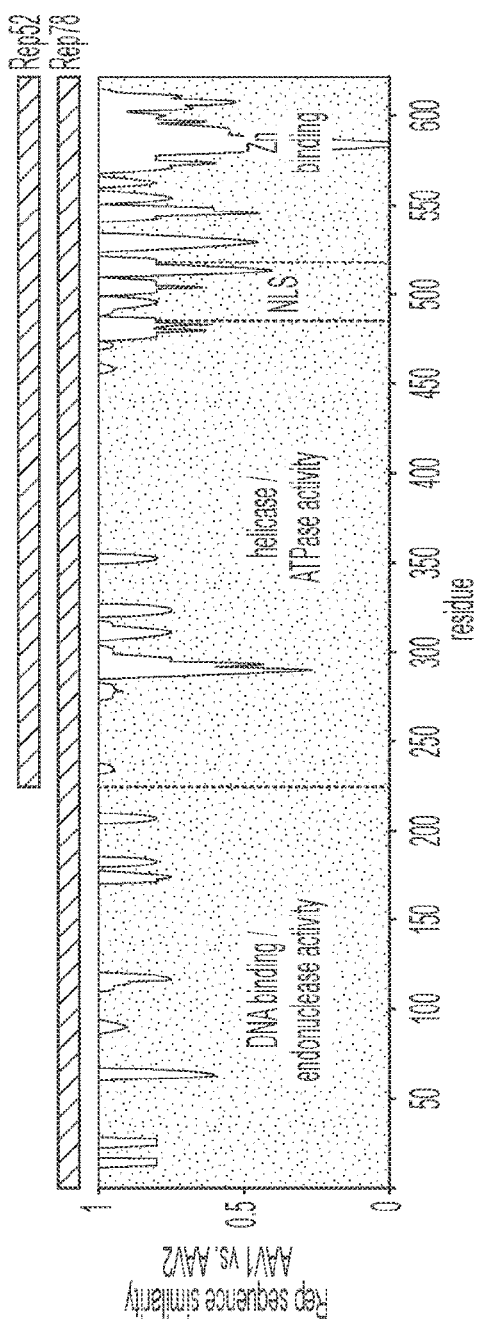
FIG. 3 shows a graphical representation of AAV1 versus AAV2 Rep protein sequence identity.

An analysis of the locations of the sequence variations within the ITRs shows minor variations in the A-region but higher variation in the D-sequence and the hairpin (B- and C-region) (FIG. 2). The D-sequence is reportedly important for AAV packaging while the sequence in the hairpin is exchangeable as long as the secondary structure is maintained. A graphical representation of the comparison of the AAV1 and AAV2, as an example, shows that variation exists in both the DNA binding and helicase domains (FIG. 3). These observations indicate a level of complexity in these essential viral elements that may relate to their function.

Example 2: Effect of Using Combination of ITRs and Rep Proteins of Different Serotypes on rAAV Particle Packaging First, a comparison between the packaging of AAV6 capsids with Rep proteins of all AAV serotypes is carried out. Vector constructs having a genome flanked by ITRs of AAV1 to AAV6 are used. Existing Rep2 (of AAV2)-cap6 (of AAV6) helper plasmids containing the AAV2 rep gene is substituted by rep genes from other AAV serotypes. These constructs are used to transfect HEK293 cells to generate rAAV6 (rAAVX/6) vectors. AAV vector genomes flanked by ITRs from alternative AAV serotypes are used for AAV6 vector production, starting with matching pairs of ITR and Rep proteins (e.g., AAV1 ITR plus AAV1 rep, or AAV3 ITR plus AAV3 rep, etc.). The resulting vectors are purified by AVB sepharose, which purifies genome-containing as well as empty (no DNA) AAV particles. The full and empty capsids are separated either by a density gradient (e.g., Iodixanol) or a sedimentation gradient (e.g., Sucrose gradient), and for each sample, a capsid ELISA (with the ADK1a antibody) is used to quantify the capsid titer. The individual vector preparations are subsequently analyzed and compared for their empty:full ratio, overall production yield, and gene expression efficiency.

If significant differences in the packaging efficiencies of the same transgenes are observed, a finer analysis of the residue differences in the two Rep domains is carried out along with mutation of certain residues to identify residues important for the differences.

Then, Rep sequences of AAV1 to AAV13 were compared to determine where differences between them are located. Their role in packaging is then examined. It is known that AAV5 ITRs can only be packaged with the AAV5 Rep proteins, thus chimeras will test both the DNA binding and helicase domains to pinpoint the determinant of this requirement. If significant differences in packaging efficiency or vector productivity are found to be dictated by serotype Rep or ITR, domains are swapped between the viruses (e.g., utilization of the AAV1 DNA binding domain and/or helicase/ATPase or the utilization of the D-sequence from AAV1) and tested for their effect on rAAV particle packaging.

Figure 4:
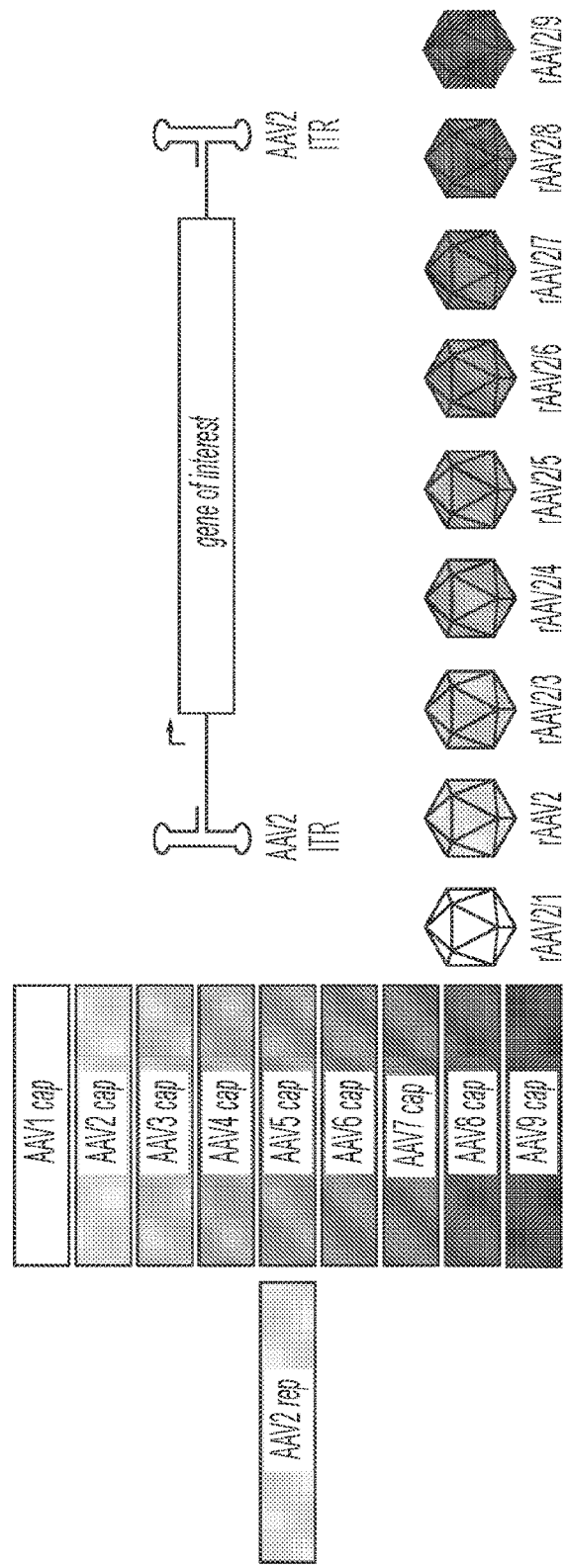
FIG. 4 is a schematic showing the standard AAV vector production system.

Example 3: Effect of Using Chimeric Rep Gene to Produce rAAV Particles of Various Serotypes FIG. 4 shows a schematic of the standard AAV productions system used to produce rAAV particles. A cell, also called a helper or producer cell, is transfected with one or more plasmids comprising genes encoding Rep and capsid proteins, and optionally, a gene of interest between ITRs so that it can be packaged within rAAV particle. The standard technique utilizes various chimeric and modified cap genes but usually rep and ITRs of serotype 2. The following describes experiments and data therefrom in which the rep gene is modified and used with ITRs having sequence of AAV2 to produce capsids of different serotypes. The modified rep genes that were tested are chimeric rep genes having domains that are substituted with domains or other serotypes.

An analysis of the DNA sequence identity for ITR AAV1-7 and Rep78 AAV1-8 was performed (FIG. 5). Sequences for AAV8 ITR, AAV9 ITR, and AAV9 Rep are not available.

Figure 6:
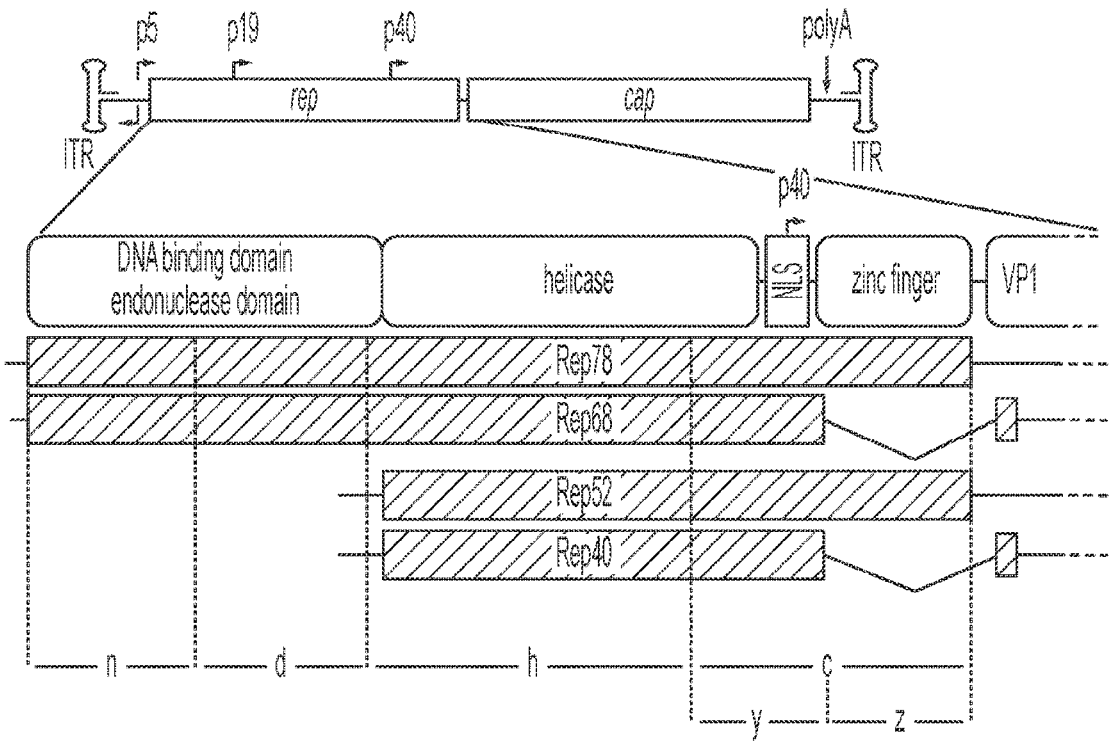
FIG. 6 shows an overview of an AAV genome is shown with its two open reading frames flanked by inverted terminal repeats (ITRs). The zoom-in shows an illustration of the domains of the Rep proteins and the transcripts leading to the expression of Rep78/68/52/40. Regions of the rep gene used for the generations of hybrids are indicated as lower case letter: n=N-terminus, d=DNA binding domain, h=helicase, c=C-terminus, y=nuclear localization signal (NLS)/p40 promoter, z=Zinc finger domain.

FIG. 5 shows percent sequence identity analysis for AAV ITR and Rep78 for AAV serotypes 1-9. FIG. 6 provides a schematic showing the arrangement of rep and cap genes in an AAV genome and various domains of AAV Rep proteins expressed from the rep gene. A schematic of AAV genome is shown with its two open reading frames flanked by inverted terminal repeats (ITRs). The zoom-in shows an illustration of the domains of the Rep proteins and the transcripts leading to the expression of Rep78/68/52/40. The specific domains of the rep gene used for the generations of hybrids are indicated by follows:
    n=N-terminus domain,
    d=DNA binding domain,
    h=helicase domain,
    y=NLS/p40 promoter domain, and
    z=Zinc finger domain;
    wherein the N-terminus as defined herein consists of domains n, d, and h; and the C-terminus (c) consists of domains y and z.

Figure 7A:
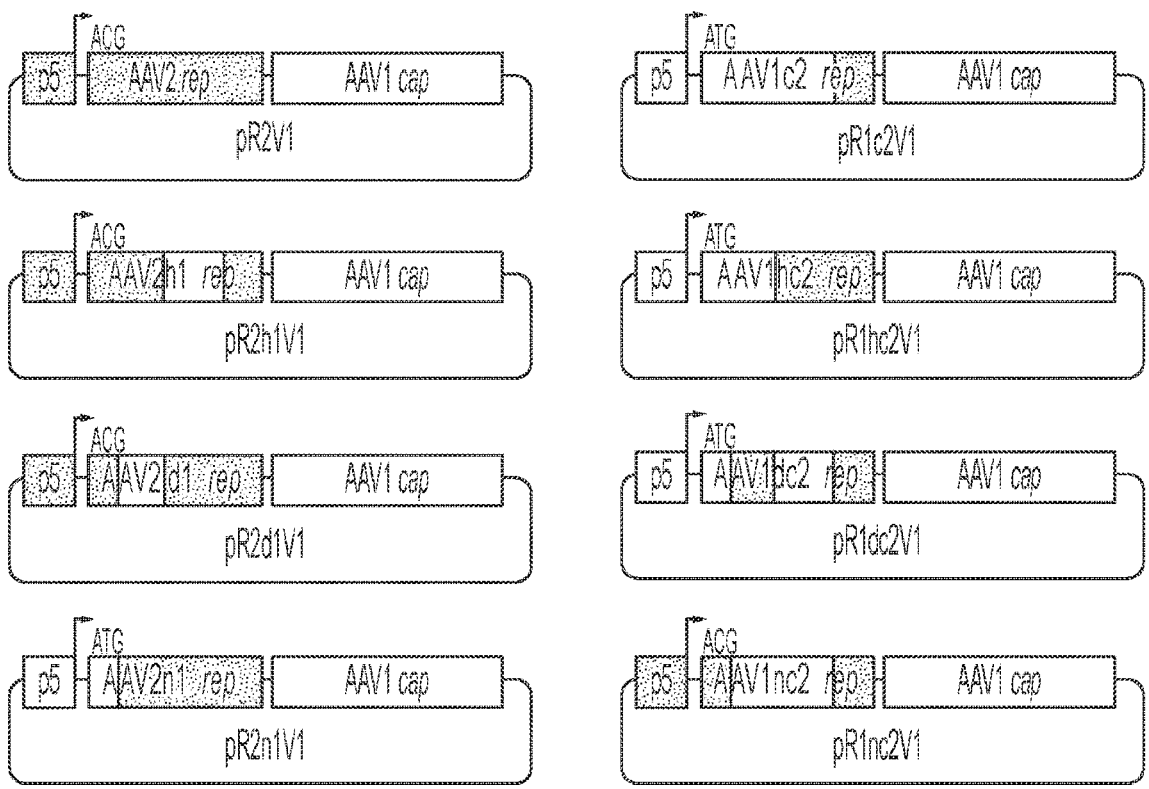
Figure 9A:
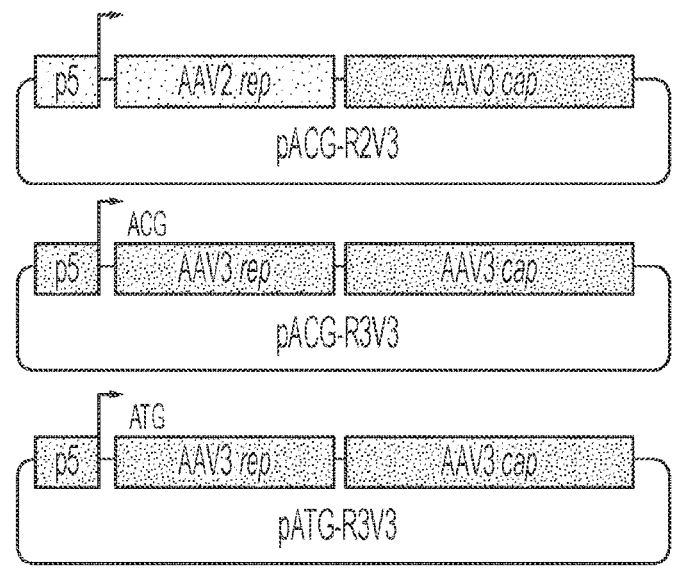
Figure 9B:
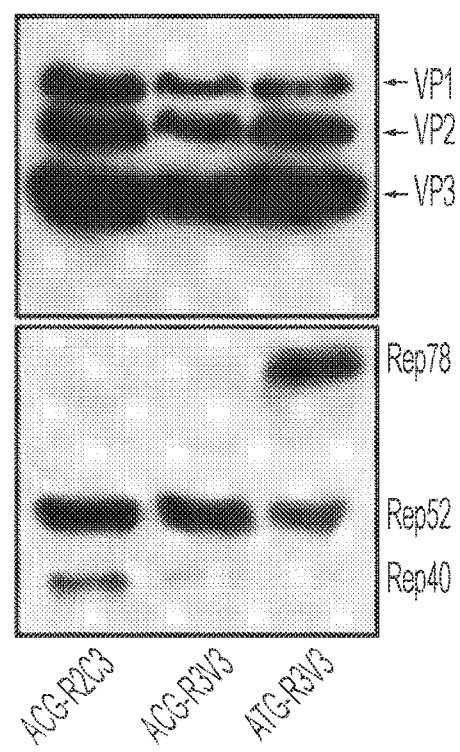
Figure 10A:
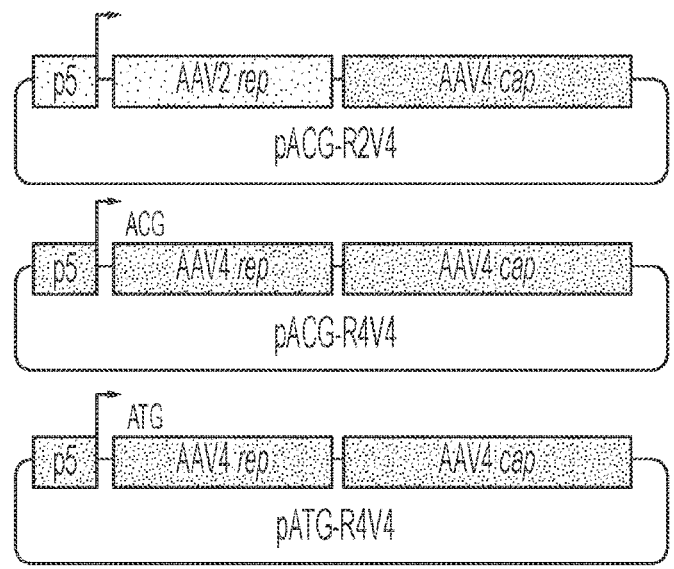
Figure 10B:
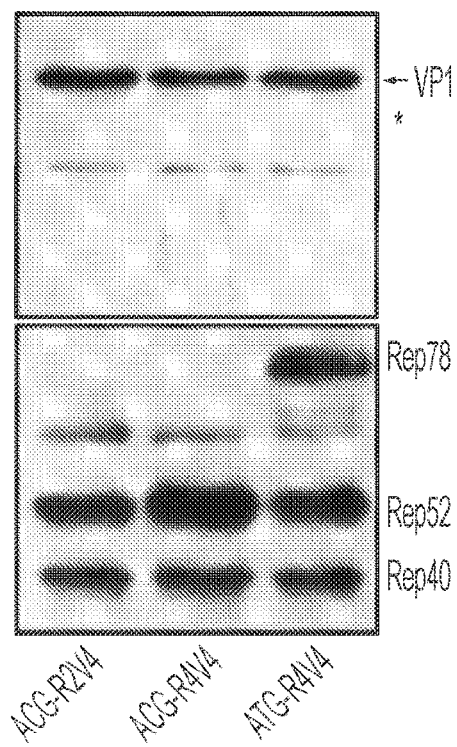
Figure 11A:
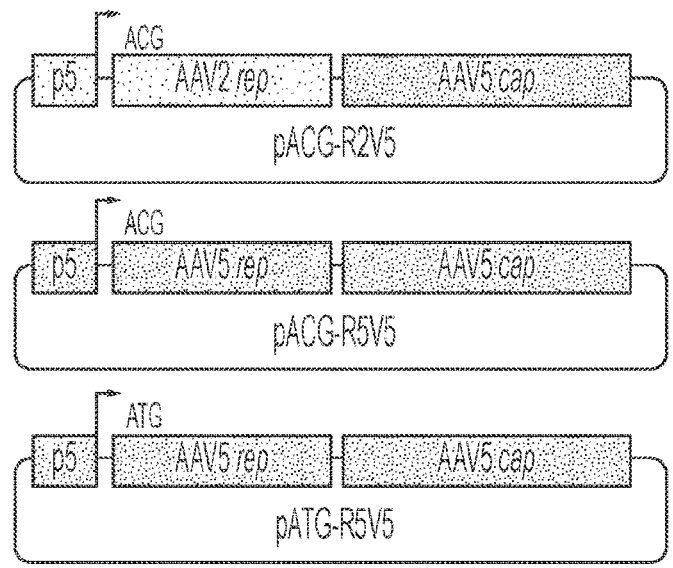
Figure 11B:
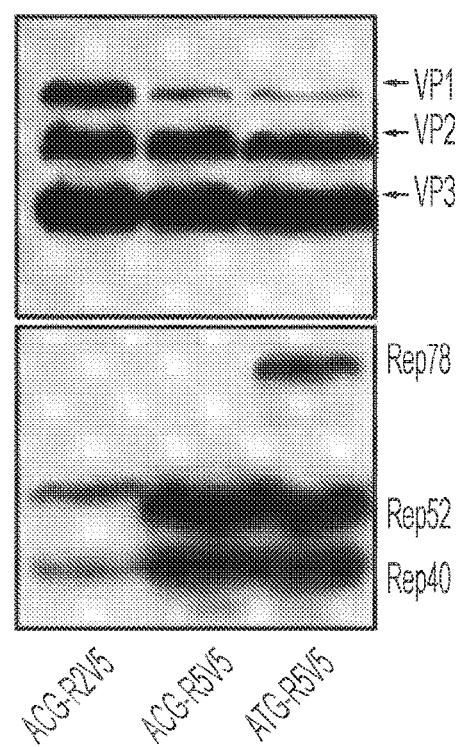

The characterization and optimization of the rep gene for AAV1 vector production is shown in FIGS. 7A-7B. Swaps between the AAV1 and AAV2 rep gene were generated to identify the domain responsible for improved genome packaging. The DNA binding domain (DBD, d) plays an important role as the AAV2 DBD significantly affects packaging. The helicase domain (h) is also likely involved with the AAV2 helicase also showing improved packaging. Overall, the variants R1hc2V1 (i.e., denoting a plasmid with a cap gene of AAV1 sequence, and a rep gene of AAV1 sequence with the exception that the C terminus (c) and the helicase domain (h) are of AAV2 sequence) and R2d1V1 (denoting a plasmid with a cap gene of AAV1 sequence, and a rep gene of AAV2 sequence with the exception that the DNA binding domain (d) is of AAV1 sequence), which both have AAV1 DBD and AAV2 helicase, have the best vector genome packaging phenotypes in AAV1 capsids. Additional data for rep modifications for producing rAAV particles of AAV1 is provided in FIG. 8. For these variants the domains in rep gene are defined as follows: n=N-terminus: aa 1-102, d=DNA-binding domain: aa 103-242, h=helicase domain: aa 243-370, c=C-terminus: aa 371-621.

The AAV2 rep gene was substituted with the AAV3 rep gene for the production of AAV3 particles (FIGS. 9A-9D). For the standard production system, an ACG-start codon for AAV2 rep was used. Both ACG and ATG start codons were tested with the AAV3 rep gene. With the ATG start codon, AAV3 Rep78 was visible and it was not seen with the ACG start codon. The VP expression of the AAV3 rep constructs was slightly lower compared to the AAV2 rep gene construct. Nonetheless, the genome titer of ATG-R3V3 was comparable to that of ACG-R2V3. Thus, the packaging was slightly better with AAV3 Rep (FIGS. 9A-9D).

Next, the AAV2 rep gene was substituted with the AAV4 rep gene for the production of AAV4 particles (FIGS. 10A-10D). Both ACG and ATG start codons were tested with the AAV4 rep gene. With the ATG start codon AAV4 Rep78 was visible and it was not seen with ACG start codon. The VP1 expression with the AAV4 rep constructs was comparable to that of the AAV2 rep gene construct. Nonetheless, the genome titer of ACG-R4V4 was higher compared to ACG-R2V4. Thus, the packaging might be better with AAV4 Rep compared to AAV2 Rep.

The AAV2 rep gene was substituted with the AAV5 rep gene for the production of AAV5 particles (FIGS. 11A-11D). Both ACG and ATG start codons were tested with the AAV5 rep gene. With the ATG start codon, AAV5 Rep78 was visible and it was not seen with ACG start codon. The VP expression with the AAV5 rep constructs appeared to be slightly lower compared to the AAV2 rep gene construct. However, no packaged genomes had been detected with the AAV5. AAV5 Rep is known to be unable to interact with AAV2 ITRs (see e.g., Chiorini et al., J Virol. 1999 May; 73(5):4293-8).

Figure 12A:
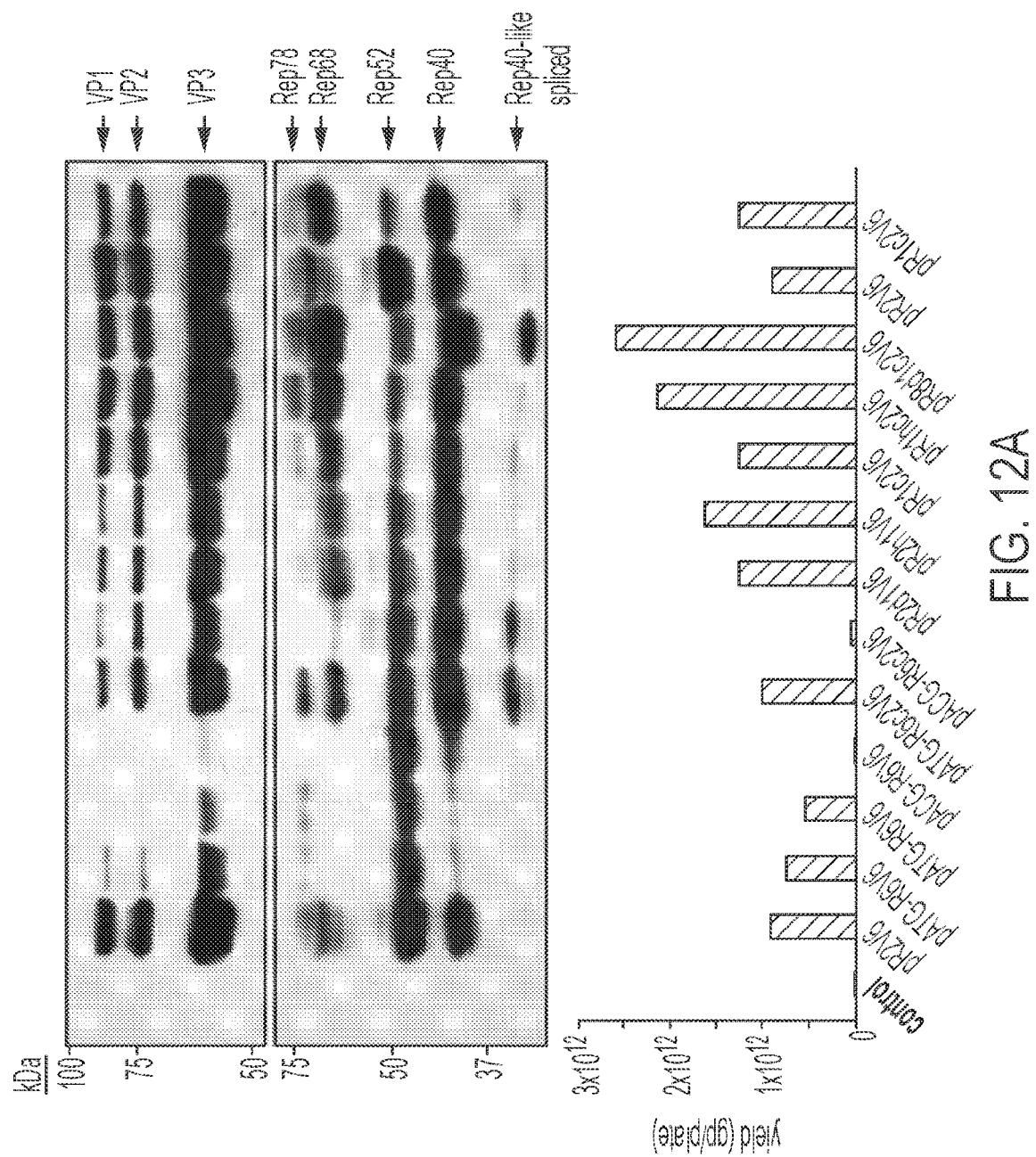
Figure 13A:
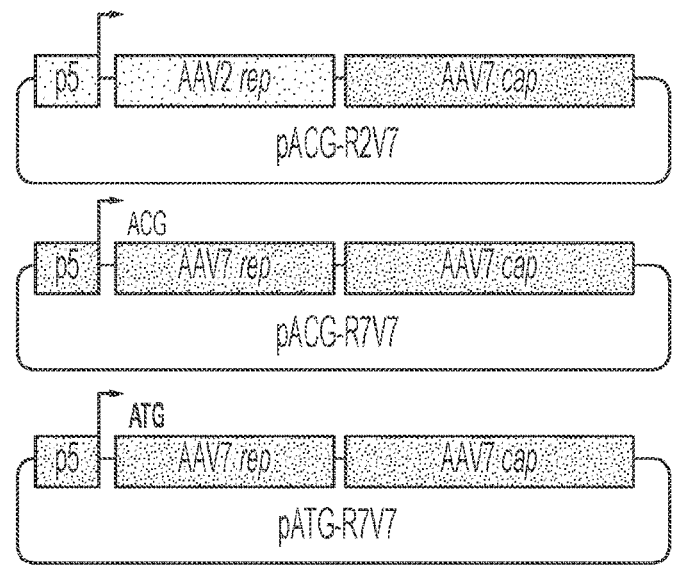
Figure 13B:
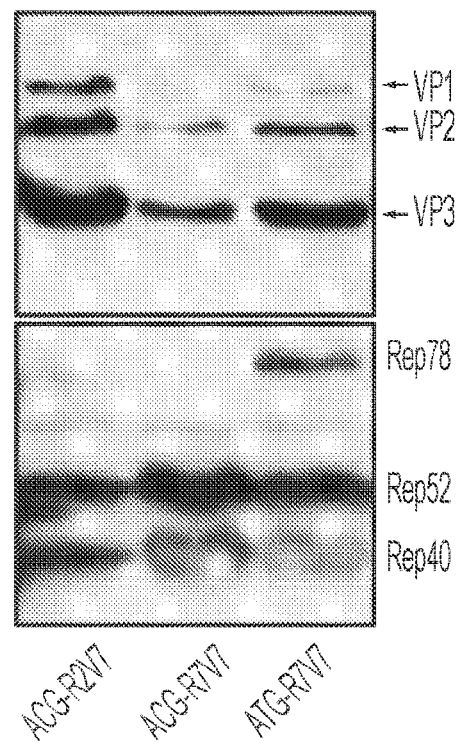

The AAV2 rep gene was substituted with the AAV6 rep gene for the production of AAV6 vectors (FIGS. 12A-12C). Both ACG and ATG start codons were tested with the AAV6 rep gene. Various Rep hybrids between the AAV serotypes AAV1, AAV2, AAV6 and AAV8 were also analyzed. The best vector genome packaging phenotypes were observed for the Rep variants plasmids R8d1c2V6 and R1hc2V6. However, both plasmids maintained high VP expression comparable to that of the reference plasmid pR2V6.

The AAV2 rep gene was substituted with the AAV7 rep gene for the production of AAV7 particles (FIGS. 13A-13D). Both ACG and ATG start codons were tested with the AAV7 rep gene. With the ATG start codon AAV7 Rep78 was visible and it was not seen with ACG start codon. The VP expression with the AAV7 rep constructs was lower compared to the AAV2 rep gene construct. Nonetheless, the genome titer of ACG-R7V7 was comparable to ACG-R2V7. Thus, the packaging was better with ACG-R7V7.

Figure 14A:
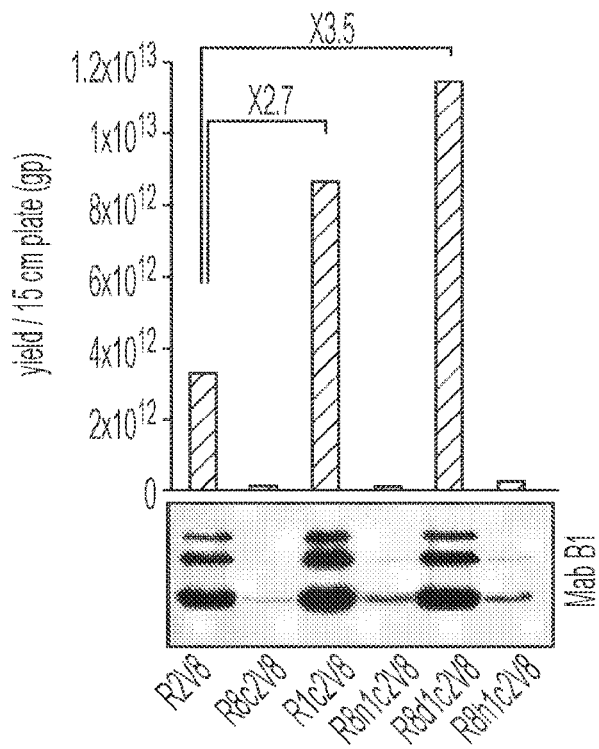
FIGS. 14A-14B provide characterization and optimization of the rep gene for AAV8 vector production.
Figure 14B:
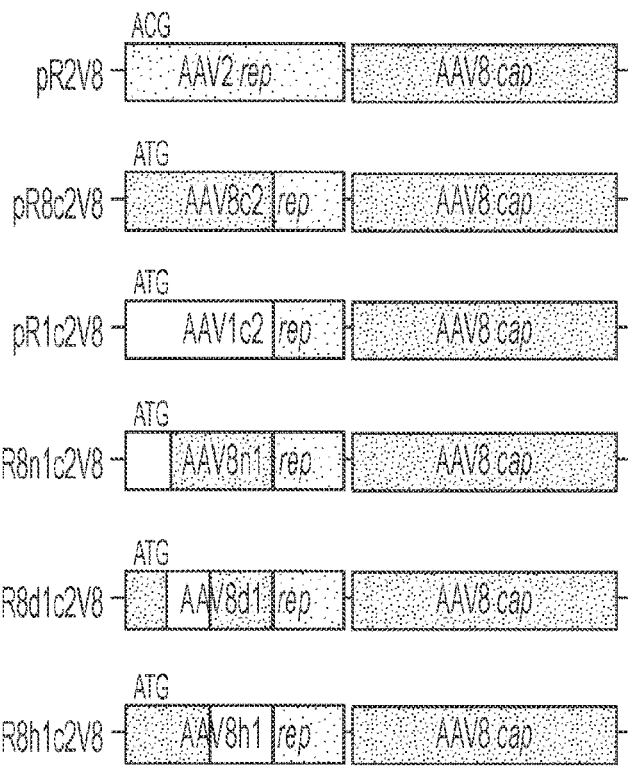

Swaps between the AAV1, AAV2, and AAV8 rep genes were generated to identify the domain responsible for improved genome packaging and to optimize the rep gene for AAV8 vector production (FIGS. 14A-14B). The DNA binding domain (DBD) appeared to play an important role for VP expression, as the substitution of the AAV8 DBD with the AAV1 DBD increased VP expression. The R1c2V8 and R8d1c2V8 hybrids/chimeras package vector genomes more efficiently into AAV8 capsids compared to the AAV2 rep gene. For these variants, the rep domains are defined as follows: n=N-terminus: aa 1-102, d=DNA-binding domain: aa 103-224, h=helicase domain: aa 225-372, c=C-terminus: aa 373-623.

The improvement in genome packaging of AAV8 particles using rep chimeras is shown in FIGS. 15A-15B. The utilization of the new rep chimeras R1c2 and R8d1c2 lead to higher percentages (3- to 4-fold) of genome containing particles.

FIGS. 16A-16B provide data for more rep chimeras to package AAV8 particles. It can be seen that the genome packaging is improved when the listed rep chimeras are used over AAV2 rep.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present application, and without departing from the spirit and scope thereof, can make various changes and modifications of the application to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present application are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present application.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B", the application also contemplates the alternative embodiments "a composition consisting of A and B" and "a composition consisting essentially of A and B".

What is claimed is:

1. A method for producing a recombinant adeno-associated virus (AAV) particle that comprises a gene of interest in a cell, the method comprising: contacting the cell with:
   (a) a first nucleic acid sequence comprising a rep gene that encodes a chimeric rep protein, wherein the rep gene comprises at least one nucleic acid sequence from a rep gene of a first AAV serotype and at least one nucleic acid sequence from a rep gene of a second AAV serotype, wherein the first AAV serotype and the second AAV serotype are different; and
   (b) a second nucleic acid sequence that comprises a gene of interest and an inverted terminal repeat (ITR),
   thereby producing the recombinant AAV particle comprising the gene of interest, wherein the first AAV serotype is AAV1 or AAV8 and wherein the second AAV serotype is AAV2.

2. The method of claim 1, wherein the at least one nucleic acid sequence from the rep gene of the first AAV serotype or the at least one nucleic acid sequence from the rep gene of the second AAV serotype encodes at least a portion of a domain selected from: a DNA binding domain, a helicase domain, a Nuclear Localization Signal domain/p40 promoter domain, and a zinc finger domain.

3. The method of claim 1, wherein the at least one nucleic acid sequence from the rep gene of the first AAV serotype or the at least one nucleic acid sequence from the rep gene of the second AAV serotype is a DNA binding domain or a zinc finger domain.

4. The method of claim 1, wherein the rep gene further comprises at least one nucleic acid sequence from a rep gene of a third AAV serotype, wherein the third AAV serotype is different from the first and the second AAV serotypes.

5. The method of claim 4, wherein the third AAV serotype is selected from the group consisting of: AAV1, AAV2, AAV3, AAV4, AAV5, AAV6, AAV7, AAV8, AAV9, AAV10, AAV11, AAV12, and AAV13, optionally wherein the third AAV serotype is AAV2.

6. The method of claim 4, wherein the first AAV serotype is AAV1, the second AAV serotype is AAV2, and the third AAV serotype is AAV8.

7. The method of claim 1, wherein the first AAV serotype is AAV1 and the second AAV serotype is AAV2.

8. The method of claim 1, wherein the first AAV serotype is AAV8 and the second AAV serotype is AAV2.

9. The method of claim 1, wherein the ITR is from the first AAV serotype or the second AAV serotype.

10. The method of claim 1, wherein the ITR is from a third AAV serotype that is different from the first AAV serotype and the second AAV serotype.

11. The method of claim 1, wherein the ITR is from AAV2 serotype.

12. The method of claim 1, wherein the first nucleic acid sequence further comprises at least a portion of a cap gene from the first AAV serotype or the second AAV serotype.

13. The method of claim 1, further comprising delivering the recombinant AAV particle comprising the gene of interest to a subject's cell.

* * * * *

SEQUENCE LISTING

```
Sequence total quantity: 199
SEQ ID NO: 1            moltype = DNA  length = 147
FEATURE                 Location/Qualifiers
source                  1..147
                        mol_type = other DNA
                        organism = synthetic construct
SEQUENCE: 1
ttgcccactc cctctctgcg cgctcgctcg ctcggtgggg cctgcggacc aaaggtccgc   60
agacggcaga gctctgctct gccggcccca ccgagcgagc gagcgcgcag agagggagtg  120
ggcaactcca tcactagggg taatcgc                                      147

SEQ ID NO: 2            moltype = DNA  length = 145
FEATURE                 Location/Qualifiers
source                  1..145
                        mol_type = other DNA
                        organism = synthetic construct
SEQUENCE: 2
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg  120
gccaactcca tcactagggg ttcct                                        145

SEQ ID NO: 3            moltype = DNA  length = 146
FEATURE                 Location/Qualifiers
source                  1..146
                        mol_type = other DNA
                        organism = synthetic construct
SEQUENCE: 3
tggccactcc ctctatgcgc actcgctcgc tcggtggggc ctggcgacca aaggtcgcca   60
gacggacgtg ctttgcacgt ccggccccac cgagcgagcg agtgcgcata gagggagtgg  120
ccaactccat cactagaggt atggca                                       146

SEQ ID NO: 4            moltype = DNA  length = 148
FEATURE                 Location/Qualifiers
source                  1..148
                        mol_type = other DNA
                        organism = synthetic construct
SEQUENCE: 4
ttggccactc cctctatgcg cgctcgctca ctcactcggc cctggagacc aaaggtctcc   60
agactgccgg cctctggccg gcagggccga gtgagtgagc gagcgcgcat agagggagtg  120
gccaactcca tcatctaggt ttgcccac                                     148

SEQ ID NO: 5            moltype = DNA  length = 176
FEATURE                 Location/Qualifiers
source                  1..176
                        mol_type = other DNA
                        organism = synthetic construct
SEQUENCE: 5
ctctcccccc tgtcgcgttc gctcgctcgc tggctcgttt gggggggtgg cagctcaaag   60
agctgccaga cgacggccct ctggccgtcg ccccccaaa cgagccagcg agcgagcgaa  120
cgcgacaggg gggagagtgc cacactctca agcaaggggg ttttgtaagc agtgat      176

SEQ ID NO: 6            moltype = DNA  length = 145
FEATURE                 Location/Qualifiers
source                  1..145
                        mol_type = other DNA
                        organism = synthetic construct
SEQUENCE: 6
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg  120
gccaactcca tcactagggg ttcct                                        145

SEQ ID NO: 7            moltype = DNA  length = 146
FEATURE                 Location/Qualifiers
```

```
source                  1..146
                        mol_type = other DNA
                        organism = synthetic construct
SEQUENCE: 7
ttggccactc cctctatgcg cgctcgctcg ctcggtgggg cctgcggacc aaaggtccgc    60
agacggcaga gctctgctct gccggcccca ccgagcgagc gagcgcgcat agagggagtg   120
gccaactcca tcactagggg taccgc                                        146

SEQ ID NO: 8            moltype = DNA  length = 1872
FEATURE                 Location/Qualifiers
source                  1..1872
                        mol_type = other DNA
                        organism = synthetic construct
SEQUENCE: 8
atgccgggct tctacgagat cgtgatcaag gtgccgagcg acctggacga gcacctgccg    60
ggcatttctg actcgtttgt gagctgggtg gccgagaagg aatgggagct gccccccggat  120
tctgacatgg atctgaatct gattgagcag gcacccctga ccgtgccgga gaagctgcag   180
cgcgacttcc tggtccaatg gcgccgcgtg agtaaggccc cggaggccct cttctttgtt   240
cagttcgaga agggcgagtc ctacttccac ctccatattc tggtggagac cacgggggtc   300
aaatccatgt tgctgggccg cttcctgagt cagattaggg acaagctggt gcagaccatc   360
taccgcggga tcgagccgac cctgcccaac tggttcgcgg tgaccaagac gcgtaatggc   420
gccggagggg ggaacaaggt ggtggacgag tgctacatcc ccaactacct cctgcccaag   480
actcagcccg agctgcagtg ggcgtggact aacatggagg agtatataag cgcctgtttg   540
aacctggccg agcgcaaacg gctcgtggcg cagcacctga cccacgtcag ccagacccag   600
gagcagaaca aggagaatct gaaccccaat tctgacgcgc tgtcatccg gtcaaaaacc   660
tccgcggct acatggacc ggtcgggtgg ctggtggaca gggcatcac ctccgagaag    720
cagtggatcc aggaggacca ggcctcgtac atctccttca acgccgcttc caactcgcgg   780
tcccagatca aggccgctct ggacaatgcc ggcaagatca tggcgctgac caaatccgcg   840
cccgactacc tggtaggccc cgctccgccc gcggacatta aaaccaaccg catctaccgc   900
atcctggagc tgaacggcta cgaacctgcc tacgccgatcc ccgtctttct cggctgtggc   960
cagaaaaggt tcgggaagcg caacaccatc tggctgtttg gccggccac cacggggcaag  1020
accaacatcg cggaagccat cgcccacgcc gtgcccttct acggctgcgt caactggacc  1080
aatgagaact tccccttcaa tgattgcgtc gacaagatgg tgatctggtg ggaggagggc  1140
aagatgacgg ccaaggttcgt ggagtccgcc aaggcattc tcggcggcag caaggtgcgc  1200
gtggaccaaa agtgcaagtc gtccgcccag atcgacccca ccccccgtgat cgtcacctcc  1260
aacaccaaca tgtgcgccgt gattgacggg aacagcacca ccttcgagca ccagcagccg  1320
ttgcaggacc ggatgttcaa atttgaactc accccgccgtc tggagcatga ctttggcaag  1380
gtgacaaagc aggaagtcaa agagttcttc cgctgggcgc aggatcacgt gaccgaggtg  1440
gcgcatgagt tctacgtcag aaagggtgga gccaacaaaa gacccgcccc cgatgacgcg  1500
gataaaagcg agcccaagcg ggcctgcccc tcagtcgcgg atccatcgac gtcagacgcg  1560
gaaggagctc cggtggactt tgccgacagg taccaaaaca aatgttctcg tcacgcgggc  1620
atgcttcaga tgctgtttcc ctgcaagaca tgcgagagaa tgaatcagaa tttcaacatt  1680
tgcttcacgc acgggacgag agactgttca gagtgcttcc ggcgtgtgc agaatctcaa  1740
ccggtcgtca gaaagaggac gtatcggaaa ctctgtgcca ttcatcatct gctggggcgg  1800
gctcccgaga ttgcttgctc ggcctgcgat ctggtcaacg tggacctgga tgactgtgtt  1860
tctgagcaat aa                                                       1872

SEQ ID NO: 9            moltype = DNA  length = 1866
FEATURE                 Location/Qualifiers
source                  1..1866
                        mol_type = other DNA
                        organism = synthetic construct
SEQUENCE: 9
atgccggggt tttacgagat tgtgattaag gtccccagcg accttgacgg gcatctgccc    60
ggcatttctg acagctttgt gaactgggtg gccgagaagg aatggagtt gccgccagat   120
tctgacatgg atctgaatct gattgagcag gcaccctga ccgtggccga gaagctgcag    180
cgcgactttc tgacggaatg gcgccgtgtg agtaaggccc cggaggccct tttctttgtg   240
caatttgaga agggagagag ctacttccac atgcacgtgc tcgtggaaac caccgggggtc  300
aaatccatgt tttgggacg tttcctgagt cagattcgcg aaaaactgat tcagagaatt   360
taccgcggga tcgagccgac tttgccaaac tggttcgcgg tcacaaagac cagaaatggc   420
gccggaggcg ggaacaaggt ggtggatgag tgctacatcc ccaattactt gctccccaaa   480
acccagcctg agctccagtg ggcgtggact aatatggaac agtatttaag cgcctgtttg   540
aatctcacgg agcgtaaacg gttggtggcg cagcatctga cgcacgtgtc gcagacgcag   600
gagcagaaca aagagaatca gaatcccaat tctgatgcgc cggtgatcag atcaaaaact   660
tcagccaggt acatggagct ggtcgggtgg ctcgtggaca gggggattac ctcggagaag   720
cagtggatcc aggaggacca ggcctcatac atctccttca tgcggcctc caactcgcgg   780
tcccaaatca aggctgcctt ggacaatgcg ggaaagatta tgagcctgac taaaaccgcc   840
cccgactacc tggtgggcca gcagcccgtg gaggacattt ccagcaatcg gatttataaa   900
attttggaac taaacgggta cgatcccaa tatgcggctc ccgtctttct gggatgggcc   960
acgaaaaagt tcggcaagag gaacaccatc tggctgtttg gcctgcaac taccgggaag  1020
accaacatcg cggaggccat agcccacact gtgcccttct acgggtgcgt aaactggacc  1080
aatgagaact ttcccttcaa cgactgtgtc gacaagatgg tgatctggtg ggaggagggg  1140
aagatgaccg ccaaggtcgt ggagtcggcc aaagccattc tcggaggaag caaggtcgc   1200
gtggacaagt ctcggccag atagaccgtg atccccgtgat cgtcacctcc              1260
aacaccaaca tgtgcgccgt gattgacggg aactcaacga ccttcgaaca ccagcagccg  1320
ttgcaagacc ggatgttcaa atttgaactc accccgccgtc tggatcatga ctttgggaag  1380
gtcaccaagc aggaagtcaa agacttttttc cggtgggcaa aggatcacgt ggttgaggtg  1440
gagcatgaat tctacgtcaa aaagggtgga gccaagaaaa gacccgcccc cagtgacgca  1500
gatataagtg agcccaaacg ggtgcgcgag tcagttcgcg agccatcgac gtcagacgcg  1560
```

```
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                              1866

SEQ ID NO: 10           moltype = DNA  length = 1875
FEATURE                 Location/Qualifiers
source                  1..1875
                        mol_type = other DNA
                        organism = synthetic construct
SEQUENCE: 10
atgccggggt tctacgagat tgtcctgaag gtcccgagtg acctggacga gcacctgccg    60
ggcatttcta actcgtttgt taactgggtg gccgagaagg aatgggagct gccgccggat   120
tctgacatgg atccgaatct gattgagcag gcaccctga ccgtggccga aaagcttcag    180
cgcgagttcc tggtggagtg gcgccgcgtg agtaaggccc ggaggccct cttttttgtc    240
cagttcgaaa aggggagac ctacttccac ctgcacgtgc tgattgagac catcgggtc     300
aaatccatgg tggtcggccg ctacgtgagc cagattaaag agaagctggt gacccgcatc   360
taccgcgggg tcgagccgca gcttccgaac tggttcgcgg tgaccaaaac gcgaaatggc   420
gccggggcg ggaacaaggt ggtggacgac tgctacatcc ccaactacct gctccccaag    480
acccagcccg agctccagtg ggcgtaggact aacatgacc agtatttaag cgcctgtttg   540
aatctcgcgg agcgtaaacg gctggtggcg cagcatctga cgcacgtgtc gcagacgcag   600
gagcagaaca agagaatca gaaccccaat tctgacgcgc cggtcatcag gtcaaaaacc    660
tcagccaggt acatggagct ggtcgggtgg ctggtggacc gcgggatcac gtcagaaaag   720
caatggattc aggaggacca ggcctcgtac atctccttca cgccgcctc caactcgcgg    780
tcccagatca aggccgcgct ggacaatgcc tccaagatca tgagcctgac aaagacggct   840
ccggactacc tggtgggcag caacccgccg gaggacatta ccaaaaatcg gatctaccaa   900
atcctggagc tgaacgggta cgatccgcag tacgcggcct ccgtcttcct gggctggggc   960
caaaagaagt tcgggaagag gaacaccatc tggctctttg ggccggccac gacgggtaaa  1020
accaacatcg cggaagccat cgcccacgcc gtgcccttct acggctgcgt aaactggacc  1080
aatgagaact ttcccttcaa cgattgcgtc gacaagatgg tgatctggtg ggaggagggc  1140
aagatgacgg ccaaggtcgt ggagagcgcc aaggccattc tgggcggaag caaggtgcgc  1200
gtggaccaaa agtgcaagtc atcggcccag atcgaaccca ctcccgtgat cgtcacctcc  1260
aacaccaaca tgtgcgcggt gattgacggg aacagcacca ccttcgagca tcagcagccg  1320
ctgcaggacc ggatgtttaa atttgaactt acccgccgtt tggaccatga ctttgggaag  1380
gtcaccaaac aggaagtaaa ggacttttc cggtgggctt ccgatcacgt gactgacgtg   1440
gctcatgagt tctacgtcag aaaggtgga gctaagaaac gccccgcctc caatgacgcg   1500
gatgtaagcg agccaaaacg gcagtgcacg tcacttgcag atcgacaaac gtcagacgcg  1560
gaagcaccgg cggactacgc ggacaggtac caaaacaaat gttctcgtca cgtgggcatg  1620
aatctgatgc ttttttccctg taaaaacatgc gagagaatga atcaaatttc caatgtctgt  1680
tttacgcatg gtcaaagaga ctgtggggaa tgcttccctg gaatgtcaga atctcaaccc  1740
gtttctgtcg tcaaaaagaa gacttatcag aaactgtgtc caattcatca tatcctggga  1800
agggcacccg agattgcctg ttcggcctgc gatttggcca atgtggactt ggatgactgt  1860
gtttctgagc aataa                                                  1875

SEQ ID NO: 11           moltype = DNA  length = 1872
FEATURE                 Location/Qualifiers
source                  1..1872
                        mol_type = other DNA
                        organism = synthetic construct
SEQUENCE: 11
atgccggggt tctacgagat cgtgctgaag gtgcccagcg acctggacga gcacctgccc    60
ggcatttctg actcttttgt gagctgggtg gccgagaagg aatgggagct gccgccggat   120
tctgacatgg acttgaatct gattgagcag gcaccccctga ccgtggccga aaagctgcaa   180
cgcgagttcc tggtcgagtg gcgccgcgtg agtaaggccc ggaggccct cttctttgtc    240
cagttcgaga aggggacag ctacttccac ctgcacatcc tggtggagac cgtgggcgtc    300
aaatccatgg tggtgggccg ctacgtgagc cagattaaag agaagctggt gacccgcatc   360
taccgcgggg tcgagccgca gcttccgaac tggttcgcgg tgaccaagac gcgtaatggc   420
gccggaggcg ggaacaaggt ggtggacgac tgctacatcc ccaactacct gctccccaag   480
acccagcccg agctccagtg ggcgtggact aacatgacc agtatataag cgcctgtttg   540
aatctcgcgg agcgtaaacg gctggtggcg cagcatctga cgcacgtgtc gcagacgcag   600
gagcagaaca aggaaaacca gaaccccaat tctgacgcgc cggtcatcag gtcaaaaacc    660
tccgccaggt acatggagct ggtcgggtgg ctggtggacc gcgggatcac gtcagaaaag   720
caatggatcc aggaggacca ggcgtcctac atctccttca cgccgcctc caactcgcgg    780
tcacaaatca aggccgcgct ggacaatgcc tccaaaatca tgagcctgac aaagacggct   840
ccggactacc tggtgggcca gaacccgccg gaggacattt ccagcaaccg catctaccga   900
atcctcgaga tgaacgggta cgatccgcag tacgcggcct ccgtcttcct gggctggggc   960
caaaagaagt tcgggaagag gaacaccatc tggctctttg gccggccac gacgggtaaa   1020
accaacatcg cggaagccat cgcccacgcc gtgcccttct acggctgcgt gaactggacc  1080
aatgagaact ttccgttcaa cgattgcgtc gacaagatgg tgatctggtg ggaggagggc  1140
aagatgacgg ccaaggtcgt agagagcgcc aaggccatcc tgggcggaag caaggtgcgc  1200
gtggaccaaa agtgcaagtc atcggcccag atcgacccaa ctcccgtgat cgtcacctcc  1260
aacaccaaca tgtgcgcggt catcgacgga aactcgacca ccttcgagca ccaacaacca  1320
ctccaggacc ggatgttcaa gttcgagctc accagcctgg tggagcacga ctttggcaag  1380
gtcaccaagc aggaagtcaa agactttttc cggtgggcgt cagatcacgt gaccgaggtg  1440
actcacgagt tttacgtcag aaaggtgga gctaagaaga gccccgcccc caatgacgca  1500
gatataagtg agcccaagcg ggcctgtccg tcagttgcgc agccatcgac gtcagacgcg  1560
gaagctccgg tggactacgc ggacaggtac caaaacaaat gttctcgtca cgtgggtatg  1620
```

```
aatctgatgc ttttccctg ccggcaatgc gagagaatga atcagaatgt ggacatttgc   1680
ttcacgcacg gggtcatgga ctgtgccgag tgcttccccg tgtcagaatc tcaacccgtg   1740
tctgtcgtca gaaagcggac gtatcagaaa ctgtgtccga ttcatcacat catggggagg   1800
gcgcccgagg tggcctgctc ggcctgcgaa ctggccaatg tggacttgga tgactgtgac   1860
atggaacaat aa                                                      1872

SEQ ID NO: 12           moltype = DNA  length = 1833
FEATURE                 Location/Qualifiers
source                  1..1833
                        mol_type = other DNA
                        organism = synthetic construct
SEQUENCE: 12
atggctacct tctatgaagt cattgttcgc gtcccatttg acgtggagga acatctgcct   60
ggaatttctg acagctttgt ggactgggta actggtcaaa tttggagct gcctccagag    120
tcagatttaa atttgactct ggttgaacag cctcagttga cggtggctga tagaattcgc   180
cgcgtgttcc tgtacgagtg gaacaaattt tccaagcagg agtccaaatt ctttgtgcag   240
tttgaaaagg gatctgaata ttttcatctg cacacgcttg tggagacctc cggcatctct   300
tccatggtcc tcggccgcta cgtagtcag attcgcgccc agctgtgtga agtggtcttc   360
cagggaattg aaccccagat caacgactgg gtcgccatcc ccaaggtaaa gaagggcgga   420
gccaataagg tggtggattc tgggtatatt cccgcctacc tgctgccgaa ggtccaaccg   480
gagcttcagt gggcgtggac aaacctggac gagtataaat tggccgccct gaatctggag   540
gagcgcaaac ggctcgtcgc gcagtttctg gcagaatcct cgcagcgctc gcaggaggcg   600
gcttcgcagc gtgagttctc ggctgacccg gtcatcaaaa gcaagacttc ccagaaatac   660
atggcgctcg tcaactggct cgtgagcac ggcatcactt ccgagaagca gtggatccag    720
gaaaatcagg agagctacct ctccttcaac tccaccggca actctcggag ccagatcaag   780
gccgcgctcg acaacgcgac caaaattatg agtctgacaa aaagcgcggt ggactacctc   840
gtggggagct ccgttcccga ggacatttca aaaaacagaa tctggcaaat ttttgagatg   900
aatggctacg acccggccta cgcgggatcc atcctctacg ctggtgtca cgctccttc     960
aacaagagga caccgtctg gctctacgga cccgccacga ccggcaagac caacatcgcg    1020
gaggccatcg cccacactgt gcccttttac ggctgcgtga gggaccaa tgaaaacttt     1080
cccttaatg actgtgtgga caaaatgctc atttggtggg aggagggaaa gatgaccaac    1140
aaggtggtta atccgccaa ggccatcctg gggggctcaa aggtgcgggt cgatcagaaa    1200
tgtaaatcct ctgttcaaat tgattctacc cctgtcattg taacttccaa tacaaacatg   1260
tgtgtggtgg tggatgggaa ttccacgacc tttgaacacc agcagccgct ggaggaccgc   1320
atgttcaaat ttgaactgac taagcggctc ccgccagatt ttggcaagat tactaagcag   1380
gaagtcaagg acttttttgc ttgggcaaag gtcaatcagg tgccggtgac tcacgagttt   1440
aaagttccca gggaattggc gggaactaaa ggggcggaga atctctaaa acgcccactg    1500
ggtgacgtca ccaatactag ctataaaagt ctggagaagc gggccaggct ctcatttgtt   1560
cccgacagcc ctcgcagttc agacgtgact gttgatccgg ctcctctgcg accgctcaat   1620
tggaattcaa ggtatgattg caaatgtgac tatcatgcctc aatttgacaa catttctaac   1680
aaatgtgatg aatgtgaata tttgaatcgg ggcaaaaatg gatgtatctg tcacaatgta   1740
actcactgtc aaatttgtca tgggattccc cctgggaaa aggaaaactt gtcagatttt    1800
gggattttg acgatgccaa taagaacag taa                                  1833

SEQ ID NO: 13           moltype = DNA  length = 1872
FEATURE                 Location/Qualifiers
source                  1..1872
                        mol_type = other DNA
                        organism = synthetic construct
SEQUENCE: 13
atgccggggt tttacgagat tgtgattaag gtccccagcg accttgacga gcatctgccc   60
ggcatttctg acagctttgt gaactggggtg gccgagaagg aatgggagtt gccgccagat  120
tctgacatgg atctgaatct gattgagcag gcacccctga ccgtggccga aagctgcag    180
cgcgacttcc tggtccagtg gcgccgcgtg agtaaggccc cggaggccct cttctttgtt   240
cagttcgaga agggcagtc ctacttccac ctccatattc cacggggggtc                300
aaatccatgg tgctgggccg cttcctgagt cagattaggg acaagctggt gcagaccatc   360
taccgcggga tcgagccgac cctgcccaac tggttcgcgg tgaccaagac gcgtaatggc   420
gccgaggggg gaacaaggt ggtggacgag tgctacatcc ccaactacct cctgcccaag    480
actcagcccg agctgcagtg ggcgtggaca aacatggagg agtataaag cgcgtgttta   540
aacctggccg agcgcaaacg gctcgtggcg cacgacctga cccacgtcag ccagaccccag  600
gagcagaaca aggagaatct gaaccccaat tctgacgcgc ctgtcatccg gtcaaaaacc   660
tccgcacgct acatggagct ggtcgggtgg ctggtggacc gggcatcac ctccgagaag    720
cagtggatcc aggaggacca ggcctcgtac atctccttca acgccgcctc caactcgcgg   780
tccagatca aggccgctct ggacaatgcc ggcaagatca tggcgctgac caaatccgcg   840
cccgactacc tggtaggccc cgctccgccc gccgacatta aaaccaaccg catttaccgg   900
atcctggagc tgaacggcta cgaccctgcc tacgccggct ccgtcttcct cggctgggcc   960
cagaaaaggt tcgaaaaacg caacaccatc tggctgtttg gccgccac cacgggcaag    1020
accaacatcg ggaagccat cgcccacgcc gtgccttcc acggctgcgt caactggacc    1080
aatgagaact ttccccttcaa cgattgcgtc gacaagatgg tgatctgtg ggaggagggc   1140
aagatgacgg ccaaggtcgt ggagtccgcc aaggccattc tcggcggcag caaggtgcgc   1200
gtggaccaaa agtgcaagtc gtccgcccag atcgatccca cccccgtgat cgtcacctcc   1260
aacaccaaca tgtgcgccgt gattgacggg aacagcacca ccttcgagca ccagcagccg   1320
ttgcaggacc ggatgttcaa atttgaactc acccgccgtg tggagcatga cttggcaag    1380
gtgacaagga aagtcaa agagttcttc gctgggcag aggatcacgt gaccgaggtg        1440
gcgcatgagt tctacgtcag aaaggggtgga gccaacaaga gacccgcccc cgatgacgtg   1500
gataaaagcg agcccaagcg ggcctgcccc tcagtcgcgg atccatcgac gtcagacgcg   1560
gaaggagctc cggtggactt tgccgacagg taccaaaca aatgttctcg tcacgcgggc    1620
atgcttcaga tgctgtttcc ctgcaaaaca tgcgagagaa tgaatcagaa tttcaacatt   1680
tgcttcacgc acgggaccag agactgttca gaatgttttcc ccggcgtgtc agaatctcaa   1740
```

```
ccggtcgtca gaaagaggac gtatcggaaa ctctgtgcca ttcatcatct gctggggcgg   1800
gctcccgaga ttgcttgctc ggcctgcgat ctggtcaacg tggatctgga tgactgtgtt   1860
tctgagcaat aa                                                        1872

SEQ ID NO: 14           moltype = DNA  length = 1872
FEATURE                 Location/Qualifiers
source                  1..1872
                        mol_type = other DNA
                        organism = synthetic construct
SEQUENCE: 14
atgccgggtt tctacgagat cgtgatcaag gtgccgagcg acctggacga gcacctgccg   60
ggcatttctg actcgtttgt gaactgggtg gccgagaagg aatgggagct gcccccggat   120
tctgacatgg atctgaatct gatcgagcag gcaccctga ccgtggccga aagctgcag    180
cgcgacttcc tggtccaatg gcgccgcgtg agtaaggccc cggaggccct gttctttgtt   240
cagttcgaga agggcgagag ctacttccac cttcacgttc tggtggagac cacggggggtc   300
aagtccatgg tgctaggccg cttcctgagt cagattcggg agaagctggt ccagaccatc   360
taccgcgggg tcgagcccac gctgcccaac tggttcgcgg tgaccaagac gcgtaatggc   420
gccgggcggg ggaacaaggt ggtggacgag tgctacatcc ccaactacct cctgcccaag   480
acccagcccg agctgcagtg ggcgtggact aacatggagg agtatataag cgcgtgtttg   540
aacctggccg aacgcaaacg gctcgtggcg cagcacctga cccacgtcag ccagacgcag   600
gagcagaaca aggagaatct gaaccccaat tctgacgcgc ccgtgatcag gtcaaaaacc   660
tccgcgcgct acatggacc ggtcgggtgg ctggtggaca gcgatcac ctccgagaag     720
cagtggatcc aggaggacca ggcctcgtac atctccttca acgccgcctc caactcgcgg   780
tcccagatca aggccgcgct ggacaatgcc ggcaagatca tggcgctgac caaatccgcg   840
cccgactacc tggtggggcc ctcgctgccc gcggacatta aaaccaaccg catctaccgc   900
atcctggagc tgaacgggta cgatcctgcc tacgccgctc ccgtctttct cggctgggcc   960
cagaaaaagt tcgggaagcg caacaccatc tggctgtttg gcccgccac accggcaag  1020
accaacattg cggaagccat cgcccacgcc gtgcccttct acggctgcgt caactggacc   1080
aatgagaact ttcccttcaa cgattgcgtc gacaagatgg tgatctggtg ggaggagggc   1140
aagtgacgg ccaaggtcgt ggagtccgcc aaggccattc tcggcggcag caaggtgccg    1200
gtggaccaaa agtgcaagtc gtccgcccag atcgacccca ccccgtgat cgtcacctcc   1260
aacaccaaca tgtgcgccgt gattgacggg aacagcacca cttcgagca ccagcagccg   1320
ttgcaggacc ggatgttcaa atttgaactc accgccgtc tggagcacga ctttggcaag   1380
gtgacgaagc aggaagtcaa agagttcttc cgctgggcca gtgatcacgt gaccgaggtg   1440
gcgcatgagt tctacgtcag aaagggcgga gccagcaaaa gacccgcccc cgatgacgcg  1500
gatataagcg agcccaagcg ggcctgcccc tcagtcgcgg atccatcgac gtcagacgcg   1560
gaaggagctc cggtggactt tgccgacagg taccaaaaca aatgttctcg tcacgcgggc   1620
atgattcaga tgctgtttcc ctgcaaaacg tgcgagagaa tgaatcagaa tttcaacatt   1680
tgcttcacac acggggtcag agactgtta gagtgtttcc ccggcgtgtc agaatctcaa   1740
ccggtcgtca gaaaaaagac gtatcggaaa ctctgcgcga ttcatcatct gctggggcgg   1800
gcgcccgaga ttgcttgctc ggcctgcgac ctggtcaacg tggatctgga cgactgcgtt   1860
tctgagcaat aa                                                        1872

SEQ ID NO: 15           moltype = DNA  length = 1878
FEATURE                 Location/Qualifiers
source                  1..1878
                        mol_type = other DNA
                        organism = synthetic construct
SEQUENCE: 15
atgccgggct tctacgagat cgtgatcaag gtgccgagcg acctggacga gcacctgccg   60
ggcatttctg actcgtttgt gaactgggtg gccgagaagg aatgggagct gcccccggat   120
tctgacatgg atcggaatct gatcgagcag gcaccctga ccgtggccga aagctgcag    180
cgcgacttcc tggtccaatg gcgccgcgtg agtaaggccc cggaggccct cttctttgtt   240
cagttcgaga agggcgagag ctactttcac ctgcacgttc tggtcgagac cacggggggtc   300
aagtccatgg tgctaggccg cttcctgagt cagattcggg aaaagcttgg tccagaccat   360
ctaccgcgg gtcgagccc accttgccc aactggttcg cggtgaccaa agacgcgta      420
atggcgccgg cggggggaa caaggtggtg gacgagtgct acatcccaa ctacctcctg   480
cccaagactc agcccgagct gcagtgggcg tggactaaca tggaggagta tataagcgcg   540
tgcttgaacc tggccgagcg caaacggctc gtggcgcagc acctgaccca cgtcaggtca   600
acgcaggagc agaacaagga gaatctgaac cccaattctg acgcgcccgt gatcaggtca   660
aaaacctccg cgcgctatat ggagctggtc gggtggctgg tggaccgggg catcacctcc   720
gagaagcagt ggatccagga ggaccaggcc tcgtacatct ccttcaacgc cgcctccaac   780
tcgcggtccc agatcaaggc cgcgctggac aatgccggca agatcatggc gctgaccaaa   840
tccgcccccg actacctggt ggggccctcg ctcccgcgg acattaccca gaaccgcatc    900
taccgcatcc tcgctctcaa cggctacgac cctgcctacg ccggctccgt ctttctcggc   960
tgggctcaga aaagttcgg gaacgcaac accatctggc tgtttggacc cgccaccacc   1020
ggcaagacca cattgcgga agccatcgcc acgccgtgc ccttctacgg ctgcgtcaac    1080
tggaccaatg agaactttcc cttcaatgat tgcgtcgaca agatggtgat ctggtgggag   1140
gagggcaaga tgacggccaa ggtcgtggag tccgccaagg ccattctcgg cggcagcaag   1200
gtgcgcgtgg accaaaagtg caagtcgtcc gcccagatcg accccacccc cgtgatcgtc   1260
acctccaaca ccaacatgtg cgccgtgatt gacgggaaca gcaccacctt cgagcaccag   1320
cagcctctcc aggaccggat gtttaagttc gaactcaccc gccgtctgga gcacgacttt   1380
ggcaaggtgc aaagcaggaa gtcaaagag ttcttccgct gggccagtga tcacgtgacc    1440
gaggtggcgc atgagtttta cgtcagaaag gccgagcca aaagacccgcccccgat      1500
gacgcggata aaagcgagcc caagcggccc tgccctcag tcgcggatcc atcgacgtca    1560
gacgcggaag gagctccggt ggactttgcc gacaggtacc aaaacaaatg ttctcgtcac   1620
gcgggcatgt tcagatgct gtttccctgc aaaacgtgcg agagaatgaa tcagaatttc   1680
aacatttgct tcacacacgg ggtcagagac tgctcagagt gtttcccggc gtgtcagaa   1740
tctcaaccgg tcgtcagaaa gaggacgtat cggaaactct gtgcgattca tcatctgctg   1800
```

```
gggcgggctc ccgagattgc ttgctcggcc tgcgatctgg tcaacgtgga cctggatgac    1860
tgtgtttctg agcaataa                                                  1878

SEQ ID NO: 16         moltype = DNA   length = 1878
FEATURE               Location/Qualifiers
source                1..1878
                      mol_type = other DNA
                      organism = synthetic construct
SEQUENCE: 16
atgccgggct tctacgagat cgtgatcaag gtgccgagcg acctggacga gcacctgccg     60
ggcatttctg actcgtttgt gaactgggtg gccgagaagg aatgggagct gccccccggat   120
tctgacatgg atcggaatct gatcgagcag gcacccctga ccgtggccga gaagctgcag    180
cgcgacttcc tggtccaatg gcgccgcgtg agtaaggccc ggaggccct cttctttgtt    240
cagttcgaga agggcgagag ctactttcac ctgcacgttc tggtcgagac cacgggggtc    300
aagtccatgg tgctaggccg cttcctgagt cagattcggg aaaagcttgg tccagaccat    360
ctacccgcgg ggtcgagccc caccttgccc aactggttcg cggtgaccaa agacgcggta    420
atggcgccgs cgggggggaa caaggtggtg gacgagtgct catcccccaa ctacctcctg    480
cccaagactc agcccgacct gcagtgggcg tggactaaca tggaggagta tataagcgcg    540
tgcttgaacc tggccgagcg caaacgcgtc gtgcgcagc acctgaccca cgtcagccag    600
acgcaggagc agaacaagga gaatctgaac cccaattctg acgcgcccgt gatcaggtca    660
aaaacctccg cgcgctatat ggagctggtc gggtggctgg tggaccgggg catcacctcc    720
gagaagcagt ggatccagga ggaccaggcc tcgtacatct ccttcaacgc cgcctccaac    780
tcgcggtccc agatcaaggc cgcgctggac aatgccggca agatcatggc gctgaccaaa    840
tccgcgcccc actaccggt gggccctcg ctgccgcgg acattcccca gaaccgcatc      900
taccgcatcc tcgctctcaa cggctacgac cctgcctacg ccggctccgt ctttctcggc    960
tgggctcaga aaagttcgg gaaacgcaac accatctcgc tgtttggacc cgccaccacc   1020
ggcaagacca acattgcgga agccatcgcc cacgccgtgc ccttctacgg ctgcgtcaac   1080
tggaccaatg agaactttcc cttcaatgat tgctgtcgaca agatggtgat ctggtgggag   1140
gagggcaaga tgacggccaa ggtcgtggag tccgccaagg ccattctcgg cggcagcaag   1200
gtgcgcgtgg accaaaagtg caagtcgtcc gcccagatcg acccccacccc cgtgatcgtc   1260
acctccaaca ccaacatgtg cgccgtgatt gacgggaaca gcaccacctt cgagcaccag   1320
cagcctctcc aggaccggat gtttaagttc gaactcaccc gccgtctgga gcacgacttt   1380
ggcaaggtga caaagcagga agtcaaagag ttcttccgct gggccagtga tcacgtgacc   1440
gaggtggcgc atgagtttta cgtcagaaag ggcggagcca gcaaaagacc cgcccccgat   1500
gacgcggata aaagcgagcc caagcgggcc tgccctcag tcgccggatcc atcgacgtca   1560
gacgcggaag gagctccggt ggactttgcc gacaggtacc aaaacaaatg ttctcgtcac   1620
gcgggcatgc ttcagatgct gtttccctgc aaaacgtgcg agagaatgaa tcagaatttc   1680
aacatttgct tcacacacgg ggtcagagac tgctcagagt gttttccccgg cgtgtcagaa   1740
tctcaaccgg tcgtcagaaa gaggacgtat cggaaactct gtgcgattca tcatctgctg   1800
gggcgggctc ccgagattgc ttgctcggcc tgcgatctgg tcaacgtgga cctggatgac   1860
tgtgtttctg agcaataa                                                 1878

SEQ ID NO: 17         moltype = DNA   length = 1869
FEATURE               Location/Qualifiers
source                1..1869
                      mol_type = other DNA
                      organism = synthetic construct
SEQUENCE: 17
atgccgggct tctacgagat cgtgatcaag gtgccgagcg acctggacga gcacctgccg     60
ggcatttctg actcgtttgt gaactgggtg gccgagaagg aatgggagct gccccccggat   120
tctgacatgg atcggaatct gatcgagcag gcacccctga ccgtggccga gaagctgcag    180
cgcgacttcc tggtccactg gcgccgcgtg agtaaggccc ggaggccct cttctttgtt    240
cagttcgaga agggcgagtc ctactttcac ctgcacgttc tggtcgagac cacgggggtc    300
aagtccatgg tcctgggccg cttcctgagt cagatcagag acaggctggt gcagaccatc    360
taccgcgggg tagagcccac gctgcccaac tggttccgtg tgaccaagac gcgaaatgcc    420
gccggcgggg ggaacaaggt ggtggacgag tgctacatcc ccaactacct cctgcccaag    480
acgcagcccg agctgcagtg ggcgtggact aacatggagg agtatataag cgcgtgtctg    540
aacctcgcgg agcgtaaacg gctcgtggcg cagcacctga cccacgtcag ccagacgcag    600
gagcagaaca aggagaatct gaacccgaat tctgacgcgc ccgtgatcag gtcaaaaacc    660
tccgcgcgct acatggagct ggtcgggtgg ctggtgaccg ggcatcac ctccgagaag     720
cagtggatcc aggaggacca ggcctcgtac atctccttca cgccgcctc caactcgcgg    780
tcccagatca aggccgcgct ggacaatgcc ggaaagatca tggcgctgac caaatccgcg    840
cccgactacc tggtaggccc gtccttaccc gcggacatta aggccaaccg catctaccgc    900
atcctggagc tcaacggcta cgacccccgc tacgccgctc ccgtcttcct gggctgggcg    960
cagaaaaagt tcggtaaaag gaatacaatt tggctgttcg gcccgccac accggcaag    1020
accaacatcg cggaagccat cgcccacgcc gtgcccttct acggctgcgt caactggacc   1080
aatgagaact ttcccttcaa cgattgcgtc gacaagatgt tgatctggtg ggaggagggc   1140
aagatgacca ccaaggtcgt ggagtccgcc aaggcattc ggggcggaag caaggtgcgc   1200
gtcgaccaaa agtgcaagtc ctcggccag atcgacccca cccgtgat cgtcacctcc    1260
aacaccaaca tgtgcgccgt gatcgacggg aacagcacca cttcgagca ccagcagccc   1320
ctgcaggacc gcatgttcaa gttcgagctc ccggccgtc tggagcacga ctttggcaag    1380
gtgaccaagc aggaagtcaa agagttcttc cgctgggctc aggatcacgt gactgaggtg   1440
acgcatgagt tctacgtcag aaagggcgga gccaccaaaa gacccgcccc cagtgacgcg   1500
gataataagc agcccaagcg ggcctgcccc tcagttgcgg agcatcgac gtcagacgcg   1560
gaagcaccgg tggactttgc ggacaggtac aaaacaaat gttctcgtca cgcgggcatg   1620
cttcagatgc tgtttccctg caagacatgc gagagaatga atcagaattt caacgtctgc   1680
ttcacgcacg gggtcagaga ctgctcagag tgcttccccg cgcgtcaga atctcaacct    1740
gtcgtcagaa aaaagacgta tcagaaactg tgcgcgattc atcatctgct ggggcgggca   1800
cccgagattg cgtgttcggc ctgcgatctc gtcaacgtgg acttggatga ctgtgtttct   1860
```

```
gagcaataa                                                          1869

SEQ ID NO: 18          moltype = DNA  length = 1869
FEATURE                Location/Qualifiers
source                 1..1869
                       mol_type = other DNA
                       organism = synthetic construct
SEQUENCE: 18
atgccgggct tctacgagat cgtgatcaag gtgccgagcg acctggacga gcacctgccg   60
ggcatttctg actcgtttgt gaactgggtg gccgagaagg aatgggagct gcccccggat   120
tctgacatgg atcggaatct gatcgagcag gcacccctga ccgtggccga gaagctgcag   180
cgcgacttcc tggtccactg gcgccgcgtg agtaaggccc ggaggccct cttctttgtt    240
cagttcgaga agggcgagtc ctacttccac ctccacgttc tcgtcgagac cacggggtc    300
aagtccatgg tcctgggccg cttcctgagt cagatcagac acggctggt cagaccatc    360
taccgcgggg tcgagcccac gctgcccaac tggttcgcgg tgaccaagac gcgaaatggc   420
gccggcgggg gaacaaggt ggtggacgag tgctacatcc caactacct cctgcccaag    480
acccagcccg agctgcagtg ggcgtggact aacatggagg agtatataag cgcgtgtcta   540
aacctcgcgg agcgtaaacg gctcgtggcg cagcacctga cccacgtcag ccagacgcag   600
gagcagaaca aggagaatct gaacccgaat tctgacgcgc ccgtgatcag gtcaaaaacc   660
tccgcgcgct acatggagct ggtcgggtgg ctggtggacc ggggcatcac ctccgagaag   720
cagtggatcc aggaggacca ggcctcgtac atctccttca acgccgcctc caactcgcgg   780
tcccagatca aggccgcgct ggacaatgcc ggaaagatca tggcgctgac caaatccgcg   840
cccgactacc tggtaggccc gtccttaccc gcggacatta aggccaaccg catctaccgc   900
atcctggagc tcaacggcta cgaccccgcc tacgccggct ccgtcttcct gggctgggcg   960
cagaaaaagt tcggtaaacg caacaccatc tggctgtttg ggcccgccac caccggcaag   1020
accaacatcg cggaagccat agcccacgcc gtgcccttct caactggctg gaactggacc   1080
aatgagaact ttcccttcaa cgattgcgtc gacaagatgg tgatctggtg ggaggagggc   1140
aagatgaccg ccaaggtcgt ggagtccgcc aaggccattc tgggcggaag caaggtgcgc   1200
gtggaccaaa agtgcaagtc ctcggcccag atcgaccccc cgcccgtgat cgtcacctcc   1260
aacaccaaca tgtgcgccgt gatcgacggg aacagcacca ccttcgagca ccagcagccg   1320
ctgcaggacc gcatgttcaa gttcgagctc acccgccgtc tggagcacga ctttggcaag   1380
gtgaccaagc aggaagtcaa agagttcttc cgctgggctc aggatcacgt gactgaggtg   1440
gcgcatgagt tctacgtcag aaagggcgga gccaccaaaa gacccgcccc cagtgacgcg   1500
gatataagcg agcccaagcg ggcctgcccc tcagttccgg agccatcgac gtcagacgcg   1560
gaagcaccgg tggactttgc ggacaggtac caaaacaaat gttctcgtca cgcgggcatg   1620
cttcagatgc tgtttccctg caagacatgc gagagaatga atcagaattt caacgtctgc   1680
ttcacgcacg gggtcagaga ctgctcagag tgcttccccg cgcgtcaga atctcaaccc    1740
gtcgtcagaa aaaagacgta tcagaaactg tgcgcgattc atcatctgct ggggcgggca   1800
cccgagattg cgtgttcggc ctgcgatctc gtcaacgtgg acttggatga ctgtgtttct   1860
gagcaataa                                                          1869

SEQ ID NO: 19          moltype = DNA  length = 1866
FEATURE                Location/Qualifiers
source                 1..1866
                       mol_type = other DNA
                       organism = synthetic construct
SEQUENCE: 19
atgccggggt tctacgaggt ggtgatcaag gtgcccagcg acctggacga gcacctgccc   60
ggcatttctg actcctttgt gaactgggtg gccgagaagg aatgggagtt gcccccggat   120
tctgacatgg atcagaatct gattgagcag gcacccctga ccgtggccga gaagctgcag   180
cgcgagttcc tggtgaatg gcgccgagtg agtaaattc tggaggccaa gttttttgtg     240
cagtttgaaa agggggactc gtactttcat ttgcatattc tgattgaaat taccggcgtg    300
aaatccatgg tggtgggccg ctacgtgagt cagattaggg ataaactgat ccagcgcatc   360
taccgcgggg tcgagcccca gctgcccaac tggttcgcgg tcacaaagac ccgaaatggc   420
gccggaggcg ggaacaaggt ggtggacgag tgctacatcc caactacct gctccccaag    480
gtccagcccg agcttcagtg ggcgtggact aacatggagg agtatataag cgcctgtttg   540
aacctcgcgg agcgtaaacg gctcgtggcg cagcacctga cgcacgtctc ccagacccag   600
gagggcgaca aggagaatct gaacccgaat tctgacgcgc cggtgatccg gtcaaaaacc   660
tccgccaggt acatggagct ggtcgggtgg ctggtggaca agggcatcac gtccgagaag   720
cagtggatcc aggaggacca ggcctcgtac atctccttca acgcggcctc caactcccgg   780
tcgcagatca aggcggccct ggacaatgcc tccaaaatca tgagcctcac caaaacggct   840
ccggactatc tcatcgggca gcagcccgtg gggacatta ccaccaaccg gatctacaaa    900
atcctggaac tgaacgggta cgaccccag tacgccgcct ccgtcttcct cggctgggcc    960
cagaaaaagt ttggaaacgc caacaccatc tggctgtttg ggccccgccac caccggcaag   1020
accaacatcg cggaagccat cgcccacgcg gtcccttct acggctgcgt caactcggacc   1080
aatgagaact ttcccttcaa cgactgcgtc gacaaaatgg tgatttggtg ggaggagggc   1140
aagatgaccg ccaaggtcgt agagtccgcc aaggccattc tgggcggcag caaggtgcgc   1200
gtggaccaaa aatgcaaggc ctcgcgcag atcgaccccc ccgtgat cgtcacctcc        1260
aacaccaaca tgtgcgccgt gattgacggg aacagcacca ccttcgagca ccagccgccc   1320
ctgcaggacc ggatgttcaa gtttgaactc acccgccgcc tcgaccacga ctttggcaag   1380
gtcaccaagc aggaagtcaa ggactttttc cggtggggcg ctgatcacgt gactgacgtg   1440
gctcatgagt tttacgtcac aaagggtgga gctaagaaaa gcccgccccc ctctgacgag   1500
gatataagcg agcccaagcg gccgcgcgtg tcatttgcgc agccggagac gtcagacgcg   1560
gaagcctccg gagacttgca ggacaggtac caaaacaaat gttctcgtca cgcgggtatg   1620
ctgcagatgc tctttccctg caagacgtgc gagagaatga atcagaattc caacgtctgc   1680
ttcacgcacg gtcagaaaga ttgcggggag tgctttcccg ggtcagaatc tcaaccggtt   1740
tctgtcgtca gaaaaacgta tcagaaactg tgcatccttc atcagctccg gggggcaccc   1800
gagatcgcct gctctgcttg cgaccaactc aaccccgatt tggacgattg ccaatttgag   1860
caataa                                                              1866
```

```
SEQ ID NO: 20          moltype = DNA  length = 1872
FEATURE                Location/Qualifiers
source                 1..1872
                       mol_type = other DNA
                       organism = synthetic construct
SEQUENCE: 20
atgccgggat tctacgagat tgtcctgaag gtgcccagcg acctggacga gcacctgcct   60
ggcatttctg actcttttgt aaactgggtg gcggagaagg aatgggagct gccgccggat   120
tctgacatgg atctgaatct gattgagcag gcacccctaa ccgtggcgga aaagctgcaa   180
cgcgaattcc tggtcgagtg gcgcgcgcgt agtaaggccc cggaggccct cttctttgtt   240
cagttcgaga aggggggacag ctacttccac ctacacattc tggtcgagac cgtgggcgtg   300
aaaatccatg tggtgggccg ctacgtgagc cagattaaag agaagctggt gacccgcatc   360
taccgcgggg tcgagccgca gcttccgaac tggttcgcgg tgaccaagac cgtaatggc    420
gccggaggcg ggaacaaggt ggtggacgac tgctacatcc ccaactacct gctcccaag    480
acccagcccg agctccagtg ggcgtggact aatatggacc agtatttaag cgcctgtttg   540
aatctcgcgg agcgtaaacg gctggtggcg cagcatctga cgcacgtgtc gcagacgcag   600
gagcagaaca aagagaacga atcccaat tctgacgcgc cggtgatcag atcaaaaacc    660
tccgcgaggt acatggagct ggtcgggtgg ctggtggacc gcgggatcac gtcagaaaag   720
caatggatcc aggaggacca ggcctcttac atctccttca cgccgcctc caactcgcgg    780
tcacaaatca aggccgcact ggacaatgcc tccaaattta tgagcctgac aaaaacggct   840
ccggactacc tggtgggaaa caacccgccg gaggacatta ccaacaaccg gatctacaaa   900
atcctcgaga tgaacgggta cgatccgcag tacgcggcct ccgtcttcct gggctgggca   960
caaaagaagt tcgggaagag gaacaccatc tggctctttg ggccggccac gacgggtaaa  1020
accaacatcg ctgaagctat cgcccacgcc gtgcctttt acggctgcgt gaactggacc   1080
aatgaaact ttccgttcaa cgattgcgtc gacaagtgg tgatctcttg ggagaaggc    1140
aagatgacga ccaaggtcgt ggagtccgcc aaggccattc tgggcggaag caaggtcgc    1200
gtggaccaaa agtgcaagtc atcggcccag atcgacccaa ctcccgtcat cgtcacctcc   1260
aacaccaaca tgtgcgcggt catcgacgga aattccacca ccttcgagca ccaacaacca   1320
ctccaagacc ggatgttcaa gttcgagctc accaagcgcc tggagcacga cttcggcaag   1380
gtcaccaagc aggaagtcaa ggactttttc cggtgggcgt cagatcacgt gactgaggtg   1440
tctcacgagt tttacgtcag aaaggggtga gctagaaaga ggccccgccc caatgacgca   1500
gatataagtg agcccaagcg ggcctgtccg tcagttgcgc agccatcgac gtcagacgcg   1560
gaagctccgg tggactacgc ggacaggtac caaaacgat gttctcgtca cgtggcatg    1620
aatctgatgc tttttccctg ccggcaatgc gagagaatga atcagaatgt ggacatttgc   1680
ttcacgcacg gggtcatgga ctgtgccgag tgcttccccg tgtcagaatc tcaacccgtg   1740
tctgtcgtca gaaagcggac atatcagaaa ctgtgtccga ttcatacat catggggagg    1800
gcgcccgagg tggcttgttc ggcctgcgat ctggccaatg tggacttgga tgactgtgac   1860
atggagcaat aa                                                        1872

SEQ ID NO: 21          moltype = AA  length = 623
FEATURE                Location/Qualifiers
source                 1..623
                       mol_type = protein
                       organism = synthetic construct
SEQUENCE: 21
MPGFYEIVIK VPSDLDEHLP GISDSFVSWV AEKEWELPPD SDMDLNLIEQ APLTVAEKLQ    60
RDFLVQWRRV SKAPEALFFV QFEKGESYFH LHILVETTGV KSMVLGRFLS QIRDKLVQTI   120
YRGIEPTLPN WFAVTKTRNG AGGGNKVVDE CYIPNYLLPK TQPELQWAWT NMEEYISACL   180
NLAERKRLVA QHLTHVSQTQ EQNKENLNPN SDAPVIRSKT SARYMELVGW LVDRGITSEK   240
QWIQEDQASY ISFNAASNSR SQIKAALDNA GKIMALTKSA PDYLVGPAPP ADIKTNRIYR   300
ILELNGYEPA YAGSVFLGWA QKRFGKRNTI WLFGPATTGK TNIAEAIAHA VPFYGCVNWT   360
NENFPFNDCV DKMVIWWEEG KMTKVVESA KAILGGSKVR VDQKCKSSAQ IDPTPVIVTS    420
NTNMCAVIDG NSTTFEHQQP LQDRMFKFEL TRRLEHDFGK VTKQEVKEFF RWAQDHVTEV   480
AHEFYVRKGG ANKRPAPDDA DKSEPKRACP SVADPSTSDA EGAPVDFADR YQNKCSRHAG   540
MLQMLFPCKT CERMNQNFNI CFTHGTRDCS ECFPGVSESQ PVVRKRTYRK LCAIHHLLGR   600
APEIACSACD LVNVDLDDCV SEQ                                            623

SEQ ID NO: 22          moltype = AA  length = 621
FEATURE                Location/Qualifiers
source                 1..621
                       mol_type = protein
                       organism = synthetic construct
SEQUENCE: 22
MPGFYEIVIK VPSDLDGHLP GISDSFVNWV AEKEWELPPD SDMDLNLIEQ APLTVAEKLQ    60
RDFLTEWRRV SKAPEALFFV QFEKGESYFH MHVLVETTGV KSMVLGRFLS QIREKLIQRI   120
YRGIEPTLPN WFAVTKTRNG AGGGNKVVDE CYIPNYLLPK TQPELQWAWT NMEQYLSACL   180
NLTERKRLVA QHLTHVSQTQ EQNKENQNPN SDAPVIRSKT SARYMELVGW LVDKGITSEK   240
QWIQEDQASY ISFNAASNSR SQIKAALDNA GKIMSLTKTA PDYLVGQQPV EDISSNRIYK   300
ILELNGYDPQ YAASVFLGWA TKKFGKRNTI WLFGPATTGK TNIAEAIAHT VPFYGCVNWT   360
NENFPFNDCV DKMVIWWEEG KMTKVVESA KAILGGSKVR VDQKCKSSAQ IDPTPVIVTS    420
NTNMCAVIDG NSTTFEHQQP LQDRMFKFEL TRRLDHDFGK VTKQEVKDFF RWAKDHVVEV   480
EHEFYVKKGG AKKRPAPSDA DISEPKRVRE SVAQPSTSDA EASINYADRY QNKCSRHVGM   540
NLMLFPCRQC ERMNQNSNIC FTHGQKDCLE CFPVSESQPV SVVKKAYQKL CYIHHIMGKV   600
PDACTACDLV NVDLDDCIFE Q                                              621

SEQ ID NO: 23          moltype = AA  length = 624
FEATURE                Location/Qualifiers
source                 1..624
```

```
                        mol_type = protein
                        organism = synthetic construct
SEQUENCE: 23
MPGFYEIVLK VPSDLDEHLP GISNSFVNWV AEKEWELPPD SDMDPNLIEQ APLTVAEKLQ    60
REFLVEWRRV SKAPEALFFV QFEKGETYFH LHVLIETIGV KSMVVGRYVS QIKEKLVTRI   120
YRGVEPQLPN WFAVTKTRNG AGGGNKVVDD CYIPNYLLPK TQPELQWAWT NMDQYLSACL   180
NLAERKRLVA QHLTHVSQTQ EQNKENQNPN SDAPVIRSKT SARYMELVGW LVDRGITSEK   240
QWIQEDQASY ISFNAASNSR SQIKAALDNA SKIMSLTKTA PDYLVGSNPP EDITKNRIYQ   300
ILELNGYDPQ YAASVFLGWA QKKFGKRNTI WLFGPATTGK TNIAEAIAHA VPFYGCVNWT   360
NENFPFNDCV DKMVIWWEEG KMTAKVVESA KAILGGSKVR VDQKCKSSAQ IEPTPVIVTS   420
NTNMCAVIDG NSTTFEHQQP LQDRMFKFEL TRRLDHDFGK VTKQEVKDFF RWASDHVTDV   480
AHEFYVRKGG AKKRPASNDA DVSEPKRQCT SLAQPTTSDA EAPADYADRY QNKCSRHVGM   540
NLMLFPCKTC ERMNQISNVC FTHGQRDCGE CFPGMSESQP VSVVKKKTYQ KLCPIHHILG   600
RAPEIACSAC DLANVDLDDC VSEQ                                         624

SEQ ID NO: 24           moltype = AA   length = 623
FEATURE                 Location/Qualifiers
source                  1..623
                        mol_type = protein
                        organism = synthetic construct
SEQUENCE: 24
MPGFYEIVLK VPSDLDEHLP GISDSFVSWV AEKEWELPPD SDMDLNLIEQ APLTVAEKLQ    60
REFLVEWRRV SKAPEALFFV QFEKGDSYFH LHILVETVGV KSMVVGRYVS QIKEKLVTRI   120
YRGVEPQLPN WFAVTKTRNG AGGGNKVVDD CYIPNYLLPK TQPELQWAWT NMDQYISACL   180
NLAERKRLVA QHLTHVSQTQ EQNKENQNPN SDAPVIRSKT SARYMELVGW LVDRGITSEK   240
QWIQEDQASY ISFNAASNSR SQIKAALDNA SKIMSLTKTA PDYLVGQNPP EDISSNRIYR   300
ILEMNGYDPQ YAASVFLGWA QKKFGKRNTI WLFGPATTGK TNIAEAIAHA VPFYGCVNWT   360
NENFPFNDCV DKMVIWWEEG KMTAKVVESA KAILGGSKVR VDQKCKSSAQ IDPTPVIVTS   420
NTNMCAVIDG NSTTFEHQQP LQDRMFKFEL TKRLEHDFGK VTKQEVKDFF RWASDHVTEV   480
THEFYVRKGG ARKRPAPNDA DISEPKRACP SVAQPSTSDA EAPVDYADRY QNKCSRHVGM   540
NLMLFPCRQC ERMNQNVDIC FTHGVMDCAE CFPVSESQPV SVVRKRTYQK LCPIHHIMGR   600
APEVACSACE LANVDLDDCD MEQ                                          623

SEQ ID NO: 25           moltype = AA   length = 610
FEATURE                 Location/Qualifiers
source                  1..610
                        mol_type = protein
                        organism = synthetic construct
SEQUENCE: 25
MATFYEVIVR VPFDVEEHLP GISDSFVDWV TGQIWELPPE SDLNLTLVEQ PQLTVADRIR    60
RVFLYEWNKF SKQESKFFVQ FEKGSEYPHL HTLVETSGIS SMVLGRYVSQ IRAQLVKVVF   120
QGIEPQINDW VAITKVKKGG ANKVVDSGYI PAYLLPKVQF ELQWAWTNLD EYKLAALNLE   180
ERKRLVAQFL AESSQRSQEA ASQREFSADP VIKSKTSQKY MALVNWLVEH GITSEKQWIQ   240
ENQESYLSFN STGNSRSQIK AALDNATKIM SLTKSAVDYL VGSSVPEDIS KNRIWQIFEM   300
NGYDPAYAGS ILYGWCQRSF NKRNTVWLYG PATTGKTNIA EAIAHTVPFY GCVNWTNENF   360
PFNDCVDKML IWWEEGKMTN KVVESAKAIL GGSKVRVDQK CKSSVQIDST PVIVTSNTNM   420
CVVVDGNSTT FEHQQPLEDR MFKFELTKRL PPDFGKITKQ EVKDFFAWAK VNQVPVTHEF   480
KVPRELAGTK GAEKSLKRPL GDVTNTSYKS LEKRARLSFV PETPRSSDVT VDPAPLRPLN   540
WNSRYDCKCD YHAQFDNISN KCDECEYLNR GKNGCICHNV THCQICHGIP PWEKENLSDF   600
GDFDDANKEQ                                                         610

SEQ ID NO: 26           moltype = AA   length = 623
FEATURE                 Location/Qualifiers
source                  1..623
                        mol_type = protein
                        organism = synthetic construct
SEQUENCE: 26
MPGFYEIVIK VPSDLDEHLP GISDSFVNWV AEKEWELPPD SDMDLNLIEQ APLTVAEKLQ    60
RDFLVQWRRV SKAPEALFFV QFEKGESYFH LHILVETTGV KSMVLGRFLS QIRDKLVQTI   120
YRGIEPTLPN WFAVTKTRNG AGGGNKVVDE CYIPNYLLPK TQPELQWAWT NMEEYISACL   180
NLAERKRLVA HDLTHVSQTQ EQNKENLNPN SDAPVIRSKT SARYMELVGW LVDRGITSEK   240
QWIQEDQASY ISFNAASNSR SQIKAALDNA GKIMALTKSA PDYLVGPAPP ADIKTNRIYR   300
ILELNGYDPA YAGSVFLGWA QKRFGKRNTI WLFGPATTGK TNIAEAIAHA VPFYGCVNWT   360
NENFPFNDCV DKMVIWWEEG KMTAKVVESA KAILGGSKVR VDQKCKSSAQ IDPTPVIVTS   420
NTNMCAVIDG NSTTFEHQQP LQDRMFKFEL TRRLEHDFGK VTKQEVKEFF RWAQDHVTEV   480
AHEFYVRKGG ANKRPAPDDA DKSEPKRACP SVADPSTSDA EGAPVDFADR YQNKCSRHAG   540
MLQMLFPCKT CERMNQNFNI CFTHGTRDCS ECFPGVSESQ PVVRKRTYRK LCAIHHLLGR   600
APEIACSACD LVNVDLDDCV SEQ                                          623

SEQ ID NO: 27           moltype = AA   length = 623
FEATURE                 Location/Qualifiers
source                  1..623
                        mol_type = protein
                        organism = synthetic construct
SEQUENCE: 27
MPGFYEIVIK VPSDLDEHLP GISDSFVNWV AEKEWELPPD SDMDLNLIEQ APLTVAEKLQ    60
RDFLVQWRRV SKAPEALFFV QFEKGESYFH LHVLVETTGV KSMVLGRFLS QIREKLVQTI   120
YRGVEPTLPN WFAVTKTRNG AGGGNKVVDE CYIPNYLLPK TQPELQWAWT NMEEYISACL   180
NLAERKRLVA QHLTHVSQTQ EQNKENLNPN SDAPVIRSKT SARYMELVGW LVDRGITSEK   240
```

```
QWIQEDQASY ISFNAASNSR SQIKAALDNA GKIMALTKSA PDYLVGPSLP ADIKTNRIYR    300
ILELNGYDPA YAGSVFLGWA QKKFGKRNTI WLFGPATTGK TNIAEAIAHA VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLEHDFGK VTKQEVKEFF RWASDHVTEV    480
AHEFYVRKGG ASKRPAPDDA DISEPKRACP SVADPSTSDA EGAPVDFADR YQNKCSRHAG    540
MIQMLFPCKT CERMNQNFNI CFTHGVRDCL ECFPGVSESQ PVVRKKTYRK LCAIHHLLGR    600
APEIACSACD LVNVDLDDCV SEQ                                           623

SEQ ID NO: 28           moltype = AA  length = 625
FEATURE                 Location/Qualifiers
source                  1..625
                        mol_type = protein
                        organism = synthetic construct
SEQUENCE: 28
MPGFYEIVIK VPSDLDEHLP GISDSFVNWV AEKEWELPPD SDMDRNLIEQ APLTVAEKLQ    60
RDFLVQWRRV SKAPEALFFV QFEKGESYFH LHVLVETTGV KSMVLGRFLS QIREKLGPDH    120
LPAGSSPTLP NWFAVTKDAV MAPAGGNKVV DECYIPNYLL PKTQPELQWA WTNMEEYISA    180
CLNLAERKRL VAQHLTHVSQ TQEQNKENLN PNSDAPVIRS KTSARYMELV GWLVDRGITS    240
EKQWIQEDQA SYISFNAASN SRSQIKAALD NAGKIMALTK SAPDYLVGPS LPADITQNRI    300
YRILALNGYD PAYAGSVFLG WAQKKFGKRN TIWLFGPATT GKTNIAEAIA HAVPFYGCVN    360
WTNENFPFND CVDKMVIWWE EGKMTAKVVE SAKAILGGSK VRVDQKCKSS AQIDPTPVIV    420
TSNTNMCAVI DGNSTTFEHQ QPLQDRMFKF ELTRRLEHDF GKVTKQEVKE FFRWASDHVT    480
EVAHEFYVRK GGASKRPAPD DADKSEPKRA CPSVADPSTS DAEGAPVDFA DRYQNKCSRH    540
AGMLQMLFPC KTCERMNQNF NICFTHGVRD CSECFPGVSE SQPVVRKRTY RKLCAIHHLL    600
GRAPEIACSA CDLVNVDLDD CVSEQ                                         625

SEQ ID NO: 29           moltype = AA  length = 622
FEATURE                 Location/Qualifiers
source                  1..622
                        mol_type = protein
                        organism = synthetic construct
SEQUENCE: 29
MPGFYEIVIK VPSDLDEHLP GISDSFVNWV AEKEWELPPD SDMDRNLIEQ APLTVAEKLR    60
DFLVQWRRVS KAPEALFFVQ FEKGESYFHL HVLVETTGVK SMVLGRFLSQ IREKLVQTIY    120
RGIEPTLPNW FAVTKTRNGA GGGNKVVDEC YIPNYLLPKT QPELQWAWTN MEEYISACLN    180
LAERKRLVAQ HLTHVSQTQE QNKENLNPNS DAPVIRSKTS ARYMELVGWL VDRGITSEKQ    240
WIQEDQASYI SFNAASNSRS QIKAALDNAG KIMALTKSAP DYLVGPSLPV DITQNRIYRI    300
LQLNGYDPAY AGSVFLGWAQ KKFGKRNTIW LFGPATTGKT NIAEAIAHAV PFYGCVNWTN    360
ENFPFNDCVD KMVIWWEEGK MTAKVVESAK AILGGSKVRV DQKCKSSAQI DPTPVIVTSN    420
TNMCAVIDGN STTFEHQQPL QDRMFKFELT RRLEHDFGKV TKQEVKEFFR WASDHVTEVA    480
HEFYVRKGGA SKRPAPDDAD KSEPKRACPS VADPSTSDAE GAPVDFADRY QNKCSRHAGM    540
LQMLLPCKTC ERMNQNFNIC FTHGVRDCSE CFPGVSESQP VVRKRTYRKL CAIHHLLGRA    600
PEIACSACDL VNVDLDDCVS EQ                                            622

SEQ ID NO: 30           moltype = AA  length = 622
FEATURE                 Location/Qualifiers
source                  1..622
                        mol_type = protein
                        organism = synthetic construct
SEQUENCE: 30
MPGFYEIVIK VPSDLDEHLP GISDSFVNWV AEKEWELPPD SDMDRNLIEQ APLTVAEKLQ    60
RDFLVHWRRV SKAPEALFFV QFEKGESYFH LHVLVETTGV KSMVLGRFLS QIRDRLVQTI    120
YRGVEPTLPN WFAVTKTRNG AGGGNKVVDE CYIPNYLLPK TQPELQWAWT NMEEYISACL    180
NLAERKRLVA QHLTHVSQTQ EQNKENLNPN SDAPVIRSKT SARYMELVGW LVDRGITSEK    240
QWIQEDQASY ISFNAASNSR SQIKAALDNA GKIMALTKSA PDYLVGPSLP ADIKANRIYR    300
ILELNGYDPA YAGSVFLGWA QKKFGKRNTI WLFGPATTGK TNIAEAIAHA VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLEHDFGK VTKQEVKEFF RWAQDHVTEV    480
THEFYVRKGG ATKRPAPSDA DISEPKRACP SVAEPSTSDA EAPVDFADRY QNKCSRHAGM    540
LQMLFPCKTC ERMNQNFNVC FTHGVRDCSE CFPGASESQP VVRKKTYQKL CAIHHLLGRA    600
PEIACSACDL VNVDLDDCVS EQ                                            622

SEQ ID NO: 31           moltype = AA  length = 622
FEATURE                 Location/Qualifiers
source                  1..622
                        mol_type = protein
                        organism = synthetic construct
SEQUENCE: 31
MPGFYEIVIK VPSDLDEHLP GISDSFVNWV AEKEWELPPD SDMDRNLIEQ APLTVAEKLQ    60
RDFLVHWRRV SKAPEALFFV QFEKGESYFH LHVLVETTGV KSMVLGRFLS QIRDRLVQTI    120
YRGVEPTLPN WFAVTKTRNG AGGGNKVVDE CYIPNYLLPK TQPELQWAWT NMEEYISACL    180
NLAERKRLVA QHLTHVSQTQ EQNKENLNPN SDAPVIRSKT SARYMELVGW LVDRGITSEK    240
QWIQEDQASY ISFNAASNSR SQIKAALDNA GKIMALTKSA PDYLVGPSLP ADIKANRIYR    300
ILELNGYDPA YAGSVFLGWA QKKFGKRNTI WLFGPATTGK TNIAEAIAHA VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLEHDFGK VTKQEVKEFF RWAQDHVTEV    480
AHEFYVRKGG ATKRPAPSDA DISEPKRACP SVPEPSTSDA EAPVDFADRY QNKCSRHAGM    540
LQMLFPCKTC ERMNQNFNVC FTHGVRDCSE CFPGASESQP VVRKKTYQKL CAIHHLLGRA    600
PEIACSACDL VNVDLDDCVS EQ                                            622
```

```
SEQ ID NO: 32              moltype = AA  length = 621
FEATURE                    Location/Qualifiers
source                     1..621
                           mol_type = protein
                           organism = synthetic construct
SEQUENCE: 32
MPGFYEVVIK VPSDLDEHLP GISDSFVNWV AEKEWELPPD SDMDQNLIEQ APLTVAEKLQ   60
REFLVEWRRV SKFLEAKFFV QFEKGDSYPH LHILIEITGV KSMVVGRYVS QIRDKLIQRI  120
YRGVEPQLPN WFAVTKTRNG AGGGNKVVDE CYIPNYLLPK VQPELQWAWT NMEEYISACL  180
NLAERKRLVA QHLTHVSQTQ EGDKENLNPN SDAPVIRSKT SARYMELVGW LVDKGITSEK  240
QWIQEDQASY ISFNAASNSR SQIKAALDNA SKIMSLTKTA PDYLIGQQPV GDITTNRIYK  300
ILELNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKASAQ IDPTPVIVTS  420
NTNMCAVIDG NSTTFEHQQP LQDRMFKFEL TRRLDHDFGK VTKQEVKDFF RWAADHVTDV  480
AHEFYVTKGG AKKRPAPSDE DISEPKRPRV SFAQPETSDA EAPGDFADRY QNKCSRHAGM  540
LQMLFPCKTC ERMNQNSNVC FTHGQKDCGE CFPGSESQPV SVVRKTYQKL CILHQLRGAP  600
EIACSACDQL NPDLDDCQFE Q                                           621

SEQ ID NO: 33              moltype = AA  length = 623
FEATURE                    Location/Qualifiers
source                     1..623
                           mol_type = protein
                           organism = synthetic construct
SEQUENCE: 33
MPGFYEIVLK VPSDLDEHLP GISDSFVNWV AEKEWELPPD SDMDLNLIEQ APLTVAEKLQ   60
REFLVEWRRV SKAPEALFFV QFEKGDSYFH LHILVETVGV KSMVVGRYVS QIKEKLVTRI  120
YRGVEPQLPN WFAVTKTRNG AGGGNKVVDD CYIPNYLLPK TQPELQWAWT NMDQYLSACL  180
NLAERKRLVA QHLTHVSQTQ EQNKENQNPN SDAPVIRSKT SARYMELVGW LVDRGITSEK  240
QWIQEDQASY ISFNAASNSR SQIKAALDNA SKFMSLTKTA PDYLVGNNPP EDITSNRIYK  300
ILEMNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TKRLEHDFGK VTKQEVKDFF RWASDHVTEV  480
SHEFYVRKGG ARKRPAPNDA DISEPKRACP SVAQPSTSDA EAPVDYADRY QNKCSRHVGM  540
NLMLFPCRQC ERMNQNVDIC FTHGVMDCAE CFPVSESQPV SVVRKRTYQK LCPIHHIMGR  600
APEVACSACD LANVDLDDCD MEQ                                         623

SEQ ID NO: 34              moltype = AA  length = 621
FEATURE                    Location/Qualifiers
source                     1..621
                           mol_type = protein
                           organism = synthetic construct
SEQUENCE: 34
MPGFYEIVIK VPSDLDEHLP GISDSFVSWV AEKEWELPPD SDMDLNLIEQ APLTVAEKLQ   60
RDFLVQWRRV SKAPEALFFV QFEKGESYFH LHILVETTGV KSMVLGRFLS QIRDKLVQTI  120
YRGIEPTLPN WFAVTKTRNG AGGGNKVVDE CYIPNYLLPK TQPELQWAWT NMEEYISACL  180
NLAERKRLVA QHLTHVSQTQ EQNKENLNPN SDAPVIRSKT SARYMELVGW LVDKGITSEK  240
QWIQEDQASY ISFNAASNSR SQIKAALDNA GKIMSLTKTA PDYLVGQQPV EDISSNRIYK  300
ILELNGYDPQ YAASVFLGWA TKKFGKRNTI WLFGPATTGK TNIAEAIAHT VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLDHDFGK VTKQEVKDFF RWAKDHVVEV  480
EHEFYVKKGG AKKRPAPSDA DISEPKRVRE SVAQPSTSDA EASINYADRY QNKCSRHVGM  540
NLMLFPCRQC ERMNQNSNIC FTHGQKDCLE CFPVSESQPV SVVKKAYQKL CYIHHIMGKV  600
PDACTACDLV NVDLDDCIFE Q                                           621

SEQ ID NO: 35              moltype = AA  length = 623
FEATURE                    Location/Qualifiers
source                     1..623
                           mol_type = protein
                           organism = synthetic construct
SEQUENCE: 35
MPGFYEIVIK VPSDLDGHLP GISDSFVNWV AEKEWELPPD SDMDLNLIEQ APLTVAEKLQ   60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEEYLSACL  180
NLTERKRLVA QHLTHVSQTQ EQNKENQNPN SDAPVIRSKT SARYMELVGW LVDRGITSEK  240
QWIQEDQASY ISFNAASNSR SQIKAALDNA GKIMALTKSA PDYLVGPAPP ADIKTNRIYR  300
ILELNGYEPA YAGSVFLGWA QKRFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWAQDHVTEV  480
AHEFYVRKGG ANKRPAPDDA DKSEPKRACP SVADPSTSDA EGAPVDFADR YQNKCSRHAG  540
MLQMLFPCKT CERMNQNFNI CFTHGTRDCS ECFPGVSESQ PVVRKRTYRK LCAIHHLLGR  600
APEIACSACD LVNVDLDDCV SEQ                                         623

SEQ ID NO: 36              moltype = AA  length = 614
FEATURE                    Location/Qualifiers
source                     1..614
                           mol_type = protein
                           organism = synthetic construct
SEQUENCE: 36
```

```
MPGFYEIVIK VPSDLDGHLP GISDSFVNWV AEKEWELPPD SDMDLNLIEQ APLTVAEKLQ    60
RDFLTEWRRV SKAPEALFFV QFEKGESYFH MHVLVETTGV KSMVLGRFLS QIREKLIQRI   120
YRGIEPTLPN WFAVTKTRNG AGGGNKVVDE CYIPNYLLPK TQPELQWAWT NMEQYLSACL   180
NLTERKRLVA QHLTHVSQTQ EQNKENQNPN SDAPVIRSKT SARYMALVNW LVEHGITSEK   240
QWIQENQESY LSFNSTGNSR SQIKAALDNA TKIMSLTKSA VDYLVGSSVP EDISKNRIWQ   300
IFEMNGYDPA YAGSILYGWC QRSFNKRNTV WLYGPATTGK TNIAEAIAHT VPFYGCVNWT   360
NENFPFNDCV DKMLIWWEEG KMTNKVVESA KAILGGSKVR VDQKCKSSVQ IDSTPVIVTS   420
NTNMCVVVDG NSTTFEHQQP LEDRMFKFEL TKRLPPDFGK ITKQEVKDFF AWAKVNQVPV   480
THEFKVPREL AGTKGAEKSL KRPLGDVTNT SYKSLEKRAR LSFVPETPRS SDVTVDPAPL   540
RPLNWNSRYD CKCDYHAQFD NISNKCDECE YLNRGKNGCI CHNVTHCQIC HGIPPWEKEN   600
LSDFGDFDDA NKEQ                                                    614

SEQ ID NO: 37        moltype = AA   length = 614
FEATURE              Location/Qualifiers
source               1..614
                     mol_type = protein
                     organism = synthetic construct
SEQUENCE: 37
MPGFYEIVIK VPSDLDGHLP GISDSFVNWV AEKEWELPPD SDMDLNLIEQ APLTVAEKLQ    60
RDFLTEWRRV SKAPEALFFV QFEKGESYFH MHVLVETTGV KSMVLGRFLS QIREKLIQRI   120
YRGIEPTLPN WFAVTKTRNG AGGGNKVVDE CYIPNYLLPK TQPELQWAWT NMEQYLSACL   180
NLTERKRLVA QHLTHVSQTQ EQNKENQNPN SDAPVIRSKT SARYMALVNW LVEHGITSEK   240
QWIQENQESY LSFNSTGNSR SQIKAALDNA TKIMSLTKSA VDYLVGSSVP EDISKNRIWQ   300
IFEMNGYDPA YAGSILYGWC QRSFNKRNTV WLYGPATTGK TNIAEAIAHT VPFYGCVNWT   360
NENFPFNDCV DKMLIWWEEG KMTNKVVESA KAILGGSKVR VDQKCKSSVQ IDSTPVIVTS   420
NTNMCVVVDG NSTTFEHQQP LEDRMFKFEL TKRLPPDFGK ITKQEVKDFF AWAKVNQVPV   480
THEFKVPREL AGTKGAEKSL KRPLGDVTNT SYKSLEKRAR LSFVPETPRS SDVTVDPAPL   540
RPLNWNSRYD CKCDYHAQFD NISNKCDECE YLNRGKNGCI CHNVTHCQIC HGIPPWEKEN   600
LSDFGDFDDA NKEQ                                                    614

SEQ ID NO: 38        moltype = AA   length = 7
FEATURE              Location/Qualifiers
source               1..7
                     mol_type = protein
                     organism = synthetic construct
SEQUENCE: 38
LARGHSL                                                              7

SEQ ID NO: 39        moltype = DNA   length = 148
FEATURE              Location/Qualifiers
source               1..148
                     mol_type = other DNA
                     organism = synthetic construct
SEQUENCE: 39
hvsbthrkkr gatctactac ctcaacsggt gagggagaka cgccgyagcg agygagysas    60
ycsggcskkc hsgtytcsdg mmskcagmcs bctggaaacc agvsggccsg rstsrctcrc   120
tcgctcrcgc gtmtctccct caccsgtt                                      148

SEQ ID NO: 40        moltype = DNA   length = 306
FEATURE              Location/Qualifiers
source               1..306
                     mol_type = other DNA
                     organism = synthetic construct
SEQUENCE: 40
atgccgggct tctacgagat cgtgatcaag gtgccgagcg acctggacga gcacctgccg    60
ggcatttctg actcgtttgt gagctgggtg gccgagaagg aatgggagct gcccccggat   120
tctgacatgg atctgaatct gattgagcag gcacccctga ccgtggccga gaagctgcag   180
cgcgacttcc tggtccaatg gcgccgcgtg agtaaggccc cggaggccct cttctttgtt   240
cagttcgaga agggcgagtc ctacttccac ctccatattc tggtggagac cacggggtc    300
aaatcc                                                              306

SEQ ID NO: 41        moltype = DNA   length = 420
FEATURE              Location/Qualifiers
source               1..420
                     mol_type = other DNA
                     organism = synthetic construct
SEQUENCE: 41
atggtgctgg gccgcttcct gagtcagatt agggacaagc tggtgcagac catctaccgc    60
atcgagcc cgaccctgcc caactggttc gcggtgacca agacgcgtaa tggcgccgga   120
ggggggaaca aggtggtgga cgagtgctac atccccaact acctcctgcc caagactcag   180
cccgagctgc agtgggcgtg gactaacatg gaggagtata taagcgcctg tttgaacctg   240
gccgagcgca acggctcgt ggcgcagcac ctgacccacg tcagcagac ccaggagcag   300
aacaaggaga atctgaaccc caattctgac gcgcctgtca tccggtcaaa aacctccgcg   360
cgctacatgg agctggtcgg gtggctggtg accggggca tcacctccga gaagcagtgg   420

SEQ ID NO: 42        moltype = DNA   length = 381
FEATURE              Location/Qualifiers
source               1..381
                     mol_type = other DNA
```

```
                        organism = synthetic construct
SEQUENCE: 42
atccaggagg accaggcctc gtacatctcc ttcaacgccg cttccaactc gcggtcccag    60
atcaaggcca ctctggacaa tgccggcaag atcatggcgc tgaccaaatc cgcgcccgac   120
tacctggtag gccccgctcc gcccgcggac attaaaacca accgcatcta ccgcatcctg   180
gagctgaacg gctacgaacc tgcctacgcc ggctccgtct ttctcggctg ggcccagaaa   240
aggttcggga gcgcaacac catctggctg tttgggccgg ccaccacggg caagaccaac    300
atcgcggaag ccatcgccca cgccgtgccc ttctacggct gcgtcaactg gaccaatgag   360
aactttccct tcaatgattg c                                             381

SEQ ID NO: 43           moltype = DNA   length = 765
FEATURE                 Location/Qualifiers
source                  1..765
                        mol_type = other DNA
                        organism = synthetic construct
SEQUENCE: 43
gtcgacaaga tggtgatctg gtgggaggag ggcaagatga cggccaaggt cgtggagtcc    60
gccaaggcca ttctcggcgg cagcaaggtg cgcgtggacc aaaagtgcaa gtcgtccgcc   120
cagatcgacc ccacccccgt gatcgtcacc tccaacacca acatgtgcgc cgtgattgac   180
gggaacagca ccaccttcga gcaccagcag ccgttgcagg accggatgtt caaatttgaa   240
ctcacccgcc gtctggagca tgactttggc aaggtgacaa agcaggaagt caaagagttc   300
ttccgctggg cgcaggatca cgtgaccgag gtggcgcatg agttctacgt cagaaagggt   360
ggagccaaca aaagacccgc ccccgatgac gcggataaaa gcgagcccaa gcgggcctgc   420
ccctcagtcg cggatccatc gacgtcagac gcggaaggag ctccggtgga ctttgccgac   480
aggtaccaaa acaaatgttc tcgtcacgcg ggcatgcttc agatgctgtt tcctgcaag    540
acatgcgaga gaatgaatca gaatttcaac atttgcttca gcacgggac gagagacttg    600
tcagagtgct tccccggcgt gtcagaatct caaccggtcg tcagaaagag gacgtatcgg   660
aaactctgtg ccattcatca tctgctgggg cgggctcccg agattgcttg ctcggcctgc   720
gatctggtca acgtggacct ggatgactgt gtttctgagc aataa                   765

SEQ ID NO: 44           moltype = DNA   length = 495
FEATURE                 Location/Qualifiers
source                  1..495
                        mol_type = other DNA
                        organism = synthetic construct
SEQUENCE: 44
gtcgacaaga tggtgatctg gtgggaggag ggcaagatga cggccaaggt cgtggagtcc    60
gccaaggcca ttctcggcgg cagcaaggtg cgcgtggacc aaaagtgcaa gtcgtccgcc   120
cagatcgacc ccacccccgt gatcgtcacc tccaacacca acatgtgcgc cgtgattgac   180
gggaacagca ccaccttcga gcaccagcag ccgttgcagg accggatgtt caaatttgaa   240
ctcacccgcc gtctggagca tgactttggc aaggtgacaa agcaggaagt caaagagttc   300
ttccgctggg cgcaggatca cgtgaccgag gtggcgcatg agttctacgt cagaaagggt   360
ggagccaaca aaagacccgc ccccgatgac gcggataaaa gcgagcccaa gcgggcctgc   420
ccctcagtcg cggatccatc gacgtcagac gcggaaggag ctccggtgga ctttgccgac   480
aggtaccaaa acaaa                                                    495

SEQ ID NO: 45           moltype = DNA   length = 270
FEATURE                 Location/Qualifiers
source                  1..270
                        mol_type = other DNA
                        organism = synthetic construct
SEQUENCE: 45
tgttctcgtc acgcgggcat gcttcagatg ctgtttccct gcaagacatg cgagagaatg    60
aatcagaatt tcaacatttg cttcacgcac gggacgagag actgttcaga gtgcttcccc   120
ggcgtgtcag aatctcaacc ggtcgtcaga aagaggacgt atcggaaact ctgtgccatt   180
catcatctgc tggggcgggc tcccgagatt gcttgctcgg cctgcgatct ggtcaacgtg   240
gacctggatg actgtgtttc tgagcaataa                                    270

SEQ ID NO: 46           moltype = AA    length = 102
FEATURE                 Location/Qualifiers
source                  1..102
                        mol_type = protein
                        organism = synthetic construct
SEQUENCE: 46
MPGFYEIVIK VPSDLDEHLP GISDSFVSWV AEKEWELPPD SDMDLNLIEQ APLTVAEKLQ    60
RDFLVQWRRV SKAPEALFFV QFEKGESYFH LHILVETTGV KS                      102

SEQ ID NO: 47           moltype = AA    length = 140
FEATURE                 Location/Qualifiers
source                  1..140
                        mol_type = protein
                        organism = synthetic construct
SEQUENCE: 47
MVLGRFLSQI RDKLVQTIYR GIEPTLPNWF AVTKTRNGAG GGNKVVDECY IPNYLLPKTQ    60
PELQWAWTNM EEYISACLNL AERKRLVAQH LTHVSQTQEQ NKENLNPNSD APVIRSKTSA   120
RYMELVGWLV DRGITSEKQW                                               140

SEQ ID NO: 48           moltype = AA    length = 127
FEATURE                 Location/Qualifiers
```

```
source                  1..127
                        mol_type = protein
                        organism = synthetic construct
SEQUENCE: 48
IQEDQASYIS FNAASNSRSQ IKAALDNAGK IMALTKSAPD YLVGPAPPAD IKTNRIYRIL    60
ELNGYEPAYA GSVFLGWAQK RFGKRNTIWL FGPATTGKTN IAEAIAHAVP FYGCVNWTNE   120
NFPFNDC                                                             127

SEQ ID NO: 49           moltype = AA   length = 254
FEATURE                 Location/Qualifiers
source                  1..254
                        mol_type = protein
                        organism = synthetic construct
SEQUENCE: 49
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VAHEFYVRKG   120
GANKRPAPDD ADKSEPKRAC PSVADPSTSD AEGAPVDFAD RYQNKCSRHA GMLQMLFPCK   180
TCERMNQNFN ICFTHGTRDC SECFPGVSES QPVVRKRTYR KLCAIHHLLG RAPEIACSAC   240
DLVNVDLDDC VSEQ                                                    254

SEQ ID NO: 50           moltype = AA   length = 165
FEATURE                 Location/Qualifiers
source                  1..165
                        mol_type = protein
                        organism = synthetic construct
SEQUENCE: 50
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VAHEFYVRKG   120
GANKRPAPDD ADKSEPKRAC PSVADPSTSD AEGAPVDFAD RYQNK                   165

SEQ ID NO: 51           moltype = AA   length = 89
FEATURE                 Location/Qualifiers
source                  1..89
                        mol_type = protein
                        organism = synthetic construct
SEQUENCE: 51
CSRHAGMLQM LFPCKTCERM NQNFNICFTH GTRDCSECFP GVSESQPVVR KRTYRKLCAI    60
HHLLGRAPEI ACSACDLVNV DLDDCVSEQ                                     89

SEQ ID NO: 52           moltype = DNA   length = 306
FEATURE                 Location/Qualifiers
source                  1..306
                        mol_type = other DNA
                        organism = synthetic construct
SEQUENCE: 52
acgccggggt tttacgagat tgtgattaag gtccccagcg accttgacga gcatctgccc    60
ggcatttctg acagctttgt gaactgggtg gccgagaagg aatgggagtt gccgccagat   120
tctgacatgg atctgaatct gattgagcag gcacccctga ccgtggccga gaagctgcag   180
cgcgactttc tgacggaatg gcgccgtgtg agtaaggccc cggaggccct tttctttgtg   240
caatttgaga agggagagag ctacttccac atgcacgtgc tcgtggaaac caccggggtg   300
aaatcc                                                              306

SEQ ID NO: 53           moltype = DNA   length = 420
FEATURE                 Location/Qualifiers
source                  1..420
                        mol_type = other DNA
                        organism = synthetic construct
SEQUENCE: 53
atggttttgg gacgtttcct gagtcagatt cgcgaaaaac tgattcagag aatttaccgc    60
gggatcgagc cgactttgcc aaactggttc gcggtcacaa agaccagaaa tggcgccgga   120
ggcgggaaca aggtggtgga tgagtgctac atccccaatt acttgctccc caaaacccag   180
cctgagctcc agtgggcgtg gactaatatg gaacagtatt taagcgcctg tttgaatctc   240
acggagcgta aacggttggt ggcgcagcat ctgacgcacg tgtcgcagac gcaggagcag   300
aacaaagaga atcagaatcc caattctgat gcgccggtga tcagatcaaa aacttcagcc   360
aggtacatgg agctggtcgg gtggctcgtg gacaagggga ttacctcgga gaagcagtgg   420

SEQ ID NO: 54           moltype = DNA   length = 381
FEATURE                 Location/Qualifiers
source                  1..381
                        mol_type = other DNA
                        organism = synthetic construct
SEQUENCE: 54
atccaggagg accaggcctc atacatctcc ttcaatgcgg cctccaactc gcggtcccaa    60
atcaaggctg ccttggacaa tgcgggaaag attatgaact tgactaaaac cgcccccgac   120
tacctggtgg gccagcagcc cgtgaggac atttccagca atcggattta aaaattttg    180
gaactaaacg gtacgatcc ccaatatgcg gcttccgtct ttctgggatg gccacgaaa    240
aagttcggca agaggaacac catctggctg tttgggcctg caactaccgg gaagaccaac   300
atcgcggagg ccatagccca cactgtgccc ttctacgggt gcgtaaactg gaccaatgag   360
aacttttccct tcaacgactg t                                            381
```

```
SEQ ID NO: 55            moltype = DNA  length = 759
FEATURE                  Location/Qualifiers
source                   1..759
                         mol_type = other DNA
                         organism = synthetic construct
SEQUENCE: 55
gtcgacaaga tggtgatctg gtgggaggag gggaagatga ccgccaaggt cgtggagtcg   60
gccaaagcca ttctcggagg aagcaaggtg cgcgtggacc agaaatgcaa gtcctcggcc  120
cagatagacc cgactcccgt gatcgtcacc tccaacacca acatgtgcgc cgtgattgac  180
gggaactcaa cgaccttcga acaccagcag ccgttgcaag accggatgtt caaatttgaa  240
ctcacccgcc gtctggatca tgactttggg aaggtcacca gcaggaagt caaagacttt   300
ttccggtggg caaggatca cgtggttgag gtggagcatg aattctacgt caaaaagggt   360
ggagccaaga aaagacccgc ccccagtgac gcagatataa gtgagcccaa acgggtgcgc  420
gagtcagttg cgcagccatc gacgtcagac gcggaagctt cgatcaacta cgcagacagg  480
taccaaaaca aatgttctcg tcacgtgggc atgaatctga tgctgtttcc ctgcagacaa  540
tgcgagagaa tgaatcagaa ttcaaatatc tgcttcactc acggacagaa agactgttta  600
gagtgctttc ccgtgtcaga atctcaaccc gtttctgtcg tcaaaaaggc gtatcagaaa  660
ctgtgctaca ttcatcatat catgggaaag gtgccagacg cttgcactgc ctgcgatctg  720
gtcaatgtgg atttggatga ctgcatcttt gaacaataa                         759

SEQ ID NO: 56            moltype = DNA  length = 492
FEATURE                  Location/Qualifiers
source                   1..492
                         mol_type = other DNA
                         organism = synthetic construct
SEQUENCE: 56
gtcgacaaga tggtgatctg gtgggaggag gggaagatga ccgccaaggt cgtggagtcg   60
gccaaagcca ttctcggagg aagcaaggtg cgcgtggacc agaaatgcaa gtcctcggcc  120
cagatagacc cgactcccgt gatcgtcacc tccaacacca acatgtgcgc cgtgattgac  180
gggaactcaa cgaccttcga acaccagcag ccgttgcaag accggatgtt caaatttgaa  240
ctcacccgcc gtctggatca tgactttggg aaggtcacca gcaggaagt caaagacttt   300
ttccggtggg caaggatca cgtggttgag gtggagcatg aattctacgt caaaaagggt   360
ggagccaaga aaagacccgc ccccagtgac gcagatataa gtgagcccaa acgggtgcgc  420
gagtcagttg cgcagccatc gacgtcagac gcggaagctt cgatcaacta cgcagacagg  480
taccaaaaca aa                                                      492

SEQ ID NO: 57            moltype = DNA  length = 267
FEATURE                  Location/Qualifiers
source                   1..267
                         mol_type = other DNA
                         organism = synthetic construct
SEQUENCE: 57
tgttctcgtc acgtgggcat gaatctgatg ctgtttccct gcagacaatg cgagagaatg   60
aatcagaatt caaatatctg cttcactcac ggacagaaag actgtttaga gtgctttccc  120
gtgtcagaat ctcaacccgt ttctgtcgtc aaaaaggcgt atcagaaact gtgctacatt  180
catcatatca tgggaaaggt gccagacgct tgcactgcct gcgatctggt caatgtggat  240
ttggatgact gcatctttga acaataa                                      267

SEQ ID NO: 58            moltype = AA  length = 102
FEATURE                  Location/Qualifiers
source                   1..102
                         mol_type = protein
                         organism = synthetic construct
SEQUENCE: 58
TPGFYEIVIK VPSDLDGHLP GISDSFVNWV AEKEWELPPD SDMDLNLIEQ APLTVAEKLQ   60
RDFLTEWRRV SKAPEALFFV QFEKGESYFH MHVLVETTGV KS                     102

SEQ ID NO: 59            moltype = AA  length = 140
FEATURE                  Location/Qualifiers
source                   1..140
                         mol_type = protein
                         organism = synthetic construct
SEQUENCE: 59
MVLGRFLSQI REKLIQRIYR GIEPTLPNWF AVTKTRNGAG GGNKVVDECY IPNYLLPKTQ   60
PELQWAWTNM EQYLSACLNL TERKRLVAQH LTHVSQTQEQ NKENQNPNSD APVIRSKTSA  120
RYMELVGWLV DKGITSEKQW                                              140

SEQ ID NO: 60            moltype = AA  length = 127
FEATURE                  Location/Qualifiers
source                   1..127
                         mol_type = protein
                         organism = synthetic construct
SEQUENCE: 60
IQEDQASYIS FNAASNSRSQ IKAALDNAGK IMSLTKTAPD YLVGQQPVED ISSNRIYKIL   60
ELNGYDPQYA ASVFLGWATK KFGKRNTIWL FGPATTGKTN IAEAIAHTVP FYGCVNWTNE  120
NFPFNDC                                                            127

SEQ ID NO: 61            moltype = AA  length = 252
```

```
FEATURE                 Location/Qualifiers
source                  1..252
                        mol_type = protein
                        organism = synthetic construct
SEQUENCE: 61
VDKMVIWWEE GKMTAKVVES AKAILGGSKV RVDQKCKSSA QIDPTPVIVT SNTNMCAVID    60
GNSTTFEHQQ PLQDRMFKFE LTRRLDHDFG KVTKQEVKDF FRWAKDHVVE VEHEFYVKKG   120
GAKKRPAPSD ADISEPKRVR ESVAQPSTSD AEASINYADR YQNKCSRHVG MNLMLFPCRQ   180
CERMNQNSNI CFTHGQKDCL ECFPVSESQP VSVVKKAYQK LCYIHHIMGK VPDACTACDL   240
VNVDLDDCIF EQ                                                       252

SEQ ID NO: 62           moltype = AA   length = 164
FEATURE                 Location/Qualifiers
source                  1..164
                        mol_type = protein
                        organism = synthetic construct
SEQUENCE: 62
VDKMVIWWEE GKMTAKVVES AKAILGGSKV RVDQKCKSSA QIDPTPVIVT SNTNMCAVID    60
GNSTTFEHQQ PLQDRMFKFE LTRRLDHDFG KVTKQEVKDF FRWAKDHVVE VEHEFYVKKG   120
GAKKRPAPSD ADISEPKRVR ESVAQPSTSD AEASINYADR YQNK                   164

SEQ ID NO: 63           moltype = AA   length = 88
FEATURE                 Location/Qualifiers
source                  1..88
                        mol_type = protein
                        organism = synthetic construct
SEQUENCE: 63
CSRHVGMNLM LFPCRQCERM NQNSNICFTH GQKDCLECFP VSESQPVSVV KKAYQKLCYI    60
HHIMGKVPDA CTACDLVNVD LDDCIFEQ                                       88

SEQ ID NO: 64           moltype = DNA   length = 306
FEATURE                 Location/Qualifiers
source                  1..306
                        mol_type = other DNA
                        organism = synthetic construct
SEQUENCE: 64
atgccggggt tctacgagat tgtcctgaag gtcccgagtg acctggacga gcacctgccg    60
ggcatttcta actcgtttgt taactgggtg gccgagaagg aatgggagct gccgccggat   120
tctgacatgg atccgaatct gattgagcag gcacccgctga ccgtggccga aaagcttcag   180
cgcgagttcc tggtggagtg gcgccgcgtg agtaaggccc cggaggccct cttttttgtc   240
cagttcgaaa aggggagac ctacttccac ctgcacgtgc tgattgagac catcggggtc   300
aaatcc                                                              306

SEQ ID NO: 65           moltype = DNA   length = 420
FEATURE                 Location/Qualifiers
source                  1..420
                        mol_type = other DNA
                        organism = synthetic construct
SEQUENCE: 65
atggtggtcg gccgctacgt gagccagatt aaagagaagc tggtgacccg catctaccgc    60
ggggtcgagc cgcagcttcc gaactggttc gcggtgacca aaacgcgaaa tggcgccgag   120
ggcgggaaca aggtggtgga cgactgctac atccccaact acctgctccc caagacccag   180
cccgagctcc agtgggcgtg gactaacatg gaccagtatt taagcgcctg tttgaatctc   240
gcggagcgta acggctggt ggcgcagcat ctgacgcacg tgtcgcagac gcaggagcag   300
aacaaagaga tcagaaaccc caattctgac gcgccggtca tcaggtcaaa aacctcagcc   360
aggtacatgg agctggtcgg gtggctggtg gaccgcggga tcacgtcaga aaagcaatgg   420

SEQ ID NO: 66           moltype = DNA   length = 381
FEATURE                 Location/Qualifiers
source                  1..381
                        mol_type = other DNA
                        organism = synthetic construct
SEQUENCE: 66
attcaggagg accaggcctc gtacatctcc ttcaacgccg cctccaactc gcggtcccag    60
atcaaggccg cgctggacaa tgcctccaag atcatgagcc tgacaaagac ggctccggac   120
tacctggtgg cagcaacccc gccggaggac attaccaaaa atcggatcta ccaaatcctg   180
gagctgaacg ggtacgatcc gcagtacgcg gcctccgtct tcctgggctg gcgcaaaag   240
aagttcggga gaggaacac catctggctc tttgggccgg ccacgacggg taaaaccaac   300
atcgcggaag ccatccccca cgccgtgccc ttctacggct gcgtaaactg gaccaatgag   360
aactttccct tcaacgattg c                                             381

SEQ ID NO: 67           moltype = DNA   length = 768
FEATURE                 Location/Qualifiers
source                  1..768
                        mol_type = other DNA
                        organism = synthetic construct
SEQUENCE: 67
gtcgacaaga tggtgatctg gtgggaggag ggcaagatga cggccaaggt cgtggagagc    60
gccaaggcca ttctgggcgg aagcaaggtg cgcgtgacc aaaagtgcaa gtcatcggcc   120
```

```
cagatcgaac ccactcccgt gatcgtcacc tccaacacca acatgtgcgc cgtgattgac    180
gggaacagca ccaccttcga gcatcagcag ccgctgcagg accggatgtt taaatttgaa    240
cttacccgcc gtttggacca tgactttggg aaggtcacca acaggaagt aaaggacttt     300
ttccggtggg cttccgatca cgtgactgac gtggctcatg agttctacgt cagaaagggt    360
ggagctaaga aacgccccgc ctccaatgaa gcggatgtaa gcgagccaaa acggcagtgc    420
acgtcacttg cgcagccgac aacgtcagac gcggaagcac cggcggacta cgcggacagg    480
taccaaaaca aatgttctcg tcacgtgggc atgaatctga tgcttttttcc ctgtaaaaca    540
tgcgagagaa tgaatcaaat ttccaatgtc tgttttacgc atggtcaaag agactgtggg    600
gaatgcttcc ctggaatgtc agaatctcaa cccgtttctg tcgtcaaaaa gaagacttat    660
cagaaactgt gtccaattca tcatatcctg ggaagggcac ccgagattgc ctgttcggcc    720
tgcgatttgg ccaatgtgga cttggatgac tgtgtttctg agcaataa                 768

SEQ ID NO: 68              moltype = DNA  length = 492
FEATURE                    Location/Qualifiers
source                     1..492
                           mol_type = other DNA
                           organism = synthetic construct
SEQUENCE: 68
gtcgacaaga tggtgatctg gtgggaggag ggcaagatga cggccaaggt cgtggagagc     60
gccaaggcca ttctgggcgg aagcaaggtg cgcgtggacc aaaagtgcaa gtcatcggcc    120
cagatcgaac ccactcccgt gatcgtcacc tccaacacca acatgtgcgc cgtgattgac    180
gggaacagca ccaccttcga gcatcagcag ccgctgcagg accggatgtt taaatttgaa    240
cttacccgcc gtttggacca tgactttggg aaggtcacca acaggaagt aaaggacttt     300
ttccggtggg cttccgatca cgtgactgac gtggctcatg agttctacgt cagaaagggt    360
ggagctaaga aacgccccgc ctccaatgac gcggatgtaa gcgagccaaa acggcagtgc    420
acgtcacttg cgcagccgac aacgtcagac gcggaagcac cggcggacta cgcggacagg    480
taccaaaaca aa                                                        492

SEQ ID NO: 69              moltype = DNA  length = 276
FEATURE                    Location/Qualifiers
source                     1..276
                           mol_type = other DNA
                           organism = synthetic construct
SEQUENCE: 69
tgttctcgtc acgtgggcat gaatctgatg cttttcccct gtaaaacatg cgagagaatg     60
aatcaaattt ccaatgtctg ttttacgcat ggtcaaagag actgtgggga atgcttccct    120
ggaatgtcag aatctcaacc cgtttctgtc gtcaaaaaga agacttatca gaaactgtgt    180
ccaattcatc atatcctggg aagggcaccc gagattgcct gttcggcctg cgatttggcc    240
aatgtggact tggatgactg tgtttctgag caataa                              276

SEQ ID NO: 70              moltype = AA  length = 102
FEATURE                    Location/Qualifiers
source                     1..102
                           mol_type = protein
                           organism = synthetic construct
SEQUENCE: 70
MPGFYEIVLK VPSDLDEHLP GISNSFVNWV AEKEWELPPD SDMDPNLIEQ APLTVAEKLQ     60
REFLVEWRRV SKAPEALFFV QFEKGETYFH LHVLIETIGV KS                       102

SEQ ID NO: 71              moltype = AA  length = 140
FEATURE                    Location/Qualifiers
source                     1..140
                           mol_type = protein
                           organism = synthetic construct
SEQUENCE: 71
MVVGRYVSQI KEKLVTRIYR GVEPQLPNWF AVTKTRNGAG GGNKVVDDCY IPNYLLPKTQ     60
PELQWAWTNM DQYLSACLNL AERKRLVAQH LTHVSQTQEQ NKENQNPNSD APVIRSKTSA    120
RYMELVGWLV DRGITSEKQW                                                140

SEQ ID NO: 72              moltype = AA  length = 127
FEATURE                    Location/Qualifiers
source                     1..127
                           mol_type = protein
                           organism = synthetic construct
SEQUENCE: 72
IQEDQASYIS FNAASNSRSQ IKAALDNASK IMSLTKTAPD YLVGSNPPED ITKNRIYQIL     60
ELNGYDPQYA ASVFLGWAQK KFGKRNTIWL FGPATTGKTN IAEAIAHAVP FYGCVNWTNE    120
NFPFNDC                                                              127

SEQ ID NO: 73              moltype = AA  length = 255
FEATURE                    Location/Qualifiers
source                     1..255
                           mol_type = protein
                           organism = synthetic construct
SEQUENCE: 73
VDKMVIWWEE GKMTAKVVES AKAILGGSKV RVDQKCKSSA QIEPTPVIVT SNTNMCAVID     60
GNSTTFEHQQ PLQDRMFKFE LTRRLDHDFG KVTKQEVKDF FRWASDHVTD VAHEFYVRKG    120
GAKKRPASND ADVSEPKRQC TSLAQPTTSD AEAPADYADR YQNKCSRHVG MNLMLFPCKT    180
CERMNQISNV CFTHGQRDCG ECFPGMSESQ PVSVVKKKTY QKLCPIHHIL GRAPEIACSA    240
```

```
CDLANVDLDD CVSEQ                                                              255

SEQ ID NO: 74             moltype = AA   length = 164
FEATURE                   Location/Qualifiers
source                    1..164
                          mol_type = protein
                          organism = synthetic construct
SEQUENCE: 74
VDKMVIWWEE GKMTAKVVES AKAILGGSKV RVDQKCKSSA QIEPTPVIVT SNTNMCAVID    60
GNSTTFEHQQ PLQDRMFKFE LTRRLDHDFG KVTKQEVKDF FRWASDHVTD VAHEFYVRKG   120
GAKKRPASND ADVSEPKRQC TSLAQPTTSD AEAPADYADR YQNK                    164

SEQ ID NO: 75             moltype = AA   length = 91
FEATURE                   Location/Qualifiers
source                    1..91
                          mol_type = protein
                          organism = synthetic construct
SEQUENCE: 75
CSRHVGMNLM LFPCKTCERM NQISNVCFTH GQRDCGECFP GMSESQPVSV VKKKTYQKLC    60
PIHHILGRAP EIACSACDLA NVDLDDCVSE Q                                   91

SEQ ID NO: 76             moltype = DNA   length = 306
FEATURE                   Location/Qualifiers
source                    1..306
                          mol_type = other DNA
                          organism = synthetic construct
SEQUENCE: 76
acgccggggt tctacgagat cgtgctgaag gtgcccagcg acctggacga gcacctgccc    60
ggcatttctg actcttttgt gagctgggtg gccgagaagg aatgggagct gccgccggat   120
tctgacatgg acttgaatct gattgagcag gcacccctga gctggccga aaagctgcaa    180
cgcgagttcc tggtcgagtg gcgccgcgtg agtaaggccc cggaggccct cttctttgtc   240
cagttcgaga gggggacag ctacttccac ctgcacatcg tggtggagac cgtgggcgtc    300
aaatcc                                                              306

SEQ ID NO: 77             moltype = DNA   length = 420
FEATURE                   Location/Qualifiers
source                    1..420
                          mol_type = other DNA
                          organism = synthetic construct
SEQUENCE: 77
atggtggtgg gccgctacgt gagccagatt aaagagaagc tggtgacccg catctaccgc    60
ggggtcgagc cgcagcttcc gaactggttc gcggtgacca gacgcgtaa tggcgccgga   120
ggcggaaca aggtggtgga cgactgctac atccccaact acctgctccc caagacccag   180
cccgagctcc agtgggcgtg gactaacatg gaccagtata taagcgcctg tttgaatctc   240
gcggagcgta acggctggt ggcgcagcat ctgacgcacg tgtcgcagac gcaggagcag    300
aacaaggaaa accagaaccc caattctgac gcgccggtca tcaggtcaaa aacctccgcc   360
aggtacatgg agctggtcgg gtggctggtg gaccgcggga tcacgtcaga aaagcaatgg   420

SEQ ID NO: 78             moltype = DNA   length = 381
FEATURE                   Location/Qualifiers
source                    1..381
                          mol_type = other DNA
                          organism = synthetic construct
SEQUENCE: 78
atccaggagg accaggcgtc ctacatctcc ttcaacgccg cctccaactc gcggtcacaa    60
atcaaggccg cgctggacaa tgcctccaaa atcatgagcc tgacaaagac ggctccggac   120
tacctggtgg gccagaaccc gccggaggac atttccagca accgcatcta ccgaatcctg   180
gagatgaacg ggtacgatcc gcagtacgcg gcctccgtct tcctgggctg gcgcaaaag   240
aagttcggga gaggaacac catctggctc tttgggccgg ccacgacggg taaaaccaac    300
atcgcggaag ccatcgccca cgccgtgccc ttctacggct gcgtgaactg gaccaatgag   360
aactttccgt tcaacgattg c                                             381

SEQ ID NO: 79             moltype = DNA   length = 765
FEATURE                   Location/Qualifiers
source                    1..765
                          mol_type = other DNA
                          organism = synthetic construct
SEQUENCE: 79
gtcgacaaga tggtgatctg gtgggaggag ggcaagatga cggccaaggt cgtagagagc    60
gccaaggcca tcctgggcgg aagcaaggtg cgcgtggacc aaaagtgcaa gtcatcggcc   120
cagatcgacc caactcccgt gatcgtcacc tccaacacaa acatgtgcgc ggtcatcgac   180
ggaaactcga ccaccttcga gcaccaacaa ccactccagg accggatgtt caagttcgag   240
ctcaccaagc gcctggagca cgactttggc aaggtcacca gcaggaagt caaagacttt   300
ttccgtgggg cgtcagatca cgtgaccgag gtgactcacg agttttacgt cagaaagggt   360
ggagctagaa agaggcccgc ccccaatgac gcagatataa gtgagcccaa gcgggcctgt   420
ccgtcagttg cgcagccatc gacgtcagac gcggaagctc cggtgactga cgggacagg   480
taccaaaaca aatgttctcg tcacgtgggt atgaatctga tgcttttcc ctgccggcaa    540
tgcgagagaa tgaatcagaa tgtggacatt tgcttcacgc acgggtcat ggactgtgcc    600
gagtgcttcc ccgtgtcaga atctcaaccc gtgtctgtcg tcagaaagcg gacgtatcag   660
```

```
aaactgtgtc cgattcatca catcatgggg agggcgcccg aggtggcctg ctcggcctgc    720
gaactggcca atgtggactt ggatgactgt gacatggaac aataa                   765

SEQ ID NO: 80           moltype = DNA   length = 492
FEATURE                 Location/Qualifiers
source                  1..492
                        mol_type = other DNA
                        organism = synthetic construct
SEQUENCE: 80
gtcgacaaga tggtgatctg gtgggaggag ggcaagatga cggccaaggt cgtagagagc    60
gccaaggcca tcctgggcgg aagcaaggtg cgcgtggacc aaaagtgcaa gtcatcggcc   120
cagatcgacc caactcccgt gatcgtcacc tccaacacca acatgtgcgc ggtcatcgac   180
ggaaactcga ccaccttcga gccaccaaca ccactccagg accggatgtt caagttcgag   240
ctcaccaagc gcctggagca cgactttggc aaggtcacca agcaggaagt caaagacttt   300
ttccggtggg cgtcagatca cgtgaccgag gtgactcacg agttttacgt cagaaagggt   360
ggagctagaa agaggcccgc ccccaatgac gcagatataa gtgagcccaa gcgggcctgt   420
ccgtcagttg cgcagccatc gacgtcagac gcggaagctc cggtggacta cgcggacagg   480
taccaaaaca aa                                                       492

SEQ ID NO: 81           moltype = DNA   length = 273
FEATURE                 Location/Qualifiers
source                  1..273
                        mol_type = other DNA
                        organism = synthetic construct
SEQUENCE: 81
tgttctctgtc acgtgggtat gaatctgatg cttttctccct gccggcaatg cgagagaatg   60
aatcagaatg tggacatttg cttcacgcac ggggtcatgg actgtgccga gtgcttcccc   120
gtgtcagaat ctcaacccgt gtctgtcgtc agaaagcgga cgtatcagaa actgtgtccg   180
attcatcaca tcatggggag ggcgcccgag gtggcctgct cggcctgcga actggccaat   240
gtggacttgg atgactgtga catggaacaa taa                                273

SEQ ID NO: 82           moltype = AA    length = 102
FEATURE                 Location/Qualifiers
source                  1..102
                        mol_type = protein
                        organism = synthetic construct
SEQUENCE: 82
TPGFYEIVLK VPSDLDEHLP GISDSFVSWV AEKEWELPPD SDMDLNLIEQ APLTVAEKLQ    60
REFLVEWRRV SKAPEALFFV QFEKGDSYFH LHILVETVGV KS                      102

SEQ ID NO: 83           moltype = AA    length = 140
FEATURE                 Location/Qualifiers
source                  1..140
                        mol_type = protein
                        organism = synthetic construct
SEQUENCE: 83
MVVGRYVSQI KEKLVTRIYR GVEPQLPNWF AVTKTRNGAG GGNKVVDDCY IPNYLLPKTQ    60
PELQWAWTNM DQYISACLNL AERKRLVAQH LTHVSQTQEQ NKENQNPNSD APVIRSKTSA   120
RYMELVGWLV DRGITSEKQW                                               140

SEQ ID NO: 84           moltype = AA    length = 127
FEATURE                 Location/Qualifiers
source                  1..127
                        mol_type = protein
                        organism = synthetic construct
SEQUENCE: 84
IQEDQASYIS FNAASNSRSQ IKAALDNASK IMSLTKTAPD YLVGQNPPED ISSNRIYRIL    60
EMNGYDPQYA ASVFLGWAQK KFGKRNTIWL FGPATTGKTN IAEAIAHAVP FYGCVNWTNE   120
NFPFNDC                                                             127

SEQ ID NO: 85           moltype = AA    length = 254
FEATURE                 Location/Qualifiers
source                  1..254
                        mol_type = protein
                        organism = synthetic construct
SEQUENCE: 85
VDKMVIWWEE GKMTAKVVES AKAILGGSKV RVDQKCKSSA QIDPTPVIVT SNTNMCAVID    60
GNSTTFEHQQ PLQDRMFKFE LTKRLEHDFG KVTKQEVKDF FRWASDHVTE VTHEFYVRKG   120
GARKRPAPND ADISEPKRAC PSVAQPSTSD AEAPVDYADR YQNKCSRHVG MNLMLFPCRQ   180
CERMNQNVDI CFTHGVMDCA ECFPVSESQP VSVVRKRTYQ KLCPIHHIMG RAPEVACSAC   240
ELANVDLDDC DMEQ                                                     254

SEQ ID NO: 86           moltype = AA    length = 164
FEATURE                 Location/Qualifiers
source                  1..164
                        mol_type = protein
                        organism = synthetic construct
SEQUENCE: 86
VDKMVIWWEE GKMTAKVVES AKAILGGSKV RVDQKCKSSA QIDPTPVIVT SNTNMCAVID    60
```

```
GNSTTFEHQQ PLQDRMFKFE LTKRLEHDFG KVTKQEVKDF FRWASDHVTE VTHEFYVRKG    120
GARKRPAPND ADISEPKRAC PSVAQPSTSD AEAPVDYADR YQNK                    164

SEQ ID NO: 87              moltype = AA   length = 90
FEATURE                    Location/Qualifiers
source                     1..90
                           mol_type = protein
                           organism = synthetic construct
SEQUENCE: 87
CSRHVGMNLM LFPCRQCERM NQNVDICFTH GVMDCAECFP VSESQPVSVV RKRTYQKLCP     60
IHHIMGRAPE VACSACELAN VDLDDCDMEQ                                      90

SEQ ID NO: 88              moltype = DNA   length = 303
FEATURE                    Location/Qualifiers
source                     1..303
                           mol_type = other DNA
                           organism = synthetic construct
SEQUENCE: 88
atggctacct tctatgaagt cattgttcgc gtcccatttg acgtggagga acatctgcct     60
ggaatttctg acagctttgt ggactgggta actggtcaaa tttgggagct gcctccagag    120
tcagatttaa atttgactct ggttgaacag cctcagttga cggtggctga tagaattcgc    180
cgcgtgttcc tgtacgagtg gaacaaattt ccaagcagg agtccaaatt ctttgtgcag     240
tttgaaaagg gatctgaata ttttcatctg cacacgcttg tggagacctc cggcatctct    300
tcc                                                                  303

SEQ ID NO: 89              moltype = DNA   length = 411
FEATURE                    Location/Qualifiers
source                     1..411
                           mol_type = other DNA
                           organism = synthetic construct
SEQUENCE: 89
atggtcctcg gccgctacgt gagtcagatt cgcgcccagc tggtgaaagt ggtcttccag     60
ggaattgaac cccagatcaa cgactgggtc gccatcacca aggtaaagaa gggcggagcc    120
aataaggtgg tggattctgg gtatattccc gcctacctgc tgccgaaggt ccaaccggag    180
cttcagtggg cgtggacaaa cctggacgag tataaattgc ccgccctgaa tctggaggag    240
cgcaaacggc tcgtcgcgca gtttctggca gaatcctcgc agcgctcgca ggaggcggct    300
tcgcagcgtg agttctcggc tgacccggtc atcaaaagca agcttcccca gaaatacatg    360
gcgctcgtca actggctcgt ggagcacggc atcacttccg agaagcagtg g             411

SEQ ID NO: 90              moltype = DNA   length = 381
FEATURE                    Location/Qualifiers
source                     1..381
                           mol_type = other DNA
                           organism = synthetic construct
SEQUENCE: 90
atccaggaaa atcaggagag ctacctctcc ttcaactcca ccggcaactc tcggagccag     60
atcaaggccg cgctcgacaa cgcgaccaaa attatgagtc tgacaaaaag cgcggtggac    120
tacctcgtgg ggagctccgt tcccgaggac atttcaaaaa acagaatctg gcaaattttt    180
gagatgaatg ctacgacccc ggcctacgcg ggatccatcc tctacggctg gtgtcagcgc    240
tccttcaaca agaggaacac cgtctggctc tacggacccg ccacgaccgg caagaccaac    300
atcgcggagg ccatcgccca cactgtgccc ttttacggct gcgtgaactg gaccaatgaa    360
aactttccct ttaatgactg t                                              381

SEQ ID NO: 91              moltype = DNA   length = 738
FEATURE                    Location/Qualifiers
source                     1..738
                           mol_type = other DNA
                           organism = synthetic construct
SEQUENCE: 91
gtggacaaaa tgctcatttg gtgggaggag ggaaagatga ccaacaaggt ggttgaatcc     60
gccaaggcca tcctgggggg ctcaaaggtg cgggtcgatc agaaatgtaa atcctctgtt    120
caaattgatt ctaccccctgt cattgtaact ccaatacaa acatgtgtgt ggtggtggat    180
gggaattcca cgacctttga acaccagcag ccgctggagg accgcatgtt caaatttgaa    240
ctgactaagc ggctcccgcc agattttggc aagattacta agcaggaagt caaggacttt    300
tttgcttggg caaaggtcaa tcaggtgccg gtgactcacg agtttaaagt tcccaggaa    360
ttggcgggaa ctaaaggggc ggagaaatct ctaaaacgcc cactgggtga cgtcaccaat    420
actagctata aaagtctgga gaagcgggcc aggctctcat tgttcccga cgcctcgc     480
agttcagacg tgactgttga tcccgctcct ctgcgaccgc tcaattggaa ttcaaggtat    540
gattgcaaat gtgactatca tgctcaattt gacaacaatt ctaacaaatg tgatgaatgt    600
gaatatttga tcggggcaa aaatggatgt atctgtcaca atgtaactca ctgtcaaatt    660
tgtcatggga ttcccccctg ggaaaaggaa aacttgtcag attttgggga ttttgacgat    720
gccaataaag aacagtaa                                                  738

SEQ ID NO: 92              moltype = DNA   length = 549
FEATURE                    Location/Qualifiers
source                     1..549
                           mol_type = other DNA
                           organism = synthetic construct
SEQUENCE: 92
```

```
gtggacaaaa tgctcatttg gtgggaggag ggaaagatga ccaacaaggt ggttgaatcc    60
gccaaggcca tcctgggggg ctcaaaggtg cgggtcgatc agaaatgtaa atcctctgtt   120
caaattgatt ctaccctgt cattgtaact tccaatacaa acatgtgtgt ggtggtggat   180
gggaattcca cgacctttga acaccagcag ccgctggagg accgcatgtt caaatttgaa   240
ctgactaagc ggctcccgcc agattttggc aagattacta agcaggaggt caaggacttt   300
tttgcttggg caaaggtcaa tcaggtgccg gtgactcacg agtttaaagt tcccagggaa   360
ttggcgggaa ctaaaggggc ggagaaatct ctaaaacgcc cactgggtga cgtcaccaat   420
actagctata aaagtctgga agcggggcc aggctctcat tgttcccga cgcctcgc       480
agttcagacg tgactgttga tcccgctcct ctgcgaccgc tcaattggaa ttcaaggtat   540
gattgcaaa                                                          549

SEQ ID NO: 93           moltype = DNA   length = 189
FEATURE                 Location/Qualifiers
source                  1..189
                        mol_type = other DNA
                        organism = synthetic construct
SEQUENCE: 93
tgtgactatc atgctcaatt tgacaacatt tctaacaaat gtgatgaatg tgaatatttg    60
aatcggggca aaaatggatg tatctgtcac aatgtaactc actgtcaaat ttgtcatggg   120
attccccct gggaaaagga aaacttgtca gattttgggg attttgacga tgccaataaa   180
gaacagtaa                                                          189

SEQ ID NO: 94           moltype = AA    length = 101
FEATURE                 Location/Qualifiers
source                  1..101
                        mol_type = protein
                        organism = synthetic construct
SEQUENCE: 94
MATFYEVIVR VPFDVEEHLP GISDSFVDWV TGQIWELPPE SDLNLTLVEQ PQLTVADRIR    60
RVFLYEWNKF SKQESKFFVQ FEKGSEYFHL HTLVETSGIS S                      101

SEQ ID NO: 95           moltype = AA    length = 137
FEATURE                 Location/Qualifiers
source                  1..137
                        mol_type = protein
                        organism = synthetic construct
SEQUENCE: 95
MVLGRYVSQI RAQLVKVVFQ GIEPQINDWV AITKVKKGGA NKVVDSGYIP AYLLPKVQPE    60
LQWAWTNLDE YKLAALNLEE RKRLVAQFLA ESSQRSQEAA SQREFSADPV IKSKTSQKYM   120
ALVNWLVEHG ITSEKQW                                                 137

SEQ ID NO: 96           moltype = AA    length = 127
FEATURE                 Location/Qualifiers
source                  1..127
                        mol_type = protein
                        organism = synthetic construct
SEQUENCE: 96
IQENQESYLS FNSTGNSRSQ IKAALDNATK IMSLTKSAVD YLVGSSVPED ISKNRIWQIF    60
EMNGYDPAYA GSILYGWCQR SFNKRNTVWL YGPATTGKTN IAEAIAHTVP FYGCVNWTNE   120
NFPFNDC                                                            127

SEQ ID NO: 97           moltype = AA    length = 245
FEATURE                 Location/Qualifiers
source                  1..245
                        mol_type = protein
                        organism = synthetic construct
SEQUENCE: 97
VDKMLIWWEE GKMTNKVVES AKAILGGSKV RVDQKCKSSV QIDSTPVIVT SNTNMCVVVD    60
GNSTTFEHQQ PLEDRMFKFE LTKRLPPDFG KITKQEVKDF FAWAKVNQVP VTHEFKVPRE   120
LAGTKGAEKS LKRPLGDVTN TSYKSLEKRA RLSFVPETPR SSDVTVDPAP LRPLNWNSRY   180
DCKCDYHAQF DNISNKCDEC EYLNRGKNGC ICHNVTHCQI CHGIPPWEKE NLSDFGDFDD   240
ANKEQ                                                              245

SEQ ID NO: 98           moltype = AA    length = 183
FEATURE                 Location/Qualifiers
source                  1..183
                        mol_type = protein
                        organism = synthetic construct
SEQUENCE: 98
VDKMLIWWEE GKMTNKVVES AKAILGGSKV RVDQKCKSSV QIDSTPVIVT SNTNMCVVVD    60
GNSTTFEHQQ PLEDRMFKFE LTKRLPPDFG KITKQEVKDF FAWAKVNQVP VTHEFKVPRE   120
LAGTKGAEKS LKRPLGDVTN TSYKSLEKRA RLSFVPETPR SSDVTVDPAP LRPLNWNSRY   180
DCK                                                                183

SEQ ID NO: 99           moltype = AA    length = 62
FEATURE                 Location/Qualifiers
source                  1..62
                        mol_type = protein
                        organism = synthetic construct
```

```
SEQUENCE: 99
CDYHAQFDNI SNKCDECEYL NRGKNGCICH NVTHCQICHG IPPWEKENLS DFGDFDDANK    60
EQ                                                                  62

SEQ ID NO: 100           moltype = DNA   length = 306
FEATURE                  Location/Qualifiers
source                   1..306
                         mol_type = other DNA
                         organism = synthetic construct
SEQUENCE: 100
atgccgggt tttacgagat tgtgattaag gtcccagcg accttgacga gcatctgccc     60
ggcatttctg acagctttgt gaactgggtg gccgagaagg aatgggagtt gccgccagat  120
tctgacatgg atctgaatct gattgagcag gcaccctga ccgtggccga aagctgcag   180
cgcgacttcc tggtccagtg gcgccgcgtg agtaaggccc cggaggccct cttctttgtt  240
cagttcgaga agggcgagtc ctacttccac ctccatattc tggtggagac cacggggtc   300
aaatcc                                                             306

SEQ ID NO: 101           moltype = DNA   length = 420
FEATURE                  Location/Qualifiers
source                   1..420
                         mol_type = other DNA
                         organism = synthetic construct
SEQUENCE: 101
atggtgctgg ccgcttcct gagtcagatt agggacaagc tggtgcagac catctaccgc    60
gggatcgagc cgaccctgcc caactggttc gcggtgacca gacgcgtaa tggcgccgga   120
ggggtggaaca aggtggtgga cgagtgctac atccccaagt acctcctgcc caagactcag  180
cccgagctgc agtgggcgtg gactaacatg gaggagtata taagcgcgtg tttaaacctg   240
gccgagcgca aacggctcgt ggcgcacgac ctgacccacg tcagccagac ccaggagcag   300
aacaaggaga atctgaaccc caattctgac gcgcctgtca tccggtcaaa aacctccgca   360
cgctacatgg agctggtcgg gtggctggtg gaccggggca tcacctccga aagcagtgg    420

SEQ ID NO: 102           moltype = DNA   length = 381
FEATURE                  Location/Qualifiers
source                   1..381
                         mol_type = other DNA
                         organism = synthetic construct
SEQUENCE: 102
atccaggagg accaggcctc gtacatctcc ttcaacgccg cctccaactc gcggtcccag   60
atcaaggccg ctctggacaa tgccggcaag atcatggcgc tgaccaaatc gcgccgac    120
tacctggtag gccccgctcc gccgccgac attaaaacca accgcattta ccgcatcctg   180
gagctgaacg gctacgaccc tgcctacgcc ggctccgtct ttctcggctg ggcccagaaa   240
aggttcgaa aacgcaacac catctggctg tttgggccgg ccaccacggg caagaccaac    300
atcgcggaag ccatcgccca cgccgtgccc ttctacggct gcgtcaactg gaccaatgag   360
aactttccct tcaacgattg c                                             381

SEQ ID NO: 103           moltype = DNA   length = 765
FEATURE                  Location/Qualifiers
source                   1..765
                         mol_type = other DNA
                         organism = synthetic construct
SEQUENCE: 103
gtcgacaaga tggtgatctg gtgggaggag ggcaagatga cggccaaggt cgtggagtcc    60
gccaaggcca ttctcggcgg cagcaaggtg cgcgtggacc aaaagtgcaa gtcgtccgcc   120
cagatcgatc ccaccccgt gatcgtcacc tccaacacca acatgtgcgc cgtgattgac    180
gggaacagca ccaccttcga gcaccagcag ccgttgcagg accggatgtt caaatttgaa   240
ctcacccgcc gtctggagca tgactttggc aaggtgacaa agcaggaagt caaagagttc   300
ttccgctggg cgcaggatca cgtgaccgag gtggcgcatg agttctacgt cagaaagggt   360
ggagccaaca gagacccgc ccccgatgac gcggataaaa gcgagcccaa gcgggcctgc   420
ccctcagtcg cggatccatc gacgtcagac gcggaaggag ctccggtgga ctttgccgac   480
aggtaccaaa acaaatgttc tcgtcacgcg ggcatgctgt agatgctgtt tccctgcaaa   540
acatgcgaga gaatgaatca gaatttcaac atttgcttca cgcacgggac cagagactgt   600
tcagaatgtt tccccggcgt gtcagaatct caaccggtcg tcagaaagag gacgtatcgg   660
aaactctgtg ccattcatca tctgctgggg cgggctcccg agattgcttg ctcggcctgc   720
gatctggtca acgtggatct ggatgactgt gtttctgagc aataa                  765

SEQ ID NO: 104           moltype = DNA   length = 495
FEATURE                  Location/Qualifiers
source                   1..495
                         mol_type = other DNA
                         organism = synthetic construct
SEQUENCE: 104
gtcgacaaga tggtgatctg gtgggaggag ggcaagatga cggccaaggt cgtggagtcc    60
gccaaggcca ttctcggcgg cagcaaggtg cgcgtggacc aaaagtgcaa gtcgtccgcc   120
cagatcgatc ccaccccgt gatcgtcacc tccaacacca acatgtgcgc cgtgattgac    180
gggaacagca ccaccttcga gcaccagcag ccgttgcagg accggatgtt caaatttgaa   240
ctcacccgcc gtctggagca tgactttggc aaggtgacaa agcaggaagt caaagagttc   300
ttccgctggg cgcaggatca cgtgaccgag gtggcgcatg agttctacgt cagaaagggt   360
ggagccaaca gagacccgc ccccgatgac gcggataaaa gcgagcccaa gcgggcctgc   420
ccctcagtcg cggatccatc gacgtcagac gcggaaggag ctccggtgga ctttgccgac   480
```

```
SEQ ID NO: 105           moltype = DNA  length = 270
FEATURE                  Location/Qualifiers
source                   1..270
                         mol_type = other DNA
                         organism = synthetic construct
SEQUENCE: 105
tgttctcgtc acgcgggcat gcttcagatg ctgtttccct gcaaaacatg cgagagaatg    60
aatcagaatt tcaacatttg cttcacgcac gggaccagag actgttcaga atgtttcccc   120
ggcgtgtcag aatctcaacc ggtcgtcaga aagaggacgt atcggaaact ctgtgccatt   180
catcatctgc tggggcgggc tcccgagatt gcttgctcgg cctgcgatct ggtcaacgtg   240
gatctggatg actgtgtttc tgagcaataa                                    270

SEQ ID NO: 106           moltype = AA  length = 102
FEATURE                  Location/Qualifiers
source                   1..102
                         mol_type = protein
                         organism = synthetic construct
SEQUENCE: 106
MPGFYEIVIK VPSDLDEHLP GISDSFVNWV AEKEWELPPD SDMDLNLIEQ APLTVAEKLQ    60
RDFLVQWRRV SKAPEALFFV QFEKGESYFH LHILVETTGV KS                      102

SEQ ID NO: 107           moltype = AA  length = 140
FEATURE                  Location/Qualifiers
source                   1..140
                         mol_type = protein
                         organism = synthetic construct
SEQUENCE: 107
MVLGRFLSQI RDKLVQTIYR GIEPTLPNWF AVTKTRNGAG GGNKVVDECY IPNYLLPKTQ    60
PELQWAWTNM EEYISACLNL AERKRLVAHD LTHVSQTQEQ NKENLNPNSD APVIRSKTSA   120
RYMELVGWLV DRGITSEKQW                                                140

SEQ ID NO: 108           moltype = AA  length = 127
FEATURE                  Location/Qualifiers
source                   1..127
                         mol_type = protein
                         organism = synthetic construct
SEQUENCE: 108
IQEDQASYIS FNAASNSRSQ IKAALDNAGK IMALTKSAPD YLVGPAPPAD IKTNRIYRIL    60
ELNGYDPAYA GSVFLGWAQK RFGKRNTIWL FGPATTGKTN IAEAIAHAVP FYGCVNWTNE   120
NFPFNDC                                                              127

SEQ ID NO: 109           moltype = AA  length = 254
FEATURE                  Location/Qualifiers
source                   1..254
                         mol_type = protein
                         organism = synthetic construct
SEQUENCE: 109
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VAHEFYVRKG   120
GANKRPAPDD ADKSEPKRAC PSVADPSTSD AEGAPVDFAD RYQNKCSRHA GMLQMLFPCK   180
TCERMNQNFN ICFTHGTRDC SECFPGVSES QPVVRKRTYR KLCAIHHLLG RAPEIACSAC   240
DLVNVDLDDC VSEQ                                                      254

SEQ ID NO: 110           moltype = AA  length = 165
FEATURE                  Location/Qualifiers
source                   1..165
                         mol_type = protein
                         organism = synthetic construct
SEQUENCE: 110
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VAHEFYVRKG   120
GANKRPAPDD ADKSEPKRAC PSVADPSTSD AEGAPVDFAD RYQNK                   165

SEQ ID NO: 111           moltype = AA  length = 89
FEATURE                  Location/Qualifiers
source                   1..89
                         mol_type = protein
                         organism = synthetic construct
SEQUENCE: 111
CSRHAGMLQM LFPCKTCERM NQNFNICFTH GTRDCSECFP GVSESQPVVR KRTYRKLCAI    60
HHLLGRAPEI ACSACDLVNV DLDDCVSEQ                                      89

SEQ ID NO: 112           moltype = DNA  length = 306
FEATURE                  Location/Qualifiers
source                   1..306
                         mol_type = other DNA
                         organism = synthetic construct
```
aggtaccaaa acaaa                                                     495

```
SEQUENCE: 112
acgccgggtt tctacgagat cgtgatcaag gtgccgagcg acctggacga gcacctgccg    60
ggcatttctg actcgtttgt gaactgggtg gccgagaagg aatgggagct gccccccggat  120
tctgacatgg atctgaatct gatcgagcag gcacccctga ccgtggccga gaagctgcag   180
cgcgacttcc tggtccaatg gcgccgcgtg agtaaggccc cggaggccct gttctttgtt   240
cagttcgaga agggcgagag ctacttccac cttcacgttc tggtggagac cacgggggtc   300
aagtcc                                                              306

SEQ ID NO: 113          moltype = DNA  length = 420
FEATURE                 Location/Qualifiers
source                  1..420
                        mol_type = other DNA
                        organism = synthetic construct
SEQUENCE: 113
atggtgctag gccgcttcct gagtcagatt cggagaagc tggtccagac catctaccgc    60
ggggtcgagc ccacgctgcc caactggttc gcggtgacca agacgcgtaa tggcgccggc   120
gggggggaaca aggtggtgga cgagtgctac atccccaact acctcctgcc caagacccag  180
cccgagctgc agtgggcgtg gactaacatg gaggagtata taagcgcgtg tttgaacctg   240
gccgaacgca aacggctcgt ggcgcagcac ctgacccacg tcagccagac gcaggagcag   300
aacaaggaga atctgaaccc caattctgac gcgcccgtga tcaggtcaaa acctccgcg    360
cgctacatgg agctggtcgg gtggctggtg gaccggggca tcacctccga aagcagtgg    420

SEQ ID NO: 114          moltype = DNA  length = 381
FEATURE                 Location/Qualifiers
source                  1..381
                        mol_type = other DNA
                        organism = synthetic construct
SEQUENCE: 114
atccaggagg accaggcctc gtacatctcc ttcaacgccg cctccaactc gcggtcccag    60
atcaaggccg cgctggacaa tgccggcaag atcatgcgcg tgaccaaatc cgcgcccgac   120
tacctggtgg ggccctcgct gcccgcggac attaaaacca accgcatcta ccgcatcctg   180
gagctgaacg ggtacgatcc tgcctacgcc ggctccgtct ttctcggctg ggcccagaaa   240
aagttcggga agcgcaacac catctggctg tttgggcccg ccaccaccgg caagaccaac   300
attgcgaag ccatcgccca cgccgtgccc ttctacggct cgtcaactg gaccaatgag    360
aactttccct tcaacgattg c                                             381

SEQ ID NO: 115          moltype = DNA  length = 765
FEATURE                 Location/Qualifiers
source                  1..765
                        mol_type = other DNA
                        organism = synthetic construct
SEQUENCE: 115
gtcgacaaga tggtgatctg gtgggaggag ggcaagatga cggccaaggt cgtggagtcc    60
gccaaggcca ttctcggcgg cagcaaggtg cgcgtggacc aaaagtgcaa gtcgtccgcc   120
cagatcgacc ccacccccgt gatcgtcacc tccaacacca catgtgcgc cgtgattgac    180
gggaacagca ccaccttcga gcaccagcag ccgttgcagg accggatgtt caaatttgaa   240
ctcacccgcc gtctggagca cgactttggc aaggtgacga gcaggaagt caaagagttc   300
ttccgctggg ccagtgatca cgtgaccgag gtggcgcatg agttctacgt cagaaagggc   360
ggagccagca aaagacccgc ccccgatgac gcggatataa gcgagcccaa gcgggcctgc   420
ccctcagtcg cggatccatc gacgtcagac gcggaaggag ctccggtgga cttgccgac   480
aggtaccaaa acaaatgttc tcgtcacgcg ggcatgattc agtatctgtt tccctgcaaa   540
acgtgcgaga gaatgaatca gaattcaac atttgcttca cacacggggt cagagactgt   600
ttagagtgtt tccccggcgt gtcagaatct caaccggtcg tcagaaaaaa gacgtatcgg   660
aaactctgcg cgattcatca tctgctgggg cgggcgccg agattgcttg ctcggcctgc   720
gacctggtca acgtggacct ggacgactgc gtttctgagc aataa                   765

SEQ ID NO: 116          moltype = DNA  length = 495
FEATURE                 Location/Qualifiers
source                  1..495
                        mol_type = other DNA
                        organism = synthetic construct
SEQUENCE: 116
gtcgacaaga tggtgatctg gtgggaggag ggcaagatga cggccaaggt cgtggagtcc    60
gccaaggcca ttctcggcgg cagcaaggtg cgcgtggacc aaaagtgcaa gtcgtccgcc   120
cagatcgacc ccacccccgt gatcgtcacc tccaacacca catgtgcgc cgtgattgac    180
gggaacagca ccaccttcga gcaccagcag ccgttgcagg accggatgtt caaatttgaa   240
ctcacccgcc gtctggagca cgactttggc aaggtgacga gcaggaagt caaagagttc   300
ttccgctggg ccagtgatca cgtgaccgag gtggcgcatg agttctacgt cagaaagggc   360
ggagccagca aaagacccgc ccccgatgac gcggatataa gcgagcccaa gcgggcctgc   420
ccctcagtcg cggatccatc gacgtcagac gcggaaggag ctccggtgga cttgccgac   480
aggtaccaaa acaaa                                                    495

SEQ ID NO: 117          moltype = DNA  length = 270
FEATURE                 Location/Qualifiers
source                  1..270
                        mol_type = other DNA
                        organism = synthetic construct
SEQUENCE: 117
tgttctcgtc acgcgggcat gattcagatg ctgtttccct gcaaaacgtg cgagagaatg    60
```

```
aatcagaatt tcaacatttg cttcacacac ggggtcagag actgtttaga gtgtttcccc    120
ggcgtgtcag aatctcaacc ggtcgtcaga aaaaagacgt atcggaaact ctgcgcgatt    180
catcatctgc tggggcgggc gcccgagatt gcttgctcgg cctgcgacct ggtcaacgtg    240
gacctggacg actgcgtttc tgagcaataa                                     270

SEQ ID NO: 118          moltype = AA   length = 102
FEATURE                 Location/Qualifiers
source                  1..102
                        mol_type = protein
                        organism = synthetic construct
SEQUENCE: 118
TPGFYEIVIK VPSDLDEHLP GISDSFVNWV AEKEWELPPD SDMDLNLIEQ APLTVAEKLQ     60
RDFLVQWRRV SKAPEALFFV QFEKGESYFH LHVLVETTGV KS                       102

SEQ ID NO: 119          moltype = AA   length = 140
FEATURE                 Location/Qualifiers
source                  1..140
                        mol_type = protein
                        organism = synthetic construct
SEQUENCE: 119
MVLGRFLSQI REKLVQTIYR GVEPTLPNWF AVTKTRNGAG GGNKVVDECY IPNYLLPKTQ     60
PELQWAWTNM EEYISACLNL AERKRLVAQH LTHVSQTQEQ NKENLNPNSD APVIRSKTSA    120
RYMELVGWLV DRGITSEKQW                                                140

SEQ ID NO: 120          moltype = AA   length = 127
FEATURE                 Location/Qualifiers
source                  1..127
                        mol_type = protein
                        organism = synthetic construct
SEQUENCE: 120
IQEDQASYIS FNAASNSRSQ IKAALDNAGK IMALTKSAPD YLVGPSLPAD IKTNRIYRIL     60
ELNGYDPAYA GSVFLGWAQK KFGKRNTIWL FGPATTGKTN IAEAIAHAVP FYGCVNWTNE    120
NFPFNDC                                                              127

SEQ ID NO: 121          moltype = AA   length = 254
FEATURE                 Location/Qualifiers
source                  1..254
                        mol_type = protein
                        organism = synthetic construct
SEQUENCE: 121
VDKMVIWWEE GKMTAKVVES AKAILGGSKV RVDQKCKSSA QIDPTPVIVT SNTNMCAVID     60
GNSTTFEHQQ PLQDRMFKFE LTRRLEHDFG KVTKQEVKEF FRWASDHVTE VAHEFYVRKG    120
GASKRPAPDD ADISEPKRAC PSVADPSTSD AEGAPVDFAD RYQNKCSRHA GMIQMLFPCK    180
TCERMNQNFN ICFTHGVRDC LECFPGVSES QPVVRKKTYR KLCAIHHLLG RAPEIACSAC    240
DLVNVDLDDC VSEQ                                                      254

SEQ ID NO: 122          moltype = AA   length = 165
FEATURE                 Location/Qualifiers
source                  1..165
                        mol_type = protein
                        organism = synthetic construct
SEQUENCE: 122
VDKMVIWWEE GKMTAKVVES AKAILGGSKV RVDQKCKSSA QIDPTPVIVT SNTNMCAVID     60
GNSTTFEHQQ PLQDRMFKFE LTRRLEHDFG KVTKQEVKEF FRWASDHVTE VAHEFYVRKG    120
GASKRPAPDD ADISEPKRAC PSVADPSTSD AEGAPVDFAD RYQNK                    165

SEQ ID NO: 123          moltype = AA   length = 89
FEATURE                 Location/Qualifiers
source                  1..89
                        mol_type = protein
                        organism = synthetic construct
SEQUENCE: 123
CSRHAGMIQM LFPCKTCERM NQNFNICFTH GVRDCLECFP GVSESQPVVR KKTYRKLCAI     60
HHLLGRAPEI ACSACDLVNV DLDDCVSEQ                                      89

SEQ ID NO: 124          moltype = DNA   length = 306
FEATURE                 Location/Qualifiers
source                  1..306
                        mol_type = other DNA
                        organism = synthetic construct
SEQUENCE: 124
atgccgggct tctacgagat cgtgatcaag gtgccgagcg acctggacga gcacctgccg     60
ggcatttctg actcgtttgt gaactgggtg gccgagaagg aatgggagct gccccccgat    120
tctgacatgg atctgaacct gatcgagcag gcacccctga ccgtggccga agctgcagga    180
cgcgacttcc tggtccaatg gcgccgcgtg agtaaggccc cggaggccct cttctttgtt    240
cagttcgaga aggcgagag ctactttcac ctgcacgttc tggtcgagac cacgggggtc    300
aagtcc                                                               306

SEQ ID NO: 125          moltype = DNA   length = 426
```

```
FEATURE               Location/Qualifiers
source                1..426
                      mol_type = other DNA
                      organism = synthetic construct
SEQUENCE: 125
atggtgctag gccgcttcct gagtcagatt cgggaaaagc ttggtccaga ccatctaccc   60
gcggggtcga gccccacctt gcccaactgg ttcgcggtga ccaaagacgc ggtaatggcg  120
ccggcggggg ggaacaaggt ggtggacgag tgctacatcc ccaactacct cctgcccaag  180
actcagcccg agctgcagtg ggcgtggact aacatggagg agtatataag cgcgtgcttg  240
aacctggccg agcgcaaacg gctcgtggcg cagcacctga cccacgtcag ccagacgcag  300
gagcagaaca aggagaatct gaaccccaat tctgacgcgc ccgtgatcag gtcaaaaacc  360
tccgcgcgct atatggagct ggtcgggtgg ctggtggacc ggggcatcac ctccgagaag  420
cagtgg                                                             426

SEQ ID NO: 126        moltype = DNA   length = 420
FEATURE               Location/Qualifiers
source                1..420
                      mol_type = other DNA
                      organism = synthetic construct
SEQUENCE: 126
atggtgctag gccgcttcct gagtcagatt cgggaaaagc tggtccagac catctaccgc   60
ggggtcgagc ccaccttgcc caactggttc gcggtgacag agcgcgtaa tggcgccggg  120
gggggaaca aggtggtgga cgagtgctac atccccaact acctcctgcc caagactcag  180
cccgagctgc agtgggcgtg gactaacatg gaggagtata aagcgcgtg cttgaacctg  240
gccgagcgca aacggctcgt ggcgcagcac ctgacccacg tcagccagac gcaggagcag  300
aacaaggaga atctgaaccc caattctgac gcgcccgtga tcaggtcaaa aacctccgcg  360
cgctatatgg agctggtcgg gtggctggtg gaccggggca tcacctccga gaagcagtgg  420

SEQ ID NO: 127        moltype = DNA   length = 381
FEATURE               Location/Qualifiers
source                1..381
                      mol_type = other DNA
                      organism = synthetic construct
SEQUENCE: 127
atccaggagg accaggcctc gtacatctcc ttcaacgccg cctccaactc gcggtcccag   60
atcaaggccg cgctggacaa tgccggcaag atcatggcgc tgaccaaatc cgcgcccgac  120
tacctggtgg ggccctcgct gcccgcggac attaccagcga accgcatcta ccgcatcctc  180
gctctcaacg gctacgaccc tgcctacgcc ggctccgtct ttctcggctg ggtcagaaa   240
aagttcggga aacgcaacac catcggctg tttggacccg ccaccaccgg caagaccaac  300
attgcggaag ccatcgccca cgccgtgccc ttctacggct gcgtcaactg gaccaatgag  360
aactttccct tcaatgattg c                                            381

SEQ ID NO: 128        moltype = DNA   length = 765
FEATURE               Location/Qualifiers
source                1..765
                      mol_type = other DNA
                      organism = synthetic construct
SEQUENCE: 128
gtcgacaaga tggtgatctg gtgggaggag ggcaagatga cggccaaggt cgtggagtcc   60
gccaaggcca ttctcggcgg cagcaaggtg cgcgtggacc aaaagtgcaa gtcgtccgcc  120
cagatcgacc caccccgt gatcgtcacc tccaacacca acatgtgcgc cgtgattgac  180
gggaacagca ccaccttcga gcaccagcag cctctccagg accggatgtt taagttcgaa  240
ctcacccgcc gtctggagca cgactttggc aaggtgacaa agcaggaagt caaagagttc  300
ttccgctggg ccagtgatca cgtgaccgag gtggcgcatg agtttacgt cagaaagggc  360
ggagccagca aaagacccgc ccccgatgac gcggataaca gcgagcccaa gcgggcctgc  420
ccctcagtcg cggatccatc gacgtcagac gcggaaggag ctccggtgga ctttgccgac  480
aggtaccaaa acaaatgttc tcgtcacgcg gcatgcttc agatgctgtt ccctgcaaa   540
acgtgcgaga gaatgaatca gaatttcaac atttgcttca cacacggggt cagagactgc  600
tcagagtgtt tccccggcgt gtcagaatct caaccggtcg tcagaaagag gacgtatcgg  660
aaactctgtg cgattcatca tctgctgggg cgggctcccg agattgcttg ctcggcctgc  720
gatctggtca acgtggacct ggatgactgt gtttctgagc ggatgactgt aataa        765

SEQ ID NO: 129        moltype = DNA   length = 495
FEATURE               Location/Qualifiers
source                1..495
                      mol_type = other DNA
                      organism = synthetic construct
SEQUENCE: 129
gtcgacaaga tggtgatctg gtgggaggag ggcaagatga cggccaaggt cgtggagtcc   60
gccaaggcca ttctcggcgg cagcaaggtg cgcgtggacc aaaagtgcaa gtcgtccgcc  120
cagatcgacc caccccgt gatcgtcacc tccaacacca acatgtgcgc cgtgattgac  180
gggaacagca ccaccttcga gcaccagcag cctctccagg accggatgtt taagttcgaa  240
ctcacccgcc gtctggagca cgactttggc aaggtgacaa agcaggaagt caaagagttc  300
ttccgctggg ccagtgatca cgtgaccgag gtggcgcatg agtttacgt cagaaagggc  360
ggagccagca aaagacccgc ccccgatgac gcggataaaa gcgagcccaa gcgggcctgc  420
ccctcagtcg cggatccatc gacgtcagac gcggaaggag ctccggtgga ctttgccgac  480
aggtaccaaa acaaa                                                   495

SEQ ID NO: 130        moltype = DNA   length = 270
```

```
FEATURE                 Location/Qualifiers
source                  1..270
                        mol_type = other DNA
                        organism = synthetic construct
SEQUENCE: 130
tgttctcgtc acgcgggcat gcttcagatg ctgtttccct gcaaaacgtg cgagagaatg   60
aatcagaatt tcaacatttg cttcacacac ggggtcagag actgctcaga gtgtttcccc  120
ggcgtgtcag aatctcaacc ggtcgtcaga aagaggacgt atcggaaact ctgtgcgatt  180
catcatctgc tggggcgggc tcccgagatt gcttgctcgg cctgcgatct ggtcaacgtg  240
gacctggatg actgtgtttc tgagcaataa                                   270

SEQ ID NO: 131          moltype = AA  length = 102
FEATURE                 Location/Qualifiers
source                  1..102
                        mol_type = protein
                        organism = synthetic construct
SEQUENCE: 131
MPGFYEIVIK VPSDLDEHLP GISDSFVNWV AEKEWELPPD SDMDRNLIEQ APLTVAEKLQ   60
RDFLVQWRRV SKAPEALFFV QFEKGESYFH LHVLVETTGV KS                    102

SEQ ID NO: 132          moltype = AA  length = 142
FEATURE                 Location/Qualifiers
source                  1..142
                        mol_type = protein
                        organism = synthetic construct
SEQUENCE: 132
MVLGRFLSQI REKLGPDHLP AGSSPTLPNW FAVTKDAVMA PAGGNKVVDE CYIPNYLLPK   60
TQPELQWAWT NMEEYISACL NLAERKRLVA QHLTHVSQTQ EQNKENLNPN SDAPVIRSKT  120
SARYMELVGW LVDRGITSEK QW                                          142

SEQ ID NO: 133          moltype = AA  length = 120
FEATURE                 Location/Qualifiers
source                  1..120
                        mol_type = protein
                        organism = synthetic construct
SEQUENCE: 133
MVLGRFLSQI REKLVQTIYR GVEPTLPNWF AVTKTRNGAG GGNKVVDECY IPNYLLPKTQ   60
PELQWAWTNM EEYISACLNL AERKRLVAQH LTHVSQTQEQ NKENLNPNSD APVIRSKTSA  120

SEQ ID NO: 134          moltype = AA  length = 147
FEATURE                 Location/Qualifiers
source                  1..147
                        mol_type = protein
                        organism = synthetic construct
SEQUENCE: 134
RYMELVGWLV DRGITSEKQW IQEDQASYIS FNAASNSRSQ IKAALDNAGK IMALTKSAPD   60
YLVGPSLPAD ITQNRIYRIL ALNGYDPAYA GSVFLGWAQK KFGKRNTIWL FGPATTGKTN  120
IAEAIAHAVP FYGCVNWTNE NFPFNDC                                     147

SEQ ID NO: 135          moltype = AA  length = 254
FEATURE                 Location/Qualifiers
source                  1..254
                        mol_type = protein
                        organism = synthetic construct
SEQUENCE: 135
VDKMVIWWEE GKMTAKVVES AKAILGGSKV RVDQKCKSSA QIDPTPVIVT SNTNMCAVID   60
GNSTTFEHQQ PLQDRMFKFE LTRRLEHDFG KVTKQEVKEF FRWASDHVTE VAHEFYVRKG  120
GASKRPAPDD ADKSEPKRAC PSVADPSTSD AEGAPVDFAD RYQNKCSRHA GMLQMLFPCK  180
TCERMQNFN ICFTHGVRDC SECFPGVSES QPVVRKRTYR KLCAIHHLLG RAPEIACSAC  240
DLVNVDLDDC VSEQ                                                   254

SEQ ID NO: 136          moltype = AA  length = 165
FEATURE                 Location/Qualifiers
source                  1..165
                        mol_type = protein
                        organism = synthetic construct
SEQUENCE: 136
VDKMVIWWEE GKMTAKVVES AKAILGGSKV RVDQKCKSSA QIDPTPVIVT SNTNMCAVID   60
GNSTTFEHQQ PLQDRMFKFE LTRRLEHDFG KVTKQEVKEF FRWASDHVTE VAHEFYVRKG  120
GASKRPAPDD ADKSEPKRAC PSVADPSTSD AEGAPVDFAD RYQNK                 165

SEQ ID NO: 137          moltype = AA  length = 89
FEATURE                 Location/Qualifiers
source                  1..89
                        mol_type = protein
                        organism = synthetic construct
SEQUENCE: 137
CSRHAGMLQM LFPCKTCERM NQNFNICFTH GVRDCSECFP GVSESQPVVR KRTYRKLCAI   60
HHLLGRAPEI ACSACDLVNV DLDDCVSEQ                                    89
```

```
SEQ ID NO: 138            moltype = DNA   length = 306
FEATURE                   Location/Qualifiers
source                    1..306
                          mol_type = other DNA
                          organism = synthetic construct
SEQUENCE: 138
atgccgggct tctacgagat cgtgatcaag gtgccgagcg acctggacga gcacctgccg     60
ggcatttctg actcgtttgt gaactgggtg gccgagaagg aatgggagct gccccggat    120
tctgacatgg atcggaatct gatcgagcag gcaccccctga ccgtggccga gaagctgcag   180
cgcgacttcc tggtccactg gcgccgcgtg agtaaggccc cggaggccct cttctttgtt   240
cagttcgaga agggcgagtc ctactttcac ctgcacgttc tggtcgagac cacggggatc   300
aagtcc                                                               306

SEQ ID NO: 139            moltype = DNA   length = 420
FEATURE                   Location/Qualifiers
source                    1..420
                          mol_type = other DNA
                          organism = synthetic construct
SEQUENCE: 139
atggtcctgg gccgcttcct gagtcagatc agagacaggc tggtgcagac catctaccgc    60
ggggtagagc ccacgctgcc caactggttc gcggtgacga agacgcgaaa tggcgccagc   120
gggggggaaca aggtggtgga cgagtgctac atccccaact acctcctgcc caagacgcag   180
cccgagctgc agtgggcgtg gactaacatg gaggagtata taagcgcgtg tctgaacctc   240
gcggagcgta acggctcgt ggcgcagcac ctgacccacg tcagccagac gcaggagcag    300
aacaaggaga atctgaaccc gaattctgac gcgcccgtga tcaggtcaaa aaccctccgcg  360
cgctacatgg agctggtcgg gtggctggtg gaccggggca tcacctccga gaagcagtgg   420

SEQ ID NO: 140            moltype = DNA   length = 381
FEATURE                   Location/Qualifiers
source                    1..381
                          mol_type = other DNA
                          organism = synthetic construct
SEQUENCE: 140
atccaggagg accaggcctc gtacatctcc ttcaacgccg cctccaactc gcggtcccag    60
atcaaggccg cgctggacaa tgccggaaag atcatggcgc tgaccaaatc gcgcccgac   120
tacctggtag gcccgtcctt acccgcggac attaaggcca accgcatcta ccgcatcctg   180
gagctcaacg gctacgaccc cgcctacgcc ggctccgtct tcctgggctg ggcgcagaaa   240
aagttcggta aaaggaatac aatttggctg ttcgggcccg ccaccaccgg caagaccaac   300
atcgcggaag ccatcgccca cgccgtgccc ttctacggct cgtcaactg gaccaatgag    360
aactttcccct tcaacgattg c                                             381

SEQ ID NO: 141            moltype = DNA   length = 762
FEATURE                   Location/Qualifiers
source                    1..762
                          mol_type = other DNA
                          organism = synthetic construct
SEQUENCE: 141
gtcgacaaga tggtgatctg gtgggaggag ggcaagatga ccgccaaggt cgtggagtcc    60
gccaaggcca ttctgggcgg aagcaaggtg cgcgtcgacc aaaagtgcaa gtcctcggcc   120
cagatcgacc ccacgcccgt gatcgtcacc tccaacacca catgtgcgc cgtgatcgac   180
gggaacagca ccaccttcga gcaccagcag cccctgcagg accgcatgtt caagttcgag   240
ctcacccgcc gtctggagca cgactttggc aaggtgacca gcaggaagt caaagagttc   300
ttccgctggg ctcaggatca cgtgactgag gtgacgcatg agttctacgt cagaaagggc   360
ggagccacca aaagacccgc ccccagtgac gcggatataa gcgagcccaa gcgggcctgc   420
ccctcagttg cggagccatc gacgtcagac gcggaagcac cggtggactt tgcggacagg   480
taccaaaaca aatgttctcg tcacgcgggc atgcttcaga tgctgttttcc ctgcaagaca   540
tgcgagagaa tgaatcagaa tttcaacgtc tgcttcacgc acggggtcag agactgctca   600
gagtgcttcc ccggcgcgtc agaatctcaa cctgtcgtca gaaaaaagac gtatcagaaa   660
ctgtgcgcga ttcatcatct gctggggcgg gcacccgaca ttgcgtgttc ggcctgcgat   720
ctcgtcaacg tggacttgga tgactgtgtt tctgagcaat aa                       762

SEQ ID NO: 142            moltype = DNA   length = 492
FEATURE                   Location/Qualifiers
source                    1..492
                          mol_type = other DNA
                          organism = synthetic construct
SEQUENCE: 142
gtcgacaaga tggtgatctg gtgggaggag ggcaagatga ccgccaaggt cgtggagtcc    60
gccaaggcca ttctgggcgg aagcaaggtg cgcgtcgacc aaaagtgcaa gtcctcggcc   120
cagatcgacc ccacgcccgt gatcgtcacc tccaacacca catgtgcgc cgtgatcgac   180
gggaacagca ccaccttcga gcaccagcag cccctgcagg accgcatgtt caagttcgag   240
ctcacccgcc gtctggagca cgactttggc aaggtgacca gcaggaagt caaagagttc   300
ttccgctggg ctcaggatca cgtgactgag gtgacgcatg agttctacgt cagaaagggc   360
ggagccacca aaagacccgc ccccagtgac gcggatataa gcgagcccaa gcgggcctgc   420
ccctcagttg cggagccatc gacgtcagac gcggaagcac cggtggactt tgcggacagg   480
taccaaaaca aa                                                         492

SEQ ID NO: 143            moltype = DNA   length = 270
```

```
FEATURE                 Location/Qualifiers
source                  1..270
                        mol_type = other DNA
                        organism = synthetic construct
SEQUENCE: 143
tgttctcgtc acgcgggcat gcttcagatg ctgtttccct gcaagacatg cgagagaatg    60
aatcagaatt tcaacgtctg cttcacgcac ggggtcagag actgctcaga gtgcttcccc   120
ggcgcgtcag aatctcaacc tgtcgtcaga aaaaagacgt atcagaaact gtgcgcgatt   180
catcatctgc tggggcgggc acccgagatt gcgtgttcgg cctgcgatct cgtcaacgtg   240
gacttggatg actgtgtttc tgagcaataa                                    270

SEQ ID NO: 144          moltype = AA  length = 102
FEATURE                 Location/Qualifiers
source                  1..102
                        mol_type = protein
                        organism = synthetic construct
SEQUENCE: 144
MPGFYEIVIK VPSDLDEHLP GISDSFVNWV AEKEWELPPD SDMDRNLIEQ APLTVAEKLQ    60
RDFLVHWRRV SKAPEALFFV QFEKGESYFH LHVLVETTGV KS                     102

SEQ ID NO: 145          moltype = AA  length = 140
FEATURE                 Location/Qualifiers
source                  1..140
                        mol_type = protein
                        organism = synthetic construct
SEQUENCE: 145
MVLGRFLSQI RDRLVQTIYR GVEPTLPNWF AVTKTRNGAG GGNKVVDECY IPNYLLPKTQ    60
PELQWAWTNM EEYISACLNL AERKRLVAQH LTHVSQTQEQ NKENLNPNSD APVIRSKTSA   120
RYMELVGWLV DRGITSEKQW                                               140

SEQ ID NO: 146          moltype = AA  length = 127
FEATURE                 Location/Qualifiers
source                  1..127
                        mol_type = protein
                        organism = synthetic construct
SEQUENCE: 146
IQEDQASYIS FNAASNSRSQ IKAALDNAGK IMALTKSAPD YLVGPSLPAD IKANRIYRIL    60
ELNGYDPAYA GSVFLGWAQK KFGKRNTIWL FGPATTGKTN IAEAIAHAVP FYGCVNWTNE   120
NFPFNDC                                                             127

SEQ ID NO: 147          moltype = AA  length = 253
FEATURE                 Location/Qualifiers
source                  1..253
                        mol_type = protein
                        organism = synthetic construct
SEQUENCE: 147
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VTHEFYVRKG   120
GATKRPAPSD ADISEPKRAC PSVAEPSTSD AEAPVDFADR YQNKCSRHAG MLQMLFPCKT   180
CERMNQNFNV CFTHGVRDCS ECFPGASESQ PVVRKKTYQK LCAIHHLLGR APEIACSACD   240
LVNVDLDDCV SEQ                                                      253

SEQ ID NO: 148          moltype = AA  length = 164
FEATURE                 Location/Qualifiers
source                  1..164
                        mol_type = protein
                        organism = synthetic construct
SEQUENCE: 148
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VTHEFYVRKG   120
GATKRPAPSD ADISEPKRAC PSVAEPSTSD AEAPVDFADR YQNK                    164

SEQ ID NO: 149          moltype = AA  length = 89
FEATURE                 Location/Qualifiers
source                  1..89
                        mol_type = protein
                        organism = synthetic construct
SEQUENCE: 149
CSRHAGMLQM LFPCKTCERM NQNFNVCFTH GVRDCSECFP GASESQPVVR KKTYQKLCAI    60
HHLLGRAPEI ACSACDLVNV DLDDCVSEQ                                      89

SEQ ID NO: 150          moltype = DNA  length = 306
FEATURE                 Location/Qualifiers
source                  1..306
                        mol_type = other DNA
                        organism = synthetic construct
SEQUENCE: 150
atgccgggct tctacgagat cgtgatcaag gtgccgagcg acctggacga gcacctgccg    60
ggcatttctg actcgtttgt gaactgggtg gccgagaagg aatgggagct gccccccggat  120
```

```
tctgacatgg atcggaatct gatcgagcag gcacccctga ccgtggccga gaagctgcag    180
cgcgacttcc tggtccactg gcgccgcgtg agtaaggccc cggaggccct cttctttgtt    240
cagttcgaga agggcgagtc ctacttccac ctccacgttc tcgtcgagac cacggggtc     300
aagtcc                                                               306

SEQ ID NO: 151           moltype = DNA   length = 420
FEATURE                  Location/Qualifiers
source                   1..420
                         mol_type = other DNA
                         organism = synthetic construct
SEQUENCE: 151
atggtcctgg ccgcttcct gagtcagatc agagacaggc tggtgcagac catctaccgc     60
ggggtcgagc ccacgctgcc caactggttc gcggtgacca agacgcgaaa tggcgccggc    120
ggggggaaca aggtggtgga cgagtgctac atccccaact acctcctgcc caagaccaag    180
cccgagctgc agtgggcgtg gactaacatg gaggagtata aagcgcgtg tctaaacctc     240
gcggagcgta aacggctcgt ggcgcagcac ctgacccacg tcagccagac gcaggagcag    300
aacaaggaga atctgaaccc gaattctgac gcgcccgtga tcaggtcaaa aacctccgcg    360
cgctacatgg agctggtcgg gtggctggtg gaccggggca tcacctccga gaagcagtgg    420

SEQ ID NO: 152           moltype = DNA   length = 381
FEATURE                  Location/Qualifiers
source                   1..381
                         mol_type = other DNA
                         organism = synthetic construct
SEQUENCE: 152
atccaggagg accaggcctc gtacatctcc ttcaacgccg cctccaactc gcggtcccag     60
atcaaggccg cgctgacaa tgccggaaag atcatggcgc tgaccaaatc cgcgcccgac    120
tacctggtag gccgtccttt acccgcggac attaaggcca accgcatcta ccgcatcctg    180
gagctcaacg gctacgaccc cgcctacgcc ggctccgtct tcctgggctg ggcgcagaaa    240
aagttcggta aacgcaacac catctggctg tttgggcccg ccaccaccgg caagaccaac    300
atcgcggaag ccatagccca cgccgtgccc ttctacggct gcgtgaactg gaccaatgag    360
aactttccct tcaacgattg c                                              381

SEQ ID NO: 153           moltype = DNA   length = 762
FEATURE                  Location/Qualifiers
source                   1..762
                         mol_type = other DNA
                         organism = synthetic construct
SEQUENCE: 153
gtcgacaaga tggtgatctg gtgggaggag ggcaagatga ccgccaaggt cgtggagtcc     60
gccaaggcca ttctgggcgg aagcaaggtg cgcgtggacc aaaagtgcaa gtcctcggcc    120
cagatcgacc ccacgcccgt gatcgtcacc tccaacacca catgtgcgc cgtgatcgac    180
gggaacagca ccaccttcga gcaccagcag ccgctgcagg accgcatgtt caagttcgag    240
ctcacccgcc gtctggagca cgactttggc aaggtgacca agcaggaagt caaagagttc    300
ttccgctggg ctcaggatca cgtgactgag gtgcgcatg agttctacgt cagaaagggc    360
ggagccacca aaagacccgc ccccagtgac gcggatataa gcgagcccaa gcgggcctgc    420
ccctcagttc cggagccatc gacgtcagac gcggaagcac cggtggactt tgcggacagg    480
taccaaaaca aatgttctcg tcacgcgggc atgcttcaga tgctgtttcc ctgcaagaca    540
tgcgagagaa tgaatcagaa tttcaacgtc tgcttcacgc acggggtcag agactgctca    600
gagtgcttcc ccgcgcgtc agaatctcaa cccgtcgtca gaaaaagac gtatcagaaa     660
ctgtgcgcga ttcatcatct gctggggcgg gcacccgaga ttgcgtgttc ggcctgcgat    720
ctcgtcaacg tggacttgga tgactgtgtt tctgagcaat aa                       762

SEQ ID NO: 154           moltype = DNA   length = 492
FEATURE                  Location/Qualifiers
source                   1..492
                         mol_type = other DNA
                         organism = synthetic construct
SEQUENCE: 154
gtcgacaaga tggtgatctg gtgggaggag ggcaagatga ccgccaaggt cgtggagtcc     60
gccaaggcca ttctgggcgg aagcaaggtg cgcgtggacc aaaagtgcaa gtcctcggcc    120
cagatcgacc ccacgcccgt gatcgtcacc tccaacacca catgtgcgc cgtgatcgac    180
gggaacagca ccaccttcga gcaccagcag ccgctgcagg accgcatgtt caagttcgag    240
ctcacccgcc gtctggagca cgactttggc aaggtgacca agcaggaagt caaagagttc    300
ttccgctggg ctcaggatca cgtgactgag gtgcgcatg agttctacgt cagaaagggc    360
ggagccacca aaagacccgc ccccagtgac gcggatataa gcgagcccaa gcgggcctgc    420
ccctcagttc cggagccatc gacgtcagac gcggaagcac cggtggactt tgcggacagg    480
taccaaaaca aa                                                        492

SEQ ID NO: 155           moltype = DNA   length = 270
FEATURE                  Location/Qualifiers
source                   1..270
                         mol_type = other DNA
                         organism = synthetic construct
SEQUENCE: 155
tgttctcgtc acgcgggcat gcttcagatg ctgtttccct gcaagacatg cgagagaatg     60
aatcagaatt tcaacgtctg cttcacgcac ggggtcagag actgctcaga gtgcttcccc    120
ggcgcgtcag aatctcaacc cgtcgtcaga aaaagacgt atcagaaact gtgcgcgatt     180
catcatctgc tggggcgggc acccgagatt gcgtgttcgg cctgcgatct cgtcaacgtg    240
```

```
gacttggatg actgtgtttc tgagcaataa                                    270

SEQ ID NO: 156          moltype = AA  length = 102
FEATURE                 Location/Qualifiers
source                  1..102
                        mol_type = protein
                        organism = synthetic construct
SEQUENCE: 156
MPGFYEIVIK VPSDLDEHLP GISDSFVNWV AEKEWELPPD SDMDRNLIEQ APLTVAEKLQ    60
RDFLVHWRRV SKAPEALFFV QFEKGESYFH LHVLVETTGV KS                      102

SEQ ID NO: 157          moltype = AA  length = 140
FEATURE                 Location/Qualifiers
source                  1..140
                        mol_type = protein
                        organism = synthetic construct
SEQUENCE: 157
MVLGRFLSQI RDRLVQTIYR GVEPTLPNWF AVTKTRNGAG GGNKVVDECY IPNYLLPKTQ    60
PELQWAWTNM EEYISACLNL AERKRLVAQH LTHVSQTQEQ NKENLNPNSD APVIRSKTSA    120
RYMELVGWLV DRGITSEKQW                                               140

SEQ ID NO: 158          moltype = AA  length = 127
FEATURE                 Location/Qualifiers
source                  1..127
                        mol_type = protein
                        organism = synthetic construct
SEQUENCE: 158
IQEDQASYIS FNAASNSRSQ IKAALDNAGK IMALTKSAPD YLVGPSLPAD IKANRIYRIL    60
ELNGYDPAYA GSVFLGWAQK KFGKRNTIWL FGPATTGKTN IAEAIAHAVP FYGCVNWTNE    120
NFPFNDC                                                             127

SEQ ID NO: 159          moltype = AA  length = 253
FEATURE                 Location/Qualifiers
source                  1..253
                        mol_type = protein
                        organism = synthetic construct
SEQUENCE: 159
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VAHEFYVRKG    120
GATKRPAPSD ADISEPKRAC PSVPEPSTSD AEAPVDFADR YQNKCSRHAG MLQMLFPCKT    180
CERMNQNFNV CFTHGVRDCS ECFPGASESQ PVVRKKTYQK LCAIHHLLGR APEIACSACD    240
LVNVDLDDCV SEQ                                                      253

SEQ ID NO: 160          moltype = AA  length = 164
FEATURE                 Location/Qualifiers
source                  1..164
                        mol_type = protein
                        organism = synthetic construct
SEQUENCE: 160
VDKMVIWWEE GKMTAKVVES AKAILGGSKV RVDQKCKSSA QIDPTPVIVT SNTNMCAVID    60
GNSTTFEHQQ PLQDRMFKFE LTRRLEHDFG KVTKQEVKEF FRWAQDHVTE VAHEFYVRKG    120
GATKRPAPSD ADISEPKRAC PSVPEPSTSD AEAPVDFADR YQNK                    164

SEQ ID NO: 161          moltype = AA  length = 89
FEATURE                 Location/Qualifiers
source                  1..89
                        mol_type = protein
                        organism = synthetic construct
SEQUENCE: 161
CSRHAGMLQM LFPCKTCERM NQNFNVCFTH GVRDCSECFP GASESQPVVR KKTYQKLCAI    60
HHLLGRAPEI ACSACDLVNV DLDDCVSEQ                                     89

SEQ ID NO: 162          moltype = DNA  length = 306
FEATURE                 Location/Qualifiers
source                  1..306
                        mol_type = other DNA
                        organism = synthetic construct
SEQUENCE: 162
atgccggggt tctacgaggt ggtgatcaag gtgcccagcg acctggacga gcacctgccc    60
ggcatttctg actcctttgt gaactgggtg gccgagaagg aatgggagtt gcccccggat    120
tctgacatgg atcagaatct gattgagcag gcacccctga ccgtggccga gaagctgcag    180
cgcgagttcc tggtgaatgg cgccgagtg agtaaattc tggaggccaa gtttttgtg     240
cagtttgaaa aggggactc gtactttcat ttgcatattc tgattgaaat taccggcgtg    300
aaatcc                                                              306

SEQ ID NO: 163          moltype = DNA  length = 420
FEATURE                 Location/Qualifiers
source                  1..420
                        mol_type = other DNA
```

```
                      organism = synthetic construct
SEQUENCE: 163
atggtggtgg gccgctacgt gagtcagatt agggataaac tgatccagcg catctaccgc     60
ggggtcgagc cccagctgcc caactggttc gcggtcacaa agacccgaaa tggcgccgga    120
ggcgggaaca aggtggtgga cgagtgctac atccccaact acctgctccc caaggtccga    180
cccgagcttc agtgggcgtg gactaacatg gaggagtata taagcgcctg tttgaacctc    240
gcggagcgta acggctcgt ggcgcagcac ctgacgcacg tctcccagac ccaggagggc    300
gacaaggaga atctgaaccc gaattctgac gcgccggtga tccggtcaaa aacctccgcc    360
aggtacatgg agctggtcgg gtggctggtg gacaagggca tcacgtccga gaagcagtgg    420

SEQ ID NO: 164            moltype = DNA    length = 381
FEATURE                   Location/Qualifiers
source                    1..381
                          mol_type = other DNA
                          organism = synthetic construct
SEQUENCE: 164
atccaggagg accaggcctc gtacatctcc ttcaacgcgg cctccaactc ccggtcgcag     60
atcaaggcgg ccctggacaa tgcctccaaa atcatgagcc tcaccaaaac ggctccggaa    120
tatctcatcg ggcagcagcc cgtggggggac attaccacca accggatcta caaaatcctg    180
gaactgaacg ggtacgaccc ccagtacgcc gcctccgtct ttctcggctg ggcccagaaa    240
aagtttggaa agcgcaacac catctggctg tttgggcccg ccaccaccgg caagaccaac    300
atcgcggaag ccatcgccca cgcggtcccc ttctacggct cgtcaactg gaccaatgag    360
aactttccct tcaacgactg c                                              381

SEQ ID NO: 165            moltype = DNA    length = 759
FEATURE                   Location/Qualifiers
source                    1..759
                          mol_type = other DNA
                          organism = synthetic construct
SEQUENCE: 165
gtcgacaaaa tggtgatttg gtgggaggag ggcaagatga ccgccaaggt cgtagagtcc     60
gccaaggcca ttctgggcgg cagcaaggtg cgcgtggacc aaaaatgcaa ggcctctgcg    120
cagatcgacc ccaccccgt gatcgtcacc tccaacacca catgtgcgc cgtgattgac    180
gggaacagca ccaccttcga gcaccagcag ccccctgcagg accggatgtt caagtttgaa    240
ctcacccgcc gcctcgacca cgactttggc aaggtcacaa agcaggaagt caaggactt    300
ttccggtggg cggctgatca cgtgactgac gtggctcatg agttttacgt cacaaagggt    360
ggagctaaga aaaggcccgc ccctctgac gaggatataa gcgagcccaa gcggccgcgc    420
gtgtcatttg cgcagccgga gacgtcagac gcggaagctc ccggagactt cgccgacagg    480
taccaaaaca aatgttctcg tcacgcgggt atgctgcaga tgctctttcc ctgcaagacg    540
tgcgagagaa tgaatcagaa ttccaacgtc tgcttcacgc acggtcagaa agattgcggg    600
gagtgctttc ccgggtcaga atctcaaccg gtttctgtcg tcagaaaaac gtatcagaaa    660
ctgtgcatcc ttcatcagct ccgggggca cccgagatcg cctgctctgc ttgcgaccaa    720
ctcaaccccg atttggacga ttgccaattt gagcaataa                           759

SEQ ID NO: 166            moltype = DNA    length = 492
FEATURE                   Location/Qualifiers
source                    1..492
                          mol_type = other DNA
                          organism = synthetic construct
SEQUENCE: 166
gtcgacaaaa tggtgatttg gtgggaggag ggcaagatga ccgccaaggt cgtagagtcc     60
gccaaggcca ttctgggcgg cagcaaggtg cgcgtggacc aaaaatgcaa ggcctctgcg    120
cagatcgacc ccaccccgt gatcgtcacc tccaacacca catgtgcgc cgtgattgac    180
gggaacagca ccaccttcga gcaccagcag ccccctgcagg accggatgtt caagtttgaa    240
ctcacccgcc gcctcgacca cgactttggc aaggtcacaa agcaggaagt caaggactt    300
ttccggtggg cggctgatca cgtgactgac gtggctcatg agttttacgt cacaaagggt    360
ggagctaaga aaaggcccgc ccctctgac gaggatataa gcgagcccaa gcggccgcgc    420
gtgtcatttg cgcagccgga gacgtcagac gcggaagctc ccggagactt cgccgacagg    480
taccaaaaca aa                                                        492

SEQ ID NO: 167            moltype = DNA    length = 267
FEATURE                   Location/Qualifiers
source                    1..267
                          mol_type = other DNA
                          organism = synthetic construct
SEQUENCE: 167
tgttctcgtc acgcgggtat gctgcagatg ctctttccct gcaagacgtg cgagagaatg     60
aatcagaatt ccaacgtctg cttcacgcac ggtcagaaag attgcgggga gtgctttccc    120
gggtcagaat ctcaaccggt ttctgtcgtc agaaaaacgt atcagaaact gtgcatcctt    180
catcagctcc gggggcacc cgagatcgcc tgctctgctt gcgaccaact caaccccgat    240
ttggacgatt gccaatttga gcaataa                                        267

SEQ ID NO: 168            moltype = AA     length = 102
FEATURE                   Location/Qualifiers
source                    1..102
                          mol_type = protein
                          organism = synthetic construct
SEQUENCE: 168
MPGFYEVVIK VPSDLDEHLP GISDSFVNWV AEKEWELPPD SDMDQNLIEQ APLTVAEKLQ     60
```

```
REFLVEWRRV SKFLEAKFFV QFEKGDSYFH LHILIEITGV KS              102

SEQ ID NO: 169          moltype = AA  length = 140
FEATURE                 Location/Qualifiers
source                  1..140
                        mol_type = protein
                        organism = synthetic construct
SEQUENCE: 169
MVVGRYVSQI RDKLIQRIYR GVEPQLPNWF AVTKTRNGAG GGNKVVDECY IPNYLLPKVQ    60
PELQWAWTNM EEYISACLNL AERKRLVAQH LTHVSQTQEG DKENLNPNSD APVIRSKTSA   120
RYMELVGWLV DKGITSEKQW                                               140

SEQ ID NO: 170          moltype = AA  length = 127
FEATURE                 Location/Qualifiers
source                  1..127
                        mol_type = protein
                        organism = synthetic construct
SEQUENCE: 170
IQEDQASYIS FNAASNSRSQ IKAALDNASK IMSLTKTAPD YLIGQQPVGD ITTNRIYKIL    60
ELNGYDPQYA ASVFLGWAQK KFGKRNTIWL FGPATTGKTN IAEAIAHAVP FYGCVNWTNE   120
NFPFNDC                                                             127

SEQ ID NO: 171          moltype = AA  length = 252
FEATURE                 Location/Qualifiers
source                  1..252
                        mol_type = protein
                        organism = synthetic construct
SEQUENCE: 171
VDKMVIWWEE GKMTAKVVES AKAILGGSKV RVDQKCKASA QIDPTPVIVT SNTNMCAVID    60
GNSTTFEHQQ PLQDRMFKFE LTRRLDHDFG KVTKQEVKDF FRWAADHVTD VAHEFYVTKG   120
GAKKRPAPSD EDISEPKRPR VSFAQPETSD AEAPGDFADR YQNKCSRHAG MLQMLFPCKT   180
CERMNQNSNV CFTHGQKDCG ECFPGSESQP VSVVRKTYQK LCILHQLRGA PEIACSACDQ   240
LNPDLDDCQF EQ                                                       252

SEQ ID NO: 172          moltype = AA  length = 164
FEATURE                 Location/Qualifiers
source                  1..164
                        mol_type = protein
                        organism = synthetic construct
SEQUENCE: 172
VDKMVIWWEE GKMTAKVVES AKAILGGSKV RVDQKCKASA QIDPTPVIVT SNTNMCAVID    60
GNSTTFEHQQ PLQDRMFKFE LTRRLDHDFG KVTKQEVKDF FRWAADHVTD VAHEFYVTKG   120
GAKKRPAPSD EDISEPKRPR VSFAQPETSD AEAPGDFADR YQNK                    164

SEQ ID NO: 173          moltype = AA  length = 88
FEATURE                 Location/Qualifiers
source                  1..88
                        mol_type = protein
                        organism = synthetic construct
SEQUENCE: 173
CSRHAGMLQM LFPCKTCERM NQNSNVCFTH GQKDCGECFP GSESQPVSVV RKTYQKLCIL    60
HQLRGAPEIA CSACDQLNPD LDDCQFEQ                                       88

SEQ ID NO: 174          moltype = DNA  length = 306
FEATURE                 Location/Qualifiers
source                  1..306
                        mol_type = other DNA
                        organism = synthetic construct
SEQUENCE: 174
atgccgggat tctacgagat tgtcctgaag gtgcccagcg acctggacga gcacctgcct    60
ggcatttctg actctttgt aaactgggtg gcggagaagg aatgggagct gccgccggat    120
tctgacatgg atctgaatct gattgagcag gcacccctaa ccgtgccga aaagctgcaa    180
cgcgaattct tggtcgagtg gcgccgcgtg agtaaggccc cggaggccct cttctttgtt    240
cagttcgaga agggggacag ctacttccac ctacacattc tggtggagac cgtgggcgtg    300
aaatcc                                                              306

SEQ ID NO: 175          moltype = DNA  length = 420
FEATURE                 Location/Qualifiers
source                  1..420
                        mol_type = other DNA
                        organism = synthetic construct
SEQUENCE: 175
atggtggtgg gccgctacgt gagccagatt aaagagaagc tggtgacccg catctaccgc    60
ggggtcgagc cgcagcttcc gaactggttc gcggtgacca agacgcgtaa tggcgccgga   120
ggcgggaaca aggtggtgga cgactgctac atccccaact acctgctccc caagaccag   180
cccgagctcc agtgggcgtg gactaatatg gaccagtatt taagcgcctg tttgaatctc   240
gcggagcgta acggctggt ggcgcagcat ctgacgcacg tgtcgcagac gcaggagcag   300
aacaaagaga ccagaatcc caattctgac gcgccggtga tcagatcaaa acctccgcg    360
aggtacatga gctggtcgg gtggctggtg gaccgcggga tcacgtcaga aaagcaatgg   420
```

```
SEQ ID NO: 176           moltype = DNA  length = 381
FEATURE                  Location/Qualifiers
source                   1..381
                         mol_type = other DNA
                         organism = synthetic construct
SEQUENCE: 176
atccaggagg accaggcctc ttacatctcc ttcaacgccg cctccaactc gcggtcacaa    60
atccaggccg cactggacaa tgcctccaaa tttatgagcc tgacaaaaac ggctccggac   120
tacctggtgg gaaacaaccc gccggaggac attaccagca accggatcta caaaatcctc   180
gagatgaacg ggtacgatcc gcagtacgcg gcctccgtct tcctgggctg ggcgcaaaag   240
aagttcggga gaggaacac catctggctc tttgggccgg ccacgacggg taaaaccaac   300
atcgctgaag ctatcgccca cgccgtgccc ttttacggct gcgtgaactg gaccaatgag   360
aactttccgt tcaacgattg c                                             381

SEQ ID NO: 177           moltype = DNA  length = 765
FEATURE                  Location/Qualifiers
source                   1..765
                         mol_type = other DNA
                         organism = synthetic construct
SEQUENCE: 177
gtcgacaaga tggtgatctg gtgggaggag ggcaagatga cggccaaggt cgtggagtcc    60
gccaaggcca ttctgggcgg aagcaaggtg cgcgtggacc aaaagtgcaa gtcatcggcc   120
cagatcgacc caactcccgt catcgtcacc tccaacacca catgtgcgc ggtcatcgac   180
ggaaattcca ccaccttcga gcaccaacaa ccactccaag accggatgtt caagttcgag   240
ctcaccaagc gcctggagca cgactttggc aaggtcacca agcaggaagt caaggacttt   300
ttccggtggg cgtcagatca cgtgactgag gtgtctcacg agttttacgt cagaaagggt   360
ggagctagaa agaggcccgc ccccaatgac gcagatataa gtgagcccaa gcgggcctgt   420
ccgtcagttg cgcagccatc gacgtcagac gcggaagctc cggtggacta cgcggacagg   480
taccaaaaca aatgttctcg tcacgtgggc atgaatctga tgcttttttcc ctgccggcaa   540
tgcgagagaa tgaatcagaa tgtggacatt tgcttcacgc acggggtcat ggactgtgcg   600
gagtgcttcc ccgtgtcaga atctcaaccc gtgtctgtcg tcagaaagcg gacatatcag   660
aaaactgtgtc cgattcatca catcatgggg agggcgcccg aggtggcttg ttcggcctgc   720
gatctggcca atgtggactt ggatgactgt gacatggagc aataa                   765

SEQ ID NO: 178           moltype = DNA  length = 492
FEATURE                  Location/Qualifiers
source                   1..492
                         mol_type = other DNA
                         organism = synthetic construct
SEQUENCE: 178
gtcgacaaga tggtgatctg gtgggaggag ggcaagatga cggccaaggt cgtggagtcc    60
gccaaggcca ttctgggcgg aagcaaggtg cgcgtggacc aaaagtgcaa gtcatcggcc   120
cagatcgacc caactcccgt catcgtcacc tccaacacca catgtgcgc ggtcatcgac   180
ggaaattcca ccaccttcga gcaccaacaa ccactccaag accggatgtt caagttcgag   240
ctcaccaagc gcctggagca cgactttggc aaggtcacca agcaggaagt caaggacttt   300
ttccggtggg cgtcagatca cgtgactgag gtgtctcacg agttttacgt cagaaagggt   360
ggagctagaa agaggcccgc ccccaatgac gcagatataa gtgagcccaa gcgggcctgt   420
ccgtcagttg cgcagccatc gacgtcagac gcggaagctc cggtggacta cgcggacagg   480
taccaaaaca aa                                                       492

SEQ ID NO: 179           moltype = DNA  length = 273
FEATURE                  Location/Qualifiers
source                   1..273
                         mol_type = other DNA
                         organism = synthetic construct
SEQUENCE: 179
tgttctcgtc acgtgggcat gaatctgatg ctttttccct gccggcaatg cgagagaatg    60
aatcagaatg tggacatttg cttcacgcac ggggtcatgg actgtgcga gtgcttccc   120
gtgtcagaat ctcaacccgt gtctgtcgtc agaaagcgga catatcagaa actgtgtc    180
attcatcaca tcatggggag ggcgcccgag gtggcttgtt cggcctgcga tctggccaat   240
gtggacttgg atgactgtga catggagcaa taa                                273

SEQ ID NO: 180           moltype = AA  length = 102
FEATURE                  Location/Qualifiers
source                   1..102
                         mol_type = protein
                         organism = synthetic construct
SEQUENCE: 180
MPGFYEIVLK VPSDLDEHLP GISDSFVNWV AEKEWELPPD SDMDLNLIEQ APLTVAEKLQ    60
REFLVEWRRV SKAPEALFFV QFEKGDSYFH LHILVETVGV KS                      102

SEQ ID NO: 181           moltype = AA  length = 140
FEATURE                  Location/Qualifiers
source                   1..140
                         mol_type = protein
                         organism = synthetic construct
SEQUENCE: 181
MVVGRYVSQI KEKLVTRIYR GVEPQLPNWF AVTKTRNGAG GGNKVVDDCY IPNYLLPKTQ    60
```

```
PELQWAWTNM DQYLSACLNL AERKRLVAQH LTHVSQTQEQ NKENQNPNSD APVIRSKTSA    120
RYMELVGWLV DRGITSEKQW                                                140

SEQ ID NO: 182          moltype = AA  length = 127
FEATURE                 Location/Qualifiers
source                  1..127
                        mol_type = protein
                        organism = synthetic construct
SEQUENCE: 182
IQEDQASYIS FNAASNSRSQ IKAALDNASK FMSLTKTAPD YLVGNNPPED ITSNRIYKIL     60
EMNGYDPQYA ASVFLGWAQK KFGKRNTIWL FGPATTGKTN IAEAIAHAVP FYGCVNWTNE    120
NFPFNDC                                                              127

SEQ ID NO: 183          moltype = AA  length = 254
FEATURE                 Location/Qualifiers
source                  1..254
                        mol_type = protein
                        organism = synthetic construct
SEQUENCE: 183
VDKMVIWWEE GKMTAKVVES AKAILGGSKV RVDQKCKSSA QIDPTPVIVT SNTNMCAVID     60
GNSTTFEHQQ PLQDRMFKFE LTKRLEHDFG KVTKQEVKDF FRWASDHVTE VSHEFYVRKG    120
GARKRPAPND ADISEPKRAC PSVAQPSTSD AEAPVDYADR YQNKCSRHVG MNLMLFPCRQ    180
CERMNQNVDI CFTHGVMDCA ECFPVSESQP VSVVRKRTYQ KLCPIHHIMG RAPEVACSAC    240
DLANVDLDDC DMEQ                                                      254

SEQ ID NO: 184          moltype = AA  length = 164
FEATURE                 Location/Qualifiers
source                  1..164
                        mol_type = protein
                        organism = synthetic construct
SEQUENCE: 184
VDKMVIWWEE GKMTAKVVES AKAILGGSKV RVDQKCKSSA QIDPTPVIVT SNTNMCAVID     60
GNSTTFEHQQ PLQDRMFKFE LTKRLEHDFG KVTKQEVKDF FRWASDHVTE VSHEFYVRKG    120
GARKRPAPND ADISEPKRAC PSVAQPSTSD AEAPVDYADR YQNK                     164

SEQ ID NO: 185          moltype = AA  length = 90
FEATURE                 Location/Qualifiers
source                  1..90
                        mol_type = protein
                        organism = synthetic construct
SEQUENCE: 185
CSRHVGMNLM LFPCRQCERM NQNVDICFTH GVMDCAECFP VSESQPVSVV RKRTYQKLCP     60
IHHIMGRAPE VACSACDLAN VDLDDCDMEQ                                      90

SEQ ID NO: 186          moltype = DNA  length = 174
FEATURE                 Location/Qualifiers
source                  1..174
                        mol_type = other DNA
                        organism = synthetic construct
SEQUENCE: 186
aagtccatgg tgctaggccg cttcctgagt cagattcggg aaaagctggt ccagaccatc     60
taccgcgggg tcgagcccac cttgcccaac tggttcgcgg tgaccaagac gcgtaatggc    120
gccggggggg ggaacaaggt ggtggacgag tgctacatcc ccaactacct cctg          174

SEQ ID NO: 187          moltype = DNA  length = 180
FEATURE                 Location/Qualifiers
source                  1..180
                        mol_type = other DNA
                        organism = synthetic construct
SEQUENCE: 187
gtcctccatc aaccctaca tcgtgagcag gtggtggaac aagggggggc ggccgcggta      60
atggcgcaga aaccagtggc gcttggtcaa cccgttccac cccgagctgg ggcgcccatc    120
taccagacct ggttcgaaaa gggcttagac tgagtccttc gccggatcgt ggtacctgaa    180

SEQ ID NO: 188          moltype = AA  length = 621
FEATURE                 Location/Qualifiers
source                  1..621
                        mol_type = protein
                        organism = synthetic construct
SEQUENCE: 188
MPGFYEIVIK VPSDLDEHLP GISDSFVSWV AEKEWELPPD SDMDLNLIEQ APLTVAEKLQ     60
RDFLVQWRRV SKAPEALFFV QFEKGESYFH LHILVETTGV KSMVLGRFLS QIRDKLVQTI    120
YRGIEPTLPN WFAVTKTRNG AGGGNKVVDE CYIPNYLLPK TQPELQWAWT NMEEYISACL    180
NLAERKRLVA QHLTHVSQTQ EQNKENLNPN SDAPVIRSKT SARYMELVGW LVDRGITSEK    240
QWIQEDQASY ISFNAASNSR SQIKAALDNA GKIMALTKSA PDYLVGPAPP ADIKTNRIYR    300
ILELNGYEPA YAGSVFLGWA QKRFGKRNTI WLFGPATTGK TNIAEAIAHA VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLDHDFGK VTKQEVKDFF RWAKDHVVEV    480
EHEFYVKKGG AKKRPAPSDA DISEPKRVRE SVAQPSTSDA EASINYADRY QNKCSRHVGM    540
```

```
NLMLFPCRQC ERMNQNSNIC FTHGQKDCLE CFPVSESQPV SVVKKAYQKL CYIHHIMGKV    600
PDACTACDLV NVDLDDCIFE Q                                              621

SEQ ID NO: 189              moltype = AA  length = 621
FEATURE                     Location/Qualifiers
source                      1..621
                            mol_type = protein
                            organism = synthetic construct
SEQUENCE: 189
MPGFYEIVIK VPSDLDEHLP GISDSFVSWV AEKEWELPPD SDMDLNLIEQ APLTVAEKLQ    60
RDFLVQWRRV SKAPEALFFV QFEKGESYFH LHILVETTGV KSMVLGRFLS QIRDKLVQTI    120
YRGIEPTLPN WFAVTKTRNG AGGGNKVVDE CYIPNYLLPK TQPELQWAWT NMEEYISACL    180
NLAERKRLVA QHLTHVSQTQ EQNKENLNPN SDAPVIRSKT SARYMELVGW LVDRGITSEK    240
QWIQEDQASY ISFNAASNSR SQIKAALDNA GKIMSLTKTA PDYLVGQQPV EDISSNRIYK    300
ILELNGYDPQ YAASVFLGWA TKKFGKRNTI WLFGPATTGK TNIAEAIAHT VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLDHDFGK VTKQEVKDFF RWAKDHVVEV    480
EHEFYVKKGG AKKRPAPSDA DISEPKRVRE SVAQPSTSDA EASINYADRY QNKCSRHVGM    540
NLMLFPCRQC ERMNQNSNIC FTHGQKDCLE CFPVSESQPV SVVKKAYQKL CYIHHIMGKV    600
PDACTACDLV NVDLDDCIFE Q                                              621

SEQ ID NO: 190              moltype = AA  length = 624
FEATURE                     Location/Qualifiers
source                      1..624
                            mol_type = protein
                            organism = synthetic construct
SEQUENCE: 190
TPGFYEIVIK VPSDLDEHLP GISDSFVNWV AEKEWELPPD SDMDLNLIEQ APLTVAEKLQ    60
RDFLTEWRRV SKAPEALFFV QFEKGESYFH MHVLVETTGV KSMVLGRFLS QIRDKLVQTI    120
YRGIEPTLPN WFAVTKTRNG AGGGNKVVDE CYIPNYLLPK TQPELQWAWT NMEEYISACL    180
NLAERKRLVA QHLTHVSQTQ EQNKENLNPN SDAPVIRSKT SARYMELVGW LVDRGITSEK    240
QWIQEDQASY ISFNAASNSR SQIKAALDNA GKIMSLTKTA PDYLVGQQPV EDISSNRIYK    300
ILELNGYDPQ YAASVFLGWA TKKFGKRNTI WLFGPATTGK TNIAEAIAHT VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLDHDFGK VTKQEVKDFF RWAKDHVVEV    480
EHEFYVKKGG AKKRPAPSDA DISEPKRVRE SVAQPSTSDA EASINYADRY QNKCSRHVGM    540
NLMLFPCRQC ERMNQNSNIC FTHGQKDCLE CFPVSEDNAS QPVSVVKKAY QKLCYIHHIM    600
GKVPDACTAC DLVNVDLDDC IFEQ                                           624

SEQ ID NO: 191              moltype = AA  length = 621
FEATURE                     Location/Qualifiers
source                      1..621
                            mol_type = protein
                            organism = synthetic construct
SEQUENCE: 191
TPGFYEIVIK VPSDLDEHLP GISDSFVNWV AEKEWELPPD SDMDLNLIEQ APLTVAEKLQ    60
RDFLTEWRRV SKAPEALFFV QFEKGESYFH MHVLVETTGV KSMVLGRFLS QIREKLIQRI    120
YRGIEPTLPN WFAVTKTRNG AGGGNKVVDE CYIPNYLLPK TQPELQWAWT NMEQYLSACL    180
NLTERKRLVA QHLTHVSQTQ EQNKENQNPN SDAPVIRSKT SARYMELVGW LVDKGITSEK    240
QWIQEDQASY ISFNAASNSR SQIKAALDNA GKIMALTKSA PDYLVGPAPP ADIKTNRIYR    300
ILELNGYEPA YAGSVFLGWA QKRFGKRNTI WLFGPATTGK TNIAEAIAHA VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLDHDFGK VTKQEVKDFF RWAKDHVVEV    480
EHEFYVKKGG AKKRPAPSDA DISEPKRVRE SVAQPSTSDA EASINYADRY QNKCSRHVGM    540
NLMLFPCRQC ERMNQNSNIC FTHGQKDCLE CFPVSESQPV SVVKKAYQKL CYIHHIMGKV    600
PDACTACDLV NVDLDDCIFE Q                                              621

SEQ ID NO: 192              moltype = AA  length = 621
FEATURE                     Location/Qualifiers
source                      1..621
                            mol_type = protein
                            organism = synthetic construct
SEQUENCE: 192
MPGFYEIVIK VPSDLDEHLP GISDSFVNWV AEKEWELPPD SDMDRNLIEQ APLTVAEKLQ    60
RDFLVQWRRV SKAPEALFFV QFEKGESYFH LHVLVETTGV KSMVLGRFLS QIRDKLVQTI    120
YRGIEPTLPN WFAVTKTRNG AGGGNKVVDE CYIPNYLLPK TQPELQWAWT NMEEYISACL    180
NLAERKRLVA QHLTHVSQTQ EQNKENLNPN SDAPVIRSKT SARYMELVGW LVDRGITSEK    240
QWIQEDQASY ISFNAASNSR SQIKAALDNA GKIMALTKSA PDYLVGPSLP ADITQNRIYR    300
ILALNGYDPA YAGSVFLGWA QKKFGKRNTI WLFGPATTGK TNIAEAIAHA VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLDHDFGK VTKQEVKDFF RWAKDHVVEV    480
EHEFYVKKGG AKKRPAPSDA DISEPKRVRE SVAQPSTSDA EASINYADRY QNKCSRHVGM    540
NLMLFPCRQC ERMNQNSNIC FTHGQKDCLE CFPVSESQPV SVVKKAYQKL CYIHHIMGKV    600
PDACTACDLV NVDLDDCIFE Q                                              621

SEQ ID NO: 193              moltype = AA  length = 621
FEATURE                     Location/Qualifiers
source                      1..621
                            mol_type = protein
```

-continued

```
                        organism = synthetic construct
SEQUENCE: 193
MPGFYEIVIK VPSDLDEHLP GISDSFVNWV AEKEWELPPD SDMDRNLIEQ APLTVAEKLQ    60
RDFLVQWRRV SKAPEALFFV QFEKGESYFH LHVLVETTGV KSMVLGRFLS QIREKLVQTI   120
YRGVEPTLPN WFAVTKTRNG AGGGNKVVDE CYIPNYLLPK TQPELQWAWT NMEEYISACL   180
NLAERKRLVA QHLTHVSQTQ EQNKENLNPN SDAPVIRSKT SARYMELVGW LVDRGITSEK   240
QWIQEDQASY ISFNAASNSR SQIKAALDNA GKIMALTKSA PDYLVGPSLP ADITQNRIYR   300
ILALNGYDPA YAGSVFLGWA QKKFGKRNTI WLFGPATTGK TNIAEAIAHA VPFYGCVNWT   360
NENFPFNDCV DKMVIWWEEG KMTAKVVESA KAILGGSKVR VDQKCKSSAQ IDPTPVIVTS   420
NTNMCAVIDG NSTTFEHQQP LQDRMFKFEL TRRLDHDFGK VTKQEVKDFF RWAKDHVVEV   480
EHEFYVKKGG AKKRPAPSDA DISEPKRVRE SVAQPSTSDA EASINYADRY QNKCSRHVGM   540
NLMLFPCRQC ERMNQNSNIC FTHGQKDCLE CFPVSESQPV SVVKKAYQKL CYIHHIMGKV   600
PDACTACDLV NVDLDDCIFE Q                                             621

SEQ ID NO: 194          moltype = DNA  length = 1866
FEATURE                 Location/Qualifiers
source                  1..1866
                        mol_type = other DNA
                        organism = synthetic construct
SEQUENCE: 194
atgccgggct tctacgagat cgtgatcaag gtgccgagcg acctggacga gcacctgccg     60
ggcatttctg actcgtttgt gagctgggtg gccgagaagg aatgggagct gccccccgga    120
tctgacatgg atctgaatct gattgagcag gcacccctga ccgtggccga gaagctgcag    180
cgcgacttcc tggtccaatg gcgccgcgtg agtaaggccc cggaggccct cttctttgtt    240
cagttcgaga agggcgagtc ctacttccac ctccatattc tggtggagac cacgggggtc    300
aaatccatgg tgctgggccg cttcctgagt cagattacaa caagctggt gcagaccatc     360
taccgcggga tcgagccgac cctgcccaac tggttcgcgg tgaccaagac gcgtaatggc    420
gccgaggggg ggaacaaggt ggtggacgag tgctacatcc caactacct cctgcccaag     480
actcagcccg agctgcagtg ggcgtggact aacatggagg agtatataag cgcctgtttg    540
aacctggcgg agcgcaaacg gctcgtggcg cagcacctga cccacgtcag ccagacccag    600
gagcagaaca aggagaatct gaaccccaat tctgacgcgc ctgtcatccg gtcaaaaacc    660
tccgcgcgct acatggagct ggtcgggtgg ctggtggacc ggggcatcac ctccgagaag    720
cagtggatcc aggaggacca ggcctcgtac atctccttca cgccgcttc caactcgcgg     780
tcccagatca aggccgctct ggacaatgcc ggcaagatca tggcgctgac caaatccgcg    840
cccgactacc tggtaggccc cgctccgccc gcggacatta aaaccaaccg catctaccgc    900
atcctggagc tgaacggcta cgaacctgcc tacgccggct ccgtctttct cggctgggcc    960
cagaaaaagg tcgggaagcg caacaccatc tggctgtttg gccggccac cacggggaag    1020
accaacatcg cggaagccat cgcccacgcc gtgcccttct acggctgcgt caactggacc    1080
aatgagaact tcccttcaa tgattcgtc gacaagatga tgatctggtg gaggaggggg     1140
aagatgaccc ccaaggtcgt ggagtcggcc aaagccattc tcggaggaag caaggtgcgc    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgcctgc tggatcatga ctttgggaag    1380
gtcaccaagc aggaagtcaa agactttttc cggtgggcaa aggatcacgt ggttgaggtg    1440
gagcatgaat ctacgtcaa aaaggggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc agacaggtac caaaacgaat gttctcgtca cgtgggcatg    1620
aatctgatgc tgtttccctg cagacaatgc gagagaatga atcagaattc aaatatctgc    1680
ttcactcacg gacagaaaga ctgtttagag tgctttcccg tgtcagaatc tcaacccgtt    1740
tctgtcgtca aaaaggcgta tcagaaactg tgctacattc atcatatcat gggaaaggtg    1800
ccagacgctt gcactgcctg cgatctggtc aatgtggatt ggatgactg catctttgaa    1860
caataa                                                              1866

SEQ ID NO: 195          moltype = DNA  length = 1866
FEATURE                 Location/Qualifiers
source                  1..1866
                        mol_type = other DNA
                        organism = synthetic construct
SEQUENCE: 195
atgccgggct tctacgagat cgtgatcaag gtgccgagcg acctggacga gcacctgccg     60
ggcatttctg actcgtttgt gagctgggtg gccgagaagg aatgggagct gccccccgga    120
tctgacatgg atctgaatct gattgagcag gcacccctga ccgtggccga gaagctgcag    180
cgcgacttcc tggtccaatg gcgccgcgtg agtaaggccc cggaggccct cttctttgtt    240
cagttcgaga agggcgagtc ctacttccac ctccatattc tggtggagac cacgggggtc    300
aaatccatgg tgctgggccg cttcctgagt cagattaggg acaagctggt gcagaccatc    360
taccgcggga tcgagccgac cctgcccaac tggttcgcgg tgaccaagac gcgtaatggc    420
gccgaggggg ggaacaaggt ggtggacgag tgctacatcc caactacct cctgcccaag     480
actcagcccg agctgcagtg ggcgtggact aacatggagg agtatataag cgcctgtttg    540
aacctggcgg agcgcaaacg gctcgtggcg cagcacctga cccacgtcag ccagacccag    600
gagcagaaca aggagaatct gaaccccaat tctgacgcgc ctgtcatccg gtcaaaaacc    660
tccgcgcgct acatggagct ggtcgggtgg ctggtggacc ggggcatcac ctccgagaag    720
cagtggatcc aggaggacca ggcctcatac atctccttca tgcggcctc caactcgcgg     780
tcccaaatca aggctgcctt ggacaatgcg ggaaagatta tgagcctgac taaaaccgcc    840
cccgactacc tgtttgggcca gcagcccgta gaggcaattt acagcaatcg gatttataaa    900
attttgaaac taaacgggta cgatcccaa tatgcggctt ccgtctttct gggatgggcc     960
acgaaaaagt tcggcaagag gaacaccatc tggctgtttg gcctgcaac taccgggaag    1020
accaacatcg cggaggccat agcccacact gtgcccttct acgggtgcgt aaactggacc    1080
aatgagaact tcccttcaa cgactgtgtc gacaagatgg tgatctggtg ggaggagggg    1140
aagatgaccc ccaaggtcgt ggagtcggcc aaagccattc tcggaggaag caaggtgcgc    1200
```

```
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agacttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                              1866

SEQ ID NO: 196        moltype = DNA  length = 1866
FEATURE               Location/Qualifiers
source                1..1866
                      mol_type = other DNA
                      organism = synthetic construct
SEQUENCE: 196
acgccggggt tttacgagat tgtgattaag gtccccagcg accttgacga gcatctgccc    60
ggcatttctg acagctttgt gaactgggtg gccgagaagg aatgggagtt gccgccagat   120
tctgacatgg atctgaatct gattgagcag gcaccctga ccgtggccga gaagctgcag   180
cgcgactttc tgacggaatg gcgccgtgtg agtaaggccc cggaggccct tttctttgtg   240
caatttgaga agggagagag ctacttccac atgcacgtgc tcgtgaaaac caccggggtg   300
aaatccatgt gctgggccg cttcctgagt cagattaggg acaagctggt gcagaccatc   360
taccgcggga tcgagccgac cctgcccaac tggttcgcgg tgaccaagac gcgtaatgcg   420
gccggagggg ggaacaaggt ggtggacgag tgctacatcc caactacctt cctgcccaag   480
actcagcccg agctgcagtg ggcgtggact aacatggagg agtatataag cgcctgtttg   540
aacctggccg agcgcaaacg gctcgtggcg cagcacctga cccacgtcag ccagacccag   600
gagcagaaca aggagaatct gaacccccaat tctgaaaccc ctgtcatccg gtcaaaaacc   660
tccgcgcgct acatggagct ggtcgggtgg ctggtggacc ggggcatcac ctccgagaag   720
cagtggatcc aggaggacca ggcctcatac atctccttca atgcggcctc caactcgcgg   780
tcccaaatca aggctgcctt ggacaatgcg ggaaagatta tgagcctgac taaaaccgcc   840
cccgactacc tggtgggcca gcagccccgtg gaggacattt ccagcaatcg gatttataaa   900
atttggaac taaacgggta cgatccccaa tatgcggctt ccgtcttctct gggatgggcc   960
acgaaaagt tcggcaagag gaacaccatc tggctgtttg ggcctgcaac taccgggaag  1020
accaacatcg cggaggccat agcccacact gtgcccttct acgggtgcgt aaactggacc  1080
aatgagaact ttcccttcaa cgactgtgtc gacaagatgt gtatctggtg ggaggagggg  1140
aagatgaccg ccaaggtcgt ggagtcggcc aaagccattc tcggaggaag caaggtgcgc  1200
gtggaccaga aatgcaagtc ctcggcccag atagacccga ctcccgtgat cgtcacctcc  1260
aacaccaaca tgtgcgccgt gattgacggg aactcaacga ccttcgaaca ccagcagccg  1320
ttgcaagacc ggatgttcaa atttgaactc acccgccgtc tggatcatga ctttgggaag  1380
gtcaccaagc aggaagtcaa agactttttc cggtgggcaa aggatcacgt ggttgaggtg  1440
gagcatgaat tctacgtcaa aaagggtgga gccaagaaaa gacccgcccc cagtgacgca  1500
gatataagtg agcccaaacg ggtgcgcgag tcagttgcgc agccatcgac gtcagacgcg  1560
gaagcttcga tcaactacgc agacaggtac caaaacaaat gttctcgtca cgtgggcatg  1620
aatctgatgc tgtttccctg cagacaatgc gagagaatga atcagaattc aaatatctgc  1680
ttcactcacg gacagaaaga ctgtttagag tgctttcccg tgtcagaatc tcaacccgtt  1740
tctgtcgtca aaaaggcgta tcagaaactg tgctacattc atcatatcat gggaaaggtg  1800
ccagacgctt gcactgcctg cgatctggtc aatgtggatt tggatgactg catctttgaa  1860
caataa                                                             1866

SEQ ID NO: 197        moltype = DNA  length = 1866
FEATURE               Location/Qualifiers
source                1..1866
                      mol_type = other DNA
                      organism = synthetic construct
SEQUENCE: 197
acgccggggt tttacgagat tgtgattaag gtccccagcg accttgacga gcatctgccc    60
ggcatttctg acagctttgt gaactgggtg gccgagaagg aatgggagtt gccgccagat   120
tctgacatgg atctgaatct gattgagcag gcaccctga ccgtggccga gaagctgcag   180
cgcgactttc tgacggaatg gcgccgtgtg agtaaggccc cggaggccct tttctttgtg   240
caatttgaga agggagagag ctacttccac atgcacgtgc tcgtgaaaac caccggggtg   300
aaatccatgt ttttgggacg tttcctgagt cagattcgcg aaaaactgat tcagagaatt   360
taccgcggga tcgagccgac tttgccaaac tggttcgcgg tcacaaagac cagaaatggc   420
gccggaggcg ggaacaaggt ggtggatgag tgctacatcc caattacttt gctccccaaa   480
acccagcctg agctccagtg ggcgtggact aatatgaac agtatttaag cgcctgtttg   540
aatctcacgg agcgtaaacg gttggtggcg cagcatctga cgcacgtgtc gcagacgcag   600
gagcagaaca aagagaatct gaatcccaat tctgaagcct cggtgatcag atcaaaaact   660
tcagccaggt acatggagct ggtcgggtgg ctcgtggaca aggggattac ctcggagaag   720
cagtggatcc aggaggacca ggcctcgtac atctccttca acgccgcttc caactcgcgg   780
tcccagatca aggccgctct ggacaatgcc ggcaagatca tggcgctgac caaatccgcg   840
cccgactacc tggtaggccc cgctccgccc gcggacatta aaaccaaccg catctaccgc   900
atcctggagc tgaacggcta cgaacctgcc tcgtcttttct ccggctgggcc   960
cagaaaaggt tcgggaagcg caacaccatc tggctgtttg gccggccac cacgggcaag  1020
accaacatcg cggaagccat cgcccacgcc gtgcccttct acggctgcgt caactggacc  1080
aatgagaact ttcccttcaa tgattgcgtc gacaagatgt gtatctggtg ggaggagggg  1140
aagatgaccg ccaaggtcgt ggagtcggcc aaagccattc tcggaggaag caaggtgcgc  1200
gtggaccaga aatgcaagtc ctcggcccag atagacccga ctcccgtgat cgtcacctcc  1260
```

```
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agacttttc cggtgggcaa aggatcacgt ggttgaggtg    1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                             1866

SEQ ID NO: 198         moltype = DNA   length = 1866
FEATURE                Location/Qualifiers
source                 1..1866
                       mol_type = other DNA
                       organism = synthetic construct
SEQUENCE: 198
atgccgggct tctacgagat cgtgatcaag gtgccgagcg acctggacga gcacctgccg   60
ggcatttctg actcgtttgt gaactgggtg gccgagaagg aatgggagct gccccccggat  120
tctgacatgg atcggaatct gatcgagcag gcaccctga ccgtggccga gaagctgcag    180
cgcgacttcc tggtccaatg gcgccgcgtg agtaaggccc ggaggccct cttctttgtt    240
cagttcgaga agggcgagag ctactttcac ctgcacgttc tggtcgagac cacggggtc    300
aagtccatgg tgctgggccg cttcctgagt cagattaggg acaagctggt gcagaccatc   360
taccgcggga tcgagccgac cctgcccaac tggttcgcgg tgaccaagac gcgtaatggc   420
gccggagggg ggaacaaggt ggtggacgag tgctacatcc ccaactacct cctgcccaag   480
actcagcccg agctgcagtg ggcgtggact aacatggagg agtatataag cgcctgtttg   540
aacctggccg agcgcaaacg gctcgtggcg cagcacctga cccacgtcag ccagacccag   600
gagcagaaca aggagaatct gaaccccaat tctgacgcgc tgtcatccg gtcaaaaacc   660
tccgcggct atatggacc ggtcgggtgg ctggtgacc ggggcatcac ctccgagaag      720
cagtggatcc aggaggacca ggcctcgtac atctccttca acgccgcctc caactcgcgg   780
tcccagatca aggccgcgct ggacaatgcc ggcaagatca tggcgctgac caaatccgcg   840
cccgactacc tggtgggcc ctcgctgccc gcggacatta cccagaaccg catctaccgc    900
atcctcgctc tcaacggcta cgaccctgcc tacgccggct ccgtctttct cggctgggct   960
cagaaaaagt tcgggaaacg caacaccatc tggctgtttg gacccgccac caccggcaag   1020
accaacattg cggaagccat cgcccacgcc gtgcccttct acggctgcgt caactggacc   1080
aatgagaact ttcccttcaa tgattgcgtc gacaagatgg tgatctggtg ggaggagggg   1140
aagatgaccg ccaaggtcgt gggagtcggcc aagccattc tcggaggaag caaggtgcgc   1200
gtggaccaga aatgcaagtc ctcggccag atagacccga ctcccgtgat cgtcacctcc    1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agacttttc cggtgggcaa aggatcacgt ggttgaggtg    1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                             1866

SEQ ID NO: 199         moltype = DNA   length = 1866
FEATURE                Location/Qualifiers
source                 1..1866
                       mol_type = other DNA
                       organism = synthetic construct
SEQUENCE: 199
atgccgggct tctacgagat cgtgatcaag gtgccgagcg acctggacga gcacctgccg   60
ggcatttctg actcgtttgt gaactgggtg gccgagaagg aatgggagct gccccccggat  120
tctgacatgg atcggaatct gatcgagcag gcaccctga ccgtggccga gaagctgcag    180
cgcgacttcc tggtccaatg gcgccgcgtg agtaaggccc ggaggccct cttctttgtt    240
cagttcgaga agggcgagag ctactttcac ctgcacgttc tggtcgagac cacggggtc    300
aagtccatgg tgctaggccg cttcctgagt cagattcggg aaaagctggt ccagaccatc   360
taccgcgggg tcgagcccac cttgcccaac tggttcgcgg tgaccaagac gcgtaatggc   420
gccgggggg ggaacaaggt ggtggacgag tgctacatcc ccaactacct cctgcccaag    480
actcagcccg agctgcagtg ggcgtggact aacatggagg agtatataag cgcgtgcttg   540
aacctggccg agcgcaaacg gctcgtggcg cagcacctga cccacgtcag ccagacgcag   600
gagcagaaca aggagaatct gaaccccaat tctgacgcgc cgtgatcag gtcaaaaacc    660
tccgcgcgct atatggacc ggtcgggtgg ctggtgacc ggggcatcac ctccgagaag     720
cagtggatcc aggaggacca ggcctcgtac atctccttca acgccgcctc caactcgcgg   780
tcccagatca aggccgcgct ggacaatgcc ggcaagatca tggcgctgac caaatccgcg   840
cccgactacc tggtgggcc ctcgctgccc gcggacatta cccagaaccg catctaccgc    900
atcctcgctc tcaacggcta cgaccctgcc tacgccggct ccgtctttct cggctgggct   960
cagaaaaagt tcgggaaacg caacaccatc tggctgtttg gacccgccac caccggcaag   1020
accaacattg cggaagccat cgcccacgcc gtgcccttct acggctgcgt caactggacc   1080
aatgagaact ttcccttcaa tgattgcgtc gacaagatgg tgatctggtg ggaggagggg   1140
aagatgaccg ccaaggtcgt gggagtcggcc aagccattc tcggaggaag caaggtgcgc   1200
gtggaccaga aatgcaagtc ctcggccag atagacccga ctcccgtgat cgtcacctcc    1260
aacaccaaca tgtgcgccgt gattgacggg aactcaacga ccttcgaaca ccagcagccg   1320
```

-continued

```
ttgcaagacc ggatgttcaa atttgaactc acccgccgtc tggatcatga ctttgggaag  1380
gtcaccaagc aggaagtcaa agactttttc cggtgggcaa aggatcacgt ggttgaggtg  1440
gagcatgaat tctacgtcaa aaagggtgga gccaagaaaa gacccgcccc cagtgacgca  1500
gatataagtg agcccaaacg ggtgcgcgag tcagttgcgc agccatcgac gtcagacgcg  1560
gaagcttcga tcaactacgc agacaggtac caaaacaaat gttctcgtca cgtgggcatg  1620
aatctgatgc tgtttccctg cagacaatgc gagagaatga atcagaattc aaatatctgc  1680
ttcactcacg gacagaaaga ctgtttagag tgctttcccg tgtcagaatc tcaacccgtt  1740
tctgtcgtca aaaaggcgta tcagaaactg tgctacattc atcatatcat gggaaaggtg  1800
ccagacgctt gcactgcctg cgatctggtc aatgtggatt tggatgactg catctttgaa  1860
caataa                                                              1866
```